United States Patent
Kang et al.

(10) Patent No.: US 10,689,630 B2
(45) Date of Patent: Jun. 23, 2020

(54) PROCESSES FOR PRODUCING FERMENTATION PRODUCTS

(71) Applicant: NOVOZYMES A/S, Bagsvaerd (DK)

(72) Inventors: Zhengfang Kang, Raleigh, NC (US); Christie Lynn Strahler, Knightdale, NC (US); James Ron Huffman, Wake Forest, NC (US); Kristian Bertel Rømer M. Krogh, Bagsvaerd (DK)

(73) Assignee: NOVOZYMES A/S, Bagsvaerd (DK)

( * ) Notice: Subject to any disclaimer, the term of this patent is extended or adjusted under 35 U.S.C. 154(b) by 0 days.

(21) Appl. No.: 16/061,149

(22) PCT Filed: Dec. 16, 2016

(86) PCT No.: PCT/US2016/067177
§ 371 (c)(1),
(2) Date: Jun. 11, 2018

(87) PCT Pub. No.: WO2017/112540
PCT Pub. Date: Jun. 29, 2017

(65) Prior Publication Data
US 2018/0371505 A1 Dec. 27, 2018

Related U.S. Application Data

(60) Provisional application No. 62/430,695, filed on Dec. 6, 2016, provisional application No. 62/324,107, filed on Apr. 18, 2016, provisional application No. 62/271,182, filed on Dec. 22, 2015, provisional application No. 62/271,063, filed on Dec. 22, 2015.

(51) Int. Cl.
| | |
|---|---|
| *C12P 7/02* | (2006.01) |
| *C12P 7/04* | (2006.01) |
| *C12N 9/24* | (2006.01) |
| *C12N 9/26* | (2006.01) |
| *C12N 9/44* | (2006.01) |
| *C12N 9/16* | (2006.01) |
| *C12P 19/14* | (2006.01) |
| *C12N 9/34* | (2006.01) |
| *C12N 9/42* | (2006.01) |
| *C12N 9/50* | (2006.01) |
| *C12N 9/20* | (2006.01) |
| *C12P 7/06* | (2006.01) |
| *C12N 9/28* | (2006.01) |

(52) U.S. Cl.
CPC .............. *C12N 9/16* (2013.01); *C12N 9/20* (2013.01); *C12N 9/2414* (2013.01); *C12N 9/2417* (2013.01); *C12N 9/2428* (2013.01); *C12N 9/2437* (2013.01); *C12N 9/2457* (2013.01); *C12N 9/50* (2013.01); *C12P 7/06* (2013.01); *C12P 19/14* (2013.01); *C12Y 301/03008* (2013.01); *C12Y 301/04* (2013.01); *C12Y 301/04011* (2013.01); *C12Y 302/01001* (2013.01); *C12Y 302/01003* (2013.01); *C12Y 302/01004* (2013.01); *C12Y 302/01008* (2013.01); *C12Y 302/01041* (2013.01); *C12Y 304/21062* (2013.01); *C12Y 304/23023* (2013.01); *C12Y 304/24039* (2013.01); *Y02E 50/17* (2013.01)

(58) Field of Classification Search
CPC .. C12N 15/8246; C12N 9/248; C12N 9/2437; C12N 9/2445
See application file for complete search history.

(56) References Cited

U.S. PATENT DOCUMENTS

| | | | |
|---|---|---|---|
| 5,688,668 A | 11/1997 | Sjoholm | |
| 2012/0258497 A1* | 10/2012 | Andersen | C12N 9/2417 435/69.6 |
| 2013/0029382 A1* | 1/2013 | Steffens | C12N 9/2434 435/94 |
| 2016/0138035 A1* | 5/2016 | Raab | C12N 9/2437 800/320.1 |
| 2016/0333332 A1 | 11/2016 | Teunissen | |
| 2016/0340664 A1 | 11/2016 | Arent Lund | |
| 2016/0345609 A1 | 12/2016 | Lorentsen | |
| 2017/0009220 A1 | 1/2017 | Lorentsen | |

FOREIGN PATENT DOCUMENTS

| | | |
|---|---|---|
| WO | 2004/087889 A1 | 10/2004 |
| WO | 06/066582 A1 | 6/2006 |
| WO | 2009/100179 A1 | 8/2009 |
| WO | 2011/082425 A2 | 7/2011 |
| WO | 2011/091260 A2 | 7/2011 |
| WO | 2012/088303 A2 | 6/2012 |
| WO | 2015/035914 A1 | 3/2015 |

OTHER PUBLICATIONS

Liang et al, 2011, J Biotechnol 154(1), 46-53.
Palackal et al, 2004, Protein Sci 13(2), 494-503.
Carl et al, 2010, Adv Appl Microbiol 70, 1-55.

* cited by examiner

*Primary Examiner* — Maryam Monshipouri
(74) *Attorney, Agent, or Firm* — David Fazzolare

(57) ABSTRACT

The present invention relates to processes for producing fermentation products from starch-containing material, wherein an alpha-amylase and a thermostable hemicellulase is present and/or added during liquefaction. The invention also relates to compositions suitable for use in processes of the invention.

29 Claims, 1 Drawing Sheet
Specification includes a Sequence Listing.

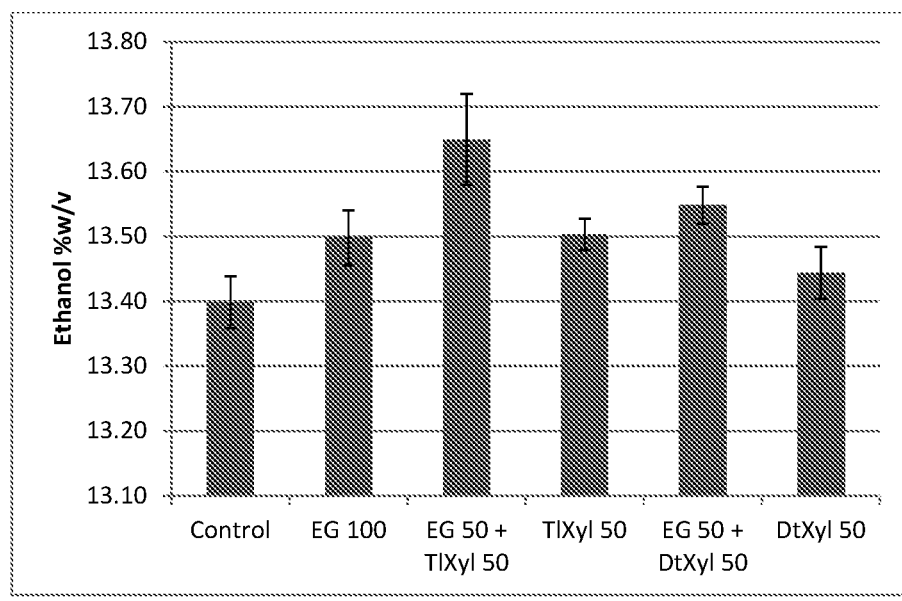

SEQUENCE LISTING

<160> NUMBER OF SEQ ID NOS: 38

<210> SEQ ID NO 1
<211> LENGTH: 515
<212> TYPE: PRT
<213> ORGANISM: Bacillus stearothermophilus
<220> FEATURE:
<221> NAME/KEY: mat_peptide
<222> LOCATION: (1)..(515)

<400> SEQUENCE: 1

Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
            20                  25                  30

Leu Ser Ser Leu Gly Ile Thr Ala Leu Trp Leu Pro Pro Ala Tyr Lys
        35                  40                  45

Gly Thr Ser Arg Ser Asp Val Gly Tyr Gly Val Tyr Asp Leu Tyr Asp
    50                  55                  60

Leu Gly Glu Phe Asn Gln Lys Gly Thr Val Arg Thr Lys Tyr Gly Thr
65                  70                  75                  80

Lys Ala Gln Tyr Leu Gln Ala Ile Gln Ala Ala His Ala Ala Gly Met
                85                  90                  95

Gln Val Tyr Ala Asp Val Val Phe Asp His Lys Gly Gly Ala Asp Gly
            100                 105                 110

Thr Glu Trp Val Asp Ala Val Glu Val Asn Pro Ser Asp Arg Asn Gln
        115                 120                 125

Glu Ile Ser Gly Thr Tyr Gln Ile Gln Ala Trp Thr Lys Phe Asp Phe
    130                 135                 140

Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
                165                 170                 175

Lys Phe Arg Gly Ile Gly Lys Ala Trp Asp Trp Glu Val Asp Thr Glu
            180                 185                 190

Asn Gly Asn Tyr Asp Tyr Leu Met Tyr Ala Asp Leu Asp Met Asp His
        195                 200                 205

Pro Glu Val Val Thr Glu Leu Lys Asn Trp Gly Lys Trp Tyr Val Asn
    210                 215                 220

Thr Thr Asn Ile Asp Gly Phe Arg Leu Asp Ala Val Lys His Ile Lys
225                 230                 235                 240

Phe Ser Phe Phe Pro Asp Trp Leu Ser Tyr Val Arg Ser Gln Thr Gly
                245                 250                 255

Lys Pro Leu Phe Thr Val Gly Glu Tyr Trp Ser Tyr Asp Ile Asn Lys
            260                 265                 270

Leu His Asn Tyr Ile Thr Lys Thr Asn Gly Thr Met Ser Leu Phe Asp
        275                 280                 285

Ala Pro Leu His Asn Lys Phe Tyr Thr Ala Ser Lys Ser Gly Gly Ala
    290                 295                 300

Phe Asp Met Arg Thr Leu Met Thr Asn Thr Leu Met Lys Asp Gln Pro
305                 310                 315                 320

Thr Leu Ala Val Thr Phe Val Asp Asn His Asp Thr Glu Pro Gly Gln
                325                 330                 335

Ala Leu Gln Ser Trp Val Asp Pro Trp Phe Lys Pro Leu Ala Tyr Ala
            340                 345                 350

```
Phe Ile Leu Thr Arg Gln Glu Gly Tyr Pro Cys Val Phe Tyr Gly Asp
            355                 360                 365

Tyr Tyr Gly Ile Pro Gln Tyr Asn Ile Pro Ser Leu Lys Ser Lys Ile
        370                 375                 380

Asp Pro Leu Leu Ile Ala Arg Arg Asp Tyr Ala Tyr Gly Thr Gln His
385                 390                 395                 400

Asp Tyr Leu Asp His Ser Asp Ile Ile Gly Trp Thr Arg Glu Gly Val
                405                 410                 415

Thr Glu Lys Pro Gly Ser Gly Leu Ala Ala Leu Ile Thr Asp Gly Pro
                420                 425                 430

Gly Gly Ser Lys Trp Met Tyr Val Gly Lys Gln His Ala Gly Lys Val
            435                 440                 445

Phe Tyr Asp Leu Thr Gly Asn Arg Ser Asp Thr Val Thr Ile Asn Ser
        450                 455                 460

Asp Gly Trp Gly Glu Phe Lys Val Asn Gly Gly Ser Val Ser Val Trp
465                 470                 475                 480

Val Pro Arg Lys Thr Thr Val Ser Thr Ile Ala Arg Pro Ile Thr Thr
                485                 490                 495

Arg Pro Trp Thr Gly Glu Phe Val Arg Trp Thr Glu Pro Arg Leu Val
            500                 505                 510

Ala Trp Pro
    515

<210> SEQ ID NO 2
<211> LENGTH: 177
<212> TYPE: PRT
<213> ORGANISM: Thermoascus aurantiacus
<220> FEATURE:
<221> NAME/KEY: mat_peptide
<222> LOCATION: (1)..(177)

<400> SEQUENCE: 2

Thr Arg Ile Ser Ser Cys Ser Gly Ser Arg Gln Ser Ala Leu Thr Thr
1               5                   10                  15

Ala Leu Arg Asn Ala Ala Ser Leu Ala Asn Ala Ala Asp Ala Ala
            20                  25                  30

Gln Ser Gly Ser Ala Ser Lys Phe Ser Glu Tyr Phe Lys Thr Thr Ser
        35                  40                  45

Ser Ser Thr Arg Gln Thr Val Ala Ala Arg Leu Arg Ala Val Ala Arg
    50                  55                  60

Glu Ala Ser Ser Ser Ser Gly Ala Thr Thr Tyr Tyr Cys Asp Asp
65                  70                  75                  80

Pro Tyr Gly Tyr Cys Ser Ser Asn Val Leu Ala Tyr Thr Leu Pro Ser
                85                  90                  95

Tyr Asn Ile Ile Ala Asn Cys Asp Ile Phe Tyr Thr Tyr Leu Pro Ala
            100                 105                 110

Leu Thr Ser Thr Cys His Ala Gln Asp Gln Ala Thr Thr Ala Leu His
        115                 120                 125

Glu Phe Thr His Ala Pro Gly Val Tyr Ser Pro Gly Thr Asp Asp Leu
    130                 135                 140

Ala Tyr Gly Tyr Gln Ala Ala Met Gly Leu Ser Ser Ser Gln Ala Val
145                 150                 155                 160

Met Asn Ala Asp Thr Tyr Ala Leu Tyr Ala Asn Ala Ile Tyr Leu Gly
                165                 170                 175

Cys
```

```
<210> SEQ ID NO 3
<211> LENGTH: 356
<212> TYPE: PRT
<213> ORGANISM: Dictyoglomus thermophilum
<220> FEATURE:
<221> NAME/KEY: SIGNAL
<222> LOCATION: (1)..(27)

<400> SEQUENCE: 3

Met Lys Lys Pro Leu Gly Lys Ile Val Ala Ser Thr Ala Leu Leu Ile
1               5                   10                  15

Ser Val Ala Phe Ser Ser Ile Ala Ser Ala Lys Glu Glu Ala Lys
            20                  25                  30

Gly Met Glu Ile Pro Ser Leu Lys Glu Val Tyr Lys Asp Tyr Phe Thr
        35                  40                  45

Ile Gly Ala Ala Val Ser His Leu Asn Ile Tyr His Tyr Glu Asn Leu
    50                  55                  60

Leu Lys Lys His Phe Asn Ser Leu Thr Pro Glu Asn Gln Met Lys Trp
65                  70                  75                  80

Glu Val Ile His Pro Lys Pro Tyr Val Tyr Asp Phe Gly Pro Ala Asp
                85                  90                  95

Glu Ile Val Asp Phe Ala Met Lys Asn Gly Met Lys Val Arg Gly His
            100                 105                 110

Thr Leu Val Trp His Asn Gln Thr Pro Gly Trp Val Tyr Ala Gly Thr
        115                 120                 125

Lys Asp Glu Ile Leu Ala Arg Leu Lys Glu His Ile Lys Glu Val Val
    130                 135                 140

Gly His Tyr Lys Gly Lys Val Tyr Ala Trp Asp Val Val Asn Glu Ala
145                 150                 155                 160

Leu Ser Asp Asn Pro Asn Glu Phe Leu Arg Arg Ala Pro Trp Tyr Asp
                165                 170                 175

Ile Cys Gly Glu Glu Val Ile Glu Lys Ala Phe Ile Trp Ala His Glu
            180                 185                 190

Val Asp Pro Asp Ala Lys Leu Phe Tyr Asn Asp Tyr Asn Leu Glu Asp
        195                 200                 205

Pro Ile Lys Arg Glu Lys Ala Tyr Lys Leu Val Lys Lys Leu Lys Asp
    210                 215                 220

Lys Gly Val Pro Ile His Gly Ile Gly Ile Gln Gly His Trp Thr Leu
225                 230                 235                 240

Ala Trp Pro Thr Pro Lys Met Leu Glu Asp Ser Ile Lys Arg Phe Ala
                245                 250                 255

Glu Leu Gly Val Glu Val Gln Val Thr Glu Phe Asp Ile Ser Ile Tyr
            260                 265                 270

Tyr Asp Arg Asn Glu Asn Asn Phe Lys Val Pro Pro Glu Asp Arg
        275                 280                 285

Leu Glu Arg Gln Ala Gln Leu Tyr Lys Glu Ala Phe Glu Ile Leu Arg
    290                 295                 300

Lys Tyr Lys Gly Ile Val Thr Gly Val Thr Phe Trp Gly Val Ala Asp
305                 310                 315                 320

Asp Tyr Thr Trp Leu Tyr Phe Trp Pro Val Arg Gly Arg Glu Asp Tyr
                325                 330                 335

Pro Leu Leu Phe Asp Lys Asn His Asn Pro Lys Lys Ala Phe Trp Glu
            340                 345                 350

Ile Val Lys Phe
            355
```

<210> SEQ ID NO 4
<211> LENGTH: 383
<212> TYPE: PRT
<213> ORGANISM: Rasamsonia byssochlamydoides
<220> FEATURE:
<221> NAME/KEY: mat_peptide
<222> LOCATION: (1)..(383)

<400> SEQUENCE: 4

```
Asp Gly Leu Asn Thr Ala Ala Lys Ala Ile Gly Lys Leu Tyr Phe Gly
 1               5                  10                  15

Thr Ala Thr Asp Asn Pro Glu Leu Ser Asp Val Ala Tyr Glu Thr Gln
            20                  25                  30

Leu Asn Asn Thr Gln Asp Phe Gly Gln Ile Thr Pro Ala Asn Ser Met
        35                  40                  45

Lys Trp Asp Ala Thr Glu Pro Glu Gln Asn Thr Phe Thr Phe Ala Ala
 50                  55                  60

Gly Asp Gln Ile Ala Asp Leu Ala Glu Ala Asn Gly Gln Ile Leu Arg
 65                  70                  75                  80

Cys His Asn Leu Val Trp Tyr Asn Gln Leu Pro Ser Trp Val Thr Ser
                85                  90                  95

Gly Ser Trp Thr Asn Glu Thr Leu Leu Ala Ala Met Lys Asn His Ile
            100                 105                 110

Thr Asn Val Val Thr His Tyr Lys Gly Arg Cys Tyr Ala Trp Asp Val
        115                 120                 125

Val Asn Glu Ala Leu Asn Asp Asp Gly Thr Tyr Arg Asp Asn Val Phe
130                 135                 140

Tyr Gln Tyr Ile Gly Glu Ala Tyr Ile Pro Ile Ala Phe Glu Thr Ala
145                 150                 155                 160

Ala Ala Ala Asp Pro Asn Val Lys Leu Tyr Tyr Asn Asp Tyr Asn Ile
                165                 170                 175

Glu Tyr Ala Gly Val Lys Ala Thr Ala Ala Gln Asn Ile Val Lys Leu
            180                 185                 190

Val Gln Ser Tyr Gly Ala Arg Ile Asp Gly Val Gly Leu Gln Ser His
        195                 200                 205

Phe Ile Val Gly Glu Thr Pro Ser Thr Ser Thr Gln Ala Ser Asn Met
210                 215                 220

Ala Ser Phe Thr Ala Leu Gly Val Glu Val Ala Ile Thr Glu Leu Asp
225                 230                 235                 240

Ile Arg Met Gln Leu Pro Glu Thr Thr Ala Leu Leu Thr Gln Gln Ser
                245                 250                 255

Thr Asp Tyr Gln Ser Thr Val Gln Ala Cys Val Asn Thr Pro Gly Cys
            260                 265                 270

Val Gly Ile Thr Leu Trp Asp Trp Thr Asp Lys Tyr Ser Trp Val Pro
        275                 280                 285

Ser Thr Phe Ser Gly Tyr Gly Asp Ala Cys Pro Trp Asp Asp Asn Tyr
290                 295                 300

Gln Lys Lys Pro Ala Tyr Tyr Gly Ile Leu Thr Ala Leu Gly Gly Ser
305                 310                 315                 320

Ala Ser Thr Thr Thr Val Gly Thr Gly Thr Thr Thr Ser Thr Ala
                325                 330                 335

Thr Thr Ser Ser Thr Gly Ser Ser Gly Thr Gly Val Ala Gln His Trp
            340                 345                 350

Gly Gln Cys Gly Gly Ile Gly Trp Thr Gly Pro Thr Val Cys Ala Ser
```

```
                355                 360                 365
Gly Tyr Thr Cys Thr Val Val Asn Pro Tyr Tyr Ser Gln Cys Leu
        370                 375                 380
```

<210> SEQ ID NO 5
<211> LENGTH: 385
<212> TYPE: PRT
<213> ORGANISM: Talaromyces leycettanus
<220> FEATURE:
<221> NAME/KEY: mat_peptide
<222> LOCATION: (1)..(385)

<400> SEQUENCE: 5

```
Ala Gly Leu Asn Thr Ala Ala Lys Ala Ile Gly Lys Leu Tyr Phe Gly
1               5                   10                  15

Thr Ala Thr Asp Asn Pro Glu Leu Ser Asp Ser Thr Tyr Met Gln Glu
            20                  25                  30

Thr Asp Asn Thr Asp Asp Phe Gly Gln Leu Thr Pro Ala Asn Ser Met
        35                  40                  45

Lys Trp Asp Ala Thr Glu Pro Ser Gln Asn Thr Phe Thr Phe Thr Asn
    50                  55                  60

Gly Asp Gln Ile Ala Asn Leu Ala Lys Ser Asn Gly Gln Met Leu Arg
65                  70                  75                  80

Cys His Asn Leu Val Trp Tyr Asn Gln Leu Pro Ser Trp Val Thr Ser
                85                  90                  95

Gly Ser Trp Thr Asn Ala Thr Leu Leu Ala Ala Met Lys Asn His Ile
            100                 105                 110

Thr Asn Val Val Thr His Tyr Lys Gly Gln Cys Tyr Ala Trp Asp Val
        115                 120                 125

Val Asn Glu Ala Leu Asn Asp Asp Gly Thr Tyr Arg Ser Asn Val Phe
    130                 135                 140

Tyr Gln Tyr Ile Gly Glu Ala Tyr Ile Pro Ile Ala Phe Ala Thr Ala
145                 150                 155                 160

Ala Ala Ala Asp Pro Asn Ala Lys Leu Tyr Tyr Asn Asp Tyr Asn Ile
                165                 170                 175

Glu Tyr Pro Gly Ala Lys Ala Thr Ala Ala Gln Asn Ile Val Lys Met
            180                 185                 190

Val Lys Ala Tyr Gly Ala Lys Ile Asp Gly Val Gly Leu Gln Ser His
        195                 200                 205

Phe Ile Val Gly Ser Thr Pro Ser Gln Ser Gln Gln Ser Asn Met
    210                 215                 220

Ala Ala Phe Thr Ala Leu Gly Val Glu Val Ala Ile Thr Glu Leu Asp
225                 230                 235                 240

Ile Arg Met Thr Leu Pro Ser Thr Ser Ala Leu Leu Ala Gln Gln Ser
                245                 250                 255

Thr Asp Tyr Gln Ser Thr Val Ser Ala Cys Val Asn Thr Pro Lys Cys
            260                 265                 270

Ile Gly Ile Thr Leu Trp Asp Trp Thr Asp Lys Tyr Ser Trp Val Pro
        275                 280                 285

Asn Thr Phe Ser Gly Gln Gly Asp Ala Cys Pro Trp Asp Ser Asn Tyr
    290                 295                 300

Gln Lys Lys Pro Ala Tyr Tyr Gly Ile Leu Thr Ala Leu Gly Gly Ser
305                 310                 315                 320

Ala Ser Thr Ser Thr Thr Thr Thr Leu Val Thr Ser Thr Arg Thr Ser
                325                 330                 335
```

```
Thr Thr Thr Ser Thr Ser Ala Thr Ser Thr Ser Thr Gly Val Ala Gln
            340                 345                 350

His Trp Gly Gln Cys Gly Gly Ile Gly Trp Thr Gly Pro Thr Thr Cys
        355                 360                 365

Ala Ser Pro Tyr Thr Cys Gln Glu Leu Asn Pro Tyr Tyr Tyr Gln Cys
    370                 375                 380

Leu
385

<210> SEQ ID NO 6
<211> LENGTH: 775
<212> TYPE: PRT
<213> ORGANISM: Talaromyces emersonii
<220> FEATURE:
<221> NAME/KEY: mat_peptide
<222> LOCATION: (1)..(775)

<400> SEQUENCE: 6

Gln Asp Asn Gln Thr Tyr Ala Asn Tyr Ser Ser Gln Ser Gln Pro Asp
1               5                   10                  15

Leu Phe Pro Arg Thr Val Ala Thr Ile Asp Leu Ser Phe Pro Asp Cys
            20                  25                  30

Glu Asn Gly Pro Leu Ser Thr Asn Leu Val Cys Asn Lys Ser Ala Asp
        35                  40                  45

Pro Trp Ala Arg Ala Glu Ala Leu Ile Ser Leu Phe Thr Leu Glu Glu
    50                  55                  60

Leu Ile Asn Asn Thr Gln Asn Thr Ala Pro Gly Val Pro Arg Leu Gly
65                  70                  75                  80

Leu Pro Gln Tyr Gln Val Trp Asn Glu Ala Leu His Gly Leu Asp Arg
                85                  90                  95

Ala Asn Phe Ser His Ser Gly Glu Tyr Ser Trp Ala Thr Ser Phe Pro
            100                 105                 110

Met Pro Ile Leu Ser Met Ala Ser Phe Asn Arg Thr Leu Ile Asn Gln
        115                 120                 125

Ile Ala Ser Ile Ile Ala Thr Gln Ala Arg Ala Phe Asn Asn Ala Gly
    130                 135                 140

Arg Tyr Gly Leu Asp Ser Tyr Ala Pro Asn Ile Asn Gly Phe Arg Ser
145                 150                 155                 160

Pro Leu Trp Gly Arg Gly Gln Glu Thr Pro Gly Glu Asp Ala Phe Phe
                165                 170                 175

Leu Ser Ser Thr Tyr Ala Tyr Glu Tyr Ile Thr Gly Leu Gln Gly Gly
            180                 185                 190

Val Asp Pro Glu His Val Lys Ile Val Ala Thr Ala Lys His Phe Ala
        195                 200                 205

Gly Tyr Asp Leu Glu Asn Trp Gly Asn Val Ser Arg Leu Gly Phe Asn
    210                 215                 220

Ala Ile Ile Thr Gln Gln Asp Leu Ser Glu Tyr Tyr Thr Pro Gln Phe
225                 230                 235                 240

Leu Ala Ser Ala Arg Tyr Ala Lys Thr Arg Ser Ile Met Cys Ser Tyr
                245                 250                 255

Asn Ala Val Asn Gly Val Pro Ser Cys Ala Asn Ser Phe Phe Leu Gln
            260                 265                 270

Thr Leu Leu Arg Glu Asn Phe Asp Phe Val Asp Gly Tyr Val Ser
        275                 280                 285

Ser Asp Cys Asp Ala Val Tyr Asn Val Phe Asn Pro His Gly Tyr Ala
    290                 295                 300
```

-continued

```
Leu Asn Gln Ser Gly Ala Ala Asp Ser Leu Leu Ala Gly Thr Asp
305                 310                 315                 320

Ile Asp Cys Gly Gln Thr Leu Pro Trp His Leu Asn Glu Ser Phe Val
                325                 330                 335

Glu Gly Tyr Val Ser Arg Gly Asp Ile Glu Lys Ser Leu Thr Arg Leu
            340                 345                 350

Tyr Ser Asn Leu Val Arg Leu Gly Tyr Phe Asp Gly Asn Asn Ser Glu
        355                 360                 365

Tyr Arg Asn Leu Asn Trp Asn Asp Val Val Thr Thr Asp Ala Trp Asn
    370                 375                 380

Ile Ser Tyr Glu Ala Ala Val Glu Gly Ile Thr Leu Leu Lys Asn Asp
385                 390                 395                 400

Gly Thr Leu Pro Leu Ser Lys Lys Val Arg Ser Ile Ala Leu Ile Gly
                405                 410                 415

Pro Trp Ala Asn Ala Thr Val Gln Met Gln Gly Asn Tyr Tyr Gly Thr
            420                 425                 430

Pro Pro Tyr Leu Ile Ser Pro Leu Glu Ala Ala Lys Ala Ser Gly Phe
        435                 440                 445

Thr Val Asn Tyr Ala Phe Gly Thr Asn Ile Ser Thr Asp Ser Thr Gln
    450                 455                 460

Trp Phe Ala Glu Ala Ile Ala Ala Ala Lys Lys Ser Asp Val Ile Ile
465                 470                 475                 480

Tyr Ala Gly Gly Ile Asp Asn Thr Ile Glu Ala Glu Gly Gln Asp Arg
                485                 490                 495

Thr Asp Leu Lys Trp Pro Gly Asn Gln Leu Asp Leu Ile Glu Gln Leu
            500                 505                 510

Ser Gln Val Gly Lys Pro Leu Val Val Leu Gln Met Gly Gly Gly Gln
        515                 520                 525

Val Asp Ser Ser Ser Leu Lys Ala Asn Lys Asn Val Asn Ala Leu Val
    530                 535                 540

Trp Gly Gly Tyr Pro Gly Gln Ser Gly Gly Ala Ala Leu Phe Asp Ile
545                 550                 555                 560

Leu Thr Gly Lys Arg Ala Pro Ala Gly Arg Leu Val Ser Thr Gln Tyr
                565                 570                 575

Pro Ala Glu Tyr Ala Thr Gln Phe Pro Ala Asn Asp Met Asn Leu Arg
            580                 585                 590

Pro Asn Gly Ser Asn Pro Gly Gln Thr Tyr Ile Trp Tyr Thr Gly Thr
        595                 600                 605

Pro Val Tyr Glu Phe Gly His Gly Leu Phe Tyr Thr Glu Phe Gln Glu
    610                 615                 620

Ser Ala Ala Ala Gly Thr Asn Lys Thr Ser Thr Phe Asp Ile Leu Asp
625                 630                 635                 640

Leu Phe Ser Thr Pro His Pro Gly Tyr Glu Tyr Ile Glu Gln Val Pro
                645                 650                 655

Phe Ile Asn Val Thr Val Asp Val Lys Asn Val Gly His Thr Pro Ser
            660                 665                 670

Pro Tyr Thr Gly Leu Leu Phe Ala Asn Thr Thr Ala Gly Pro Lys Pro
        675                 680                 685

Tyr Pro Asn Lys Trp Leu Val Gly Phe Asp Trp Leu Pro Thr Ile Gln
    690                 695                 700

Pro Gly Glu Thr Ala Lys Leu Thr Ile Pro Val Pro Leu Gly Ala Ile
705                 710                 715                 720
```

-continued

```
Ala Trp Ala Asp Glu Asn Gly Asn Lys Val Phe Pro Gly Asn Tyr
            725                 730                 735

Glu Leu Ala Leu Asn Asn Glu Arg Ser Val Val Ser Phe Thr Leu
            740                 745                 750

Thr Gly Asp Ala Ala Thr Leu Glu Lys Trp Pro Leu Trp Glu Gln Ala
            755                 760                 765

Val Pro Gly Val Leu Gln Gln
        770             775

<210> SEQ ID NO 7
<211> LENGTH: 282
<212> TYPE: PRT
<213> ORGANISM: Trichoderma reesei
<220> FEATURE:
<221> NAME/KEY: mat_peptide
<222> LOCATION: (1)..(282)

<400> SEQUENCE: 7

Ser Pro Val Asp Gly Glu Thr Val Val Lys Arg Gln Cys Pro Ala Ile
  1               5                  10                  15

His Val Phe Gly Ala Arg Glu Thr Thr Val Ser Gln Gly Tyr Gly Ser
             20                  25                  30

Ser Ala Thr Val Val Asn Leu Val Ile Gln Ala His Pro Gly Thr Thr
         35                  40                  45

Ser Glu Ala Ile Val Tyr Pro Ala Cys Gly Gly Gln Ala Ser Cys Gly
     50                  55                  60

Gly Ile Ser Tyr Ala Asn Ser Val Val Asn Gly Thr Asn Ala Ala Ala
 65                  70                  75                  80

Ala Ala Ile Asn Asn Phe His Asn Ser Cys Pro Asp Thr Gln Leu Val
                 85                  90                  95

Leu Val Gly Tyr Ser Gln Gly Ala Gln Ile Phe Asp Asn Ala Leu Cys
            100                 105                 110

Gly Gly Gly Asp Pro Gly Glu Gly Ile Thr Asn Thr Ala Val Pro Leu
        115                 120                 125

Thr Ala Gly Ala Val Ser Ala Val Lys Ala Ala Ile Phe Met Gly Asp
    130                 135                 140

Pro Arg Asn Ile His Gly Leu Pro Tyr Asn Val Gly Thr Cys Thr Thr
145                 150                 155                 160

Gln Gly Phe Asp Ala Arg Pro Ala Gly Phe Val Cys Pro Ser Ala Ser
                165                 170                 175

Lys Ile Lys Ser Tyr Cys Asp Ala Ala Asp Pro Tyr Cys Cys Thr Gly
            180                 185                 190

Asn Asp Pro Asn Val His Gln Gly Tyr Gly Gln Glu Tyr Gly Gln Gln
        195                 200                 205

Ala Leu Ala Phe Ile Asn Ser Gln Leu Ser Ser Gly Gly Ser Gln Pro
    210                 215                 220

Pro Gly Gly Gly Pro Thr Ser Thr Ser Arg Pro Thr Ser Thr Arg Thr
225                 230                 235                 240

Gly Ser Ser Pro Gly Pro Thr Gln Thr His Trp Gly Gln Cys Gly Gly
                245                 250                 255

Gln Gly Trp Thr Gly Pro Thr Cys Glu Ser Gly Thr Cys Gln
            260                 265                 270

Val Ile Ser Gln Trp Tyr Ser Gln Cys Leu
        275                 280

<210> SEQ ID NO 8
```

```
<211> LENGTH: 378
<212> TYPE: PRT
<213> ORGANISM: Aspergillus fumigatus
<220> FEATURE:
<221> NAME/KEY: mat_peptide
<222> LOCATION: (1)..(378)

<400> SEQUENCE: 8

Ala Gly Leu Asn Thr Ala Ala Lys Ala Lys Gly Leu Lys Tyr Phe Gly
1               5                   10                  15

Ser Ala Thr Asp Asn Pro Glu Leu Thr Asp Ser Ala Tyr Val Ala Gln
            20                  25                  30

Leu Ser Asn Thr Asp Asp Phe Gly Gln Ile Thr Pro Gly Asn Ser Met
        35                  40                  45

Lys Trp Asp Ala Thr Glu Pro Ser Gln Asn Ser Phe Ser Phe Ala Asn
50                  55                  60

Gly Asp Ala Val Val Asn Leu Ala Asn Lys Asn Gly Gln Leu Met Arg
65                  70                  75                  80

Cys His Thr Leu Val Trp His Ser Gln Leu Pro Asn Trp Val Ser Ser
                85                  90                  95

Gly Ser Trp Thr Asn Ala Thr Leu Leu Ala Ala Met Lys Asn His Ile
            100                 105                 110

Thr Asn Val Val Thr His Tyr Lys Gly Lys Cys Tyr Ala Trp Asp Val
        115                 120                 125

Val Asn Glu Ala Leu Asn Glu Asp Gly Thr Phe Arg Asn Ser Val Phe
130                 135                 140

Tyr Gln Ile Ile Gly Pro Ala Tyr Ile Pro Ile Ala Phe Ala Thr Ala
145                 150                 155                 160

Ala Ala Ala Asp Pro Asp Val Lys Leu Tyr Tyr Asn Asp Tyr Asn Ile
                165                 170                 175

Glu Tyr Ser Gly Ala Lys Ala Thr Ala Ala Gln Asn Ile Val Lys Met
            180                 185                 190

Ile Lys Ala Tyr Gly Ala Lys Ile Asp Gly Val Gly Leu Gln Ala His
        195                 200                 205

Phe Ile Val Gly Ser Thr Pro Ser Gln Ser Asp Leu Thr Thr Val Leu
210                 215                 220

Lys Gly Tyr Thr Ala Leu Gly Val Glu Val Ala Tyr Thr Glu Leu Asp
225                 230                 235                 240

Ile Arg Met Gln Leu Pro Ser Thr Ala Ala Lys Leu Ala Gln Gln Ser
                245                 250                 255

Thr Asp Phe Gln Gly Val Ala Ala Ala Cys Val Ser Thr Thr Gly Cys
            260                 265                 270

Val Gly Val Thr Ile Trp Asp Trp Thr Asp Lys Tyr Ser Trp Val Pro
        275                 280                 285

Ser Val Phe Gln Gly Tyr Gly Ala Pro Leu Pro Trp Asp Glu Asn Tyr
290                 295                 300

Val Lys Lys Pro Ala Tyr Asp Gly Leu Met Ala Gly Leu Gly Ala Ser
305                 310                 315                 320

Gly Ser Gly Thr Thr Thr Thr Thr Thr Thr Ser Thr Thr Thr Gly
                325                 330                 335

Gly Thr Asp Pro Thr Gly Val Ala Gln Lys Trp Gly Gln Cys Gly Gly
            340                 345                 350

Ile Gly Trp Thr Gly Pro Thr Thr Cys Val Ser Gly Thr Thr Cys Gln
        355                 360                 365

Lys Leu Asn Asp Trp Tyr Ser Gln Cys Leu
```

<210> SEQ ID NO 9
<211> LENGTH: 409
<212> TYPE: PRT
<213> ORGANISM: Talaromyces leycettanus
<220> FEATURE:
<221> NAME/KEY: SIGNAL
<222> LOCATION: (1)..(18)
<220> FEATURE:
<221> NAME/KEY: mat_peptide
<222> LOCATION: (19)..(409)

<400> SEQUENCE: 9

Met Lys Phe Ser Asn Val Ile Leu Ala Ala Ser Ala Ser Ser Leu Val
            -15                 -10                 -5

Leu Ala Ala Pro Lys Ser Lys Thr Lys Arg Thr Ser Ala Phe Gln Trp
     -1   1               5                  10

Phe Gly Ala Asn Glu Ser Gly Ala Glu Phe Gly Asn Gln Asn Ile Pro
 15                  20                  25                  30

Gly Thr Leu Gly Thr Asp Tyr Thr Trp Pro Asp Thr Ser Thr Ile Gln
                 35                  40                  45

Thr Leu Arg Asn Ala Gly Met Asn Ile Phe Arg Val Pro Phe Leu Met
             50                  55                  60

Glu Arg Leu Val Pro Asn Gln Met Thr Gly Ser Pro Asp Pro Thr Tyr
 65                  70                  75

Leu Ala Asp Leu Lys Ser Thr Val Asn Phe Ile Thr Gly Thr Gly Ala
         80                  85                  90

Tyr Ala Val Val Asp Pro His Asn Tyr Gly Arg Tyr Tyr Asn Asn Ile
 95                 100                 105                 110

Ile Thr Ser Thr Ser Asp Phe Ala Ala Phe Trp Thr Thr Val Ala Ser
                115                 120                 125

Gln Phe Ala Ser Asn Pro Arg Val Ile Phe Asp Thr Asn Asn Glu Tyr
            130                 135                 140

Asn Asn Met Asp Gln Thr Leu Val Leu Asn Leu Asn Gln Ala Ala Ile
            145                 150                 155

Asn Ala Ile Arg Ala Ala Gly Ala Thr Ser Gln Tyr Ile Phe Ala Glu
            160                 165                 170

Gly Asn Ser Trp Thr Gly Ala Trp Thr Trp Thr Ser Val Asn Asp Asn
175                 180                 185                 190

Met Lys Gln Leu Thr Asp Pro Ser Asn Lys Leu Val Tyr Glu Met His
                195                 200                 205

Gln Tyr Leu Asp Ser Asp Gly Ser Thr Ser Asp Gln Cys Val Asn
            210                 215                 220

Ser Thr Ile Gly Tyr Asp Arg Ile Val Ser Ala Thr Gln Trp Leu Gln
            225                 230                 235

Ala Asn Gly Lys Val Ala Phe Leu Gly Glu Phe Ala Gly Gly Ser Asn
            240                 245                 250

Ser Val Cys Glu Ala Ala Val Thr Gly Met Leu Asp Tyr Met Glu Gln
255                 260                 265                 270

Asn Ser Asp Val Trp Leu Gly Ala Glu Trp Trp Ala Ala Gly Pro Trp
                275                 280                 285

Trp Gly Asn Tyr Ile Tyr Ser Met Glu Pro Pro Ser Gly Ile Ala Tyr
            290                 295                 300

Gln Asn Tyr Leu Ser Ile Leu Glu Pro Tyr Phe Pro Gly Gly Ser Tyr
            305                 310                 315

```
Ser Gly Gly Thr Gly Ser Gly Ser Gly Ser Thr Thr Thr Ala Thr
    320             325             330
Thr Thr Thr Thr Lys Val Pro Pro Thr Thr Thr Ser Ser Ala Ser
335             340             345             350
Ser Thr Gly Thr Gly Val Ala Gln His Trp Gly Gln Cys Gly Gly Gln
            355             360             365
Gly Trp Thr Gly Pro Thr Thr Cys Val Ser Pro Tyr Thr Cys Gln Glu
        370             375             380
Leu Asn Pro Tyr Tyr Tyr Gln Cys Leu
        385             390

<210> SEQ ID NO 10
<211> LENGTH: 4014
<212> TYPE: DNA
<213> ORGANISM: Thermococcus hydrothermalis
<220> FEATURE:
<221> NAME/KEY: CDS
<222> LOCATION: (1)..(4011)
<220> FEATURE:
<221> NAME/KEY: misc_signal
<222> LOCATION: (1)..(81)
<220> FEATURE:
<221> NAME/KEY: mat_peptide
<222> LOCATION: (82)..(4014)

<400> SEQUENCE: 10
```

| | | |
|---|---|---|
| atg agg cgg gtg gtt gcc ctc ttc att gca att ttg atg ctt gga agc<br>Met Arg Arg Val Val Ala Leu Phe Ile Ala Ile Leu Met Leu Gly Ser<br>    -25                -20                -15 | | 48 |
| atc gtt gga gcg aac gtt aag agc gtt ggc gcg gcg gag ccg aag ccg<br>Ile Val Gly Ala Asn Val Lys Ser Val Gly Ala Ala Glu Pro Lys Pro<br>-10                -5                -1  1                5 | | 96 |
| ctc aac gtc ata ata gtc tgg cac cag cac cag ccc tac tac tac gac<br>Leu Asn Val Ile Ile Val Trp His Gln His Gln Pro Tyr Tyr Tyr Asp<br>              10                15                20 | | 144 |
| cct gtc cag gac gtc tac acc agg ccc tgg gtc agg ctc cac gcg gcg<br>Pro Val Gln Asp Val Tyr Thr Arg Pro Trp Val Arg Leu His Ala Ala<br>              25                30                35 | | 192 |
| aac aac tac tgg aag atg gcc cac tac ctg agc cag tac ccg gag gtt<br>Asn Asn Tyr Trp Lys Met Ala His Tyr Leu Ser Gln Tyr Pro Glu Val<br>    40                45                50 | | 240 |
| cac gcc acc att gac ctc tcg ggt tcg ctg ata gcc cag ctt gcc gac<br>His Ala Thr Ile Asp Leu Ser Gly Ser Leu Ile Ala Gln Leu Ala Asp<br>55                60                65 | | 288 |
| tac atg aac ggc aag aag gac acc tac cag ata atc acc gag aag ata<br>Tyr Met Asn Gly Lys Lys Asp Thr Tyr Gln Ile Ile Thr Glu Lys Ile<br>70                75                80                85 | | 336 |
| gcc aac ggg gaa ccc ctc acc gtc gac gag aag tgg ttc atg ctc cag<br>Ala Asn Gly Glu Pro Leu Thr Val Asp Glu Lys Trp Phe Met Leu Gln<br>              90                95                100 | | 384 |
| gca ccg gga ggg ttc ttc gac aac acc atc ccc tgg aac ggt gaa ccg<br>Ala Pro Gly Gly Phe Phe Asp Asn Thr Ile Pro Trp Asn Gly Glu Pro<br>              105                110                115 | | 432 |
| ata acc gac ccc aac ggc aac ccg ata agg gac ttc tgg gac cgc tac<br>Ile Thr Asp Pro Asn Gly Asn Pro Ile Arg Asp Phe Trp Asp Arg Tyr<br>120                125                130 | | 480 |
| acg gag ctg aag aac aag atg ctc agc gca aag gcc aag tac gca aac<br>Thr Glu Leu Lys Asn Lys Met Leu Ser Ala Lys Ala Lys Tyr Ala Asn<br>135                140                145 | | 528 |
| ttc gtg act gag agc cag aag gtc gct gtg acg aac gag ttc aca gag<br>Phe Val Thr Glu Ser Gln Lys Val Ala Val Thr Asn Glu Phe Thr Glu<br>150                155                160                165 | | 576 |

-continued

| | |
|---|---|
| cag gac tac ata gac cta gcg gtt ctc ttc aat ctc gct tgg att gac<br>Gln Asp Tyr Ile Asp Leu Ala Val Leu Phe Asn Leu Ala Trp Ile Asp<br>              170                        175                        180 | 624 |
| tac aat tac atc acg agc acg ccg gag ttc aag gcc ctc tac gac aag<br>Tyr Asn Tyr Ile Thr Ser Thr Pro Glu Phe Lys Ala Leu Tyr Asp Lys<br>              185                        190                        195 | 672 |
| gtt gac gag ggc ggc tat aca agg gcg gac gtc aaa acc gtt ctc gac<br>Val Asp Glu Gly Gly Tyr Thr Arg Ala Asp Val Lys Thr Val Leu Asp<br>              200                        205                        210 | 720 |
| gcc cag atc tgg ctt ctc aac cac acc ttc gag gag cac gag aag ata<br>Ala Gln Ile Trp Leu Leu Asn His Thr Phe Glu Glu His Glu Lys Ile<br>              215                        220                        225 | 768 |
| aac ctc ctc ctc gga aac ggc aac gtc gag gtc acg gtc gtt ccc tac<br>Asn Leu Leu Leu Gly Asn Gly Asn Val Glu Val Thr Val Val Pro Tyr<br>230                        235                        240                        245 | 816 |
| gcc cac ccg ata ggc ccg ata ctc aac gac ttc ggc tgg gac agc gac<br>Ala His Pro Ile Gly Pro Ile Leu Asn Asp Phe Gly Trp Asp Ser Asp<br>                      250                        255                        260 | 864 |
| ttc aac gac cag gtc aag aag gcc gac gaa ctg tac aag ccg tac ctc<br>Phe Asn Asp Gln Val Lys Lys Ala Asp Glu Leu Tyr Lys Pro Tyr Leu<br>              265                        270                        275 | 912 |
| ggc ggc ggc acc gcg gtt cca aaa ggc gga tgg gcg gct gag agc gcc<br>Gly Gly Gly Thr Ala Val Pro Lys Gly Gly Trp Ala Ala Glu Ser Ala<br>              280                        285                        290 | 960 |
| ctc aac gac aaa act ctg gag atc ctc gcc gag aac ggc tgg gag tgg<br>Leu Asn Asp Lys Thr Leu Glu Ile Leu Ala Glu Asn Gly Trp Glu Trp<br>295                        300                        305 | 1008 |
| gtc atg acc gac cag atg gtt ctc gga aag ctc ggc att gag gga acc<br>Val Met Thr Asp Gln Met Val Leu Gly Lys Leu Gly Ile Glu Gly Thr<br>310                        315                        320                        325 | 1056 |
| gtc gag aac tac cac aag ccc tgg gtg gcc gag ttc aac gga aag aag<br>Val Glu Asn Tyr His Lys Pro Trp Val Ala Glu Phe Asn Gly Lys Lys<br>              330                        335                        340 | 1104 |
| ata tac ctc ttc cca aga aat cac gat cta agt gac aga gtt ggc ttt<br>Ile Tyr Leu Phe Pro Arg Asn His Asp Leu Ser Asp Arg Val Gly Phe<br>              345                        350                        355 | 1152 |
| acc tac agc gga atg aac cag cag cag gcc gtt gag gac ttc gtc aac<br>Thr Tyr Ser Gly Met Asn Gln Gln Gln Ala Val Glu Asp Phe Val Asn<br>                      360                        365                        370 | 1200 |
| gag ctc ctc aag ctc cag aag cag aac tac gat ggc tcg ctg gtt tac<br>Glu Leu Leu Lys Leu Gln Lys Gln Asn Tyr Asp Gly Ser Leu Val Tyr<br>375                        380                        385 | 1248 |
| gtg gtc acg ctc gac ggc gag aac ccc gtg gag aac tac ccc tac gac<br>Val Val Thr Leu Asp Gly Glu Asn Pro Val Glu Asn Tyr Pro Tyr Asp<br>390                        395                        400                        405 | 1296 |
| ggg gag ctc ttc ctc acc gaa ctc tac aag aag ctg acc gaa ctc cag<br>Gly Glu Leu Phe Leu Thr Glu Leu Tyr Lys Lys Leu Thr Glu Leu Gln<br>              410                        415                        420 | 1344 |
| gag cag ggt ctc ata aga acc ctc acc ccg agc gag tac atc cag ctc<br>Glu Gln Gly Leu Ile Arg Thr Leu Thr Pro Ser Glu Tyr Ile Gln Leu<br>              425                        430                        435 | 1392 |
| tac ggc gac aag gcc aac aag ctc aca cct cgg atg atg gag cgc ctt<br>Tyr Gly Asp Lys Ala Asn Lys Leu Thr Pro Arg Met Met Glu Arg Leu<br>              440                        445                        450 | 1440 |
| gac ctc acc gga gac aac gtt aac gcc ctc ctc aag gcc cag agc ctc<br>Asp Leu Thr Gly Asp Asn Val Asn Ala Leu Leu Lys Ala Gln Ser Leu<br>              455                        460                        465 | 1488 |
| ggc gaa ctc tac gac atg acc ggc gtt aag gag gag atg cag tgg ccc<br>Gly Glu Leu Tyr Asp Met Thr Gly Val Lys Glu Glu Met Gln Trp Pro | 1536 |

```
                                                     -continued 470               475               480               485
gag agc agc tgg ata gac gga acc ctc tcc acg tgg ata ggc gag ccc        1584
Glu Ser Ser Trp Ile Asp Gly Thr Leu Ser Thr Trp Ile Gly Glu Pro
                490               495               500 cag gag aac tac ggc tgg tac tgg ctc tac atg gcc agg aag gcc ctt        1632
Gln Glu Asn Tyr Gly Trp Tyr Trp Leu Tyr Met Ala Arg Lys Ala Leu
        505               510               515 atg gag aac aag gat aaa atg agc cag gcg gac tgg gag aag gcc tac        1680
Met Glu Asn Lys Asp Lys Met Ser Gln Ala Asp Trp Glu Lys Ala Tyr
            520               525               530 gag tac ctg ctc cgc gcc gag gca agc gac tgg ttc tgg tgg tac gga        1728
Glu Tyr Leu Leu Arg Ala Glu Ala Ser Asp Trp Phe Trp Trp Tyr Gly
        535               540               545 agc gac cag gac agc ggc cag gac tac acc ttc gac cgc tac ctg aag        1776
Ser Asp Gln Asp Ser Gly Gln Asp Tyr Thr Phe Asp Arg Tyr Leu Lys
550               555               560               565 acc tac ctc tac gag atg tac aag ctg gca gga gtc gag ccg ccg agc        1824
Thr Tyr Leu Tyr Glu Met Tyr Lys Leu Ala Gly Val Glu Pro Pro Ser
                570               575               580 tac ctc ttc ggc aac tac ttc ccg gac gga gag ccc tac acc acg agg        1872
Tyr Leu Phe Gly Asn Tyr Phe Pro Asp Gly Glu Pro Tyr Thr Thr Arg
            585               590               595 ggc ctg gtc gga ctc aag gac ggc gag atg aag aac ttc tcc agc atg        1920
Gly Leu Val Gly Leu Lys Asp Gly Glu Met Lys Asn Phe Ser Ser Met
        600               605               610 tcc ccg ctg gca aag ggc gtg agc gtc tat ttc gac ggc gag ggg ata        1968
Ser Pro Leu Ala Lys Gly Val Ser Val Tyr Phe Asp Gly Glu Gly Ile
    615               620               625 cac ttc ata gtg aaa ggg aac ctg gac agg ttc gag gtg agc atc tgg        2016
His Phe Ile Val Lys Gly Asn Leu Asp Arg Phe Glu Val Ser Ile Trp
630               635               640               645 gag aag gat gag cgc gtt ggc aac acg ttc acc cgc ctc caa gag aag        2064
Glu Lys Asp Glu Arg Val Gly Asn Thr Phe Thr Arg Leu Gln Glu Lys
                650               655               660 ccg gac gag ttg agc tat ttc atg ttc cca ttc tca agg gac agc gtt        2112
Pro Asp Glu Leu Ser Tyr Phe Met Phe Pro Phe Ser Arg Asp Ser Val
            665               670               675 ggt ctc ctc ata acc aag cac gtc gtg tac gag aac gga aag gcc gag        2160
Gly Leu Leu Ile Thr Lys His Val Val Tyr Glu Asn Gly Lys Ala Glu
        680               685               690 ata tac ggc gcc acc gac tac gag aag agc gag aag ctt ggg gaa gcc        2208
Ile Tyr Gly Ala Thr Asp Tyr Glu Lys Ser Glu Lys Leu Gly Glu Ala
    695               700               705 acc gtc aag aac acg agc gaa gga atc gaa gtc gtc ctt ccc ttt gac        2256
Thr Val Lys Asn Thr Ser Glu Gly Ile Glu Val Val Leu Pro Phe Asp
710               715               720               725 tac ata gaa aac ccc tcc gac ttc tac ttc gct gtc tcg acg gtc aaa        2304
Tyr Ile Glu Asn Pro Ser Asp Phe Tyr Phe Ala Val Ser Thr Val Lys
                730               735               740 gat gga gac ctt gag gtg ata agc act cct gtg gag ctc aag ctc ccg        2352
Asp Gly Asp Leu Glu Val Ile Ser Thr Pro Val Glu Leu Lys Leu Pro
            745               750               755 acc gag gtc aag gga gtc gtc ata gcc gat ata acc gac cca gaa ggc        2400
Thr Glu Val Lys Gly Val Val Ile Ala Asp Ile Thr Asp Pro Glu Gly
        760               765               770 gac gac cat ggg ccc gga aac tac act tat ccc acg gac aag gtc ttc        2448
Asp Asp His Gly Pro Gly Asn Tyr Thr Tyr Pro Thr Asp Lys Val Phe
    775               780               785 aag cca ggt gtt ttc gac ctc ctc cgc ttc agg atg ctc gaa cag acg        2496
```

-continued

| | | |
|---|---|---|
| Lys Pro Gly Val Phe Asp Leu Leu Arg Phe Arg Met Leu Glu Gln Thr<br>790                 795                800                 805 | | |
| gag agc tac gtc atg gag ttc tac ttc aag gac cta ggt ggt aac ccg<br>Glu Ser Tyr Val Met Glu Phe Tyr Phe Lys Asp Leu Gly Gly Asn Pro<br>                810                           815                       820 | | 2544 |
| tgg aac gga ccc aac ggc ttc agc ctc cag ata atc gag gtc tac ctc<br>Trp Asn Gly Pro Asn Gly Phe Ser Leu Gln Ile Ile Glu Val Tyr Leu<br>               825                         830                       835 | | 2592 |
| gac ttc aag gac ggt gga aac agt tcg gcc att aag atg ttc ccc gac<br>Asp Phe Lys Asp Gly Gly Asn Ser Ser Ala Ile Lys Met Phe Pro Asp<br>           840                        845                    850 | | 2640 |
| gga ccg gga gcc aac gtc aac ctc gac ccc gag cat cca tgg gac gtt<br>Gly Pro Gly Ala Asn Val Asn Leu Asp Pro Glu His Pro Trp Asp Val<br>855                 860                       865 | | 2688 |
| gcc ttc agg ata gcg ggc tgg gac tac gga aac ctc atc atc ctg ccg<br>Ala Phe Arg Ile Ala Gly Trp Asp Tyr Gly Asn Leu Ile Ile Leu Pro<br>870                875                    880                  885 | | 2736 |
| aac gga acg gcc atc cag ggc gag atg cag att tcc gca gat ccg gtt<br>Asn Gly Thr Ala Ile Gln Gly Glu Met Gln Ile Ser Ala Asp Pro Val<br>                 890                        895                    900 | | 2784 |
| aag aac gcc ata ata gtc aag gtt cca aag aag tac atc gcc ata aac<br>Lys Asn Ala Ile Ile Val Lys Val Pro Lys Lys Tyr Ile Ala Ile Asn<br>           905                        910                    915 | | 2832 |
| gag gac tac ggc ctc tgg gga gac gtc ctc gtc ggc tcg cag gac ggc<br>Glu Asp Tyr Gly Leu Trp Gly Asp Val Leu Val Gly Ser Gln Asp Gly<br>920                 925                    930 | | 2880 |
| tac ggc ccg gac aag tgg aga acg gcg gca gtg gat gcg gag cag tgg<br>Tyr Gly Pro Asp Lys Trp Arg Thr Ala Ala Val Asp Ala Glu Gln Trp<br>935                 940                    945 | | 2928 |
| aag ctt gga ggt gcg gac ccg cag gca gtc ata aac ggc gtg gcc ccg<br>Lys Leu Gly Gly Ala Asp Pro Gln Ala Val Ile Asn Gly Val Ala Pro<br>950                 955                    960                  965 | | 2976 |
| cgc gtc att gat gag ctg gtt ccg cag ggc ttt gaa ccg acc cag gag<br>Arg Val Ile Asp Glu Leu Val Pro Gln Gly Phe Glu Pro Thr Gln Glu<br>                 970                        975                    980 | | 3024 |
| gag cag ctg agc agc tac gat gca aac gac atg aag ctc gcc act gtc<br>Glu Gln Leu Ser Ser Tyr Asp Ala Asn Asp Met Lys Leu Ala Thr Val<br>           985                        990                    995 | | 3072 |
| aag gcg ctg cta ctc ctc aag cag ggc atc gtt gtg acc gac ccg<br>Lys Ala Leu Leu Leu Leu Lys Gln Gly Ile Val Val Thr Asp Pro<br>1000                 1005                 1010 | | 3117 |
| gag gga gac gac cac ggg ccg gga acg tac acc tat ccg acg gac<br>Glu Gly Asp Asp His Gly Pro Gly Thr Tyr Thr Tyr Pro Thr Asp<br>           1015                 1020                 1025 | | 3162 |
| aaa gtt ttc aag ccc ggt gtt ttc gac ctc ctc aag ttc aag gtg<br>Lys Val Phe Lys Pro Gly Val Phe Asp Leu Leu Lys Phe Lys Val<br>           1030                 1035                 1040 | | 3207 |
| acc gag gga agc gac gac tgg acg ctg gag ttc cac ttc aaa gac<br>Thr Glu Gly Ser Asp Asp Trp Thr Leu Glu Phe His Phe Lys Asp<br>           1045                 1050                 1055 | | 3252 |
| ctc ggt gga aac ccg tgg aac ggg ccg aac ggc ttc agc ctg cag<br>Leu Gly Gly Asn Pro Trp Asn Gly Pro Asn Gly Phe Ser Leu Gln<br>           1060                 1065                 1070 | | 3297 |
| ata atc gag gta tac ttc gac ttc aag gag ggc ggg aac gtc tcg<br>Ile Ile Glu Val Tyr Phe Asp Phe Lys Glu Gly Gly Asn Val Ser<br>           1075                 1080                 1085 | | 3342 |
| gcc att aag atg ttc ccg gat ggg ccc gga agc aac gtc cgt ctt<br>Ala Ile Lys Met Phe Pro Asp Gly Pro Gly Ser Asn Val Arg Leu<br>           1090                 1095                 1100 | | 3387 |

-continued

| | | |
|---|---|---|
| gat cca aat cac cca tgg gac ctg gcg ctt agg ata gcc ggc tgg<br>Asp Pro Asn His Pro Trp Asp Leu Ala Leu Arg Ile Ala Gly Trp<br>    1105             1110             1115 | 3432 | |
| gac tac gga aac ctg ata att ctg ccc gac gga acc gcc tac caa<br>Asp Tyr Gly Asn Leu Ile Ile Leu Pro Asp Gly Thr Ala Tyr Gln<br>1120             1125             1130 | 3477 | |
| ggc gag atg cag att tcc gca gat ccg gtt aag aac gcc ata ata<br>Gly Glu Met Gln Ile Ser Ala Asp Pro Val Lys Asn Ala Ile Ile<br>    1135             1140             1145 | 3522 | |
| gtc aag gtt cca aag aag tac ctg aac ata tcc gac tac gga ctc<br>Val Lys Val Pro Lys Lys Tyr Leu Asn Ile Ser Asp Tyr Gly Leu<br>1150             1155             1160 | 3567 | |
| tac acc gcc gtc atc gtg ggt tcc caa gac ggg tac ggc ccg gac<br>Tyr Thr Ala Val Ile Val Gly Ser Gln Asp Gly Tyr Gly Pro Asp<br>    1165             1170             1175 | 3612 | |
| aag tgg agg ccc gtg gcc gct gag gcc gag cag tgg aag ctc gga<br>Lys Trp Arg Pro Val Ala Ala Glu Ala Glu Gln Trp Lys Leu Gly<br>1180             1185             1190 | 3657 | |
| ggc gca gac ccc cag gcg gtc ata gac aac ctc gta cca agg gtc<br>Gly Ala Asp Pro Gln Ala Val Ile Asp Asn Leu Val Pro Arg Val<br>    1195             1200             1205 | 3702 | |
| gtt gat gaa ctc gtg ccg gag ggc ttc aag cca acg cag gag gag<br>Val Asp Glu Leu Val Pro Glu Gly Phe Lys Pro Thr Gln Glu Glu<br>1210             1215             1220 | 3747 | |
| cag ctg agc agc tac gac ctt gag aag aag acc ctg gcg acg gtg<br>Gln Leu Ser Ser Tyr Asp Leu Glu Lys Lys Thr Leu Ala Thr Val<br>    1225             1230             1235 | 3792 | |
| ctc atg gta ccg ctc gtc aat ggg act ggc ggc gag gaa cca acg<br>Leu Met Val Pro Leu Val Asn Gly Thr Gly Gly Glu Glu Pro Thr<br>1240             1245             1250 | 3837 | |
| ccg acg gag agc cca acg gaa acg acg aca acc aca ccc agc gaa<br>Pro Thr Glu Ser Pro Thr Glu Thr Thr Thr Thr Thr Pro Ser Glu<br>    1255             1260             1265 | 3882 | |
| aca acc acc aca act tca acg acc acc ggc cca agc tca acg acc<br>Thr Thr Thr Thr Thr Ser Thr Thr Thr Gly Pro Ser Ser Thr Thr<br>1270             1275             1280 | 3927 | |
| acc agc aca ccc ggc gga gga atc tgc ggc cca ggc att ata gcg<br>Thr Ser Thr Pro Gly Gly Gly Ile Cys Gly Pro Gly Ile Ile Ala<br>    1285             1290             1295 | 3972 | |
| ggc ctg gcc ctg ata ccg ctc ctc ctc aag agg agg aac tga<br>Gly Leu Ala Leu Ile Pro Leu Leu Leu Lys Arg Arg Asn<br>1300             1305             1310 | 4014 | |

<210> SEQ ID NO 11
<211> LENGTH: 1337
<212> TYPE: PRT
<213> ORGANISM: Thermococcus hydrothermalis

<400> SEQUENCE: 11

Met Arg Arg Val Val Ala Leu Phe Ile Ala Ile Leu Met Leu Gly Ser
        -25                 -20                 -15

Ile Val Gly Ala Asn Val Lys Ser Val Gly Ala Ala Glu Pro Lys Pro
    -10                 -5              -1   1               5

Leu Asn Val Ile Ile Val Trp His Gln His Gln Pro Tyr Tyr Tyr Asp
                10                  15                  20

Pro Val Gln Asp Val Tyr Thr Arg Pro Trp Val Arg Leu His Ala Ala
            25                  30                  35

Asn Asn Tyr Trp Lys Met Ala His Tyr Leu Ser Gln Tyr Pro Glu Val
        40                  45                  50

```
His Ala Thr Ile Asp Leu Ser Gly Ser Leu Ile Ala Gln Leu Ala Asp
    55                      60                  65

Tyr Met Asn Gly Lys Lys Asp Thr Tyr Gln Ile Ile Thr Glu Lys Ile
70                  75                  80                  85

Ala Asn Gly Glu Pro Leu Thr Val Asp Glu Lys Trp Phe Met Leu Gln
                90                  95                  100

Ala Pro Gly Gly Phe Phe Asp Asn Thr Ile Pro Trp Asn Gly Glu Pro
            105                 110                 115

Ile Thr Asp Pro Asn Gly Asn Pro Ile Arg Asp Phe Trp Asp Arg Tyr
        120                 125                 130

Thr Glu Leu Lys Asn Lys Met Leu Ser Ala Lys Ala Lys Tyr Ala Asn
    135                 140                 145

Phe Val Thr Glu Ser Gln Lys Val Ala Val Thr Asn Glu Phe Thr Glu
150                 155                 160                 165

Gln Asp Tyr Ile Asp Leu Ala Val Leu Phe Asn Leu Ala Trp Ile Asp
            170                 175                 180

Tyr Asn Tyr Ile Thr Ser Thr Pro Glu Phe Lys Ala Leu Tyr Asp Lys
            185                 190                 195

Val Asp Glu Gly Gly Tyr Thr Arg Ala Asp Val Lys Thr Val Leu Asp
        200                 205                 210

Ala Gln Ile Trp Leu Leu Asn His Thr Phe Glu Glu His Glu Lys Ile
    215                 220                 225

Asn Leu Leu Leu Gly Asn Gly Asn Val Glu Val Thr Val Val Pro Tyr
230                 235                 240                 245

Ala His Pro Ile Gly Pro Ile Leu Asn Asp Phe Gly Trp Asp Ser Asp
                250                 255                 260

Phe Asn Asp Gln Val Lys Lys Ala Asp Glu Leu Tyr Lys Pro Tyr Leu
            265                 270                 275

Gly Gly Gly Thr Ala Val Pro Lys Gly Gly Trp Ala Ala Glu Ser Ala
        280                 285                 290

Leu Asn Asp Lys Thr Leu Glu Ile Leu Ala Glu Asn Gly Trp Glu Trp
    295                 300                 305

Val Met Thr Asp Gln Met Val Leu Gly Lys Leu Gly Ile Glu Gly Thr
310                 315                 320                 325

Val Glu Asn Tyr His Lys Pro Trp Val Ala Glu Phe Asn Gly Lys Lys
                330                 335                 340

Ile Tyr Leu Phe Pro Arg Asn His Asp Leu Ser Asp Arg Val Gly Phe
            345                 350                 355

Thr Tyr Ser Gly Met Asn Gln Gln Ala Val Glu Asp Phe Val Asn
        360                 365                 370

Glu Leu Leu Lys Leu Gln Lys Gln Asn Tyr Asp Gly Ser Leu Val Tyr
    375                 380                 385

Val Val Thr Leu Asp Gly Glu Asn Pro Val Glu Asn Tyr Pro Tyr Asp
390                 395                 400                 405

Gly Glu Leu Phe Leu Thr Glu Leu Tyr Lys Lys Leu Thr Glu Leu Gln
                410                 415                 420

Glu Gln Gly Leu Ile Arg Thr Leu Thr Pro Ser Glu Tyr Ile Gln Leu
            425                 430                 435

Tyr Gly Asp Lys Ala Asn Lys Leu Thr Pro Arg Met Glu Arg Leu
        440                 445                 450

Asp Leu Thr Gly Asp Asn Val Asn Ala Leu Leu Lys Ala Gln Ser Leu
    455                 460                 465

Gly Glu Leu Tyr Asp Met Thr Gly Val Lys Glu Glu Met Gln Trp Pro
```

-continued

```
            470                 475                 480                 485
        Glu Ser Ser Trp Ile Asp Gly Thr Leu Ser Thr Trp Ile Gly Glu Pro
                        490                 495                 500
        Gln Glu Asn Tyr Gly Trp Tyr Trp Leu Tyr Met Ala Arg Lys Ala Leu
                        505                 510                 515
        Met Glu Asn Lys Asp Lys Met Ser Gln Ala Asp Trp Glu Lys Ala Tyr
                        520                 525                 530
        Glu Tyr Leu Leu Arg Ala Glu Ala Ser Asp Trp Phe Trp Trp Tyr Gly
                        535                 540                 545
        Ser Asp Gln Asp Ser Gly Gln Asp Tyr Thr Phe Asp Arg Tyr Leu Lys
        550                 555                 560                 565
        Thr Tyr Leu Tyr Glu Met Tyr Lys Leu Ala Gly Val Glu Pro Pro Ser
                            570                 575                 580
        Tyr Leu Phe Gly Asn Tyr Phe Pro Asp Gly Glu Pro Tyr Thr Thr Arg
                        585                 590                 595
        Gly Leu Val Gly Leu Lys Asp Gly Glu Met Lys Asn Phe Ser Ser Met
                        600                 605                 610
        Ser Pro Leu Ala Lys Gly Val Ser Val Tyr Phe Asp Gly Glu Gly Ile
                        615                 620                 625
        His Phe Ile Val Lys Gly Asn Leu Asp Arg Phe Glu Val Ser Ile Trp
        630                 635                 640                 645
        Glu Lys Asp Glu Arg Val Gly Asn Thr Phe Thr Arg Leu Gln Glu Lys
                            650                 655                 660
        Pro Asp Glu Leu Ser Tyr Phe Met Phe Pro Phe Ser Arg Asp Ser Val
                        665                 670                 675
        Gly Leu Leu Ile Thr Lys His Val Val Tyr Glu Asn Gly Lys Ala Glu
                        680                 685                 690
        Ile Tyr Gly Ala Thr Asp Tyr Glu Lys Ser Glu Lys Leu Gly Glu Ala
                        695                 700                 705
        Thr Val Lys Asn Thr Ser Glu Gly Ile Glu Val Val Leu Pro Phe Asp
        710                 715                 720                 725
        Tyr Ile Glu Asn Pro Ser Asp Phe Tyr Phe Ala Val Ser Thr Val Lys
                            730                 735                 740
        Asp Gly Asp Leu Glu Val Ile Ser Thr Pro Val Glu Leu Lys Leu Pro
                        745                 750                 755
        Thr Glu Val Lys Gly Val Val Ile Ala Asp Ile Thr Asp Pro Glu Gly
                        760                 765                 770
        Asp Asp His Gly Pro Gly Asn Tyr Thr Tyr Pro Thr Asp Lys Val Phe
        775                 780                 785
        Lys Pro Gly Val Phe Asp Leu Leu Arg Phe Arg Met Leu Glu Gln Thr
        790                 795                 800                 805
        Glu Ser Tyr Val Met Glu Phe Tyr Phe Lys Asp Leu Gly Gly Asn Pro
                            810                 815                 820
        Trp Asn Gly Pro Asn Gly Phe Ser Leu Gln Ile Ile Glu Val Tyr Leu
                        825                 830                 835
        Asp Phe Lys Asp Gly Gly Asn Ser Ser Ala Ile Lys Met Phe Pro Asp
                        840                 845                 850
        Gly Pro Gly Ala Asn Val Asn Leu Asp Pro Glu His Pro Trp Asp Val
                        855                 860                 865
        Ala Phe Arg Ile Ala Gly Trp Asp Tyr Gly Asn Leu Ile Ile Leu Pro
        870                 875                 880                 885
        Asn Gly Thr Ala Ile Gln Gly Glu Met Gln Ile Ser Ala Asp Pro Val
                            890                 895                 900
```

-continued

```
Lys Asn Ala Ile Ile Val Lys Val Pro Lys Lys Tyr Ile Ala Ile Asn
                905                 910                 915
Glu Asp Tyr Gly Leu Trp Gly Asp Val Leu Val Gly Ser Gln Asp Gly
        920                 925                 930
Tyr Gly Pro Asp Lys Trp Arg Thr Ala Ala Val Asp Ala Glu Gln Trp
    935                 940                 945
Lys Leu Gly Gly Ala Asp Pro Gln Ala Val Ile Asn Gly Val Ala Pro
950                 955                 960                 965
Arg Val Ile Asp Glu Leu Val Pro Gln Gly Phe Pro Thr Gln Glu
                970                 975                 980
Glu Gln Leu Ser Ser Tyr Asp Ala Asn Asp Met Lys Leu Ala Thr Val
            985                 990                 995
Lys Ala Leu Leu Leu Leu Lys Gln Gly Ile Val Val Thr Asp Pro
        1000                1005                1010
Glu Gly Asp Asp His Gly Pro Gly Thr Tyr Thr Tyr Pro Thr Asp
        1015                1020                1025
Lys Val Phe Lys Pro Gly Val Phe Asp Leu Leu Lys Phe Lys Val
        1030                1035                1040
Thr Glu Gly Ser Asp Asp Trp Thr Leu Glu Phe His Phe Lys Asp
        1045                1050                1055
Leu Gly Gly Asn Pro Trp Asn Gly Pro Asn Gly Phe Ser Leu Gln
        1060                1065                1070
Ile Ile Glu Val Tyr Phe Asp Phe Lys Glu Gly Gly Asn Val Ser
        1075                1080                1085
Ala Ile Lys Met Phe Pro Asp Gly Pro Gly Ser Asn Val Arg Leu
        1090                1095                1100
Asp Pro Asn His Pro Trp Asp Leu Ala Leu Arg Ile Ala Gly Trp
        1105                1110                1115
Asp Tyr Gly Asn Leu Ile Ile Leu Pro Asp Gly Thr Ala Tyr Gln
        1120                1125                1130
Gly Glu Met Gln Ile Ser Ala Asp Pro Val Lys Asn Ala Ile Ile
        1135                1140                1145
Val Lys Val Pro Lys Lys Tyr Leu Asn Ile Ser Asp Tyr Gly Leu
        1150                1155                1160
Tyr Thr Ala Val Ile Val Gly Ser Gln Asp Gly Tyr Gly Pro Asp
        1165                1170                1175
Lys Trp Arg Pro Val Ala Ala Glu Ala Glu Gln Trp Lys Leu Gly
        1180                1185                1190
Gly Ala Asp Pro Gln Ala Val Ile Asp Asn Leu Val Pro Arg Val
        1195                1200                1205
Val Asp Glu Leu Val Pro Glu Gly Phe Lys Pro Thr Gln Glu Glu
        1210                1215                1220
Gln Leu Ser Ser Tyr Asp Leu Glu Lys Lys Thr Leu Ala Thr Val
        1225                1230                1235
Leu Met Val Pro Leu Val Asn Gly Thr Gly Gly Glu Pro Thr
        1240                1245                1250
Pro Thr Glu Ser Pro Thr Glu Thr Thr Thr Thr Pro Ser Glu
        1255                1260                1265
Thr Thr Thr Thr Thr Ser Thr Thr Thr Gly Pro Ser Thr Thr
        1270                1275                1280
Thr Ser Thr Pro Gly Gly Gly Ile Cys Gly Pro Gly Ile Ile Ala
        1285                1290                1295
```

```
Gly Leu Ala Leu Ile Pro Leu Leu Leu Lys Arg Arg Asn
        1300            1305            1310
```

<210> SEQ ID NO 12
<211> LENGTH: 809
<212> TYPE: PRT
<213> ORGANISM: Artificial Sequence
<220> FEATURE:
<223> OTHER INFORMATION: Hybrid pullulanase of Thermoccus hydrothermalis
      and Thermococcus litoralis
<220> FEATURE:
<221> NAME/KEY: SIGNAL
<222> LOCATION: (1)..(27)
<220> FEATURE:
<221> NAME/KEY: mat_peptide
<222> LOCATION: (28)..(809)

<400> SEQUENCE: 12

```
Met Lys Lys Pro Leu Gly Lys Ile Val Ala Ser Thr Ala Leu Leu Ile
        -25            -20            -15

Ser Val Ala Phe Ser Ser Ile Ala Ser Ala Glu Glu Pro Lys Pro
    -10            -5          -1  1              5

Leu Asn Val Ile Ile Val Trp His Gln His Gln Pro Tyr Tyr Tyr Asp
                10              15              20

Pro Ile Gln Asp Ile Tyr Thr Arg Pro Trp Val Arg Leu His Ala Ala
            25              30              35

Asn Asn Tyr Trp Lys Met Ala Asn Tyr Leu Ser Lys Tyr Pro Asp Val
            40              45              50

His Val Ala Ile Asp Leu Ser Gly Ser Leu Ile Ala Gln Leu Ala Asp
        55              60              65

Tyr Met Asn Gly Lys Lys Asp Thr Tyr Gln Ile Val Thr Glu Lys Ile
70              75              80              85

Ala Asn Gly Glu Pro Leu Thr Leu Glu Asp Lys Trp Phe Met Leu Gln
            90              95              100

Ala Pro Gly Gly Phe Phe Asp His Thr Ile Pro Trp Asn Gly Glu Pro
            105             110             115

Val Ala Asp Glu Asn Gly Asn Pro Tyr Arg Glu Gln Trp Asp Arg Tyr
            120             125             130

Ala Glu Leu Lys Asp Lys Arg Asn Asn Ala Phe Lys Lys Tyr Ala Asn
135             140             145

Leu Pro Leu Asn Glu Gln Lys Val Lys Ile Thr Ala Glu Phe Thr Glu
150             155             160             165

Gln Asp Tyr Ile Asp Leu Ala Val Leu Phe Asn Leu Ala Trp Ile Asp
            170             175             180

Tyr Asn Tyr Ile Ile Asn Thr Pro Glu Leu Lys Ala Leu Tyr Asp Lys
            185             190             195

Val Asp Val Gly Gly Tyr Thr Lys Glu Asp Val Ala Thr Val Leu Lys
            200             205             210

His Gln Met Trp Leu Leu Asn His Thr Phe Glu Glu His Glu Lys Ile
        215             220             225

Asn Tyr Leu Leu Gly Asn Gly Asn Val Glu Val Thr Val Pro Tyr
230             235             240             245

Ala His Pro Ile Gly Pro Leu Asn Asp Phe Gly Trp Tyr Glu Asp
            250             255             260

Phe Asp Ala His Val Lys Lys Ala His Glu Leu Tyr Lys Lys Tyr Leu
            265             270             275

Gly Asp Asn Arg Val Glu Pro Gln Gly Gly Trp Ala Ala Glu Ser Ala
            280             285             290
```

```
Leu Asn Asp Lys Thr Leu Glu Ile Leu Thr Asn Asn Gly Trp Lys Trp
    295                 300                 305

Val Met Thr Asp Gln Met Val Leu Asp Ile Leu Gly Ile Pro Asn Thr
310                 315                 320                 325

Val Glu Asn Tyr Tyr Lys Pro Trp Val Ala Glu Phe Asn Gly Lys Lys
                330                 335                 340

Ile Tyr Leu Phe Pro Arg Asn His Asp Leu Ser Asp Arg Val Gly Phe
                345                 350                 355

Arg Tyr Ser Gly Met Asn Gln Tyr Gln Ala Val Glu Asp Phe Val Asn
            360                 365                 370

Glu Leu Leu Lys Val Gln Lys Glu Asn Tyr Asp Gly Ser Leu Val Tyr
    375                 380                 385

Val Val Thr Leu Asp Gly Glu Asn Pro Trp Glu His Tyr Pro Phe Asp
390                 395                 400                 405

Gly Lys Ile Phe Leu Glu Glu Leu Tyr Lys Lys Leu Thr Glu Leu Gln
                410                 415                 420

Lys Gln Gly Leu Ile Arg Thr Val Thr Pro Ser Glu Tyr Ile Gln Met
            425                 430                 435

Tyr Gly Asp Lys Ala Asn Lys Leu Thr Pro Arg Met Met Glu Arg Leu
            440                 445                 450

Asp Leu Thr Gly Asp Asn Val Asn Ala Leu Leu Lys Ala Gln Ser Leu
    455                 460                 465

Gly Glu Leu Tyr Asp Met Thr Gly Val Lys Glu Met Gln Trp Pro
470                 475                 480                 485

Glu Ser Ser Trp Ile Asp Gly Thr Leu Ser Thr Trp Ile Gly Glu Pro
                490                 495                 500

Gln Glu Asn Tyr Gly Trp Tyr Trp Leu Tyr Met Ala Arg Lys Ala Leu
                505                 510                 515

Met Glu Asn Lys Asp Lys Met Ser Gln Ala Asp Trp Glu Lys Ala Tyr
            520                 525                 530

Glu Tyr Leu Leu Arg Ala Glu Ala Ser Asp Trp Phe Trp Trp Tyr Gly
    535                 540                 545

Ser Asp Gln Asp Ser Gly Gln Asp Tyr Thr Phe Asp Arg Tyr Leu Lys
550                 555                 560                 565

Thr Tyr Leu Tyr Glu Met Tyr Lys Leu Ala Gly Val Glu Pro Pro Ser
                570                 575                 580

Tyr Leu Phe Gly Asn Tyr Phe Pro Asp Gly Glu Pro Tyr Thr Thr Arg
                585                 590                 595

Gly Leu Val Gly Leu Lys Asp Gly Glu Met Lys Asn Phe Ser Ser Met
            600                 605                 610

Ser Pro Leu Ala Lys Gly Val Ser Val Tyr Phe Asp Gly Glu Gly Ile
    615                 620                 625

His Phe Ile Val Lys Gly Asn Leu Asp Arg Phe Glu Val Ser Ile Trp
630                 635                 640                 645

Glu Lys Asp Glu Arg Val Gly Asn Thr Phe Thr Arg Leu Gln Glu Lys
                650                 655                 660

Pro Asp Glu Leu Ser Tyr Phe Met Phe Pro Phe Ser Arg Asp Ser Val
                665                 670                 675

Gly Leu Leu Ile Thr Lys His Val Val Tyr Glu Asn Gly Lys Ala Glu
            680                 685                 690

Ile Tyr Gly Ala Thr Asp Tyr Glu Lys Ser Glu Lys Leu Gly Glu Ala
    695                 700                 705
```

-continued

```
Thr Val Lys Asn Thr Ser Glu Gly Ile Glu Val Leu Pro Phe Asp
710                 715                 720                 725

Tyr Ile Glu Asn Pro Ser Asp Phe Tyr Phe Ala Val Ser Thr Lys
                730                 735                 740

Asp Gly Asp Leu Glu Val Ile Ser Thr Pro Val Glu Leu Lys Leu Pro
            745                 750                 755

Thr Glu Val Lys Gly Val Val Ile Ala Asp Ile Thr Asp Pro Glu Gly
                760                 765                 770

Asp Asp His Gly Pro Gly Asn Tyr Thr
    775                 780

<210> SEQ ID NO 13
<211> LENGTH: 412
<212> TYPE: PRT
<213> ORGANISM: Pyrococcus furiosus
<220> FEATURE:
<221> NAME/KEY: mat_peptide
<222> LOCATION: (1)..(412)
<223> OTHER INFORMATION: Pyrococcus furiosus protease (Pfu)

<400> SEQUENCE: 13

Ala Glu Leu Glu Gly Leu Asp Glu Ser Ala Ala Gln Val Met Ala Thr
1               5                   10                  15

Tyr Val Trp Asn Leu Gly Tyr Asp Gly Ser Gly Ile Thr Ile Gly Ile
                20                  25                  30

Ile Asp Thr Gly Ile Asp Ala Ser His Pro Asp Leu Gln Gly Lys Val
            35                  40                  45

Ile Gly Trp Val Asp Phe Val Asn Gly Arg Ser Tyr Pro Tyr Asp Asp
50                  55                  60

His Gly His Gly Thr His Val Ala Ser Ile Ala Ala Gly Thr Gly Ala
65                  70                  75                  80

Ala Ser Asn Gly Lys Tyr Lys Gly Met Ala Pro Gly Ala Lys Leu Ala
                85                  90                  95

Gly Ile Lys Val Leu Gly Ala Asp Gly Ser Gly Ser Ile Ser Thr Ile
            100                 105                 110

Ile Lys Gly Val Glu Trp Ala Val Asp Asn Lys Asp Lys Tyr Gly Ile
        115                 120                 125

Lys Val Ile Asn Leu Ser Leu Gly Ser Ser Gln Ser Ser Asp Gly Thr
130                 135                 140

Asp Ala Leu Ser Gln Ala Val Asn Ala Ala Trp Asp Ala Gly Leu Val
145                 150                 155                 160

Val Val Val Ala Ala Gly Asn Ser Gly Pro Asn Lys Tyr Thr Ile Gly
                165                 170                 175

Ser Pro Ala Ala Ala Ser Lys Val Ile Thr Val Gly Ala Val Asp Lys
            180                 185                 190

Tyr Asp Val Ile Thr Ser Phe Ser Ser Arg Gly Pro Thr Ala Asp Gly
        195                 200                 205

Arg Leu Lys Pro Glu Val Val Ala Pro Gly Asn Trp Ile Ile Ala Ala
    210                 215                 220

Arg Ala Ser Gly Thr Ser Met Gly Gln Pro Ile Asn Asp Tyr Tyr Thr
225                 230                 235                 240

Ala Ala Pro Gly Thr Ser Met Ala Thr Pro His Val Ala Gly Ile Ala
                245                 250                 255

Ala Leu Leu Leu Gln Ala His Pro Ser Trp Thr Pro Asp Lys Val Lys
            260                 265                 270

Thr Ala Leu Ile Glu Thr Ala Asp Ile Val Lys Pro Asp Glu Ile Ala
```

```
                275                 280                 285
Asp Ile Ala Tyr Gly Ala Gly Arg Val Asn Ala Tyr Lys Ala Ile Asn
290                 295                 300

Tyr Asp Asn Tyr Ala Lys Leu Val Phe Thr Gly Tyr Val Ala Asn Lys
305                 310                 315                 320

Gly Ser Gln Thr His Gln Phe Val Ile Ser Gly Ala Ser Phe Val Thr
                325                 330                 335

Ala Thr Leu Tyr Trp Asp Asn Ala Asn Ser Asp Leu Asp Leu Tyr Leu
                340                 345                 350

Tyr Asp Pro Asn Gly Asn Gln Val Asp Tyr Ser Tyr Thr Ala Tyr Tyr
                355                 360                 365

Gly Phe Glu Lys Val Gly Tyr Tyr Asn Pro Thr Asp Gly Thr Trp Thr
                370                 375                 380

Ile Lys Val Val Ser Tyr Ser Gly Ser Ala Asn Tyr Gln Val Asp Val
385                 390                 395                 400

Val Ser Asp Gly Ser Leu Ser Gln Pro Gly Ser Ser
                405                 410

<210> SEQ ID NO 14
<211> LENGTH: 595
<212> TYPE: PRT
<213> ORGANISM: Penicillium oxalicum
<220> FEATURE:
<221> NAME/KEY: mat_peptide
<222> LOCATION: (1)..(595)
<223> OTHER INFORMATION: mature Penicillium oxalicum glucoamylase
      sequence

<400> SEQUENCE: 14

Arg Pro Asp Pro Lys Gly Gly Asn Leu Thr Pro Phe Ile His Lys Glu
1               5                   10                  15

Gly Glu Arg Ser Leu Gln Gly Ile Leu Asp Asn Leu Gly Gly Arg Gly
                20                  25                  30

Lys Lys Thr Pro Gly Thr Ala Ala Gly Leu Phe Ile Ala Ser Pro Asn
            35                  40                  45

Thr Glu Asn Pro Asn Tyr Tyr Tyr Thr Trp Thr Arg Asp Ser Ala Leu
50                  55                  60

Thr Ala Lys Cys Leu Ile Asp Leu Phe Glu Asp Ser Arg Ala Lys Phe
65                  70                  75                  80

Pro Ile Asp Arg Lys Tyr Leu Glu Thr Gly Ile Arg Asp Tyr Lys Ser
                85                  90                  95

Ser Gln Ala Ile Leu Gln Ser Val Ser Asn Pro Ser Gly Thr Leu Lys
            100                 105                 110

Asp Gly Ser Gly Leu Gly Glu Pro Lys Phe Glu Ile Asp Leu Asn Pro
        115                 120                 125

Phe Ser Gly Ala Trp Gly Arg Pro Gln Arg Asp Gly Pro Ala Leu Arg
130                 135                 140

Ala Thr Ala Met Ile Thr Tyr Ala Asn Tyr Leu Ile Ser His Gly Gln
145                 150                 155                 160

Lys Ser Asp Val Ser Gln Val Met Trp Pro Ile Ile Ala Asn Asp Leu
                165                 170                 175

Ala Tyr Val Gly Gln Tyr Trp Asn Asn Thr Gly Phe Asp Leu Trp Glu
            180                 185                 190

Glu Val Asp Gly Ser Ser Phe Phe Thr Ile Ala Val Gln His Arg Ala
        195                 200                 205

Leu Val Glu Gly Ser Gln Leu Ala Lys Lys Leu Gly Lys Ser Cys Asp
```

```
            210                 215                 220
Ala Cys Asp Ser Gln Pro Gln Ile Leu Cys Phe Leu Gln Ser Phe
225                 230                 235                 240

Trp Asn Gly Lys Tyr Ile Thr Ser Asn Ile Asn Thr Gln Ala Ser Arg
                245                 250                 255

Ser Gly Ile Asp Leu Asp Ser Val Leu Gly Ser Ile His Thr Phe Asp
            260                 265                 270

Pro Glu Ala Ala Cys Asp Asp Ala Thr Phe Gln Pro Cys Ser Ala Arg
        275                 280                 285

Ala Leu Ala Asn His Lys Val Tyr Val Asp Ser Phe Arg Ser Ile Tyr
    290                 295                 300

Lys Ile Asn Ala Gly Leu Ala Glu Gly Ser Ala Ala Asn Val Gly Arg
305                 310                 315                 320

Tyr Pro Glu Asp Val Tyr Gln Gly Gly Asn Pro Trp Tyr Leu Ala Thr
                325                 330                 335

Leu Gly Ala Ser Glu Leu Leu Tyr Asp Ala Leu Tyr Gln Trp Asp Arg
            340                 345                 350

Leu Gly Lys Leu Glu Val Ser Glu Thr Ser Leu Ser Phe Phe Lys Asp
        355                 360                 365

Phe Asp Ala Thr Val Lys Ile Gly Ser Tyr Ser Arg Asn Ser Lys Thr
    370                 375                 380

Tyr Lys Lys Leu Thr Gln Ser Ile Lys Ser Tyr Ala Asp Gly Phe Ile
385                 390                 395                 400

Gln Leu Val Gln Gln Tyr Thr Pro Ser Asn Gly Ser Leu Ala Glu Gln
                405                 410                 415

Tyr Asp Arg Asn Thr Ala Ala Pro Leu Ser Ala Asn Asp Leu Thr Trp
            420                 425                 430

Ser Phe Ala Ser Phe Leu Thr Ala Thr Gln Arg Arg Asp Ala Val Val
        435                 440                 445

Pro Pro Ser Trp Gly Ala Lys Ser Ala Asn Lys Val Pro Thr Thr Cys
    450                 455                 460

Ser Ala Ser Pro Val Val Gly Thr Tyr Lys Ala Pro Thr Ala Thr Phe
465                 470                 475                 480

Ser Ser Lys Thr Lys Cys Val Pro Ala Lys Asp Ile Val Pro Ile Thr
                485                 490                 495

Phe Tyr Leu Ile Glu Asn Thr Tyr Tyr Gly Glu Asn Val Phe Met Ser
            500                 505                 510

Gly Asn Ile Thr Ala Leu Gly Asn Trp Asp Ala Lys Lys Gly Phe Pro
        515                 520                 525

Leu Thr Ala Asn Leu Tyr Thr Gln Asp Gln Asn Leu Trp Phe Ala Ser
    530                 535                 540

Val Glu Phe Ile Pro Ala Gly Thr Pro Phe Glu Tyr Lys Tyr Tyr Lys
545                 550                 555                 560

Val Glu Pro Asn Gly Asp Ile Thr Trp Glu Lys Gly Pro Asn Arg Val
                565                 570                 575

Phe Val Ala Pro Thr Gly Cys Pro Val Gln Pro His Ser Asn Asp Val
            580                 585                 590

Trp Gln Phe
        595

<210> SEQ ID NO 15
<211> LENGTH: 49
<212> TYPE: DNA
<213> ORGANISM: artificial sequence
```

<220> FEATURE:
<223> OTHER INFORMATION: Prot F primer

<400> SEQUENCE: 15
aacgacggta cccggggatc ggatccatgc ggctcgttgc ttccctaac          49

<210> SEQ ID NO 16
<211> LENGTH: 48
<212> TYPE: DNA
<213> ORGANISM: artificial sequence
<220> FEATURE:
<223> OTHER INFORMATION: Prot R primer

<400> SEQUENCE: 16
ctaattacat gatgcggccc ttaattaatt agcaaccaag gtatatgg           48

<210> SEQ ID NO 17
<211> LENGTH: 20
<212> TYPE: DNA
<213> ORGANISM: Artificial sequence
<220> FEATURE:
<223> OTHER INFORMATION: AM34 Primer

<400> SEQUENCE: 17
taggagttta gtgaacttgc                                          20

<210> SEQ ID NO 18
<211> LENGTH: 18
<212> TYPE: DNA
<213> ORGANISM: Artificial sequence
<220> FEATURE:
<223> OTHER INFORMATION: AM35 Primer

<400> SEQUENCE: 18
ttcgagcgtc ccaaaacc                                            18

<210> SEQ ID NO 19
<211> LENGTH: 25
<212> TYPE: DNA
<213> ORGANISM: Artificial Primer
<220> FEATURE:
<223> OTHER INFORMATION: Sense Primer

<400> SEQUENCE: 19
atgcgtctca ctctattatc aggtg                                    25

<210> SEQ ID NO 20
<211> LENGTH: 39
<212> TYPE: DNA
<213> ORGANISM: Artificial sequence
<220> FEATURE:
<223> OTHER INFORMATION: Primer F

<400> SEQUENCE: 20
acacaactgg ggatccacca tgcgtctcac tctattatc                     39

<210> SEQ ID NO 21
<211> LENGTH: 37
<212> TYPE: DNA
<213> ORGANISM: Artificial Primer
<220> FEATURE:
<223> OTHER INFORMATION: Primer R

<400> SEQUENCE: 21
agatctcgag aagcttaaaa ctgccacacg tcgttgg                       37

<210> SEQ ID NO 22
<211> LENGTH: 18
<212> TYPE: DNA
<213> ORGANISM: Artificial sequence
<220> FEATURE:
<223> OTHER INFORMATION: Primer

<400> SEQUENCE: 22
gcagtctttc caattgac                                                 18

<210> SEQ ID NO 23
<211> LENGTH: 18
<212> TYPE: DNA
<213> ORGANISM: Artificial sequence
<220> FEATURE:
<223> OTHER INFORMATION: Primer

<400> SEQUENCE: 23
aattggaaag actgcccg                                                 18

<210> SEQ ID NO 24
<211> LENGTH: 39
<212> TYPE: DNA
<213> ORGANISM: Artificial sequence
<220> FEATURE:
<223> OTHER INFORMATION: Primer

<400> SEQUENCE: 24
acacaactgg ggatccacca tgcgtctcac tctattatc                           39

<210> SEQ ID NO 25
<211> LENGTH: 37
<212> TYPE: DNA
<213> ORGANISM: Artificial sequence
<220> FEATURE:
<223> OTHER INFORMATION: Primer

<400> SEQUENCE: 25
agatctcgag aagcttaaaa ctgccacacg tcgttgg                             37

<210> SEQ ID NO 26
<211> LENGTH: 574
<212> TYPE: PRT
<213> ORGANISM: Trametes cingulata

<400> SEQUENCE: 26

Met Arg Phe Thr Leu Leu Thr Ser Leu Leu Gly Leu Ala Leu Gly Ala
1               5                   10                  15

Phe Ala Gln Ser Ser Ala Ala Asp Ala Tyr Val Ala Ser Glu Ser Pro
            20                  25                  30

Ile Ala Lys Ala Gly Val Leu Ala Asn Ile Gly Pro Ser Gly Ser Lys
        35                  40                  45

Ser Asn Gly Ala Lys Ala Gly Ile Val Ile Ala Ser Pro Ser Thr Ser
    50                  55                  60

Asn Pro Asn Tyr Leu Tyr Thr Trp Thr Arg Asp Ser Ser Leu Val Phe
65                  70                  75                  80

Lys Ala Leu Ile Asp Gln Phe Thr Thr Gly Glu Asp Thr Ser Leu Arg
                85                  90                  95

Thr Leu Ile Asp Glu Phe Thr Ser Ala Glu Ala Ile Leu Gln Gln Val
            100                 105                 110

Pro Asn Pro Ser Gly Thr Val Ser Thr Gly Gly Leu Gly Glu Pro Lys
        115                 120                 125

```
Phe Asn Ile Asp Glu Thr Ala Phe Thr Asp Ala Trp Gly Arg Pro Gln
    130                 135                 140

Arg Asp Gly Pro Ala Leu Arg Ala Thr Ala Ile Ile Thr Tyr Ala Asn
145                 150                 155                 160

Trp Leu Leu Asp Asn Lys Asn Thr Thr Tyr Val Thr Asn Thr Leu Trp
                165                 170                 175

Pro Ile Ile Lys Leu Asp Leu Asp Tyr Val Ala Ser Asn Trp Asn Gln
            180                 185                 190

Ser Thr Phe Asp Leu Trp Glu Glu Ile Asn Ser Ser Ser Phe Phe Thr
        195                 200                 205

Thr Ala Val Gln His Arg Ala Leu Arg Glu Gly Ala Thr Phe Ala Asn
    210                 215                 220

Arg Ile Gly Gln Thr Ser Val Val Ser Gly Tyr Thr Thr Gln Ala Asn
225                 230                 235                 240

Asn Leu Leu Cys Phe Leu Gln Ser Tyr Trp Asn Pro Thr Gly Gly Tyr
                245                 250                 255

Ile Thr Ala Asn Thr Gly Gly Arg Ser Gly Lys Asp Ala Asn Thr
            260                 265                 270

Val Leu Thr Ser Ile His Thr Phe Asp Pro Ala Ala Gly Cys Asp Ala
        275                 280                 285

Val Thr Phe Gln Pro Cys Ser Asp Lys Ala Leu Ser Asn Leu Lys Val
    290                 295                 300

Tyr Val Asp Ala Phe Arg Ser Ile Tyr Ser Ile Asn Ser Gly Ile Ala
305                 310                 315                 320

Ser Asn Ala Ala Val Ala Thr Gly Arg Tyr Pro Glu Asp Ser Tyr Met
                325                 330                 335

Gly Gly Asn Pro Trp Tyr Leu Thr Thr Ser Ala Val Ala Glu Gln Leu
            340                 345                 350

Tyr Asp Ala Leu Ile Val Trp Asn Lys Leu Gly Ala Leu Asn Val Thr
        355                 360                 365

Ser Thr Ser Leu Pro Phe Phe Gln Gln Phe Ser Ser Gly Val Thr Val
    370                 375                 380

Gly Thr Tyr Ala Ser Ser Ser Thr Phe Lys Thr Leu Thr Ser Ala
385                 390                 395                 400

Ile Lys Thr Phe Ala Asp Gly Phe Leu Ala Val Asn Ala Lys Tyr Thr
                405                 410                 415

Pro Ser Asn Gly Gly Leu Ala Glu Gln Tyr Ser Arg Ser Asn Gly Ser
            420                 425                 430

Pro Val Ser Ala Val Asp Leu Thr Trp Ser Tyr Ala Ala Ala Leu Thr
        435                 440                 445

Ser Phe Ala Ala Arg Ser Gly Lys Thr Tyr Ala Ser Trp Gly Ala Ala
    450                 455                 460

Gly Leu Thr Val Pro Thr Thr Cys Ser Gly Ser Gly Gly Ala Gly Thr
465                 470                 475                 480

Val Ala Val Thr Phe Asn Val Gln Ala Thr Val Phe Gly Glu Asn
                485                 490                 495

Ile Tyr Ile Thr Gly Ser Val Pro Ala Leu Gln Asn Trp Ser Pro Asp
            500                 505                 510

Asn Ala Leu Ile Leu Ser Ala Ala Asn Tyr Pro Thr Trp Ser Ile Thr
        515                 520                 525

Val Asn Leu Pro Ala Ser Thr Thr Ile Glu Tyr Lys Tyr Ile Arg Lys
    530                 535                 540
```

```
Phe Asn Gly Ala Val Thr Trp Glu Ser Asp Pro Asn Asn Ser Ile Thr
545                 550                 555                 560

Thr Pro Ala Ser Gly Thr Phe Thr Gln Asn Asp Thr Trp Arg
                565                 570

<210> SEQ ID NO 27
<211> LENGTH: 583
<212> TYPE: PRT
<213> ORGANISM: Rhizomucor pusillus

<400> SEQUENCE: 27

Ala Thr Ser Asp Asp Trp Lys Gly Lys Ala Ile Tyr Gln Leu Leu Thr
1               5                   10                  15

Asp Arg Phe Gly Arg Ala Asp Asp Ser Thr Ser Asn Cys Ser Asn Leu
                20                  25                  30

Ser Asn Tyr Cys Gly Gly Thr Tyr Glu Gly Ile Thr Lys His Leu Asp
            35                  40                  45

Tyr Ile Ser Gly Met Gly Phe Asp Ala Ile Trp Ile Ser Pro Ile Pro
50                  55                  60

Lys Asn Ser Asp Gly Gly Tyr His Gly Tyr Trp Ala Thr Asp Phe Tyr
65                  70                  75                  80

Gln Leu Asn Ser Asn Phe Gly Asp Glu Ser Gln Leu Lys Ala Leu Ile
                85                  90                  95

Gln Ala Ala His Glu Arg Asp Met Tyr Val Met Leu Asp Val Val Ala
                100                 105                 110

Asn His Ala Gly Pro Thr Ser Asn Gly Tyr Ser Gly Tyr Thr Phe Gly
            115                 120                 125

Asp Ala Ser Leu Tyr His Pro Lys Cys Thr Ile Asp Tyr Asn Asp Gln
130                 135                 140

Thr Ser Ile Glu Gln Cys Trp Val Ala Asp Gly Leu Pro Asp Ile Asp
145                 150                 155                 160

Thr Glu Asn Ser Asp Asn Val Ala Ile Leu Asn Asp Ile Val Ser Gly
                165                 170                 175

Trp Val Gly Asn Tyr Ser Phe Asp Gly Ile Arg Ile Asp Thr Val Lys
            180                 185                 190

His Ile Arg Lys Asp Phe Trp Thr Gly Tyr Ala Glu Ala Ala Gly Val
        195                 200                 205

Phe Ala Thr Gly Glu Val Phe Asn Gly Asp Pro Ala Tyr Val Gly Pro
210                 215                 220

Tyr Gln Lys Tyr Leu Pro Ser Leu Ile Asn Tyr Pro Met Tyr Tyr Ala
225                 230                 235                 240

Leu Asn Asp Val Phe Val Ser Lys Ser Lys Gly Phe Ser Arg Ile Ser
                245                 250                 255

Glu Met Leu Gly Ser Asn Arg Asn Ala Phe Glu Asp Thr Ser Val Leu
            260                 265                 270

Thr Thr Phe Val Asp Asn His Asp Asn Pro Arg Phe Leu Asn Ser Gln
        275                 280                 285

Ser Asp Lys Ala Leu Phe Lys Asn Ala Leu Thr Tyr Val Leu Leu Gly
    290                 295                 300

Glu Gly Ile Pro Ile Val Tyr Tyr Gly Ser Glu Gln Gly Phe Ser Gly
305                 310                 315                 320

Gly Ala Asp Pro Ala Asn Arg Glu Val Leu Trp Thr Thr Asn Tyr Asp
                325                 330                 335

Thr Ser Ser Asp Leu Tyr Gln Phe Ile Lys Thr Val Asn Ser Val Arg
            340                 345                 350
```

```
Met Lys Ser Asn Lys Ala Val Tyr Met Asp Ile Tyr Val Gly Asp Asn
            355                 360                 365

Ala Tyr Ala Phe Lys His Gly Asp Ala Leu Val Val Leu Asn Asn Tyr
    370                 375                 380

Gly Ser Gly Ser Thr Asn Gln Val Ser Phe Ser Val Ser Gly Lys Phe
385                 390                 395                 400

Asp Ser Gly Ala Ser Leu Met Asp Ile Val Ser Asn Ile Thr Thr Thr
                405                 410                 415

Val Ser Ser Asp Gly Thr Val Thr Phe Asn Leu Lys Asp Gly Leu Pro
            420                 425                 430

Ala Ile Phe Thr Ser Ala Thr Gly Gly Thr Thr Thr Ala Thr Pro
            435                 440                 445

Thr Gly Ser Gly Ser Val Thr Ser Thr Ser Lys Thr Thr Ala Thr Ala
    450                 455                 460

Ser Lys Thr Ser Thr Ser Thr Ser Ser Thr Ser Cys Thr Thr Pro Thr
465                 470                 475                 480

Ala Val Ala Val Thr Phe Asp Leu Thr Ala Thr Thr Thr Tyr Gly Glu
                485                 490                 495

Asn Ile Tyr Leu Val Gly Ser Ile Ser Gln Leu Gly Asp Trp Glu Thr
            500                 505                 510

Ser Asp Gly Ile Ala Leu Ser Ala Asp Lys Tyr Thr Ser Ser Asp Pro
        515                 520                 525

Leu Trp Tyr Val Thr Val Thr Leu Pro Ala Gly Glu Ser Phe Glu Tyr
    530                 535                 540

Lys Phe Ile Arg Ile Glu Ser Asp Ser Val Glu Trp Glu Ser Asp
545                 550                 555                 560

Pro Asn Arg Glu Tyr Thr Val Pro Gln Ala Cys Gly Thr Ser Thr Ala
                565                 570                 575

Thr Val Thr Asp Thr Trp Arg
            580

<210> SEQ ID NO 28
<211> LENGTH: 618
<212> TYPE: PRT
<213> ORGANISM: Talaromyces emersonii

<400> SEQUENCE: 28

Met Ala Ser Leu Val Ala Gly Ala Leu Cys Ile Leu Gly Leu Thr Pro
1               5                   10                  15

Ala Ala Phe Ala Arg Ala Pro Val Ala Ala Arg Ala Thr Gly Ser Leu
            20                  25                  30

Asp Ser Phe Leu Ala Thr Glu Thr Pro Ile Ala Leu Gln Gly Val Leu
        35                  40                  45

Asn Asn Ile Gly Pro Asn Gly Ala Asp Val Ala Gly Ala Ser Ala Gly
    50                  55                  60

Ile Val Val Ala Ser Pro Ser Arg Ser Asp Pro Asn Tyr Phe Tyr Ser
65                  70                  75                  80

Trp Thr Arg Asp Ala Ala Leu Thr Ala Lys Tyr Leu Val Asp Ala Phe
                85                  90                  95

Ile Ala Gly Asn Lys Asp Leu Glu Gln Thr Ile Gln Gln Tyr Ile Ser
            100                 105                 110

Ala Gln Ala Lys Val Gln Thr Ile Ser Asn Pro Ser Gly Asp Leu Ser
        115                 120                 125

Thr Gly Gly Leu Gly Glu Pro Lys Phe Asn Val Asn Glu Thr Ala Phe
```

```
              130                 135                 140
Thr Gly Pro Trp Gly Arg Pro Gln Arg Asp Gly Pro Ala Leu Arg Ala
145                 150                 155                 160

Thr Ala Leu Ile Ala Tyr Ala Asn Tyr Leu Ile Asp Asn Gly Glu Ala
                165                 170                 175

Ser Thr Ala Asp Glu Ile Ile Trp Pro Ile Val Gln Asn Asp Leu Ser
            180                 185                 190

Tyr Ile Thr Gln Tyr Trp Asn Ser Ser Thr Phe Asp Leu Trp Glu Glu
        195                 200                 205

Val Glu Gly Ser Ser Phe Phe Thr Thr Ala Val Gln His Arg Ala Leu
    210                 215                 220

Val Glu Gly Asn Ala Leu Ala Thr Arg Leu Asn His Thr Cys Ser Asn
225                 230                 235                 240

Cys Val Ser Gln Ala Pro Gln Val Leu Cys Phe Leu Gln Ser Tyr Trp
                245                 250                 255

Thr Gly Ser Tyr Val Leu Ala Asn Phe Gly Gly Ser Gly Arg Ser Gly
            260                 265                 270

Lys Asp Val Asn Ser Ile Leu Gly Ser Ile His Thr Phe Asp Pro Ala
        275                 280                 285

Gly Gly Cys Asp Asp Ser Thr Phe Gln Pro Cys Ser Ala Arg Ala Leu
    290                 295                 300

Ala Asn His Lys Val Val Thr Asp Ser Phe Arg Ser Ile Tyr Ala Ile
305                 310                 315                 320

Asn Ser Gly Ile Ala Glu Gly Ser Ala Val Ala Val Gly Arg Tyr Pro
                325                 330                 335

Glu Asp Val Tyr Gln Gly Gly Asn Pro Trp Tyr Leu Ala Thr Ala Ala
            340                 345                 350

Ala Ala Glu Gln Leu Tyr Asp Ala Ile Tyr Gln Trp Lys Lys Ile Gly
        355                 360                 365

Ser Ile Ser Ile Thr Asp Val Ser Leu Pro Phe Phe Gln Asp Ile Tyr
    370                 375                 380

Pro Ser Ala Ala Val Gly Thr Tyr Asn Ser Gly Ser Thr Thr Phe Asn
385                 390                 395                 400

Asp Ile Ile Ser Ala Val Gln Thr Tyr Gly Asp Gly Tyr Leu Ser Ile
                405                 410                 415

Val Glu Lys Tyr Thr Pro Ser Asp Gly Ser Leu Thr Glu Gln Phe Ser
            420                 425                 430

Arg Thr Asp Gly Thr Pro Leu Ser Ala Ser Ala Leu Thr Trp Ser Tyr
        435                 440                 445

Ala Ser Leu Leu Thr Ala Ser Ala Arg Arg Gln Ser Val Val Pro Ala
    450                 455                 460

Ser Trp Gly Glu Ser Ala Ser Ser Val Pro Ala Val Cys Ser Ala
465                 470                 475                 480

Thr Ser Ala Thr Gly Pro Tyr Ser Thr Ala Thr Asn Thr Val Trp Pro
                485                 490                 495

Ser Ser Gly Ser Gly Ser Ser Thr Thr Thr Ser Ser Ala Pro Cys Thr
            500                 505                 510

Thr Pro Thr Ser Val Ala Val Thr Phe Asp Glu Ile Val Ser Thr Ser
        515                 520                 525

Tyr Gly Glu Thr Ile Tyr Leu Ala Gly Ser Ile Pro Glu Leu Gly Asn
    530                 535                 540

Trp Ser Thr Ala Ser Ala Ile Pro Leu Arg Ala Asp Ala Tyr Thr Asn
545                 550                 555                 560
```

```
Ser Asn Pro Leu Trp Tyr Val Thr Val Asn Leu Pro Pro Gly Thr Ser
                565                 570                 575

Phe Glu Tyr Lys Phe Phe Lys Asn Gln Thr Asp Gly Thr Ile Val Trp
            580                 585                 590

Glu Asp Asp Pro Asn Arg Ser Tyr Thr Val Pro Ala Tyr Cys Gly Gln
        595                 600                 605

Thr Thr Ala Ile Leu Asp Asp Ser Trp Gln
    610                 615

<210> SEQ ID NO 29
<211> LENGTH: 863
<212> TYPE: PRT
<213> ORGANISM: Aspergillus fumigatus

<400> SEQUENCE: 29

Met Arg Phe Gly Trp Leu Glu Val Ala Ala Leu Thr Ala Ala Ser Val
1               5                   10                  15

Ala Asn Ala Gln Glu Leu Ala Phe Ser Pro Pro Phe Tyr Pro Ser Pro
            20                  25                  30

Trp Ala Asp Gly Gln Gly Glu Trp Ala Asp Ala His Arg Arg Ala Val
        35                  40                  45

Glu Ile Val Ser Gln Met Thr Leu Ala Glu Lys Val Asn Leu Thr Thr
    50                  55                  60

Gly Thr Gly Trp Glu Met Asp Arg Cys Val Gly Gln Thr Gly Ser Val
65                  70                  75                  80

Pro Arg Leu Gly Ile Asn Trp Gly Leu Cys Gly Gln Asp Ser Pro Leu
                85                  90                  95

Gly Ile Arg Phe Ser Asp Leu Asn Ser Ala Phe Pro Ala Gly Thr Asn
            100                 105                 110

Val Ala Ala Thr Trp Asp Lys Thr Leu Ala Tyr Leu Arg Gly Lys Ala
        115                 120                 125

Met Gly Glu Glu Phe Asn Asp Lys Gly Val Asp Ile Leu Leu Gly Pro
    130                 135                 140

Ala Ala Gly Pro Leu Gly Lys Tyr Pro Asp Gly Gly Arg Ile Trp Glu
145                 150                 155                 160

Gly Phe Ser Pro Asp Pro Val Leu Thr Gly Val Leu Phe Ala Glu Thr
                165                 170                 175

Ile Lys Gly Ile Gln Asp Ala Gly Val Ile Ala Thr Ala Lys His Tyr
            180                 185                 190

Ile Leu Asn Glu Gln Glu His Phe Arg Gln Val Gly Glu Ala Gln Gly
        195                 200                 205

Tyr Gly Tyr Asn Ile Thr Glu Thr Ile Ser Ser Asn Val Asp Asp Lys
    210                 215                 220

Thr Met His Glu Leu Tyr Leu Trp Pro Phe Ala Asp Ala Val Arg Ala
225                 230                 235                 240

Gly Val Gly Ala Val Met Cys Ser Tyr Asn Gln Ile Asn Asn Ser Tyr
                245                 250                 255

Gly Cys Gln Asn Ser Gln Thr Leu Asn Lys Leu Leu Lys Ala Glu Leu
            260                 265                 270

Gly Phe Gln Gly Phe Val Met Ser Asp Trp Ser Ala His His Ser Gly
        275                 280                 285

Val Gly Ala Ala Leu Ala Gly Leu Asp Met Ser Met Pro Gly Asp Ile
    290                 295                 300

Ser Phe Asp Asp Gly Leu Ser Phe Trp Gly Thr Asn Leu Thr Val Ser
```

```
            305                 310                 315                 320
        Val Leu Asn Gly Thr Val Pro Ala Trp Arg Val Asp Asp Met Ala Val
                        325                 330                 335
        Arg Ile Met Thr Ala Tyr Tyr Lys Val Gly Arg Asp Arg Leu Arg Ile
                        340                 345                 350
        Pro Pro Asn Phe Ser Ser Trp Thr Arg Asp Glu Tyr Gly Trp Glu His
                        355                 360                 365
        Ser Ala Val Ser Glu Gly Ala Trp Thr Lys Val Asn Asp Phe Val Asn
                        370                 375                 380
        Val Gln Arg Ser His Ser Gln Ile Ile Arg Glu Ile Gly Ala Ala Ser
        385                 390                 395                 400
        Thr Val Leu Leu Lys Asn Thr Gly Ala Leu Pro Leu Thr Gly Lys Glu
                        405                 410                 415
        Val Lys Val Gly Val Leu Gly Glu Asp Ala Gly Ser Asn Pro Trp Gly
                        420                 425                 430
        Ala Asn Gly Cys Pro Asp Arg Gly Cys Asp Asn Gly Thr Leu Ala Met
                        435                 440                 445
        Ala Trp Gly Ser Gly Thr Ala Asn Phe Pro Tyr Leu Val Thr Pro Glu
                        450                 455                 460
        Gln Ala Ile Gln Arg Glu Val Ile Ser Asn Gly Gly Asn Val Phe Ala
        465                 470                 475                 480
        Val Thr Asp Asn Gly Ala Leu Ser Gln Met Ala Asp Val Ala Ser Gln
                        485                 490                 495
        Ser Ser Val Ser Leu Val Phe Val Asn Ala Asp Ser Gly Glu Gly Phe
                        500                 505                 510
        Ile Ser Val Asp Gly Asn Glu Gly Asp Arg Lys Asn Leu Thr Leu Trp
                        515                 520                 525
        Lys Asn Gly Glu Ala Val Ile Asp Thr Val Val Ser His Cys Asn Asn
                        530                 535                 540
        Thr Ile Val Val Ile His Ser Val Gly Pro Val Leu Ile Asp Arg Trp
        545                 550                 555                 560
        Tyr Asp Asn Pro Asn Val Thr Ala Ile Ile Trp Ala Gly Leu Pro Gly
                        565                 570                 575
        Gln Glu Ser Gly Asn Ser Leu Val Asp Val Leu Tyr Gly Arg Val Asn
                        580                 585                 590
        Pro Ser Ala Lys Thr Pro Phe Thr Trp Gly Lys Thr Arg Glu Ser Tyr
                        595                 600                 605
        Gly Ala Pro Leu Leu Thr Glu Pro Asn Asn Gly Asn Gly Ala Pro Gln
                        610                 615                 620
        Asp Asp Phe Asn Glu Gly Val Phe Ile Asp Tyr Arg His Phe Asp Lys
        625                 630                 635                 640
        Arg Asn Glu Thr Pro Ile Tyr Glu Phe Gly His Gly Leu Ser Tyr Thr
                        645                 650                 655
        Thr Phe Gly Tyr Ser His Leu Arg Val Gln Ala Leu Asn Ser Ser Ser
                        660                 665                 670
        Ser Ala Tyr Val Pro Thr Ser Gly Glu Thr Lys Pro Ala Pro Thr Tyr
                        675                 680                 685
        Gly Glu Ile Gly Ser Ala Ala Asp Tyr Leu Tyr Pro Glu Gly Leu Lys
                        690                 695                 700
        Arg Ile Thr Lys Phe Ile Tyr Pro Trp Leu Asn Ser Thr Asp Leu Glu
        705                 710                 715                 720
        Asp Ser Ser Asp Asp Pro Asn Tyr Gly Trp Glu Asp Ser Glu Tyr Ile
                        725                 730                 735
```

```
Pro Glu Gly Ala Arg Asp Gly Ser Pro Gln Pro Leu Lys Ala Gly
            740                 745                 750

Gly Ala Pro Gly Gly Asn Pro Thr Leu Tyr Gln Asp Leu Val Arg Val
            755                 760                 765

Ser Ala Thr Ile Thr Asn Thr Gly Asn Val Ala Gly Tyr Glu Val Pro
    770                 775                 780

Gln Leu Tyr Val Ser Leu Gly Pro Asn Glu Pro Arg Val Val Leu
785             790                 795                 800

Arg Lys Phe Asp Arg Ile Phe Leu Ala Pro Gly Glu Gln Lys Val Trp
                805                 810                 815

Thr Thr Thr Leu Asn Arg Arg Asp Leu Ala Asn Trp Asp Val Glu Ala
            820                 825                 830

Gln Asp Trp Val Ile Thr Lys Tyr Pro Lys Lys Val His Val Gly Ser
            835                 840                 845

Ser Ser Arg Lys Leu Pro Leu Arg Ala Pro Leu Pro Arg Val Tyr
    850                 855                 860

<210> SEQ ID NO 30
<211> LENGTH: 250
<212> TYPE: PRT
<213> ORGANISM: Thermoascus aurantiacus

<400> SEQUENCE: 30

Met Ser Phe Ser Lys Ile Ile Ala Thr Ala Gly Val Leu Ala Ser Ala
1               5                   10                  15

Ser Leu Val Ala Gly His Gly Phe Val Gln Asn Ile Val Ile Asp Gly
            20                  25                  30

Lys Lys Tyr Tyr Gly Gly Tyr Leu Val Asn Gln Tyr Pro Tyr Met Ser
        35                  40                  45

Asn Pro Pro Glu Val Ile Ala Trp Ser Thr Thr Ala Thr Asp Leu Gly
    50                  55                  60

Phe Val Asp Gly Thr Gly Tyr Gln Thr Pro Asp Ile Ile Cys His Arg
65                  70                  75                  80

Gly Ala Lys Pro Gly Ala Leu Thr Ala Pro Val Ser Pro Gly Gly Thr
                85                  90                  95

Val Glu Leu Gln Trp Thr Pro Trp Pro Asp Ser His His Gly Pro Val
            100                 105                 110

Ile Asn Tyr Leu Ala Pro Cys Asn Gly Asp Cys Ser Thr Val Asp Lys
        115                 120                 125

Thr Gln Leu Glu Phe Phe Lys Ile Ala Glu Ser Gly Leu Ile Asn Asp
    130                 135                 140

Asp Asn Pro Pro Gly Ile Trp Ala Ser Asp Asn Leu Ile Ala Ala Asn
145                 150                 155                 160

Asn Ser Trp Thr Val Thr Ile Pro Thr Thr Ile Ala Pro Gly Asn Tyr
                165                 170                 175

Val Leu Arg His Glu Ile Ile Ala Leu His Ser Ala Gln Asn Gln Asp
            180                 185                 190

Gly Ala Gln Asn Tyr Pro Gln Cys Ile Asn Leu Gln Val Thr Gly Gly
        195                 200                 205

Gly Ser Asp Asn Pro Ala Gly Thr Leu Gly Thr Ala Leu Tyr His Asp
    210                 215                 220

Thr Asp Pro Gly Ile Leu Ile Asn Ile Tyr Gln Lys Leu Ser Ser Tyr
225                 230                 235                 240

Ile Ile Pro Gly Pro Pro Leu Tyr Thr Gly
                245                 250
```

```
<210> SEQ ID NO 31
<211> LENGTH: 253
<212> TYPE: PRT
<213> ORGANISM: Penicillium emersonii

<400> SEQUENCE: 31

Met Leu Ser Ser Thr Thr Arg Thr Leu Ala Phe Thr Gly Leu Ala Gly
1               5                   10                  15

Leu Leu Ser Ala Pro Leu Val Lys Ala His Gly Phe Val Gln Gly Ile
            20                  25                  30

Val Ile Gly Asp Gln Phe Tyr Ser Gly Tyr Ile Val Asn Ser Phe Pro
        35                  40                  45

Tyr Glu Ser Asn Pro Pro Val Ile Gly Trp Ala Thr Thr Ala Thr
    50                  55                  60

Asp Leu Gly Phe Val Asp Gly Thr Gly Tyr Gln Gly Pro Asp Ile Ile
65                  70                  75                  80

Cys His Arg Asn Ala Thr Pro Ala Pro Leu Thr Ala Pro Val Ala Ala
                85                  90                  95

Gly Gly Thr Val Glu Leu Gln Trp Thr Pro Trp Pro Asp Ser His His
            100                 105                 110

Gly Pro Val Ile Thr Tyr Leu Ala Pro Cys Asn Gly Asn Cys Ser Thr
        115                 120                 125

Val Asp Lys Thr Thr Leu Glu Phe Phe Lys Ile Asp Gln Gln Gly Leu
130                 135                 140

Ile Asp Asp Thr Ser Pro Pro Gly Thr Trp Ala Ser Asp Asn Leu Ile
145                 150                 155                 160

Ala Asn Asn Asn Ser Trp Thr Val Thr Ile Pro Asn Ser Val Ala Pro
                165                 170                 175

Gly Asn Tyr Val Leu Arg His Glu Ile Ile Ala Leu His Ser Ala Asn
            180                 185                 190

Asn Lys Asp Gly Ala Gln Asn Tyr Pro Gln Cys Ile Asn Ile Glu Val
        195                 200                 205

Thr Gly Gly Gly Ser Asp Ala Pro Glu Gly Thr Leu Gly Glu Asp Leu
    210                 215                 220

Tyr His Asp Thr Asp Pro Gly Ile Leu Val Asp Ile Tyr Glu Pro Ile
225                 230                 235                 240

Ala Thr Tyr Thr Ile Pro Gly Pro Glu Pro Thr Phe
                245                 250

<210> SEQ ID NO 32
<211> LENGTH: 532
<212> TYPE: PRT
<213> ORGANISM: Aspergillus fumigatus

<400> SEQUENCE: 32

Met Leu Ala Ser Thr Phe Ser Tyr Arg Met Tyr Lys Thr Ala Leu Ile
1               5                   10                  15

Leu Ala Ala Leu Leu Gly Ser Gly Gln Ala Gln Gln Val Gly Thr Ser
            20                  25                  30

Gln Ala Glu Val His Pro Ser Met Thr Trp Gln Ser Cys Thr Ala Gly
        35                  40                  45

Gly Ser Cys Thr Thr Asn Asn Gly Lys Val Val Ile Asp Ala Asn Trp
    50                  55                  60

Arg Trp Val His Lys Val Gly Asp Tyr Thr Asn Cys Tyr Thr Gly Asn
```

-continued

```
            65                  70                  75                  80
Thr Trp Asp Thr Thr Ile Cys Pro Asp Asp Ala Thr Cys Ala Ser Asn
                    85                  90                  95

Cys Ala Leu Glu Gly Ala Asn Tyr Glu Ser Thr Tyr Gly Val Thr Ala
                   100                 105                 110

Ser Gly Asn Ser Leu Arg Leu Asn Phe Val Thr Thr Ser Gln Gln Lys
                   115                 120                 125

Asn Ile Gly Ser Arg Leu Tyr Met Met Lys Asp Asp Ser Thr Tyr Glu
            130                 135                 140

Met Phe Lys Leu Leu Asn Gln Glu Phe Thr Phe Asp Val Asp Val Ser
145                 150                 155                 160

Asn Leu Pro Cys Gly Leu Asn Gly Ala Leu Tyr Phe Val Ala Met Asp
                   165                 170                 175

Ala Asp Gly Gly Met Ser Lys Tyr Pro Thr Asn Lys Ala Gly Ala Lys
                   180                 185                 190

Tyr Gly Thr Gly Tyr Cys Asp Ser Gln Cys Pro Arg Asp Leu Lys Phe
                   195                 200                 205

Ile Asn Gly Gln Ala Asn Val Glu Gly Trp Gln Pro Ser Ser Asn Asp
            210                 215                 220

Ala Asn Ala Gly Thr Gly Asn His Gly Ser Cys Cys Ala Glu Met Asp
225                 230                 235                 240

Ile Trp Glu Ala Asn Ser Ile Ser Thr Ala Phe Thr Pro His Pro Cys
                   245                 250                 255

Asp Thr Pro Gly Gln Val Met Cys Thr Gly Asp Ala Cys Gly Gly Thr
                   260                 265                 270

Tyr Ser Ser Asp Arg Tyr Gly Gly Thr Cys Asp Pro Asp Gly Cys Asp
                   275                 280                 285

Phe Asn Ser Phe Arg Gln Gly Asn Lys Thr Phe Tyr Gly Pro Gly Met
            290                 295                 300

Thr Val Asp Thr Lys Ser Lys Phe Thr Val Thr Gln Phe Ile Thr
305                 310                 315                 320

Asp Asp Gly Thr Ser Ser Gly Thr Leu Lys Glu Ile Lys Arg Phe Tyr
                   325                 330                 335

Val Gln Asn Gly Lys Val Ile Pro Asn Ser Glu Ser Thr Trp Thr Gly
                   340                 345                 350

Val Ser Gly Asn Ser Ile Thr Thr Glu Tyr Cys Thr Ala Gln Lys Ser
                   355                 360                 365

Leu Phe Gln Asp Gln Asn Val Phe Glu Lys His Gly Gly Leu Glu Gly
            370                 375                 380

Met Gly Ala Ala Leu Ala Gln Gly Met Val Leu Val Met Ser Leu Trp
385                 390                 395                 400

Asp Asp His Ser Ala Asn Met Leu Trp Leu Asp Ser Asn Tyr Pro Thr
                   405                 410                 415

Thr Ala Ser Ser Thr Pro Gly Val Ala Arg Gly Thr Cys Asp Ile
                   420                 425                 430

Ser Ser Gly Val Pro Ala Asp Val Glu Ala Asn His Pro Asp Ala Tyr
            435                 440                 445

Val Val Tyr Ser Asn Ile Lys Val Gly Pro Ile Gly Ser Thr Phe Asn
450                 455                 460

Ser Gly Gly Ser Asn Pro Gly Gly Thr Thr Thr Thr Thr Thr
465                 470                 475                 480

Gln Pro Thr Thr Thr Thr Thr Ala Gly Asn Pro Gly Gly Thr Gly
                   485                 490                 495
```

-continued

Val Ala Gln His Tyr Gly Gln Cys Gly Gly Ile Gly Trp Thr Gly Pro
                500                 505                 510

Thr Thr Cys Ala Ser Pro Tyr Thr Cys Gln Lys Leu Asn Asp Tyr Tyr
            515                 520                 525

Ser Gln Cys Leu
    530

<210> SEQ ID NO 33
<211> LENGTH: 454
<212> TYPE: PRT
<213> ORGANISM: Aspergillus fumigatus

<400> SEQUENCE: 33

Met Lys His Leu Ala Ser Ser Ile Ala Leu Thr Leu Leu Pro Ala
1               5                   10                  15

Val Gln Ala Gln Gln Thr Val Trp Gly Gln Cys Gly Gly Gln Gly Trp
            20                  25                  30

Ser Gly Pro Thr Ser Cys Val Ala Gly Ala Ala Cys Ser Thr Leu Asn
        35                  40                  45

Pro Tyr Tyr Ala Gln Cys Ile Pro Gly Ala Thr Ala Thr Ser Thr Thr
    50                  55                  60

Leu Thr Thr Thr Thr Ala Ala Thr Thr Thr Ser Gln Thr Thr Thr Lys
65                  70                  75                  80

Pro Thr Thr Thr Gly Pro Thr Thr Ser Ala Pro Thr Val Thr Ala Ser
                85                  90                  95

Gly Asn Pro Phe Ser Gly Tyr Gln Leu Tyr Ala Asn Pro Tyr Tyr Ser
            100                 105                 110

Ser Glu Val His Thr Leu Ala Met Pro Ser Leu Pro Ser Ser Leu Gln
        115                 120                 125

Pro Lys Ala Ser Ala Val Ala Glu Val Pro Ser Phe Val Trp Leu Asp
    130                 135                 140

Val Ala Ala Lys Val Pro Thr Met Gly Thr Tyr Leu Ala Asp Ile Gln
145                 150                 155                 160

Ala Lys Asn Lys Ala Gly Ala Asn Pro Pro Ile Ala Gly Ile Phe Val
                165                 170                 175

Val Tyr Asp Leu Pro Asp Arg Asp Cys Ala Ala Leu Ala Ser Asn Gly
            180                 185                 190

Glu Tyr Ser Ile Ala Asn Asn Gly Val Ala Asn Tyr Lys Ala Tyr Ile
        195                 200                 205

Asp Ala Ile Arg Ala Gln Leu Val Lys Tyr Ser Asp Val His Thr Ile
    210                 215                 220

Leu Val Ile Glu Pro Asp Ser Leu Ala Asn Leu Val Thr Asn Leu Asn
225                 230                 235                 240

Val Ala Lys Cys Ala Asn Ala Gln Ser Ala Tyr Leu Glu Cys Val Asp
                245                 250                 255

Tyr Ala Leu Lys Gln Leu Asn Leu Pro Asn Val Ala Met Tyr Leu Asp
            260                 265                 270

Ala Gly His Ala Gly Trp Leu Gly Trp Pro Ala Asn Leu Gly Pro Ala
        275                 280                 285

Ala Thr Leu Phe Ala Lys Val Tyr Thr Asp Ala Gly Ser Pro Ala Ala
    290                 295                 300

Val Arg Gly Leu Ala Thr Asn Val Ala Asn Tyr Asn Ala Trp Ser Leu
305                 310                 315                 320

Ser Thr Cys Pro Ser Tyr Thr Gln Gly Asp Pro Asn Cys Asp Glu Lys

```
                     325                 330                 335
Lys Tyr Ile Asn Ala Met Ala Pro Leu Leu Lys Glu Ala Gly Phe Asp
                340                 345                 350

Ala His Phe Ile Met Asp Thr Ser Arg Asn Gly Val Gln Pro Thr Lys
                355                 360                 365

Gln Asn Ala Trp Gly Asp Trp Cys Asn Val Ile Gly Thr Gly Phe Gly
            370                 375                 380

Val Arg Pro Ser Thr Asn Thr Gly Asp Pro Leu Gln Asp Ala Phe Val
385                 390                 395                 400

Trp Ile Lys Pro Gly Gly Glu Ser Asp Gly Thr Ser Asn Ser Thr Ser
                405                 410                 415

Pro Arg Tyr Asp Ala His Cys Gly Tyr Ser Asp Ala Leu Gln Pro Ala
                420                 425                 430

Pro Glu Ala Gly Thr Trp Phe Gln Ala Tyr Phe Glu Gln Leu Leu Thr
                435                 440                 445

Asn Ala Asn Pro Ser Phe
                450

<210> SEQ ID NO 34
<211> LENGTH: 203
<212> TYPE: PRT
<213> ORGANISM: Dictyoglomus thermophilum
<220> FEATURE:
<221> NAME/KEY: mat_peptide
<222> LOCATION: (1)..(203)

<400> SEQUENCE: 34

Gln Thr Ser Ile Thr Leu Thr Ser Asn Ala Ser Gly Thr Phe Asp Gly
1               5                   10                  15

Tyr Tyr Tyr Glu Leu Trp Lys Asp Thr Gly Asn Thr Thr Met Thr Val
                20                  25                  30

Tyr Thr Gln Gly Arg Phe Ser Cys Gln Trp Ser Asn Ile Asn Asn Ala
            35                  40                  45

Leu Phe Arg Thr Gly Lys Lys Tyr Asn Gln Asn Trp Gln Ser Leu Gly
    50                  55                  60

Thr Ile Arg Ile Thr Tyr Ser Ala Thr Tyr Asn Pro Asn Gly Asn Ser
65                  70                  75                  80

Tyr Leu Cys Ile Tyr Gly Trp Ser Thr Asn Pro Leu Val Glu Phe Tyr
                85                  90                  95

Ile Val Glu Ser Trp Gly Asn Trp Arg Pro Pro Gly Ala Thr Ser Leu
            100                 105                 110

Gly Gln Val Thr Ile Asp Gly Gly Thr Tyr Asp Ile Tyr Arg Thr Thr
        115                 120                 125

Arg Val Asn Gln Pro Ser Ile Val Gly Thr Ala Thr Phe Asp Gln Tyr
130                 135                 140

Trp Ser Val Arg Thr Ser Lys Arg Thr Ser Gly Thr Val Thr Val Thr
145                 150                 155                 160

Asp His Phe Arg Ala Trp Ala Asn Arg Gly Leu Asn Leu Gly Thr Ile
                165                 170                 175

Asp Gln Ile Thr Leu Cys Val Glu Gly Tyr Gln Ser Ser Gly Ser Ala
            180                 185                 190

Asn Ile Thr Gln Asn Thr Phe Ser Gln Gly Ser
        195                 200

<210> SEQ ID NO 35
<211> LENGTH: 334
```

<212> TYPE: PRT
<213> ORGANISM: Penicillium aculeatum
<220> FEATURE:
<221> NAME/KEY: SIGNAL
<222> LOCATION: (1)..(18)
<220> FEATURE:
<221> NAME/KEY: mat_peptide
<222> LOCATION: (19)..(334)

<400> SEQUENCE: 35

```
Met Lys Phe Ser Asn Leu Val Ala Leu Ala Ala Ala Ser Ser Ala
        -15                 -10                  -5

Met Ala Leu Pro Leu Thr Lys Lys His Ala Lys Arg Ala Ser Ser Phe
 -1   1              5                  10

Glu Trp Phe Gly Ser Asn Glu Ser Gly Ala Glu Phe Gly Ser Gly Asn
 15                  20                  25                  30

Ile Pro Gly Val Tyr Gly Thr Asp Tyr Ile Phe Pro Ser Thr Ser Ala
                 35                  40                  45

Ile Gln Thr Leu Ile Asn Asn Gly Met Asn Ile Phe Arg Val Thr Phe
             50                  55                  60

Met Met Glu Arg Leu Val Pro Asn Thr Met Thr Gly Ser Phe Asp Ala
         65                  70                  75

Glu Tyr Leu Ser Asn Leu Thr Ser Val Val Asn Tyr Ile Thr Glu Ala
 80                  85                  90

Gly Ala His Ala Val Ile Asp Pro His Asn Tyr Gly Arg Tyr Tyr Gly
 95                 100                 105                 110

Ser Ile Ile Ser Ser Thr Ser Asp Phe Gln Thr Phe Trp Lys Asn Val
                115                 120                 125

Ala Gly Gln Phe Lys Ser Asn Ser Leu Val Ile Phe Asp Thr Asn Asn
            130                 135                 140

Glu Tyr His Asp Met Asp Gln Thr Leu Val Leu Asn Leu Asn Gln Ala
            145                 150                 155

Ala Ile Asn Gly Ile Arg Ala Ala Gly Ala Thr Ser Gln Tyr Ile Phe
            160                 165                 170

Val Glu Gly Asn Ser Tyr Thr Gly Ala Trp Thr Trp Ala Asp Val Asn
175                 180                 185                 190

Asp Asn Leu Lys Asn Leu Thr Asp Pro Gln Asn Lys Ile Val Tyr Glu
                195                 200                 205

Met His Gln Tyr Leu Asp Ser Asp Gly Ser Gly Thr Ser Ala Thr Cys
            210                 215                 220

Val Ser Thr Thr Ile Gly Lys Glu Arg Val Thr Ser Ala Thr Gln Trp
            225                 230                 235

Leu Gln Lys Asn Gly Lys Val Gly Ile Leu Gly Glu Phe Ala Gly Gly
            240                 245                 250

Val Asn Asp Gln Cys Lys Thr Ala Ile Thr Gly Met Leu Ser Tyr Leu
255                 260                 265                 270

Glu Asp Asn Ser Asp Val Trp Arg Gly Ala Met Trp Trp Ala Ala Gly
                275                 280                 285

Pro Trp Trp Gly Asp Tyr Ile Phe Ser Leu Glu Pro Pro Ser Gly Thr
            290                 295                 300

Ala Tyr Thr Gly Met Trp Ser Thr Leu Lys Ser Tyr Leu Ala
            305                 310                 315
```

<210> SEQ ID NO 36
<211> LENGTH: 394
<212> TYPE: PRT
<213> ORGANISM: Trichophaea saccata

```
<220> FEATURE:
<221> NAME/KEY: SIGNAL
<222> LOCATION: (1)..(20)
<220> FEATURE:
<221> NAME/KEY: mat_peptide
<222> LOCATION: (21)..(394)

<400> SEQUENCE: 36
```

Met His Ser Phe Phe Ser Leu Ala Leu Ala Val Ala Gly Leu Pro Ala
-20             -15                 -10                 -5

Leu Ile Asn Ala Gln Gln Ser Ala Trp Gly Gln Cys Gly Gly Val Gly
            -1  1               5                   10

Trp Thr Gly Ala Thr Thr Cys Val Ser Gly Tyr Tyr Cys Ser Lys Leu
            15              20                  25

Asn Asp Tyr Tyr Ser Gln Cys Ile Pro Gly Thr Ala Ser Thr Thr Thr
        30              35                  40

Ser Ala Val Ser Thr Thr Thr Ala Thr Ser Pro Thr Gly Ser Val
45              50              55                  60

Cys Ser Gly Asn Arg Thr Lys Phe Lys Tyr Phe Gly Val Asn Glu Ser
                65              70                  75

Gly Ala Glu Phe Gly Asn Asn Val Val Pro Gly Thr Leu Gly Lys Asp
            80                  85                  90

Tyr Thr Trp Pro Thr Thr Asp Ser Val Asp Phe Phe Leu Gly Lys Gly
            95                  100                 105

Met Asn Thr Phe Arg Ile Ala Phe Leu Met Glu Arg Leu Ser Pro Pro
        110                 115                 120

Ala Gly Gly Leu Thr Gly Thr Phe Asp Pro Thr Tyr Leu Ala Ser Leu
125             130                 135                 140

Lys Asn Ile Ala Ser Tyr Ile Thr Gly Lys Gly Gly Tyr Ala Ile Ile
                145                 150                 155

Asp Pro His Asn Tyr Gly Arg Tyr Asn Gly Asn Ile Ile Thr Asp Tyr
                160                 165                 170

Thr Ser Phe Gly Thr Trp Cys Lys Asn Leu Ala Ser Gln Phe Lys Ser
        175                 180                 185

Asp Ser His Ile Ile Phe Asp Thr Asn Asn Glu Tyr His Asp Met Asp
        190                 195                 200

Glu Thr Leu Val Phe Asn Leu Asn Gln Ala Cys Ile Asn Gly Ile Arg
205                 210                 215                 220

Ala Ala Gly Ala Thr Ser Gln Leu Ile Leu Ile Glu Gly Asn Ser Trp
                225                 230                 235

Thr Gly Ala Trp Thr Trp Ile Ser Ser Gly Asn Ala Ala Ser Leu Ile
            240                 245                 250

Asn Leu Thr Asp Pro Asn Asn Asn Ile Ala Tyr Glu Met His Gln Tyr
            255                 260                 265

Leu Asp Ser Asp Gly Ser Gly Thr Ser Pro Thr Cys Val Ser Ser Thr
270                 275                 280

Ile Gly Ala Glu Arg Leu Ala Ala Ala Thr Ala Trp Leu Gln Ala Asn
285                 290                 295                 300

Asn Lys Lys Gly Phe Leu Gly Glu Ile Gly Ala Gly Ser Asn Asp Asp
                305                 310                 315

Cys Ile Ala Ala Val Lys Gly Ala Leu Cys Ser Met Gln Glu Ala Gly
                320                 325                 330

Gly Val Trp Leu Gly Ala Leu Trp Trp Ala Ala Gly Pro Trp Trp Gly
            335                 340                 345

Asp Tyr Tyr Gln Ser Ile Glu Pro Pro Asp Gly Ala Ala Ile Ala Arg

```
                350                 355                 360

Ile Leu Pro Glu Ala Leu Leu Pro Phe Leu
365                 370

<210> SEQ ID NO 37
<211> LENGTH: 278
<212> TYPE: PRT
<213> ORGANISM: Thielavia terrestris
<220> FEATURE:
<221> NAME/KEY: mat_peptide
<222> LOCATION: (1)..(278)

<400> SEQUENCE: 37

Ala Ser Gly Ser Gly Gln Ser Thr Arg Tyr Trp Asp Cys Cys Lys Pro
1               5                   10                  15

Ser Cys Ala Trp Pro Gly Lys Ala Ala Val Ser Gln Pro Val Tyr Ala
            20                  25                  30

Cys Asp Ala Asn Phe Gln Arg Leu Ser Asp Phe Asn Val Gln Ser Gly
        35                  40                  45

Cys Asn Gly Gly Ser Ala Tyr Ser Cys Ala Asp Gln Thr Pro Trp Ala
    50                  55                  60

Val Asn Asp Asn Leu Ala Tyr Gly Phe Ala Ala Thr Ser Ile Ala Gly
65                  70                  75                  80

Gly Ser Glu Ser Ser Trp Cys Cys Ala Cys Tyr Ala Leu Thr Phe Thr
                85                  90                  95

Ser Gly Pro Val Ala Gly Lys Thr Met Val Val Gln Ser Thr Ser Thr
            100                 105                 110

Gly Gly Asp Leu Gly Ser Asn His Phe Asp Ile Ala Met Pro Gly Gly
        115                 120                 125

Gly Val Gly Ile Phe Asn Gly Cys Ser Ser Gln Phe Gly Gly Leu Pro
    130                 135                 140

Gly Ala Gln Tyr Gly Gly Ile Ser Ser Arg Asp Gln Cys Asp Ser Phe
145                 150                 155                 160

Pro Ala Pro Leu Lys Pro Gly Cys Gln Trp Arg Phe Asp Trp Phe Gln
                165                 170                 175

Asn Ala Asp Asn Pro Thr Phe Thr Phe Gln Gln Val Gln Cys Pro Ala
            180                 185                 190

Glu Ile Val Ala Arg Ser Gly Cys Lys Arg Asn Asp Asp Ser Ser Phe
        195                 200                 205

Pro Val Phe Thr Pro Pro Ser Gly Asn Gly Gly Thr Gly Thr Pro
    210                 215                 220

Thr Ser Thr Ala Pro Gly Ser Gly Gln Thr Ser Pro Gly Gly Gly Ser
225                 230                 235                 240

Gly Cys Thr Ser Gln Lys Trp Ala Gln Cys Gly Gly Ile Gly Phe Ser
                245                 250                 255

Gly Cys Thr Thr Cys Val Ser Gly Thr Thr Cys Gln Lys Leu Asn Asp
            260                 265                 270

Tyr Tyr Ser Gln Cys Leu
        275

<210> SEQ ID NO 38
<211> LENGTH: 294
<212> TYPE: PRT
<213> ORGANISM: Sordaria fimicola
<220> FEATURE:
<221> NAME/KEY: SIGNAL
<222> LOCATION: (1)..(21)
<220> FEATURE:
```

```
<221> NAME/KEY: mat_peptide
<222> LOCATION: (22)..(294)

<400> SEQUENCE: 38

Met Arg Ser Ser Thr Ile Leu Gln Thr Gly Leu Val Ala Val Leu Pro
    -20              -15              -10

Phe Ala Val Gln Ala Ala Ser Gly Ser Gly Lys Ser Thr Arg Tyr Trp
 -5          -1   1               5                       10

Asp Cys Cys Lys Pro Ser Cys Ala Trp Ser Gly Lys Ala Ser Val Asn
            15              20              25

Arg Pro Val Leu Ala Cys Asp Ala Asn Asn Asn Pro Leu Asn Asp Ala
            30              35              40

Asn Val Lys Ser Gly Cys Asp Gly Gly Ser Ala Tyr Thr Cys Ala Asn
 45              50                  55

Asn Ser Pro Trp Ala Val Asn Asp Asn Leu Ala Tyr Gly Phe Ala Ala
 60               65              70              75

Thr Lys Leu Ser Gly Gly Thr Glu Ser Ser Trp Cys Cys Ala Cys Tyr
                80              85              90

Ala Leu Thr Phe Thr Ser Gly Pro Val Ser Gly Lys Thr Leu Val Val
             95              100             105

Gln Ser Thr Ser Thr Gly Gly Asp Leu Gly Ser Asn His Phe Asp Leu
            110             115             120

Asn Met Pro Gly Gly Gly Val Gly Leu Phe Asp Gly Cys Lys Arg Glu
    125             130             135

Phe Gly Gly Leu Pro Gly Ala Gln Tyr Gly Gly Ile Ser Ser Arg Ser
140             145             150             155

Glu Cys Asp Ser Phe Pro Ala Ala Leu Lys Pro Gly Cys Gln Trp Arg
                160             165             170

Phe Asp Trp Phe Lys Asn Ala Asp Asn Pro Glu Phe Thr Phe Lys Gln
            175             180             185

Val Gln Cys Pro Ser Glu Leu Thr Ser Arg Thr Gly Cys Lys Arg Asn
        190             195             200

Asp Asp Ser Gln Phe Pro Ala Phe Thr Pro Pro Ser Gly Gly Gly Ser
    205             210             215

Asn Pro Ser Thr Pro Thr Thr Pro Pro Ser Ser Gly Gly Gly Gly Ser
220             225             230             235

Gly Cys Ala Ala Ala Met Tyr Ala Gln Cys Gly Gly Ser Gly Phe Ser
            240             245             250

Gly Cys Thr Asn Cys Pro Ser Gly Ser Thr Cys Lys Ala Ile Asn Asp
            255             260             265

Tyr Tyr His Gln Cys Ala
            270
```

US 10,689,630 B2

PROCESSES FOR PRODUCING FERMENTATION PRODUCTS

CROSS-REFERENCE TO RELATED APPLICATIONS

This application is a 35 U.S.C. 371 national application of international application no. PCT/US2016/067177 filed Dec. 16, 2016, which claims priority or the benefit under 35 U.S.C. 119 of U.S. application nos. 62/271,182, 62/271,063, 62/324,107 and 62/430,695, filed Dec. 22, 2015, Dec. 22, 2015, Apr. 18, 2016 and Dec. 6, 2016, respectively, the contents of which are fully incorporated herein by reference.

FIELD OF THE INVENTION

The present invention relates to processes for producing fermentation products, especially ethanol, from starch-containing material. The invention also relates to compositions suitable for use in a process of the invention and the use of compositions of the invention.

REFERENCE TO A SEQUENCE LISTING

This application contains a Sequence Listing in computer readable form. The computer readable form is incorporated herein by reference.

BACKGROUND OF THE INVENTION

Production of fermentation products, such as ethanol, from starch-containing material is well-known in the art. Industrially two different kinds of processes are used today. The most commonly used process, often referred to as a "conventional process", includes liquefying gelatinized starch at high temperature using typically a bacterial alpha-amylase, followed by simultaneous saccharification and fermentation carried out in the presence of a glucoamylase and a fermentation organism. Another well-known process, often referred to as a "raw starch hydrolysis"-process (RSH process), includes simultaneously saccharifying and fermenting granular starch below the initial gelatinization temperature typically in the presence of at least a glucoamylase.

Despite significant improvement of fermentation product production processes over the past decade a significant amount of residual starch material is not converted into the desired fermentation product, such as ethanol.

Therefore, there is still a desire and need for providing processes for producing fermentation products, such as ethanol, from starch-containing material that can provide a higher fermentation product yield, or other advantages, compared to conventional processes.

SUMMARY OF THE INVENTION

The present invention relates to processes of producing fermentation products, such as especially ethanol, from starch-containing material using a fermenting organism. The invention also relates to compositions for use in processes of the invention.

In the first aspect the invention relates to processes for producing fermentation products, such as preferably ethanol, from starch-containing material comprising the steps of:
i) liquefying the starch-containing material at a temperature above the initial gelatinization temperature, preferably between 80-90° C., using:
   an alpha-amylase, such as a bacterial alpha-amylase;
   a hemicellulase, preferably a xylanase, having a Melting Point (DSC) above 80° C.;
   optionally an endoglucanase having Melting Point (DSC) above 70° C.;
ii) saccharifying using a carbohydrate-source generating enzyme;
iii) fermenting using a fermenting organism.

In a preferred embodiment the hemicellulase is a xylanase, in particular a GH10 xylanase or a GH11 xylanase.

The hemicellulase, in particular a xylanase, especially GH10 or GH11 xylanase, preferably has a Melting Point (DSC) above 82° C., such as above 84° C., such as above 86° C., such as above 88° C., such as above 88° C., such as above 90° C., such as above 92° C., such as above 94° C., such as above 96° C., such as above 98° C., such as above 100° C., such as between 80° C. and 110° C., such as between 82° C. and 110° C., such as between 84° C. and 110° C.

Examples of suitable hemicellulases, in particular xylanases, include the xylanase shown in SEQ ID NOs: 3 herein or SEQ ID NO: 34 herein derived from a strain of *Dictyoglomus thermophilum*; the xylanase shown in SEQ ID NO: 4 herein derived from a strain of *Rasomsonia byssochlamydoides*; the xylanase shown in SEQ ID NO: 5 herein derived from a strain of *Talaromyces leycettanus*; the xylanase shown in SEQ ID NO: 8 herein derived from a strain of *Aspergillus fumigatus* or a polypeptide having hemicellulase activity, preferably xylanase activity, having at least 60%, such as at least 70%, such as at least 75% identity, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, such as 100% identity to the mature part of the polypeptides of SEQ ID NOs: 3, 4, 5, 8 and 34 herein.

In another aspect the invention relates to compositions comprising:
   an alpha-amylase;
   a hemicellulase, in particular a xylanase, having a Melting Point (DSC) above 80° C., preferably above 85° C., especially above 90° C., in particular above 95° C.;
   optionally an endoglucanase;
   optionally a protease;
   optionally a carbohydrate-source generating enzyme.

Other enzymes such as pullulanases and phytases may also be comprised in the composition of the invention.

In a preferred embodiment the composition of the invention comprises
   an alpha-amylase, preferably a bacterial alpha-amylase;
   a hemicellulase having a Melting Point (DSC) above 80° C., preferably above 85° C., especially above 90° C., in particular above 95° C.;
   an endoglucanase having Melting Point (DSC) above 70° C., preferably above 75° C., especially above 80° C., in particular above 85° C.

BRIEF DESCRIPTION OF THE FIGURES

FIG. 1 shows the ethanol yield with Tl EG (SEQ ID NO: 9) and Tl xylanase (SEQ ID NO: 5) or Dt xylanase (SEQ ID NO: 34) addition in liquefaction, and SSF with Glucoamylase SA (GSA).

DETAILED DESCRIPTION OF THE INVENTION

The present invention relates to processes of producing fermentation products, such as ethanol, from starch-containing material using a fermenting organism. The invention also relates to compositions for use in processes of the invention.

The inventors have found that increased ethanol yield is obtained when liquefying starch-containing material using an alpha-amylase in the presence of a thermostable hemicellulase (see Example 19). It was also found that when additionally adding a thermostable endoglucase the ethanol yield increased even more.

In the first aspect the invention relates to processes for producing fermentation products, such as preferably ethanol, from starch-containing material comprising the steps of:
i) liquefying the starch-containing material at a temperature above the initial gelatinization temperature, such as between 80-90° C., using:
an alpha-amylase, such as a bacterial alpha-amylase;
a hemicellulase having a Melting Point (DSC) above 80° C.;
ii) saccharifying using a carbohydrate-source generating enzyme;
iii) fermenting using a fermenting organism.

Steps ii) and iii) may be carried out either sequentially or simultaneously. In a preferred embodiment steps ii) and iii) are carried out simultaneously. The alpha-amylase, the hemicellulase, preferably xylanase, having a Melting Point (DSC) above 80° C.; and optionally a thermostable endoglucanase having a Melting Point (DSC) above 70° C., may be added before and/or during liquefaction step i). Optionally a protease, a carbohydrate-source generating enzyme, preferably a glucoamylase, a pullulanase, and/or a phytase may be present and/or added as well. In a preferred embodiment a composition of the invention defined below may suitably be used in liquefaction in a process of the invention. The enzymes may be added individually or as one or more blend compositions comprising an alpha-amylase, hemicellulase, preferably xylanase, having a Melting Point (DSC) above 80° C., and optional endoglucanase and optionally a protease, a carbohydrate-source generating enzyme, a pullulanase and/or a phytase.

Examples of alpha-amylases can be found in the "Alpha-Amylase Present and/or Added During Liquefaction"-section below.

In an embodiment the alpha-amylase is a variant of the alpha-amylase shown in SEQ ID NO: 1 herein, such as one derived from a strain *Bacillus stearomthermphilus*, with mutations selected from the group of:
I181*+G182*;
I181*+G182*+N193F;
preferably
I181*+G182*+E129V+K177L+R179E;
I181*+G182*+N193F+E129V+K177L+R179E;
I181*+G182*+N193F+V59A+Q89R+E129V+K177L+R179E+H208Y+K220P+N224L+Q254S;
I181*+G182*+N193F+V59A+Q89R+E129V+K177L+R179E+Q254S+M284V; and
I181*+G182*+N193F+E129V+K177L+R179E+K220P+N224L+S242Q+Q254S (using SEQ ID NO: 1 herein for numbering).

*Bacillus stearothermophilus* alpha-amylases are typically naturally truncated when produced to be around 491 amino acids long (compared to SEQ ID NO: 3 in WO 99/19467 or SEQ ID NO: 1 herein), such as from about 480-495 amino acids long.

In an embodiment the bacterial alpha-amylase, e.g., *Bacillus* alpha-amylase, such as especially *Bacillus stearothermophilus* alpha-amylase, is dosed in liquefaction in a concentration between 0.01-10 KNU-A/g DS, e.g., between 0.02 and 5 KNU-A/g DS, such as 0.03 and 3 KNU-A, preferably 0.04 and 2 KNU-A/g DS, such as especially 0.01 and 2 KNU-A/g DS.

In an embodiment the bacterial alpha-amylase, e.g., *Bacillus* alpha-amylase, such as especially *Bacillus stearothermophilus* alpha-amylase, is dosed in liquefaction in a concentration of between 0.0001-1 mg EP (Enzyme Protein)/g DS, e.g., 0.0005-0.5 mg EP/g DS, such as 0.001-0.1 mg EP/g DS.

Examples of suitable hemicellulases, such as xylanases, having a Melting Point (DSC) above 80° C. can be found in the "Thermostable Hemicellulases Present and/or Added During Liquefaction"-section below.

Specific examples of suitable hemicellulases, in particular xylanases, include the xylanases shown in SEQ ID NOs: 3 herein and SEQ ID NO: 34 herein, e.g., derived from a strain of *Dictyogilomus thermophilum*; the xylanase shown in SEQ ID NO: 4 herein, e.g., derived from a strain of *Rasomsonia byssochiamydoides*; the xylanase shown in SEQ ID NO: 5 herein, e.g., derived from a strain of *Talaromyces leycettanus*; the xylanase shown in SEQ ID NO: 8 herein, e.g., derived from a strain of *Aspergillus fumigatus* or polypeptides having hemicellulase, preferably xylanase activity, having at least 60%, such as at least 70%, such as at least 75% identity, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, such as 100% identity to the mature part of any of the polypeptides of SEQ ID NOs: 3, 4, 5, 8 and 34 herein, respectively.

Examples of suitable optional endoglucanases having a Melting Point (DSC) above 70° C. can be found in the "Thermostable Endoglucanase Present and/or Added During Liquefaction"-section below.

In a preferred embodiment the endoglucanase is the one shown in SEQ ID NO: 9 herein, such as one derived from a strain of *Talaromyces leycettanus* (WO2013/019780), or an endoglucanase having at least 80% identity to SEQ ID NO: 9 herein.

In a preferred embodiment the endoglucanase is the one shown in SEQ ID NO: 9 herein, such as one derived from a strain of *Talaromyces leycettanus* (WO2013/019780—hereby incorporated by reference), or an endoglucanase having at least 90% identity to SEQ ID NO: 9 herein having a Melting Point (DSC) above 70° C.

Examples of optional proteases can be found in the "Protease Present and/or Added During Liquefaction"-section below.

Examples of suitable optional carbohydrate-source generating enzymes, preferably thermostable carbohydrate-source generating enzymes, in particularglucoamylases, can be found in the "Carbohydrate-Source Generating Enzymes Present and/or Added During Liquefaction"-section below.

A suitable optional pullulanase can be found in the "Pullulanase Present and/or Added During Liquefaction"-section below. In a preferred embodiment the pullulanase is derived from *Bacillus* sp.

Examples of optional phytases can be found in the "Phytase Present and/or Added During Liquefaction"-section below. In a preferred embodiment the phytase is derived from a strain of *Buttiauxella*.

A suitable cellulase or cellulolytic enzyme composition present and/or added during saccharification and/or fermentation or simultaneous saccharification and fermentation (SSF) can be found in the "Cellulase or Cellulolytic Enzyme Composition Present and/or Added During Saccharification and/or Fermentation or SSF"-section below. In an embodiment the cellulase or cellulolytic enzyme composition is derived from *Trichoderma reesei*.

In a preferred embodiment the cellulase or cellulolytic enzyme composition is a *Trichoderma reesei* cellulolytic enzyme composition, further comprising *Thermoascus aurantiacus* GH61A polypeptide having cellulolytic enhancing activity (SEQ ID NO: 2 in WO 2005/074656 or SEQ ID NO: 30 herein) and *Aspergillus fumigatus* beta-glucosidase (SEQ ID NO: 2 of WO 2005/047499 or SEQ ID NO: 29 herein).

In an embodiment the cellulase or cellulolytic enzyme composition is a *Trichoderma reesei* cellulolytic enzyme composition further comprising *Penicillium emersonii* GH61A polypeptide disclosed as SEQ ID NO: 2 in WO 2011/041397 or SEQ ID NO: 31 herein, and *Aspergillus fumigatus* beta-glucosidase disclosed as SEQ ID NO: 2 in WO 2005/047499 or SEQ ID NO: 29 herein, or a variant thereof, which variant has one of, preferably all of, the following substitutions: F100D, S283G, N456E, F512Y (using SEQ ID NO: 29 herein for numbering).

According to the process of the invention the pH during liquefaction may be between 4.0-6.5, such as 4.5-6.2, such as above 4.8-6.0, such as between 5.0-5.8.

According to the invention the temperature is above the initial gelatinization temperature. The term "initial gelatinization temperature" refers to the lowest temperature at which solubilization of starch, typically by heating, begins. The temperature can vary for different starches. The initial gelanitization temperature may be from 50-70° C.

In an embodiment the temperature during liquefaction step i) is in the range from 70-100° C., such as between 70-95° C., such as between 75-90° C., preferably between 80-90° C., such as around 85° C.

In an embodiment, the process of the invention further comprises, prior to the step i), the steps of:

a) reducing the particle size of the starch-containing material, preferably by dry milling;

b) forming a slurry comprising the starch-containing material and water.

The starch-containing starting material, such as whole grains, may be reduced in particle size, e.g., by milling, in order to open up the structure, to increase the surface area and allowing for further processing. Generally, there are two types of processes: wet and dry milling. In dry milling whole kernels are milled and used. Wet milling gives a good separation of germ and meal (starch granules and protein). Wet milling is often applied at locations where the starch hydrolysate is used in production of, e.g., syrups. Both dry and wet millings are well known in the art of starch processing. According to the present invention dry milling is preferred. The particle size may be reduced even further, for example, by Turkish grinding. In an embodiment the particle size is reduced to between 0.05 to 3.0 mm, preferably 0.1-0.5 mm, or so that at least 30%, preferably at least 50%, more preferably at least 70%, even more preferably at least 90% of the starch-containing material fit through a sieve with a 0.05 to 3.0 mm screen, preferably 0.1-0.5 mm screen. In another embodiment at least 50%, preferably at least 70%, more preferably at least 80%, especially at least 90% of the starch-containing material fit through a sieve with #6 screen. In an embodiment, at least 75% of the starch-containing material fit through a sieve with less than a 0.5 mm screen, more preferably at least 79% or 80% of the starch-containing material fit through a sieve with less than a 0.425 mm screen. In an embodiment, at least 50% of the starch-containing material fit through a sieve with a 0.25 to 0.425 mm screen, more preferably at least 59% or 60% of the starch-containing material fit through a sieve with a 0.25 to 0.425 mm screen.

The aqueous slurry may contain from 10-55 w/w-% dry solids (DS), preferably 25-45 w/w-% dry solids (DS), more preferably 30-40 w/w-% dry solids (DS) of starch-containing material.

The slurry may be heated to above the initial gelatinization temperature, preferably to between 70-95° C., such as between 80-90° C., between pH 5.0-7.0, preferably between 5.0 and 6.0, for 30 minutes to 5 hours, such as around 2 hours.

In an embodiment liquefaction step i) is carried out for 0.5-5 hours at a temperature from 70-95° C. at a pH from 4-6.

In a preferred embodiment liquefaction step i) is carried out for 0.5-3 hours at a temperature from 80-90° C. at a pH from 4-6.

The alpha-amylase and hemicellulase and optional thermostable endoglucanase, optional protease, optional carbohydrate-source generating enzyme, in particular glucoamylase, optional pullulanase, and/or optional phytase, may initially be added to the aqueous slurry to initiate liquefaction (thinning). In an embodiment only a portion of the enzymes is added to the aqueous slurry, while the rest of the enzymes are added during liquefaction step i).

The aqueous slurry may in an embodiment be jet-cooked to further gelatinize the slurry before being subjected to liquefaction in step i). The jet-cooking may be carried out at a temperature between 95-160° C., such as between 110-145° C., preferably 120-140° C., such as 125-135° C., preferably around 130° C. for about 1-15 minutes, preferably for about 3-10 minutes, especially around about 5 minutes.

Saccharification and Fermentation

According to the process of the invention one or more carbohydrate-source generating enzymes, in particular glucoamylase, may be present and/or added during saccharification step ii) and/or fermentation step iii). The carbohydrate-source generating enzyme may preferably be a glucoamylase, but may also be an enzyme selected from the group consisting of: beta-amylase, maltogenic amylase and alpha-glucosidase. The carbohydrate-source generating enzyme added during saccharification step ii) and/or fermentation step iii) is typically different from the optional carbohydrate-source generating enzyme, in particular glucoamylase, optionally added during liquefaction step i). In an embodiment the carbohydrate-source generating enzymes, in particular glucoamylase, is added together with a fungal alpha-amylase.

Examples of carbohydrate-source generating enzymes, including glucoamylases, can be found in the "Carbohydrate-Source Generating Enzyme Present and/or Added During Saccharification and/or Fermentation"-section below.

When doing sequential saccharification and fermentation, saccharification step ii) may be carried out at conditions well-known in the art. For instance, the saccharification step ii) may last up to from about 24 to about 72 hours.

In an embodiment a pre-saccharification step is done. In an embodiment a carbohydrate-source generating enzyme is added during pre-saccharification carried out before saccharification step ii) and/or fermentation step iii). The carbohydrate-source generating enzyme may also be added during pre-saccharification carried out before simultaneous saccharification and fermentation (SSF).

In an embodiment a carbohydrate-source generating enzyme, preferably glucoamylase, and/or the cellulase or cellulolytic enzyme composition, are added during pre-saccharification carried out before saccharification step ii) and/or fermentation step iii). The carbohydrate-source generating enzyme, preferably glucoamylase, and the cellulase or cellulolytic enzyme composition may also be added during pre-saccharification carried out before simultaneous saccharification and fermentation (SSF). Pre-saccharification is typically done for 40-90 minutes at a temperature between 30-65° C., typically around 60° C. Pre-saccharification may be followed by saccharification during fermentation in simultaneous saccharification and fermentation ("SSF). Saccharification is typically carried out at temperatures from 20-75° C., preferably from 40-70° C., typically around 60° C., and at a pH between 4 and 5, such as around pH 4.5.

Simultaneous saccharification and fermentation ("SSE") is widely used in industrial scale fermentation product production processes, especially ethanol production processes. When doing SSF the saccharification step ii) and the fermentation step iii) are carried out simultaneously. There may be no holding stage for the saccharification, meaning that a fermenting organism, such as yeast, and enzyme(s), in a preferred embodiment according to the invention a glucoamylase and a cellulase or cellulolytic enzyme composition, may be added together. However, it is also contemplated to add the fermenting organism and enzyme(s) separately. Fermentation or SSF may, according to the invention, typically be carried out at a temperature from 25° C. to 40° C., such as from 28° C. to 35° C., such as from 30° C. to 34° C., preferably around about 32° C. In an embodiment fermentation is ongoing for 6 to 120 hours, in particular 24 to 96 hours. In an embodiment the pH is between 3.5-5, in particular between 3.8 and 4.3.

Fermentation Medium

"Fermentation media" or "fermentation medium" refers to the environment in which fermentation is carried out. The fermentation medium includes the fermentation substrate, that is, the carbohydrate source that is metabolized by the fermenting organism. According to the invention the fermentation medium may comprise nutrients and growth stimulator(s) for the fermenting organism(s). Nutrient and growth stimulators are widely used in the art of fermentation and include nitrogen sources, such as ammonia; urea, vitamins and minerals, or combinations thereof.

Fermenting Organisms

The term "fermenting organism" refers to any organism, including bacterial and fungal organisms, especially yeast, suitable for use in a fermentation process and capable of producing the desired fermentation product. Especially suitable fermenting organisms are able to ferment, i.e., convert, sugars, such as glucose or maltose, directly or indirectly into the desired fermentation product, such as ethanol. Examples of fermenting organisms include fungal organisms, such as yeast. Preferred yeast includes strains of *Saccharomyces* spp., in particular, *Saccharomyces cerevisiae*.

Suitable concentrations of the viable fermenting organism during fermentation, such as SSF, are well known in the art or can easily be determined by the skilled person in the art. In one embodiment the fermenting organism, such as ethanol fermenting yeast, (e.g., *Saccharomyces cerevisiae*) is added to the fermentation medium so that the viable fermenting organism, such as yeast, count per mL of fermentation medium is in the range from $10^5$ to $10^{12}$, preferably from $10^7$ to $10^{10}$, especially about $5 \times 10^7$.

Examples of commercially available yeast includes, e.g., RED STAR™ and ETHANOL RED™ yeast (available from Fermentis/Lesaffre, USA), FALI (available from Fleischmann's Yeast, USA), SUPERSTART and THERMOSACC™ fresh yeast (available from Ethanol Technology, WI, USA), BIOFERM AFT and XR (available from NABC—North American Bioproducts Corporation, GA, USA), GERT STRAND (available from Gert Strand AB, Sweden), and FERMIOL (available from DSM Specialties).

Starch-Containing Materials

Any suitable starch-containing material may be used according to the present invention. The starting material is generally selected based on the desired fermentation product. Examples of starch-containing materials, suitable for use in a process of the invention, include whole grains, corn, wheat, barley, rye, milo, sago, cassava, tapioca, sorghum, rice, peas, beans, or sweet potatoes, or mixtures thereof or starches derived therefrom, or cereals. Contemplated are also waxy and non-waxy types of corn and barley.

In a preferred embodiment the starch-containing material, used for ethanol production according to the invention, is corn or wheat.

Fermentation Products

The term "fermentation product" means a product produced by a process including a fermentation step using a fermenting organism. Fermentation products contemplated according to the invention include alcohols (e.g., ethanol, methanol, butanol; polyols such as glycerol, sorbitol and inositol); organic acids (e.g., citric acid, acetic acid, itaconic acid, lactic acid, succinic acid, gluconic acid); ketones (e.g., acetone); amino acids (e.g., glutamic acid); gases (e.g., $H_2$ and $CO_2$); antibiotics (e.g., penicillin and tetracycline); enzymes; vitamins (e.g., riboflavin, $B_{12}$, beta-carotene); and hormones. In a preferred embodiment the fermentation product is ethanol, e.g., fuel ethanol; drinking ethanol, i.e., potable neutral spirits; or industrial ethanol or products used in the consumable alcohol industry (e.g., beer and wine), dairy industry (e.g., fermented dairy products), leather industry and tobacco industry. Preferred beer types comprise ales, stouts, porters, lagers, bitters, malt liquors, happoushu, high-alcohol beer, low-alcohol beer, low-calorie beer or light beer. Preferably processes of the invention are used for producing an alcohol, such as ethanol. The fermentation product, such as ethanol, obtained according to the invention, may be used as fuel, which is typically blended with gasoline. However, in the case of ethanol it may also be used as potable ethanol.

Recovery

Subsequent to fermentation, or SSF, the fermentation product may be separated from the fermentation medium. The slurry may be distilled to extract the desired fermentation product (e.g., ethanol). Alternatively the desired fermentation product may be extracted from the fermentation medium by micro or membrane filtration techniques. The fermentation product may also be recovered by stripping or other method well known in the art.

Alpha-Amylase Present and/or Added During Liquefaction

According to the invention an alpha-amylase is present and/or added in liquefaction together with a hemicellulase, preferably xylanase, having a Melting Point (DSC) above 80° C., such as between 80° C. and 95° C., and an optional endoglucanase, an optional protease, an optional carbohydrate-source generating enzyme, in particular a glucoamylase, an optional pullulanase, and/or an optional phytase.

The alpha-amylase added during liquefaction step i) may be any alpha-amylase. Preferred are bacterial alpha-amylases, such as especially *Bacillus* alpha-amylases, such as *Bacillus stearothermophilus* alpha-amylases, which are stable at temperature used during liquefaction.

Bacterial Alpha-Amylase

The term "bacterial alpha-amylase" means any bacterial alpha-amylase classified under EC 3.2.1.1. A bacterial alpha-amylase used according to the invention may, e.g., be derived from a strain of the genus *Bacillus*, which is sometimes also referred to as the genus *Geobacillus*. In an embodiment the *Bacillus* alpha-amylase is derived from a strain of *Bacillus amyloliquefaciens, Bacillus licheniformis, Bacillus stearothermophilus, Bacillus* sp. TS-23, or *Bacillus subtilis*, but may also be derived from other *Bacillus* sp.

Specific examples of bacterial alpha-amylases include the *Bacillus stearothermophilus* alpha-amylase of SEQ ID NO: 3 in WO 99/19467 or SEQ ID NO: 1 herein, the *Bacillus amyloliquefaciens* alpha-amylase of SEQ ID NO: 5 in WO 99/19467, and the *Bacillus licheniformis* alpha-amylase of SEQ ID NO: 4 in WO 99/19467 and the *Bacillus* sp. TS-23 alpha-amylase disclosed as SEQ ID NO: 1 in WO 2009/061380 (all sequences are hereby incorporated by reference).

In an embodiment the bacterial alpha-amylase may be an enzyme having a degree of identity of at least 60%, e.g., at least 70%, at least 80%, at least 90%, at least 95%, at least 96%, at least 97%, at least 98% or at least 99% to any of the sequences shown in SEQ ID NOS: 3, 4 or 5, respectively, in WO 99/19467 and SEQ ID NO: 1 in WO 2009/061380.

In an embodiment the alpha-amylase may be an enzyme having a degree of identity of at least 60%, e.g., at least 70%, at least 80%, at least 90%, at least 91%, at least 92%, at least 93%, at least 94%, at least 95%, at least 96%, at least 97%, at least 98% or at least 99% to any of the sequences shown in SEQ ID NO: 3 in WO 99/19467 or SEQ ID NO: 1 herein.

In a preferred embodiment the alpha-amylase is derived from *Bacillus stearothermophilus*. The *Bacillus stearothermophilus* alpha-amylase may be a mature wild-type or a mature variant thereof. The mature *Bacillus stearothermophilus* alpha-amylases, or variant thereof, may be naturally truncated during recombinant production. For instance, the mature *Bacillus stearothermophilus* alpha-amylase may be truncated at the C-terminal so it is around 491 amino acids long (compared to SEQ ID NO: 3 in WO 99/19467 or SEQ ID NO: 1 herein), such as from 480-495 amino acids long.

The *Bacillus* alpha-amylase may also be a variant and/or hybrid. Examples of such a variant can be found in any of WO 96/23873, WO 96/23874, WO 97/41213, WO 99/19467, WO 00/60059, WO 02/10355 and WO2009/061380 (all documents are hereby incorporated by reference). Specific alpha-amylase variants are disclosed in U.S. Pat. Nos. 6,093,562, 6,187,576, 6,297,038, and 7,713,723 (hereby incorporated by reference) and include *Bacillus stearothermophilus* alpha-amylase (often referred to as BSG alpha-amylase) variants having a deletion of one or two amino acids at any of positions R179, G180, I181 and/or G182, preferably the double deletion disclosed in WO 96/23873—see, e.g., page 20, lines 1-10 (hereby incorporated by reference), preferably corresponding to deletion of positions I181 and G182 compared to the amino acid sequence of *Bacillus stearothermophilus* alpha-amylase set forth in SEQ ID NO: 3 disclosed in WO 99/19467 or SEQ ID NO: 1 herein or the deletion of amino acids R179 and G180 using SEQ ID NO: 3 in WO 99/19467 or SEQ ID NO: 1 herein. Even more preferred are *Bacillus* alpha-amylases, especially *Bacillus stearothermophilus* (BSG) alpha-amylases, which have at one or two amino acid deletions corresponding to positions R179, G180, I181 and G182, preferably which have a double deletion corresponding to R179 and G180, or preferably a deletion of positions 181 and 182 (denoted I181*+G182*), and optionally further comprises a N193F substitution (denoted I181*+G182*+N193F) compared to the wild-type BSG alpha-amylase amino acid sequence set forth in SEQ ID NO: 3 disclosed in WO 99/19467 or SEQ ID NO: 1 herein. The bacterial alpha-amylase may also have a substitution in a position corresponding to S239 in the *Bacillus licheniformis* alpha-amylase shown in SEQ ID NO: 4 in WO 99/19467, or a S242 variant in the *Bacillus stearothermophilus* alpha-amylase of SEQ ID NO: 3 in WO 99/19467 or SEQ ID NO: 1 herein.

In an embodiment the variant is a S242A, E or Q variant, preferably a S242Q or A variant, of the *Bacillus stearothermophilus* alpha-amylase (using SEQ ID NO: 1 herein for numbering).

In an embodiment the variant is a position E188 variant, preferably E188P variant of the *Bacillus stearothermophilus* alpha-amylase (using SEQ ID NO: 1 herein for numbering).

Other contemplated variant are *Bacillus* sp. TS-23 variant disclosed in WO2009/061380, especially variants defined in claim 1 of WO2009/061380 (hereby incorporated by reference).

Bacterial Hybrid Alpha-Amylases

The bacterial alpha-amylase may also be a hybrid bacterial alpha-amylase, e.g., an alpha-amylase comprising 445 C-terminal amino acid residues of the *Bacillus licheniformis* alpha-amylase (shown in SEQ ID NO: 4 of WO 99/19467) and the 37 N-terminal amino acid residues of the alpha-amylase derived from *Bacillus amyloliquefaciens* (shown in SEQ ID NO: 5 of WO 99/19467). In a preferred embodiment this hybrid has one or more, especially all, of the following substitutions:

G48A+T49I+G107A+H156Y+A181T+N190F+I201F+A209V+Q264S (using the *Bacillus licheniformis* numbering in SEQ ID NO: 4 of WO 99/19467). Also preferred are variants having one or more of the following mutations (or corresponding mutations in other *Bacillus* alpha-amylases): H154Y, A181T, N190F, A209V and Q264S and/or the deletion of two residues between positions 176 and 179, preferably the deletion of E178 and G179 (using SEQ ID NO: 5 of WO 99/19467 for position numbering).

In an embodiment the bacterial alpha-amylase is the mature part of the chimeric alpha-amylase disclosed in Richardson et al., 2002, *The Journal of Biological Chemistry* 277(29): 267501-26507, referred to as BD5088 or a variant thereof. This alpha-amylase is the same as the one shown in SEQ ID NO: 2 in WO 2007134207. The mature enzyme sequence starts after the initial "Met" amino acid in position 1.

Thermostable Alpha-Amylase

According to the invention the alpha-amylase is used in combination with a hemicellulase, preferably xylanase, having a Melting Point (DSC) above 80° C. Optionally an endoglucanase having a Melting Point (DSC) above 70° C., such as above 75° C., in particular above 80° C. may be included. The thermostable alpha-amylase, such as a bacterial an alpha-amylase, is preferably derived from *Bacillus stearothermophilus* or *Bacillus* sp. TS-23. In an embodiment the alpha-amylase has a T½ (min) at pH 4.5, 85° C., 0.12 mM CaCl₂ of at least 10.

In an embodiment the alpha-amylase has a T½ (min) at pH 4.5, 85° C., 0.12 mM CaCl₂, of at least 15.

In an embodiment the alpha-amylase has a T½ (min) at pH 4.5, 85° C., 0.12 mM CaCl₂, of at least 20.

In an embodiment the alpha-amylase has a T½ (min) at pH 4.5, 85° C., 0.12 mM CaCl₂, of at least 25.

In an embodiment the alpha-amylase has a T½ (min) at pH 4.5, 85° C., 0.12 mM CaCl₂, of at least 30.

In an embodiment the alpha-amylase has a T½ (min) at pH 4.5, 85° C., 0.12 mM CaCl₂, of at least 40.

In an embodiment the alpha-amylase has a T½ (min) at pH 4.5, 85° C., 0.12 mM CaCl₂, of at least 50.

In an embodiment the alpha-amylase has a T½ (min) at pH 4.5, 85° C., 0.12 mM CaCl₂, of at least 60.

In an embodiment the alpha-amylase has a T½ (min) at pH 4.5, 85° C., 0.12 mM CaCl₂, between 10-70.

In an embodiment the alpha-amylase has a T½ (min) at pH 4.5, 85° C., 0.12 mM CaCl₂, between 15-70.

In an embodiment the alpha-amylase has a T½ (min) at pH 4.5, 85° C., 0.12 mM CaCl₂, between 20-70.

In an embodiment the alpha-amylase has a T½ (min) at pH 4.5, 85° C., 0.12 mM CaCl₂, between 25-70.

In an embodiment the alpha-amylase has a T½ (min) at pH 4.5, 85° C., 0.12 mM CaCl₂, between 30-70.

In an embodiment the alpha-amylase has a T½ (min) at pH 4.5, 85° C., 0.12 mM CaCl₂, between 40-70.

In an embodiment the alpha-amylase has a T½ (min) at pH 4.5, 85° C., 0.12 mM CaCl₂, between 50-70.

In an embodiment the alpha-amylase has a T½ (min) at pH 4.5, 85° C., 0.12 mM CaCl₂, between 60-70.

In an embodiment the alpha-amylase is a bacterial alpha-amylase, preferably derived from the genus *Bacillus*, especially a strain of *Bacillus stearothermophilus*, in particular the *Bacillus stearothermophilus* as disclosed in WO 99/19467 as SEQ ID NO: 3 or SEQ ID NO: 1 herein with one or two amino acids deleted at positions R179, G180, I181 and/or G182, in particular with R179 and G180 deleted, or with I181 and G182 deleted, with mutations in below list of mutations. In preferred embodiments the *Bacillus stearothermophilus* alpha-amylases have double deletion I181+G182, and optional substitution N193F, optionally further comprising mutations selected from below list:

V59A + Q89R + G112D + E129V + K177L + R179E + K220P + N224L + Q254S;
V59A + Q89R + E129V + K177L + R179E + H208Y + K220P + N224L + Q254S;
V59A + Q89R + E129V + K177L + R179E + K220P + N224L + Q254S + D269E + D281N;
V59A + Q89R + E129V + K177L + R179E + K220P + N224L + Q254S + I270L;
V59A + Q89R + E129V + K177L + R179E + K220P + N224L + Q254S + H274K;
V59A + Q89R + E129V + K177L + R179E + K220P + N224L + Q254S + Y276F;
V59A + E129V + R157Y + K177L + R179E + K220P + N224L + S242Q + Q254S;
V59A + E129V + K177L + R179E + H208Y + K220P + N224L + S242Q + Q254S;
V59A + E129V + K177L + R179E + K220P + N224L + S242Q + Q254S;
V59A + E129V + K177L + R179E + K220P + N224L + S242Q + Q254S + H274K;
V59A + E129V + K177L + R179E + K220P + N224L + S242Q + Q254S + Y276F;
V59A + E129V + K177L + R179E + K220P + N224L + S242Q + Q254S + D281N;
V59A + E129V + K177L + R179E + K220P + N224L + S242Q + Q254S + M284T;
V59A + E129V + K177L + R179E + K220P + N224L + S242Q + Q254S + G416V;
V59A + E129V + K177L + R179E + K220P + N224L + Q254S;
V59A + E129V + K177L + R179E + K220P + N224L + Q254S + M284T;
A91L + M96I + E129V + K177L + R179E + K220P + N224L + S242Q + Q254S;
E129V + K177L + R179E;
E129V + K177L + R179E + K220P + N224L + S242Q + Q254S;
E129V + K177L + R179E + K220P + N224L + S242Q + Q254S + Y276F + L427M;
E129V + K177L + R179E + K220P + N224L + S242Q + Q254S + M284T;
E129V + K177L + R179E + K220P + N224L + S242Q + Q254S + N376* + I377*;
E129V + K177L + R179E + K220P + N224L + Q254S;
E129V + K177L + R179E + K220P + N224L + Q254S + M284T;
E129V + K177L + R179E + S242Q;
E129V + K177L + R179V + K220P + N224L + S242Q + Q254S;
K220P + N224L + S242Q + Q254S;
M284V;
V59A + Q89R + E129V + K177L + R179E + Q254S + M284V.

In an embodiment the alpha-amylase is selected from the group of *Bacillus stearomthermphilus* alpha-amylase variants:
I181w+G182*;
I181*+G182*+N193F;
preferably
I181*+G182*+E129V+K177L+R179E;
I181*+G182*+N193F+E129V+K177L+R179E;
I181*+G182*+N193F+V59A+Q89R+E129V+K177L+R179E+H208Y+K220P+N224L+Q254S;
I181*+G182*+N193F+V59A+Q89R+E129V+K177L+R179E+Q254S+M284V; and
I181*+G182*+N193F+E129V+K177L+R179E+K220P+N224L+S242Q+Q254S (using SEQ ID NO: 1 herein for numbering).

In an embodiment the bacterial alpha-amylase, such as *Bacillus* alpha-amylase, such as as *Bacillus stearomthermphilus* alpha-amylase has at least 60%, such as at least 70%, such as at least 75% identity, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, such as 100% identity to the mature part of the polypeptide of SEQ ID NO: 1 herein.

In an embodiment the bacterial alpha-amylase variant, such as *Bacillus* alpha-amylase variant, such as *Bacillus stearomthermphilus* alpha-amylase variant has at least 60%, such as at least 70%, such as at least 75% identity, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the mature part of the polypeptide of SEQ ID NO: 1 herein.

It should be understood that when referring to *Bacillus stearothermophilus* alpha-amylase and variants thereof they are normally produced naturally in truncated form. In particular, the truncation may be so that the *Bacillus stearo-*

*thermophilus* alpha-amylase shown in SEQ ID NO: 3 in WO 99/19467 or SEQ ID NO: 1 herein, or variants thereof, are truncated in the C-terminal and are typically around 491 amino acids long, such as from 480-495 amino acids long.

Thermostable Hemicellulase Present and/or Added During Liquefaction

According to the invention a hemicellulase, preferably xylanase, having a Melting Point (DSC) above 80° C. is present and/or added to liquefaction step i) in combination with an alpha-amylase, such as a bacterial alpha-amylase (described above).

The thermostability of a hemicellulase, preferably xylanase may be determined as described in the "Materials & Methods"-section under "Determination of $T_d$ by Differential Scanning calorimetry for Endoglucanases and Hemicellulases".

In an embodiment the hemicellulase, in particular xylanase, especially GH10 or GH11 xylanase has a Melting Point (DSC) above 82° C., such as above 84° C., such as above 86° C., such as above 88° C., such as above 88° C., such as above 90° C., such as above 92° C., such as above 94° C., such as above 96° C., such as above 98° C., such as above 100° C., such as between 80° C. and 110° C., such as between 82° C. and 110° C., such as between 84° C. and 110° C.

In a preferred embodiment the hemicellulase, in particular xylanase, especially GH10 xylanase has at least 60%, such as at least 70%, such as at least 75%, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, such as 100% identity to the mature part of the polypeptide of SEQ ID NO: 3 herein, preferably derived from a strain of the genus *Dictyoglomus*, such as a strain of *Dictyogllomus thermophilum*.

In a preferred embodiment the hemicellulase, in particular xylanase, especially GH11 xylanase has at least 60%, such as at least 70%, such as at least 75%, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, such as 100% identity to the mature part of the polypeptide of SEQ ID NO: 34 herein, preferably derived from a strain of the genus *Dictyoglomus*, such as a strain of *Dictyogitomus thermophlium*.

In a preferred embodiment the hemicellulase, in particular xylanase, especially GH10 xylanase has at least 60%, such as at least 70%, such as at least 75% identity, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, such as 100% identity to the mature part of the polypeptide of SEQ ID NO: 4 herein, preferably derived from a strain of the genus *Rasamsonia*, such as a strain of *Rasomsonia byssochiamydoides*.

In a preferred embodiment the hemicellulase, in particular xylanase, especially GH10 xylanase has at least 60%, such as at least 70%, such as at least 75% identity, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, such as 100% identity to the mature part of the polypeptide of SEQ ID NO: 5 herein, preferably derived from a strain of the genus *Talaromyces*, such as a strain of *Talaromyces leycettanus*.

In a preferred embodiment the hemicellulase, in particular xylanase, especially GH10 xylanase has at least 60%, such as at least 70%, such as at least 75% identity, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, such as 100% identity to the mature part of the polypeptide of SEQ ID NO: 8 herein, preferably derived from a strain of the genus *Aspergillus*, such as a strain of *Aspergillus fumigatus*.

Thermostable Endoglucanase Present and/or Added During Liquefaction

According to the invention an optional endoglucanase ("EG") having a Melting Point (DSC) above 70° C., such as between 70° C. and 95° C. may be present and/or added in liquefaction step i) in combination with an alpha-amylase, such as a thermostable bacterial alpha-amylase and a hemicellulase, preferably xylanase, having a Melting Point (DSC) above 80° C.

The thermostability of an endoglucanase may be determined as described in the "Materials & Methods"—section under "Determination of $T_d$ by Differential Scanning calorimetry for Endoglucanases and Hemicellulases".

In an embodiment the endoglucanase has a Melting Point (DSC) above 72° C., such as above 74° C., such as above 76° C., such as above 78° C., such as above 80° C., such as above 82° C., such as above 84° C., such as above 86° C., such as above 88° C., such as between 70° C. and 95° C., such as between 76° C. and 94° C., such as between 78° C. and 93° C., such as between 80° C. and 92° C., such as between 82° C. and 91° C., such as between 84° C. and 90° C.

In a preferred embodiment the endogluconase used in a process of the invention or comprised in a composition of the invention is a Glycoside Hydrolase Family 5 endoglucnase or GH5 endoglucanase (see the CAZy database on the "www.cazy.org" webpage.

In an embodiment the GH5 endoglucanase is from family EG II, such as the *Taiaromyces ieycettanus* endoglucanase shown in SEQ ID NO: 9 herein; *Penicillium capsulatum* endoglucanase shown in SEQ ID NO: 35 herein, and *Trichophaea saccata* endoglucanase shown in SEQ ID NO: 36 herein.

In an embodiment the endoglucanase is a family GH45 endoglucanase. In an embodiment the GH45 endoglucanase is from family EG V, such as the *Sordaria fimicola* shown in SEQ ID NO: 38 herein or the *Thielavia terrestris* endoglucanase shown in SEQ ID NO: 37 herein.

In an embodiment the endoglucanase has at least 60%, such as at least 70%, such as at least 75% identity, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, such as 100% identity to the mature part of the polypeptide of SEQ ID NO: 9 herein. In an embodiment the endoglucanase is derived from a strain of the genus *Talaromyces*, such as a strain of *Talaromyces leycettanus*.

In an embodiment the endoglucanase has at least 60%, such as at least 70%, such as at least 75% identity, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, such as 100% identity to the mature part of the polypeptide of SEQ ID NO: 35 herein, preferably derived from a strain of the genus *Penicillium*, such as a strain of *Penicillium capsulatum*.

In an embodiment the endoglucanase has at least 60%, such as at least 70%, such as at least 75% identity, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, such as 100% identity to the mature part of the polypeptide of SEQ ID NO: 36 herein, preferably derived from a strain of the genus *Trichophaea*, such as a strain of *Trichophaea saccata*.

In an embodiment the endoglucanase has at least 60%, such as at least 70%, such as at least 75% identity, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, such as 100% identity to the mature part of the polypeptide of SEQ ID NO: 37 herein, preferably derived from a strain of the genus *Thielavia*, such as a strain of *Thielavia terrestris*.

In an embodiment the endoglucanase has at least 60%, such as at least 70%, such as at least 75% identity, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, such as 100% identity to the mature part of the polypeptide of SEQ ID NO: 38 herein, preferably derived from a strain of the genus *Sordaria*, such as a strain of *Sordaria fimicola*.

In an embodiment the endoglucanase is added in liquefaction step i) at a dose from 1-10,000 μg EP (Enzymes Protein)/g DS), such as 10-1,000 μg EP/g DS.

Protease Present and/or Added During Liquefaction

In an embodiment of the invention an optional protease, such as a thermostable protease, may be present and/or added in liquefaction together with an alpha-amylase, such as a thermostable alpha-amylase, and a hemicellulase, preferably xylanase, having a melting point (DSC) above 80° C., and optionally an endoglucanase, a carbohydrate-source generating enzyme, in particular a glucoamylase, optionally a pullulanase and/or optionally a phytase.

Proteases are classified on the basis of their catalytic mechanism into the following groups: Serine proteases (S), Cysteine proteases (C), Aspartic proteases (A), Metallo proteases (M), and Unknown, or as yet unclassified, proteases (U), see Handbook of Proteolytic Enzymes, A. J. Barrett, N. D. Rawlings, J. F. Woessner (eds), Academic Press (1998), in particular the general introduction part.

In a preferred embodiment the thermostable protease used according to the invention is a "metallo protease" defined as a protease belonging to EC 3.4.24 (metalloendopeptidases); preferably EC 3.4.24.39 (acid metallo proteinases).

To determine whether a given protease is a metallo protease or not, reference is made to the above "Handbook of Proteolytic Enzymes" and the principles indicated therein. Such determination can be carried out for all types of proteases, be it naturally occurring or wild-type proteases; or genetically engineered or synthetic proteases.

Protease activity can be measured using any suitable assay, in which a substrate is employed, that includes peptide bonds relevant for the specificity of the protease in question. Assay-pH and assay-temperature are likewise to be adapted to the protease in question. Examples of assay-pH-values are pH 6, 7, 8, 9, 10, or 11. Examples of assay-temperatures are 30, 35, 37, 40, 45, 50, 55, 60, 65, 70 or 80° C.

Examples of protease substrates are casein, such as Azurine-Crosslinked Casein (AZCL-casein). Two protease assays are described below in the "Materials & Methods"-section, of which the so-called "AZCL-Casein Assay" is the preferred assay.

In an embodiment the thermostable protease has at least 20%, such as at least 30%, such as at least 40%, such as at least 50%, such as at least 60%, such as at least 70%, such as at least 80%, such as at least 90%, such as at least 95%, such as at least 100% of the protease activity of the JTP196 variant (Example 2) or Protease Pfu (SEQ ID NO: 13 herein) determined by the AZCL-casein assay described in the "Materials & Methods"-section.

There are no limitations on the origin of the thermostable protease used in a process or composition of the invention as long as it fulfills the thermostability properties defined below.

In one embodiment the protease is of fungal origin.

In a preferred embodiment the thermostable protease is a variant of a metallo protease as defined above. In an embodiment the thermostable protease used in a process or composition of the invention is of fungal origin, such as a fungal metallo protease, such as a fungal metallo protease derived from a strain of the genus *Thermoascus*, preferably a strain of *Thermoascus aurantiacus*, especially *Thermoascus aurantiacus* CGMCC No. 0670 (classified as EC 3.4.24.39).

In an embodiment the thermostable protease is a variant of the mature part of the metallo protease shown in SEQ ID NO: 2 disclosed in WO 2003/048353 or the mature part of SEQ ID NO: 1 in WO 2010/008841 and shown as SEQ ID NO: 2 herein further with mutations selected from below list:

S5*+D79L+S87P+A112P+D142L;
D79L+S87P+A112P+T124V+D142L;
S5*+N26R+D79L+S87P+A112P+D142L;
N26R+T46R+D79L+S87P+A112P+D142L;
T46R+D79L+S87P+T116V+D142L;
D79L+P81R+S87P+A112P+D142L;
A27K+D79L+S87P+A112P+T124V+D142L;
D79L+Y82F+S87P+A112P+T124V+D142L;
D79L+Y82F+S87P+A112P+T124V+D142L;
D79L+S87P+A112P+T124V+A126V+D142L;
D79L+S87P+A112P+D142L;
D79L+Y82F+S87P+A112P+D142L;
S38T+D79L+S87P+A112P+A126V+D142L;
D79L+Y82F+S87P+A112P+A126V+D142L;
A27K+D79L+S87P+A112P+A126V+D142L;
D79L+S87P+N98C+A112P+G135C+D142L;
D79L+S87P+A112P+D142L+T141C+M161C;
S36P+D79L+S87P+A112P+D142L;
A37P+D79L+S87P+A112P+D142L;
S49P+D79L+S87P+A112P+D142L;
S50P+D79L+S87P+A112P+D142L;
D79L+S87P+D104P+A112P+D142L;

D79L+Y82F+S87G+A112P+D142L;
S70V+D79L+Y82F+S87G+Y97W+A112P+D142L;
D79L+Y82F+S87G+Y97W+D104P+A112P+D142L;
S70V+D79L+Y82F+S87G+A112P+D142L;
D79L+Y82F+S87G+D104P+A112P+D142L;
D79L+Y82F+S87G+A112P+A126V+D142L;
Y82F+S87G+S70V+D79L+D104P+A112P+D142L;
Y82F+S87G+D79L+D104P+A112P+A126V+D142L;
A27K+D79L+Y82F+S87G+D104P+A112P+A126V+D142L;
A27K+Y82F+S87G+D104P+A112P+A126V+D142L:
A27K+D79L+Y82F+D104P+A112P+A126V+D142L;
A27K+Y82F+D104P+A112P+A126V+D142L;
A27K+D79L+S87P+A112P+D142L;
D79L+S87P+D142L.

In a preferred embodiment the thermostable protease is a variant of the mature metallo protease disclosed as the mature part of SEQ ID NO: 2 disclosed in WO 2003/048353 or the mature part of SEQ ID NO: 1 in WO 2010/008841 or SEQ ID NO: 2 herein with the following mutations:
D79L+S87P+A112P+D142L;
D79L+S87P+D142L; or
A27K+D79L+Y82F+S87G+D104P+A112P+A126V+D142L.

In an embodiment the protease variant has at least 75% identity preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the mature part of the polypeptide of SEQ ID NO: 2 disclosed in WO 2003/048353 or the mature part of SEQ ID NO: 1 in WO 2010/008841 or SEQ ID NO: 2 herein.

The thermostable protease may also be derived from any bacterium as long as the protease has the thermostability properties defined according to the invention.

In an embodiment the thermostable protease is derived from a strain of the bacterium *Pyrococcus*, such as a strain of *Pyrococcus furiosus* (pfu protease).

In an embodiment the protease is one shown as SEQ ID NO: 1 in U.S. Pat. No. 6,358,726-B1 (Takara Shuzo Company) and SEQ ID NO: 13 herein.

In an embodiment the thermostable protease is one disclosed in SEQ ID NO: 13 herein or a protease having at least 80% identity, such as at least 85%, such as at least 90%, such as at least 95%, such as at least 96%, such as at least 97%, such as at least 98%, such as at least 99% identity to SEQ ID NO: 1 in U.S. Pat. No. 6,358,726-B1 or SEQ ID NO: 13 herein. The *Pyroccus furiosus* protease can be purchased from Takara Bio, Japan.

The *Pyrococcus furiosus* protease is a thermostable protease according to the invention. The commercial product *Pyrococcus furiosus* protease (Pfu S) was found (see Example 5) to have a thermostability of 110% (80° C./70° C.) and 103% (90° C./70° C.) at pH 4.5 determined as described in Example 2.

In one embodiment a thermostable protease has a thermostability value of more than 20% determined as Relative Activity at 80° C./70° C. determined as described in Example 2.

In an embodiment the protease has a thermostability of more than 30%, more than 40%, more than 50%, more than 60%, more than 70%, more than 80%, more than 90%, more than 100%, such as more than 105%, such as more than 110%, such as more than 115%, such as more than 120% determined as Relative Activity at 80° C./70° C.

In an embodiment protease has a thermostability of between 20 and 50%, such as between 20 and 40%, such as 20 and 30% determined as Relative Activity at 80° C./70° C.

In an embodiment the protease has a thermostability between 50 and 115%, such as between 50 and 70%, such as between 50 and 60%, such as between 100 and 120%, such as between 105 and 115% determined as Relative Activity at 80° C./70° C.

In an embodiment the protease has a thermostability value of more than 10% determined as Relative Activity at 85° C./70° C. determined as described in Example 2.

In an embodiment the protease has a thermostability of more than 10%, such as more than 12%, more than 14%, more than 16%, more than 18%, more than 20%, more than 30%, more than 40%, more that 50%, more than 60%, more than 70%, more than 80%, more than 90%, more than 100%, more than 110% determined as Relative Activity at 85° C./70° C.

In an embodiment the protease has a thermostability of between 10 and 50%, such as between 10 and 30%, such as between 10 and 25% determined as Relative Activity at 85° C./70° C.

In an embodiment the protease has more than 20%, more than 30%, more than 40%, more than 50%, more than 60%, more than 70%, more than 80%, more than 90% determined as Remaining Activity at 80° C.; and/or In an embodiment the protease has more than 20%, more than 30%, more than 40%, more than 50%, more than 60%, more than 70%, more than 80%, more than 90% determined as Remaining Activity at 84° C.

Determination of "Relative Activity" and "Remaining Activity" is done as described in Example 2.

In an embodiment the protease may have a themostability for above 90, such as above 100 at 85° C. as determined using the Zein-BCA assay as disclosed in Example 3.

In an embodiment the protease has a themostability above 60%, such as above 90%, such as above 100%, such as above 110% at 85° C. as determined using the Zein-BCA assay.

In an embodiment protease has a themostability between 60-120, such as between 70-120%, such as between 80-120%, such as between 90-120%, such as between 100-120%, such as 110-120% at 85° C. as determined using the Zein-BCA assay.

In an embodiment the thermostable protease has at least 20%, such as at least 30%, such as at least 40%, such as at least 50%, such as at least 60%, such as at least 70%, such as at least 80%, such as at least 90%, such as at least 95%, such as at least 100% of the activity of the JTP196 protease variant or Protease Pfu determined by the AZCL-casein assay described in the "Materials & Methods"-section.

Carbohydrate-Source Generating Enzyme Present and/or Added During Liquefaction

According to the invention an optional carbohydrate-source generating enzyme, in particular a glucoamylase, preferably a thermostable glucoamylase, may be present and/or added in liquefaction together with an alpha-amylase and hemicellulase, preferably xylanase, having a Melting Point (DSC) above 80° C., and an optional endoglucanase having a Melting Point (DSC) above 70° C., and an optional a pullulanase and/or optional phytase.

The term "carbohydrate-source generating enzyme" includes any enzymes generating fermentable sugars. A carbohydrate-source generating enzyme is capable of producing a carbohydrate that can be used as an energy-source by the fermenting organism(s) in question, for instance, when used in a process of the invention for producing a fermentation product, such as ethanol. The generated carbohydrates may be converted directly or indirectly to the desired fermentation product, preferably ethanol. According to the invention a mixture of carbohydrate-source generating enzymes may be used, Specific examples include glucoamylase (being glucose generators), beta-amylase and maltogenic amylase (being maltose generators).

In a preferred embodiment the carbohydrate-source generating enzyme is thermostable. The carbohydrate-source generating enzyme, in particular thermostable glucoamylase, may be added together with or separately from the alpha-amylase and the thermostable protease.

In an embodiment the carbohydrate-source generating enzyme, preferably a thermostable glucoamylase, has a Relative Activity heat stability at 85° C. of at least 20%, at least 30%, preferably at least 35% determined as described in Example 4 (heat stability).

In an embodiment the carbohydrate-source generating enzyme is a glucoamylase having a relative activity pH optimum at pH 5.0 of at least 90%, preferably at least 95%, preferably at least 97%, such as 100% determined as described in Example 4 (pH optimum).

In an embodiment the carbohydrate-source generating enzyme is a glucoamylase having a pH stability at pH 5.0 of at least at least 80%, at least 85%, at least 90% determined as described in Example 4 (pH stability).

In a specific and preferred embodiment the carbohydrate-source generating enzyme is a thermostable glucoamylase, preferably of fungal origin, preferably a filamentous fungi, such as from a strain of the genus *Penicillium*, especially a strain of *Penicillium oxalicum*, in particular the *Penicillium oxalicum* glucoamylase disclosed as SEQ ID NO: 2 in WO 2011/127802 (which is hereby incorporated by reference) and shown in SEQ ID NO: 14 herein.

In an embodiment the thermostable glucoamylase has at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99% or 100% identity to the mature polypeptide shown in SEQ ID NO: 2 in WO 2011/127802 or SEQ ID NOs: 14 herein.

In an embodiment the carbohydrate-source generating enzyme, in particular thermostable glucoamylase, is the *Penicillium oxalicum* glucoamylase shown in SEQ ID NO: 14 herein.

In a preferred embodiment the carbohydrate-source generating enzyme is a variant of the *Penicillium oxalicum* glucoamylase disclosed as SEQ ID NO: 2 in WO 2011/127802 and shown in SEQ ID NO: 14 herein, having a K79V substitution (referred to as "PE001") (using the mature sequence shown in SEQ ID NO: 14 for numbering). The K79V glucoamylase variant has reduced sensitivity to protease degradation relative to the parent as disclosed in WO 2013/036526 (which is hereby incorporated by reference).

Contemplated *Penicillium oxalicum* glucoamylase variants are disclosed in WO 2013/053801 (which is hereby incorporated by reference).

In an embodiment these variants have reduced sensitivity to protease degradation.

In an embodiment these variant have improved thermostability compared to the parent.

More specifically, in an embodiment the glucoamylase has a K79V substitution (using SEQ ID NO: 14 herein for numbering), corresponding to the PE001 variant, and further comprises at least one of the following substitutions or combination of substitutions:

T65A; Q327F; E501V; Y504T; Y504*; T65A+Q327F; T65A+E501V; T65A+Y504T; T65A+Y504*; Q327F+E501V; Q327F+Y504T; Q327F+Y504*; E501V+Y504T; E501V+Y504*; T65A+Q327F+E501V; T65A+Q327F+Y504T; T65A+E501V+Y504T; Q327F+E501V+Y504T; T65A+Q327F+Y504*; T65A+E501V+Y504*; Q327F+E501V+Y504*; T65A+Q327F+E501V+Y504T; T65A+Q327F+E501V+Y504*; E501V+Y504T; T65A+K161S; T65A+Q405T; T65A+Q327W; T65A+Q327F; T65A+Q327Y; P11F+T65A+Q327F; R1K+D3W+K5Q+G7V+N8S+T10K+P11S+T65A+Q327F; P2N+P4S+P11F+T65A+Q327F; P11F+D26C+K33C+T65A+Q327F; P2N+P4S+P11F+T65A+Q327W+E501V+Y504T; R1E+D3N+P4G+G6R+G7A+N8A+T10D+P11D+T65A+Q327F; P11F+T65A+Q327W; P2N+P4S+P11F+T65A+Q327F+E501V+Y504T; P11F+T65A+Q327W+E501V+Y504T; T65A+Q327F+E501V+Y504T; T65A+S105P+Q327W; T65A+S105P+Q327F; T65A+Q327W+S364P; T65A+Q327F+S364P; T65A+S103N+Q327F; P2N+P4S+P11F+K34Y+T65A+Q327F; P2N+P4S+P11F+T65A+Q327F+D445N+V447S; P2N+P4S+P11F+T65A+I172V+Q327F; P2N+P4S+P11F+T65A+Q327F+N502*; P2N+P4S+P11F+T65A+Q327F+N502T+P563S+K571E; P2N+P4S+P11F+R31S+K33V+T65A+Q327F+N564D+K571S; P2N+P4S+P11F+T65A+Q327F+S377T; P2N+P4S+P11F+T65A+V325T+Q327W; P2N+P4S+P11F+T65A+Q327F+D445N+V447S+E501V+Y504T; P2N+P4S+P11F+T65A+I172V+Q327F+E501V+Y504T; P2N+P4S+P11F+T65A+Q327F+S377T+E501V+Y504T; P2N+P4S+P11F+Q26N+K34Y+T65A+Q327F; P2N+P4S+P11F+T65A+Q327F+I375A+E501V+Y504T; P2N+P4S+P11F+T65A+K218A+K221D+Q327F+E501V+Y504T; P2N+P4S+P11F+T65A+S103N+Q327F+E501V+Y504T; P2N+P4S+T10D+T65A+Q327F+E501V+Y504T; P2N+P4S+F12Y+T65A+Q327F+E501V+Y504T; K5A+P11F+T65A+Q327F+E501V+Y504T; P2N+P4S+T10E+E18N+T65A+Q327F+E501V+Y504T; P2N+T10E+E18N+T65A+Q327F+E501V+Y504T; P2N+P4S+P11F+T65A+Q327F+E501V+Y504T+T568N; P2N+P4S+P11F+T65A+Q327F+E501V+Y504T+K524T+G526A; P2N+P4S+P11F+K34Y+T65A+Q327F+D445N+V447S+E501V+Y504T; P2N+P4S+P11F+R31S+K33V+T65A+Q327F+D445N+V447S+E501V+Y504T; P2N+P4S+P11F+D26N+K34Y+T65A+Q327F+E501V+Y504T; P2N+P4S+P11F+T65A+F80*+Q327F+E501V+Y504T; P2N+P4S+P11F+T65A+K112S+Q327F+E501V+Y504T; P2N+P4S+P11F+T65A+Q327F+E501V+Y504T+T516P+K524T+G526A; P2N+P4S+P11F+T65A+Q327F+E501V+N502T+Y504*; P2N+P4S+P11F+T65A+Q327F+E501V+Y504T; P2N+P4S+P11F+T65A+S103N+Q327F+E501V+Y504T; K5A+P11F+T65A+Q327F+E501V+Y504T; P2N+P4S+P11F+T65A+Q327F+E501V+Y504T+T516P+K524T+G526A; P2N+P4S+P11F+T65A+V79A+Q327F+E501V+Y504T; P2N+P4S+P11F+T65A+V79G+Q327F+E501V+Y504T; P2N+P4S+P11F+T65A+V79I+Q327F+E501V+Y504T; P2N+P4S+P11F+T65A+V79L+Q327F+E501V+Y504T; P2N+P4S+P11F+T65A+V79S+Q327F+E501V+Y504T; P2N+P4S+P11F+T65A+L72V+Q327F+E501V+Y504T; S255N+Q327F+E501V+Y504T; P2N+P4S+P11F+T65A+E74N+Q327F+E501V+Y504T; P2N+P4S+P11F+T65A+G220N+Q327F+E501V+Y504T; P2N+P4S+P11F+T65A+Y245N+Q327F+E501V+Y504T; P2N+

P4S+P11F+T65A+Q253N+Q327F+E501V+Y504T;
P2N+P4S+P11F+T65A+D279N+Q327F+E501V+Y504T; P2N+P4S+P11F+I65A+Q327F+S359N+E501V+Y504T; P2N+P4S+P11F+T65A+Q327F+D370N+E501V+Y504T; P2N+P4S+P11F+T65A+Q327F+V460S+E501V+Y504T; P2N+P4S+P11F+T65A+Q327F+V460T+P468T+E501V+Y504T; P2N+P4S+P11F+T65A+Q327F+T463N+E501V+Y504T; P2N+P4S+P11F+T65A+Q327F+S465N+E501V+Y504T; or P2N+P4S+P11F+T65A+Q327F+T477N+E501V+Y504T.

In a preferred embodiment the *Penicillium oxalicum* glucoamylase variant has a K79V substitution using SEQ ID NO: 14 herein for numbering (PE001 variant), and further comprises one of the following mutations:
P11F+T65A+Q327F;
P2N+P4S+P11F+T65A+Q327F;
P11F+D26C+K33C+T65A+Q327F;
P2N+P4S+P11F+T65A+Q327W+E501V+Y504T;
P2N+P4S+P11F+T65A+Q327F+E501V+Y504T; or
P11F+T65A+Q327W+E501V+Y504T.

In an embodiment the glucoamylase variant, such as *Penicillium oxalicum* glucoamylase variant has at least 60%, such as at least 70%, such as at least 75% identity, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the mature polypeptide of SEQ ID NO: 14 herein.

The carbohydrate-source generating enzyme, in particular glycoamylase, may be added in amounts from 0.1-100 micrograms EP/g DS, such as 0.5-50 micrograms EP/g DS, such as 1-25 micrograms EP/g DS, such as 2-12 micrograms EP/g DS.

Pullulanase Present and/or Added During Liquefaction

Optionally a pullulanase may be present and/or added during liquefaction step i) together with an alpha-amylase and a hemicellulase, preferably xylanase, having a melting point (DSC) above 80° C. As mentioned above a protease, a carbohydrate-source generating enzyme, preferably a thermostable glucoamylase, may also optionally be present and/or added during liquefaction step i).

The pullulanase may be present and/or added during liquefaction step i) and/or saccharification step ii) or simultaneous saccharification and fermentation.

Pullulanases (E.C. 3.2.1.41, pullulan 6-glucano-hydrolase), are debranching enzymes characterized by their ability to hydrolyze the alpha-1,6-glycosidic bonds in, for example, amylopectin and pullulan.

Contemplated pullulanases according to the present invention include the pullulanases from *Bacillus amyloderamificans* disclosed in U.S. Pat. No. 4,560,651 (hereby incorporated by reference), the pullulanase disclosed as SEQ ID NO: 2 in WO 01/151620 (hereby incorporated by reference), the *Bacillus deramificans* disclosed as SEQ ID NO: 4 in WO 01/151620 (hereby incorporated by reference), and the pullulanase from *Bacillus acidopullulyticus* disclosed as SEQ ID NO: 6 in WO 01/151620 (hereby incorporated by reference) and also described in FEMS Mic. Let. (1994) 115, 97-106.

Additional pullulanases contemplated according to the present invention included the pullulanases from *Pyrococcus woesei*, specifically from *Pyrococcus woesei* DSM No. 3773 disclosed in WO 92/02614.

In an embodiment the pullulanase is a family GH57 pullulanase. In an embodiment the pullulanase includes an X47 domain as disclosed in WO 2011/087836 (which are hereby incorporated by reference). More specifically the pullulanase may be derived from a strain of the genus *Thermococcus*, including *Thermococcus litoralis* and *Thermococcus hydrothermalis*, such as the *Thermococcus hydrothermalis* pullulanase shown WO 2011/087836 truncated at the X4 site right after the X47 domain. The pullulanase may also be a hybrid of the *Thermococcus litoralis* and *Thermococcus hydrothermalis* pullulanases or a *T. hydrothermalis/T. litoralis* hybrid enzyme with truncation site X4 disclosed in WO 2011/087836 (which is hereby incorporated by reference).

In another embodiment the pullulanase is one comprising an X46 domain disclosed in WO 2011/076123 (Novozymes).

The pullulanase may be according to the invention be added in an effective amount which include the preferred amount of about 0.0001-10 mg enzyme protein per gram DS, preferably 0.0001-0.10 mg enzyme protein per gram DS, more preferably 0.0001-0.010 mg enzyme protein per gram DS. Pullulanase activity may be determined as NPUN. An Assay for determination of NPUN is described in the "Materials & Methods"-section below.

Suitable commercially available pullulanase products include PROMOZYME 400L, PROMOZYME™ D2 (Novozymes A/S, Denmark), OPTIMAX L-300 (Genencor Int., USA), and AMANO 8 (Amano, Japan).

Phytase Present and/or Added During Liquefaction

Optionally a phytase may be present and/or added in liquefaction in combination with an alpha-amylase and hemicellulase, preferably xylanase, having a melting point (DSC) above 80° C.

A phytase used according to the invention may be any enzyme capable of effecting the liberation of inorganic phosphate from phytic acid (myo-inositol hexakisphosphate) or from any salt thereof (phytates). Phytases can be classified according to their specificity in the initial hydrolysis step, viz. according to which phosphate-ester group is hydrolyzed first. The phytase to be used in the invention may have any specificity, e.g., be a 3-phytase (EC 3.1.3.8), a 6-phytase (EC 3.1.3.26) or a 5-phytase (no EC number). In an embodiment the phytase has a temperature optimum above 50° C., such as in the range from 50-90° C.

The phytase may be derived from plants or microorganisms, such as bacteria or fungi, e.g., yeast or filamentous fungi.

A plant phytase may be from wheat-bran, maize, soy bean or lily pollen. Suitable plant phytases are described in Thomlinson et al, Biochemistry, 1 (1962), 166-171; Barrientos et al, Plant. Physiol., 106 (1994), 1489-1495; WO 98/05785; WO 98/20139.

A bacterial phytase may be from genus *Bacillus*, *Citrobacter*, *Hafnia*, *Pseudomonas*, *Buttiauxella* or *Escherichia*, specifically the species *Bacillus subtilis*, *Citrobacter braakii*, *Citrobacter freundii*, *Hafnia alvei*, *Buttiauxella gaviniae*, *Buttiauxella agrestis*, *Buttiauxella noackies* and *E. coli*. Suitable bacterial phytases are described in Paver and Jagannathan, 1982, Journal of Bacteriology 151:1102-1108; Cosgrove, 1970, Australian Journal of Biological Sciences 23:1207-1220; Greiner et al, Arch. Biochem. Biophys., 303, 107-113, 1993; WO 1997/33976; WO 1997/48812, WO 1998/06856, WO 1998/028408; WO 2004/085638, WO 2006/037327, WO 2006/038062, WO 2006/063588, WO 2008/092901, WO 2008/116878; and WO 2010/034835.

A yeast phytase may be derived from genus *Saccharomyces* or *Schwanniomyces*, specifically species *Saccharomyces cerevisiae* or *Schwanniomyces occidentails*. The former enzyme has been described as a Suitable yeast phytases are described in Nayini et al, 1984, Lebensmittel Wissenschaft and Technologie 17:24-26; Wodzinski et al, Adv. Appl. Microbiol., 42, 263-303; AU-A-24840/95;

Phytases from filamentous fungi may be derived from the fungal phylum of *Ascomycota* (*ascomycetes*) or the phylum *Basidiomycota*, e.g., the genus *Aspergillus, Thermomyces* (also called *Humicola*), *Myceliophthora, Manascus, Penicillium, Peniophora, Agrocybe, Paxillus*, or *Trametes*, specifically the species *Aspergillus terreus, Aspergillus niger, Aspergillus niger* var. awamori, *Aspergillus ficuum, Aspergillus fumigatus, Aspergillus oryzae, T. lanuginosus* (also known as *H. lanuginosa*), *Myceliophthora thermophila, Peniophora lycii, Agrocybe pediades, Manascus anka, Paxillus involtus*, or *Trametes pubescens*. Suitable fungal phytases are described in Yamada et al., 1986, Agric. Biol. Chem. 322:1275-1282; Piddington et al., 1993, Gene 133: 55-62; EP 684,313; EP 0 420 358; EP 0 684 313; WO 1998/28408; WO 1998/28409; JP 7-67635; WO 1998/44125; WO 1997/38096; WO 1998/13480.

In a preferred embodiment the phytase is derived from *Buttiauxella*, such as *Buttiauxella gaviniae, Buttiauxella agrestis*, or *Buttiauxella noackies*, such as the ones disclosed as SEQ ID NO: 2, SEQ ID NO: 4 and SEQ ID NO: 6, respectively, in WO 2008/092901 (hereby incorpotared by reference).

In a preferred embodiment the phytase is derived from *Citrobacter*, such as *Citrobacter braakii*, such as one disclosed in WO 2006/037328 (hereby incorporated by reference).

Modified phytases or phytase variants are obtainable by methods known in the art, in particular by the methods disclosed in EP 897010; EP 897985; WO 99/49022; WO 99/48330, WO 2003/066847, WO 2007/112739, WO 2009/129489, and WO 2010/034835.

Commercially available phytase containing products include BIO-FEED PHYTASE™, PHYTASE NOVO™ CT or L (all from Novozymes), LIQMAX (DuPont) or RONOZYME™ NP, RONOZYME® HiPhos, RONOZYME® P5000 (CT), NATUPHOS™ NG 5000 (from DSM).

Carbohydrate-Source Generating Enzyme Present and/or Added During Saccharification and/or Fermentation According to the invention a carbohydrate-source generating enzyme, preferably a glucoamylase, is present and/or added during saccharification and/or fermentation.

In a preferred embodiment the carbohydrate-source generating enzyme is a glucoamylase, of fungal origin, preferably from a stain of *Aspergillus*, preferably *A. niger, A. awamori*, or *A. oryzae*; or a strain of *Trichoderma*, preferably *T. reesei*; or a strain of *Talaromyces*, preferably *T. emersonii*.

Glucoamylase

According to the invention the glucoamylase present and/or added in saccharification and/or fermentation may be derived from any suitable source, e.g., derived from a microorganism or a plant. Preferred glucoamylases are of fungal or bacterial origin, selected from the group consisting of *Aspergillus* glucoamylases, in particular *Aspergillus niger* G1 or G2 glucoamylase (Boel et al. (1984), EMBO J. 3 (5), p. 1097-1102), or variants thereof, such as those disclosed in WO 92/00381, WO 00/04136 and WO 01/04273 (from Novozymes, Denmark); the *A. awamori* glucoamylase disclosed in WO 84/02921, *Aspergillus oryzae* glucoamylase (Agric. Biol. Chem. (1991), 55 (4), p. 941-949), or variants or fragments thereof. Other *Aspergillus* glucoamylase variants include variants with enhanced thermal stability: G137A and G139A (Chen et al. (1996), Prot. Eng. 9, 499-505); D257E and D293E/Q (Chen et al. (1995), Prot. Eng. 8, 575-582); N182 (Chen et al. (1994), Biochem. J. 301, 275-281); disulphide bonds, A246C (Fierobe et al. (1996), Biochemistry, 35, 8698-8704; and introduction of Pro residues in position A435 and S436 (Li et al. (1997), Protein Eng. 10, 1199-1204.

Other glucoamylases include *Athelia rolfsii* (previously denoted *Corticium rolfsii*) glucoamylase (see U.S. Pat. No. 4,727,026 and (Nagasaka et al. (1998) "Purification and properties of the raw-starch-degrading glucoamylases from *Corticium rolfsii*, Appl Microbiol Biotechnol 50:323-330), *Talaromyces* glucoamylases, in particular derived from *Talaromyces emersonii* (WO 99/28448), *Talaromyces leycettanus* (U.S. Pat. No. Re. 32,153), *Talaromyces duponti, Talaromyces thermophilus* (U.S. Pat. No. 4,587,215). In a preferred embodiment the glucoamylase used during saccharification and/or fermentation is the *Talaromyces emersonii* glucoamylase disclosed in WO 99/28448.

Bacterial glucoamylases contemplated include glucoamylases from the genus *Clostridium*, in particular *C. thermoamylolyticum* (EP 135,138), and *C. thermohydrosulfuricum* (WO 86/01831).

Contemplated fungal glucoamylases include *Trametes cingulata, Pachykytospora papyracea*; and *Leucopaxillus giganteus* all disclosed in WO 2006/069289; and *Peniophora rufomarginata* disclosed in WO2007/124285; or a mixture thereof. Also hybrid glucoamylase are contemplated according to the invention. Examples include the hybrid glucoamylases disclosed in WO 2005/045018. Specific examples include the hybrid glucoamylase disclosed in Table 1 and 4 of Example 1 (which hybrids are hereby incorporated by reference).

In an embodiment the glucoamylase is derived from a strain of the genus *Pycnoporus*, in particular a strain of *Pycnoporus* as described in WO 2011/066576 (SEQ ID NOs 2, 4 or 6), or from a strain of the genus *Gloephyllum*, in particular a strain of *Gloephyllum* as described in WO 2011/068803 (SEQ ID NO: 2, 4, 6, 8, 10, 12, 14 or 16) or a strain of the genus *Nigrofomes*, in particular a strain of *Nigrofomes* sp, disclosed in WO 2012/064351 (SEQ ID NO: 2) (all references hereby incorporated by reference). Contemplated are also glucoamylases which exhibit a high identity to any of the above-mentioned glucoamylases, i.e., at least 70%, at least 75%, at least 80%, at least 85%, at least 90%, at least 95%, at least 96%, at least 97%, at least 98%, at least 99%, such as 100% identity to any one of the mature parts of the enzyme sequences mentioned above.

Glucoamylases may in an embodiment be added to the saccharification and/or fermentation in an amount of 0.0001-20 AGU/g DS, preferably 0.001-10 AGU/g DS, especially between 001-5 AGU/g DS, such as 0.1-2 AGU/g DS.

Commercially available compositions comprising glucoamylase include AMG 200L; AMG 300 L; SAN™ SUPER, SAN™ EXTRA L, SPIRIZYME™ PLUS, SPIRIZYME™ FUEL, SPIRIZYME™ B4U, SPIRIZYME™ ULTRA, SPIRIZYME™ EXCEL, SPIRIZYME™ ACHIEVE and AMG™ E (from Novozymes A/S); OPTIDEX™ 300, GC480, GC417 (from Genencor Int.); AMIGASE™ and AMIGASE™ PLUS (from DSM); G-ZYME™ G900, G-ZYME™ and G990 ZR (from Danisco US).

Maltogenic Amylase

The carbohydrate-source generating enzyme present and/or added during saccharification and/or fermentation may also be a maltogenic alpha-amylase. A "maltogenic alpha-amylase" (glucan 1,4-alpha-maltohydrolase, E.C. 3.2.1.133) is able to hydrolyze amylose and amylopectin to maltose in the alpha-configuration. A maltogenic amylase from *Bacillus stearothermophilus* strain NCIB 11837 is commercially available from Novozymes A/S. Maltogenic alpha-amylases are described in U.S. Pat. Nos. 4,598,048, 4,604,355 and 6,162,628, which are hereby incorporated by reference. The maltogenic amylase may in a preferred embodiment be added in an amount of 0.05-5 mg total protein/gram DS or 0.05-5 MANU/g DS.

Cellulase or Cellulolytic Enzyme Composition Present and/or Added during Saccharification and/or Fermentation or SSF In a preferred embodiment of the invention a cellulase or cellulolytic enzyme composition is present and/or added in saccharification in step ii) and/or fermentation in step iii) or SSF.

The cellulase or cellulolytic enzyme composition may comprise one or more cellulolytic enzymes. The cellulase or cellulolytic enzyme composition may be of any origin. In a preferred embodiment the cellulase or cellulolytic enzyme composition comprises cellulolytic enzymes of fungal origin. In an embodiment the cellulase or cellulolytic enzyme composition is derived from a strain of *Trichoderma*, such as *Trichoderma reesei*; or a strain of *Humicola*, such as *Humicola insolens*: or a strain of *Chrysosporium*, such as *Chrysosporium lucknowense*; or a strain of *Penicillium*, such as *Penicillium decumbens*. In a preferred embodiment the cellulolytic enzyme composition is derived from a strain of *Trichoderma reesei*. The cellulase may be a beta-glucosidase, a cellobiohydrolase, and an endoglucanase or a combination thereof. The cellulolytic enzyme composition may comprise a beta-glucosidase, a cellobiohydrolase, and an endoglucanase.

In an embodiment the cellulase or cellulolytic enzyme composition comprising one or more polypeptides selected from the group consisting of:
  beta-glucosidase;
  cellobiohydrolase I;
  cellobiohydrolase II;
  or a mixture thereof.

In a preferred embodiment the cellulase or cellulolytic enzyme composition further comprises a GH61 polypeptide having cellulolytic enhancing activity. Cellulolytic enhancing activity is defined and determined as described in WO 2011/041397 (incorporated by reference).

The term "GH61 polypeptide having cellulolytic enhancing activity" means a GH61 polypeptide that enhances the hydrolysis of a cellulosic material by enzymes having cellulolytic activity. For purposes of the present invention, cellulolytic enhancing activity may be determined by measuring the increase in reducing sugars or the increase of the total of cellobiose and glucose from hydrolysis of a cellulosic material by cellulolytic enzyme under the following conditions: 1-50 mg of total protein/g of cellulose in PCS (Pretreated Corn Stover), wherein total protein is comprised of 50-99.5% w/w cellulolytic enzyme protein and 0.5-50% w/w protein of a GH61 polypeptide having cellulolytic enhancing activity for 1-7 days at 50° C. compared to a control hydrolysis with equal total protein loading without cellulolytic enhancing activity (1-50 mg of cellulolytic protein/g of cellulose in PCS). In a preferred aspect, a mixture of CELLUCLAST™ 1.5 L (Novozymes A/S, Bagsværd, Denmark) in the presence of 2-3% of total protein weight *Aspergillus oryzae* beta-glucosidase (recombinantly produced in *Aspergillus oryzae* according to WO 02/095014) or 2-3% of total protein weight *Aspergillus fumigatus* beta-glucosidase (recombinantly produced in *Aspergillus oryzae* as described in WO 2002/095014) of cellulase protein loading is used as the source of the cellulolytic activity.

The cellulolytic enzyme composition may comprise a beta-glucosidase, preferably one derived from a strain of the genus *Aspergillus*, such as *Aspergillus oryzae*, such as the one disclosed in WO 2002/095014 or the fusion protein having beta-glucosidase activity disclosed in WO 2008/057637 (see SEQ ID NOs: 74 or 76), or *Aspergillus fumigatus*, such as one disclosed in SEQ ID NO: 2 in WO 2005/047499 or SEQ ID NO: 29 herein; or an *Aspergillus fumigatus* beta-glucosidase variant disclosed in WO 2012/044915; or a strain of the genus a strain *Penicillium*, such as a strain of the *Penicillium brasilianum* disclosed in WO 2007/019442, or a strain of the genus *Trichoderma*, such as a strain of *Trichoderma reesei*.

In an embodiment the beta-glucosidase is from a strain of *Aspergillus*, such as a strain of *Aspergillus fumigatus*, such as *Aspergillus fumigatus* beta-glucosidase (SEQ ID NO: 29 herein), or a variant thereof, which variant comprises one or more substitutions selected from the group consisting of L89M, G91L, F100D, I140V, I186V, S283G, N456E, and F512Y; such as a variant thereof with the following substitutions:
  F100D+S283G+N456E+F512Y;
  L89M+G91L+I186V+I140V;
  I186V+L89M+I140V+F100D+S283G+N456E+F512Y
(using SEQ ID NO: 29 herein for numbering).

The parent beta-glucosidase may have at least 60% identity, such as at least 70%, such as at least 80%, such as at least 90%, such as at least 95%, such as at least 96%, such as at least 97%, such as at least 98%, such as at least 99%, such as 100% identity to the mature polypeptide of SEQ ID NO: 29 herein.

In case the beta-glucosidase is a beta-glucosidase variant it may have at least 60% identity, such as at least 70%, such as at least 80%, such as at least 90%, such as at least 95%, such as at least 96%, such as at least 97%, such as at least 98%, such as at least 99%, but less than 100% identity to the mature polypeptide of SEQ ID NO: 29 herein.

In case the cellulolytic enzyme composition may comprise a GH61 polypeptide, it may be one derived from the genus *Thermoascus*, such as a strain of *Thermoascus aurantiacus*, such as the one described in WO 2005/074656 as SEQ ID NO: 2 or SEQ ID NO: 30 herein; or one derived from the genus *Thielavia*, such as a strain of *Thielavia terrestris*, such as the one described in WO 2005/074647 as SEQ ID NO: 7 and SEQ ID NO: 8; or one derived from a strain of *Aspergillus*, such as a strain of *Aspergillus fumigatus*, such as the one described in WO 2010/138754 as SEQ ID NO: 1 and SEQ ID NO: 2; or one derived from a strain derived from *Penicillium*, such as a strain of *Penicillium emersonii*, such as the one disclosed in WO 2011/041397 as SEQ ID NO: 2 or SEQ ID NO: 31 herein.

In a preferred embodiment the GH61 polypeptide, such as one derived from a strain of *Penicillium*, preferably a strain of *Penicillium emersonii*, is selected from the group consisting of:
(i) a GH61 polypeptide comprising the mature polypeptide of SEQ ID NO: 31 herein;
(ii) a GH61 polypeptide comprising an amino acid sequence having at least 60%, such as at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 31 herein.

In an embodiment the cellulolytic enzyme composition comprises a cellobiohydrolase I (CBH I), such as one derived from a strain of the genus *Aspergillus*, such as a strain of *Aspergillus fumigatus*, such as the Cel7a CBH I disclosed in SEQ ID NO: 6 in WO 2011/057140 or SEQ ID NO: 32 herein, or a strain of the genus *Trichoderma*, such as a strain of *Trichoderma reesei*.

In a preferred embodiment the cellobiohydrolase I, such as one derived from a strain of *Aspergillus*, preferably a strain of *Aspergillus fumigatus*, is selected from the group consisting of:
(i) a cellobiohydrolase I comprising the mature polypeptide of SEQ ID NO: 32 herein;
(ii) a cellobiohydrolase I comprising an amino acid sequence having at least 60%, such as at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 32 herein.

In an embodiment the cellulolytic enzyme composition comprises a cellobiohydrolase II (CBH II), such as one derived from a strain of the genus *Aspergillus*, such as a strain of *Aspergillus fumigatus*; such as the one disclosed as SEQ ID NO: 33 herein or a strain of the genus *Trichoderma*, such as *Trichoderma reesei*, or a strain of the genus *Thielavia*, such as a strain of *Thielavia terrestris*, such as cellobiohydrolase II CEL6A from *Thielavia terrestris*.

In a preferred embodiment cellobiohydrolase II, such as one derived from a strain of *Aspergillus*, preferably a strain of *Aspergillus fumigatus*, is selected from the group consisting of:
(i) a cellobiohydrolase II comprising the mature polypeptide of SEQ ID NO: 33 herein.
(ii) a cellobiohydrolase II comprising an amino acid sequence having at least 60%, such as at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 33 herein.

In an embodiment the cellulolytic enzyme composition comprises a GH61 polypeptide having cellulolytic enhancing activity and a beta-glucosidase.

In an embodiment the cellulolytic enzyme composition comprises a GH61 polypeptide having cellulolytic enhancing activity derived from a strain of *Penicillium*, such as a strain of *Penicillium emersonii*, such as the one disclosed as SEQ ID NO: 2 in WO 2011/041397 or SEQ ID NO: 31 herein, and a beta-glucosidase.

In an embodiment the cellulolytic enzyme composition comprises a GH61 polypeptide having cellulolytic enhancing activity, a beta-glucosidase, and a CBH I.

In an embodiment the cellulolytic enzyme composition comprises a GH61 polypeptide having cellulolytic enhancing activity derived from a strain of *Penicillium*, such as a strain of *Penicillium emersonii*, such as the one disclosed as SEQ ID NO: 2 in WO 2011/041397 or SEQ ID NO: 31 herein, a beta-glucosidase, and a CBHI.

In an embodiment the cellulolytic enzyme composition comprises a GH61 polypeptide having cellulolytic enhancing activity, a beta-glucosidase, a CBHI, and a CBHII.

In an embodiment the cellulolytic enzyme composition comprises a GH61 polypeptide having cellulolytic enhancing activity derived from a strain of *Penicillium*, such as a strain of *Penicillium emersonii*, such as the one disclosed as SEQ ID NO: 2 in WO 2011/041397 or SEQ ID NO: 31 herein, a beta-glucosidase, a CBHI, and a CBHIII.

In an embodiment the cellulolytic enzyme composition is a *Trichoderma reesei* cellulolytic enzyme composition, further comprising *Thermoascus aurantiacus* GH61A polypeptide (SEQ ID NO: 2 in WO 2005/074656 or SEQ ID NO: 30 herein), and *Aspergillus oryzae* beta-glucosidase fusion protein (WO 2008/057637).

In an embodiment the cellulolytic enzyme composition is a *Trichoderma reesei* cellulolytic enzyme composition, further comprising *Thermoascus aurantiacus* GH61A polypeptide having cellulolytic enhancing activity (SEQ ID NO: 2 in WO 2005/074656 or SEQ ID NO: 30 herein) and *Aspergillus fumigatus* beta-glucosidase (SEQ ID NO: 2 of WO 2005/047499 or SEQ ID NO: 29 herein).

In an embodiment the cellulolytic enzyme composition is a *Trichoderma reesei* cellulolytic enzyme composition further comprising *Penicillium emersonii* GH61A polypeptide disclosed as SEQ ID NO: 2 in WO 2011/041397 or SEQ ID NO: 31 herein, and *Aspergillus fumigatus* beta-glucosidase disclosed as SEQ ID NO: 2 in WO 2005/047499 or SEQ ID NO: 29 herein, or a variant thereof, which variant has one of, preferably all of, the following substitutions: F100D, S283G, N456E, F512Y.

In an embodiment the cellulolytic enzyme composition comprises one or more of the following components:
(i) an *Aspergillus fumigatus* cellobiohydrolase I;
(ii) an *Aspergillus fumigatus* cellobiohydrolase II;
(iii) an *Aspergillus fumigatus* beta-glucosidase or variant thereof.

In an embodiment the *Aspergillus fumigatus* beta-glucosidase (SEQ ID NO: 29 herein), comprises one or more substitutions selected from the group consisting of L89M, G91L, F100D, I140V, I186V, S283G, N456E, and F512Y; such as a variant thereof, with the following substitutions:
F100D+S283G+N456E+F512Y;
L89M+G91L+I186V+I140V; or
I186V+L89M+G91L+I140V+F100D+S283G+N456E+F512Y.

In an embodiment the cellulolytic enzyme composition further comprises the *Penicillium* sp. GH61 polypeptide shown in SEQ ID NO: 31 herein; or a GH61 polypeptide comprising an amino acid sequence having at least 60%, such as at least 70%, e.g., at least 75%, at least 80%, at least 85%, at least 90%, at least 91%, at least 92%, at least 93%, at least 94%, at least 95%, at least 96%, at least 97%, at least 98%, or at least 99%, such as 100% identity to the mature polypeptide of SEQ ID NO: 31 herein.

In an embodiment the cellulolytic enzyme composition comprising the following components:
(i) *Aspergillus fumigatus* cellobiohydrolase I shown in SEQ ID NO: 32 herein;
(ii) *Aspergillus fumigatus* cellobiohydrolase II shown in SEQ ID NO: 33 herein;
(iii) a variant of *Aspergillus fumigatus* beta-glucosidase shown in SEQ ID NO: 29 with the following substitutions: F100D+S283G+N456E+F512Y; and
(iv) *Penicillium* sp. GH61 polypeptide shown in SEQ ID NO: 31 herein.

In an embodiment cellulolytic enzyme composition is dosed (i.e, during saccharification in step ii) and/or fermentation in step iii) or SSF) from 0.0001-3 mg EP/g DS, preferably 0.0005-2 mg EP/g DS, preferably 0.001-1 mg/g DS, more preferred from 0.005-0.5 mg EP/g DS, even more preferred 0.01-0.1 mg EP/g DS.

Examples of Preferred Processes of the Invention

In a preferred embodiment the invention relates to a process for producing fermentation products from starch-containing material comprising the steps of:

i) liquefying the starch-containing material at a pH in the range between from above 4.0-6.5 at a temperature in the range from 70-100° C. using:

an alpha-amylase derived from *Bacillus stearothermophilus;* a hemicellulase, preferably xylanase, having a Melting Point (DSC) above 80° C.

an optional endoglucanase having a Melting Point (DSC) above 70° C.;

ii) saccharifying using a glucoamylase enzyme;

iii) fermenting using a fermenting organism.

In a preferred embodiment the process of the invention comprises the steps of:

i) liquefying the starch-containing material at a pH in the range between from above 4.5-6.2 at a temperature above the initial gelatinization temperature using:

an alpha-amylase, preferably derived from *Bacillus stearothermophilus*, having a T½ (min) at pH 4.5, 85° C., 0.12 mM CaCl$_2$ of at least 10;

a hemicellulase, preferably xylanase, having a Melting Point (DSC) above 80° C.;

an optional endoglucanase having a Melting Point (DSC) above 70° C.;

ii) saccharifying using a glucoamylase enzyme;

iii) fermenting using a fermenting organism.

In a preferred embodiment the process of the invention comprises the steps of:

i) liquefying the starch-containing material at a pH in the range between from above 4.0-6.5 at a temperature between 70-100° C.:

a bacterial alpha-amylase, preferably derived from *Bacillus stearothermophilus*, having a T½ (min) at pH 4.5, 85° C., 0.12 mM CaCl$_2$ of at least 10;

a hemicellulase, preferably xylanase, having a Melting Point (DSC) above 80° C.; —an optional endoglucanase having a Melting Point (DSC), between 70° C. and 95° C.;

optionally a protease, preferably derived from *Pyrococcus furiosus* or *Thermoascus aurantiacus*, having a thermostability value of more than 20% determined as Relative Activity at 80° C./70° C.;

ii) saccharifying using a glucoamylase enzyme;

iii) fermenting using a fermenting organism.

In a preferred embodiment the process of the invention comprises the steps of:

i) liquefying the starch-containing material at a pH in the range between from above 4.0-6.5 at a temperature above the initial gelatinization temperature using:

an alpha-amylase shown in SEQ ID NO: 1 having a double deletion in positions R179+G180 or I181+G182, and optional substitution N193F; and optionally further one of the following set of substitutions:

E129V+K177L+R179E;

V59A+Q89R+E129V+K177L+R179E+H208Y+K220P+N224L+Q254S;

E129V+K177L+R179E+K220P+N224L+S242Q+Q254S;

V59A+Q89R+E129V+K177L+R179E+Q254S+M284V (using SEQ ID NO: 1 herein for numbering);

a hemicellulase, preferably xylanase, having a Melting Point (DSC) above 80° C.; such as an xylanase having at least 60%, such as at least 70%, such as at least 75% identity, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, such as 100% identity to the mature part of the polypeptide of SEQ ID NOs: 3, 4, 5, 8 and 34 herein; preferably SEQ ID NO: 5 herein;

an optional endoglucanase having a Melting Point (DSC), between 70° C. and 95° C.; such as an endoglucanase having at least 60%, such as at least 70%, such as at least 75% identity, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, such as 100% to the mature part of the any of the polypeptides shown in SEQ ID NOs: 9, 35, 36, 37 or 38 herein;

optionally a protease having a thermostability value of more than 20% determined as Relative Activity at 80° C./70° C. derived from *Pyrococcus furiosus* and/or *Thermoascus aurantiacus;* optionally a *Penicillium oxalicum* glucoamylase in SEQ ID NO: 14 herein, preferably having substitutions selected from the group of:

K79V;

K79V+P11F+T65A+Q327F; or

K79V+P2N+P4S+P11F+T65A+Q327F; (using SEQ ID NO: 14 for numbering);

ii) saccharifying using a glucoamylase enzyme;

iii) fermenting using a fermenting organism.

In a preferred embodiment the process of the invention comprises the steps of:

i) liquefying the starch-containing material at a pH in the range between from above 4.0-6.5 at a temperature between 70-100° C. using:

an alpha-amylase derived from *Bacillus stearothermophilus* having a double deletion in positions I181+G182, and optional substitution N193F; and optionally further one of the following set of substitutions:

V59A+Q89R+E129V+K177L+R179E+H208Y+K220P+N224L+Q254S: or

V59A+Q89R+E129V+K177L+R179E+Q254S+M284V (using SEQ ID NO: 1 herein (using SEQ ID NO: 1 herein for numbering);

a hemicellulase, preferably xylanase, having a Melting Point (DSC) above 80° C.;

such as an xylanase having at least 60%, such as at least 70%, such as at least 75% identity, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, such as 100% identity to the mature part of the polypeptide of SEQ ID NOs: 3, 4, 5, 8 and 34 herein; preferably SEQ ID NO: 5 herein an optional endoglucanase having a Melting Point (DSC), between 70° C. and 95° C.; preferably having at least 90% identity to the mature part of the polypeptide of SEQ ID NO: 9 herein;

a optional protease having a thermostability value of more than 20% determined as Relative Activity at 80° C./70° C. derived from *Pyrococcus furiosus* and/or *Thermoascus aurantiacus*; and optionally a *Penicillium oxalicum* glucoamylase in SEQ ID NO: 14 herein, preferably having substitutions selected from the group of:
K79V; or
K79V+P11F+T65A+Q327F; or
K79V+P2N+P4S+P11F+T65A+Q327F (using SEQ ID NO: 14 herein for numbering);

ii) saccharifying using a glucoamylase enzyme;
iii) fermenting using a fermenting organism.

In a preferred embodiment the process of the invention comprises the steps of:

i) liquefying the starch-containing material at a pH in the range between from above 4.0-6.5 at a temperature between 70-100° C. using:

an alpha-amylase derived from *Bacillus stearothermophilus* having a double deletion in positions I181+G182, and optional substitution N193F; and optionally further one of the following set of substitutions:
E129V+K177L+R179E;
V59A+Q89R+E129V+K177L+R179E+H208Y+K220P+N224L+Q254S;
V59A+Q89R+E129V+K177L+R179E+Q254S+M284V;
E129V+K177L+R179E+K220P+N224L+S242Q+Q254S (using SEQ ID NO: 1 herein for numbering);

a hemicellulase, preferably xylanase, having a Melting Point (DSC) above 80° C.;

an optional endoglucanase having a Melting Point (DSC), between 70° C. and 95° C.; preferably having at least 90% identity to the mature part of the polypeptide of SEQ ID NO: 9 herein;

a protease having a thermostability value of more than 20% determined as Relative Activity at 80° C./70° C. derived from *Pyrococcus furiosus*;

a *Penicillium oxalicum* glucoamylase in SEQ ID NO: 14 herein, preferably having substitutions selected from the group of:
K79V;
K79V+P11F+T65A+Q327F; or
K79V+P2N+P4S+P11F+T65A+Q327F; or
K79V+P11F+D26C+K33C+T65A+Q327F; or
K79V+P2N+P4S+P11F+T65A+Q327W+E501V+Y504T; or
K79V+P2N+P4S+P11F+T65A+Q327F+E501V+Y504T; or
K79V+P11F+T65A+Q327W+E501V+Y504T (using SEQ ID NO: 14 herein for numbering);

ii) saccharifying using a glucoamylase enzyme;
iii) fermenting using a fermenting organism.

In a preferred embodiment a cellulase or cellulolytic enzyme composition is present and/or added during fermentation or simultaneous saccharification and fermentation.

In a preferred embodiment a cellulase or cellulolytic enzyme composition derived from *Trichoderma reesei* is present and/or added during fermentation or simultaneous saccharification and fermentation (SSF).

In a preferred embodiment a cellulase or cellulolytic enzyme composition and a glucoamylase are present and/or added during fermentation or simultaneous saccharification and fermentation.

In an embodiment the cellulase or cellulolytic enzyme composition is derived from *Trichoderma reesei, Humicola insolens, Chrysosporium lucknowense* or *Penicillium decumbens*.

A Composition of the Invention

A composition of the invention comprises an alpha-amylase, such as a thermostable alpha-amylase, and a hemicellulase, preferably xylanase, having a Melting Point (DSC) above 80° C.; an optional endoglucanase having a Melting Point (DSC) above 70° C.; an optional protease, such as a thermostable protease. The composition may also further comprise a carbohydrate-source generating enzyme, in particular a glucoamylase, optionally a pullulanase and optionally a phytase too.

Therefore, in this aspect the invention relates to composition comprising:
an alpha-amylase;
a hemicellulase, preferably xylanase, having a Melting Point (DSC) above 80° C.
an optional endoglucanase having a Melting Point (DSC) above 70° C.;
optionally a protease;
optionally a carbohydrate-source generating enzyme.

Alpha-amylase: The alpha-amylase may be any alpha-amylase. In a preferred embodiment the alpha-amylase is a bacterial alpha-amylases, such as alpha-amylases derived from the genus *Bacillus*, such as *Bacillus stearomthermphilus*, preferably the one shown in SEQ ID NO: 1 herein.

The alpha-amylase may be a thermostable alpha-amylase. The thermostable alpha-amylase may have a T½ (min) at pH 4.5, 85° C., 0.12 mM $CaCl_2$) of at least 10, such as at least 15, such as at least 20, such as at least 25, such as at least 30, such as at least 40, such as at least 50, such as at least 60, such as between 10-70, such as between 15-70, such as between 20-70, such as between 25-70, such as between 30-70, such as between 40-70, such as between 50-70, such as between 60-70.

In an embodiment the alpha-amylase is selected from the group of *Bacillus stearomthermphilus* alpha-amylase variants, in particular truncated to be 491 amino acids long, such as from 480 to 495 amino acids long, with mutations selected from the group of:
I181*+G182*;
I181*+G182*+N193F;
preferably
I181*+G182*+E129V+K177L+R179E;
I181*+G182*+N193F+E129V+K177L+R179E;
I181*+G182*+N193F+V59A+Q89R+E129V+K177L+R179E+H208Y+K220P+N224L+Q254S;
I181*+G182*+N193F+V59A Q89R+E129V+K177L+R179E+Q254S+M284V; and
I181*+G182*+N193F+E129V+K177L+R179E+K220P+N224L+S242Q+Q254S (using SEQ ID NO: 1 herein for numbering).

It should be understood that these alpha-amylases are only specific examples. Any alpha-amylase disclosed above in the "Alpha-Amylase Present and/or Added During Liquefaction"-section above may be used as the alpha-amylase component in a composition of the invention.

Endocilucanase: According to the invention an optional endoglucanase component may be comprised in the composition. It may be any endoglucanase having a Melting Point (DSC) above 70° C., such as above 75° C., in particular above 80° C., such as between 70° C. and 95° C., determined using the "Differential Scanning calorimetry (DSC) Assay" described in the "Materials & Methods"—section below.

In an embodiment the endoglucanase has a Melting Point (DSC) above 72° C., such as above 74° C., such as above 76° C., such as above 78° C., such as above 80° C., such as above 82° C. such as above 84° C., such as above 86° C., such as above 88° C., such as between 70° C. and 95° C., such as between 76° C. and 94° C., such as between 78° C. and 93° C., such as between 80° C. and 92° C., such as between 82° C. and 91° C., such as between 84° C. and 90° C.

In a preferred embodiment the endoglucanase used in a process of the invention comprised in a composition of the invention is a Glycoside Hydrolase Family 5 endoglucnase or GH5 endoglucanase (see the CAZy database on the "www.cazy.org" webpage. In an embodiment the GH5 endoglocianase is from family EG II, such as the *Talaromyces leycettanus* endoglucanase shown in SEQ ID NO: 9 herein; *Penicillium capsulatum* endoglucanase show in SEQ ID NO: 35 herein, and *Trichophaea saccata* endoglucanase shown in SEQ ID NO: 36 herein.

In an embodiment the endoglucanase is a family GH45 endoglucanase. In an embodiment the GH45 endoglocianase is from family EG V, such as the *Sordana fimicola* shown in SEQ ID NO: 38 herein or *Thielavia terrestris* endoglucnase shown in SEQ ID NO: 37 herein.

In an embodiment the endoglucanase has at least 60%, such as at least 70%, such as at least 75% identity, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, such as 100% identity to the mature part of the polypeptide of SEQ ID NO: 9 herein. In an embodiment the endoglucanase is derived from a strain of the genus *Talaromyces*, such as a strain of *Talaromyces leycettanus*.

In an embodiment the endoglucanase has at least 60%, such as at least 70%, such as at least 75% identity, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, such as 100% identity to the mature part of the polypeptide of SEQ ID NO: 35 herein, preferably derived from a strain of the genus *Penicillium*, such as a strain of *Penicillium capsulatum*.

In an embodiment the endoglucanase has at least 60%, such as at least 70%, such as at least 75% identity, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, such as 100% identity to the mature part of the polypeptide of SEQ ID NO: 36 herein, preferably derived from a strain of the genus *Trichophaea*, such as a strain of *Trichophaea saccata*.

In an embodiment the endoglucanase has at least 60%, such as at least 70%, such as at least 75% identity, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, such as 100% identity to the mature part of the polypeptide of SEQ ID NO: 37 herein, preferably derived from a strain of the genus *Thielavia*, such as a strain of *Thielavia terrestris*.

In an embodiment the endoglucanase has at least 60%, such as at least 70%, such as at least 75% identity, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, such as 100% identity to the mature part of the polypeptide of SEQ ID NO: 38 herein, preferably derived from a strain of the genus *Sordaria*, such as a strain of *Sordaria fimicola*.

It should be understood that these endoglucanases are only specific examples. Any endoglucanase disclosed above in the "Thermostable Endoglucanase Present and/or Added During Liquefaction"-section above may be used as the optional endoglucoanase component in a composition of the invention.

In an especially preferred embodiment the endoglucanase (EG) has at least 90% identity to the mature part of the polypeptide of SEQ ID NO: 9 herein derived from a strain of *Talaromyces leycettanus* having a Melting Point (DSC) above 80° C.

Protease: A composition of the invention may optionally comprise a protease, such as a thermosyable protease. There is no limitation on the origin of the protease component as long as it fulfills the thermostability properties defined herein.

In an embodiment the protease is of fungal origin. In an embodiment the protease is a metallo protease. In an embodiment the protease is derived from *Thermoascus aurantiacus* shown in SEQ ID NO: 2 herein.

In a preferred embodiment the protease is a variant of the *Thermoascus aurantiacus* protease mentioned above having a thermostability value of more than 20% determined as Relative Activity at 80° C./70° C. determined as described in Example 2.

In a specific preferred embodiment the protease is a variant of the metallo protease derived from *Thermoascus aurantiacus* disclosed as the mature part of SEQ ID NO: 2 disclosed in WO 2003/048353 or the mature part of SEQ ID NO: 1 in WO 2010/008841 or SEQ ID NO: 2 herein with mutations selected from the group of:
D79L+S87P+A112P+D142L;
D79L+S87P+D142L; and
A27K+D79L+Y82F+S87G+D104P+A112P+A126V+D142L.

In another embodiment the protease is a bacterial protease. In another embodiment the protease is a serine protease. In a preferred embodiment the protease is derived from a strain of *Pyrococcus furiosus*, such as the one shown in SEQ ID NO: 1 in U.S. Pat. No. 6,358,726 or SEQ ID NO: 13 herein.

It should be understood that these proteases are only examples. Any protease disclosed above in the "Protease Present and/or Added During Liquefaction" section above may be used as the protease component in a composition of the invention.

Carbohydrate-source generating enzymes: A composition of the invention may optionally further comprise a carbohydrate-source generating enzyme, in particular a glucoamylase, such as a thermostable glucoamylase which has a heat stability at 85° C., pH 5.3, of at least 30%, preferably at least 35%.

Said carbohydrate-source generating enzyme may be a thermostable glucoamylase having a Relative Activity heat stability at 85° C. of at least 20%, at least 30%, preferably at least 35% determined as described in Example 4 (Heat stability).

In an embodiment the carbohydrate-source generating enzyme is a glucoamylase having a relative activity pH optimum at pH 5.0 of at least 90%, preferably at least 95%, preferably at least 97%, such as 100% determined as described in Example 4 (pH optimum).

In an embodiment the carbohydrate-source generating enzyme is a glucoamylase having a pH stability at pH 5.0 of at least at least 80%, at least 85%, at least 90% determined as described in Example 4 (pH stability).

In a preferred embodiment the carbohydrate-source generating enzyme is a thermostable glucoamylase, preferably of fungal origin, preferably a filamentous fungi, such as from a strain of the genus *Penicillium*, especially a strain of *Penicillium oxalicum* disclosed as SEQ ID NO: 2 in WO 2011/127802 (which is hereby incorporated by reference), or a variant thereof, and shown in SEQ ID NO: 14 herein.

In an embodiment the glucoamylase, or a variant thereof, may have at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, such as 100% identity to the mature polypeptide shown in SEQ ID NO: 2 in WO 2011/127802 or SEQ ID NO: 14 herein.

In a specific and preferred embodiment the carbohydrate-source generating enzyme is a variant of the *Penicillium oxalicum* glucoamylase disclosed as SEQ ID NO: 2 in WO 2011/127802 and shown in SEQ ID NO: 14 herein, having a K79V substitution (using the mature sequence shown in SEQ ID NO: 14 herein for numbering). The K79V glucoamylase variant has reduced sensitivity to protease degradation relative to the parent as disclosed in WO 2013/036526 (which is hereby incorporated by reference).

Examples of suitable thermostable *Penicillium oxalicum* glucoamylase variants are listed above and in Examples 17 and 18 below.

In an embodiment the carbohydrate-source generating enzyme, such as glucoamyase, such as *Penicillium oxalicum* glucoamylase, has pullulanase side-activity.

It should be understood that these carbohydrate-source generating enzymes, in particular glucoamylases, are only examples. Any carbohydrate-source generating enzyme disclosed above in the "Carbohydrate-source generating enzyme Present and/or Added During Liquefaction" section above may be used as component in a composition of the invention.

In a preferred embodiment the the carbohydrate-source generating enzyme is the *Penicillium oxalicum* glucoamylase shown in SEQ ID NO: 14 herein or a sequence having at least 90% identity thereto further comprising a K79V substitution.

Pullulanase: A composition of the invention may optionally further comprise a pullulanase. The pullulanase may be of any origin.

In an embodiment the pullulanase is of bacterial origin. In an embodiment the pullulanase is derived from a strain of *Bacillus* sp.

In an embodiment the pullulanase is a family GH57 pullulanase. In a preferred embodiment the pullulanase includes an X47 domain as disclosed in WO 2011/087836 (which is hereby incorporated by reference).

Specifically the pullulanase may be derived from a strain from the genus *Thermococcus*, including *Thermococcus litoralis* and *Thermococcus hydrothermalis* or a hybrid thereof.

The pullulanase may be *Thermococcus hydrothermalis* pullulanase shown in SEQ ID NO: 11 herein truncated at site X4 or a *Thermococcus hydrothermalis/T. litoralis* hybrid enzyme (SEQ ID NO: 12 herein) with truncation site X4 as disclosed in WO 2011/087836.

The another embodiment the pullulanase is one comprising an X46 domain disclosed in WO 2011/076123 (Novozymes).

It should be understood that these pullulanases are only specific examples. Any pullulanase disclosed above in the "Pullulanase Present and/or Added During Liquefaction"-section above may be used as the optional pullulanase component in a composition of the invention.

Phytase: A composition of the invention may optionally further comprise a phytase. The phytase may be of any origin.

In an embodiment the phytase is of bacterial origin. In an embodiment the phytase is derived from a strain of from *Buttiauxella*, such as *Buttiauxella gaviniae*, such as the one disclosed as SEQ ID NO: 2 (amino acids 1-33 are expected signal peptide) in WO 2008/092901; or *Buttiauxella agrestis*, such as the one shown as SEQ ID NO: 4 (amino acids −9 to −1 are expected to be a part of the signal peptide) in WO 2008/092901; or *Buttiauxella noackies*, such as the one shown as SEQ ID NO: 6 in WO 2008/092901.

In another embodiment the phytase is derived from a strain of *Citrobacter*, such as a strain of *Citrobacter braakii*, such as ones disclosed as SEQ ID NOs: 2 or 4 in WO 2006/037328 (hereby incorporated by reference).

It should be understood that these phytases are only specific examples. Any phytase disclosed above in the "Phytase Present and/or Added During Liquefaction"-section above may be used as the optional pullulanase component in a composition of the invention.

In a preferred embodiment the phytase is derived from a strain of *Buttiauxella*.

Examples of Preferred Embodiments of the Composition of the Invention

In a preferred embodiment the composition of the invention comprises
- an alpha-amylase derived from *Bacillus stearothermophilus*;
- a hemicellulase, preferably xylanase, having a Melting Point (DSC) above 80° C.;
- an optional endoglucanase having a Melting Point (DSC) above 70° C., such as between 70° C. and 95° C.;
- optionally a protease having a thermostability value of more than 20% determined as Relative Activity at 80° C./70° C. derived from *Pyrococcus furiosus* or *Thermoascus auranticus*; and
- optionally a glucoamylase, such as one derived from *Penicillium oxalicum*.

In another embodiment the composition of the invention comprises
- an alpha-amylase, preferably derived from *Bacillus stearothermophilus*; having a T½ (min) at pH 4.5, 85° C., 0.12 mM CaCl$_2$ of at least 10;
- a hemicellulase, preferably a xylanase, having a Melting Point (DSC) above 80° C.;
- an optional endoglucanase having a Melting Point (DSC) between 70° C. and 95° C.;
- an optional protease, preferably derived from *Pyrococcus furiosus* or *Thermoascus aurantiacus*, having a thermostability value of more than 20% determined as Relative Activity at 80° C./70° C.; and
- optionally a glucoamylase, e.g., derived from *Penicillium oxalicum*.

In another embodiment the composition of the invention comprises an alpha-amylase derived from *Bacillus stearothermophilus* having a double deletion in positions I181+G182, and optionally substitution N193F; and optionally further one of the following set of substitutions:

E129V+K177L+R179E;

V59A+Q89R+E129V+K177L+R179E+H208Y+K220P+N224L+Q254S;

V59A+Q89R+E129V+K177L+R179E+Q254S+M284V; and

E129V+K177L+R179E+K220P+N224L+S242Q+Q254S (using SEQ ID NO: 1 herein for numbering);

a hemicellulase having a Melting Point (DSC) above 80° C.;

an optional endoglucanase having a Melting Point (DSC) above 70° C.;

optionally a protease, preferably derived from *Pyrococcus furiosus* and/or *Thermoascus aurantiacus*, having a thermostability value of more than 20% determined as Relative Activity at 80° C./70° C.; and optionally a *Penicillium oxalicum* glucoamylase in SEQ ID NO: 14 having substitutions selected from the group of:

K79V;

K79V+P11F+T65A+Q327F; or

K79V+P2N+P4S+P11F+T65A+Q327F; or

K79V+P11F+D26C+K33C+T65A+Q327F; or

K79V+P2N+P4S+P11F+T65A+Q327W+E501V+Y504T, or

K79V+P2N+P4S+P11F+T65A+Q327F+E501V+Y504T, or

K79V+P11F+T65A+Q327W+E501V+Y504T (using SEQ ID NO: 14 for numbering).

In an embodiment the *Bacillus stearothermophilus* alpha-amylase (SEQ ID NO: 1 herein), or a variant thereof, is the mature alpha-amylase or corresponding mature alpha-amylases having at least 80% identity, at least 90% identity, at least 95% identity at least 96% identity at least 97% identity at least 99% identity to the SEQ ID NO: 1 herein.

In an embodiment the hemicellulase, in particular xylanase, especially GH10 or GH11 xylanase has a Melting Point (DSC) above 82° C., such as above 84° C., such as above 86° C., such as above 88° C., such as above 88° C., such as above 90° C., such as above 92° C., such as above 94° C., such as above 96° C., such as above 98° C., such as above 100° C., such as between 80° C. and 110° C., such as between 82° C. and 110° C., such as between 84° C. and 110° C.

Examples of suitable hemicellulases, in particular xylanases, include the xylanase shown in SEQ ID NOs: 3 herein or SEQ ID NO: 34 herein derived from a strain of *Dictyogllomus thermophilum*; the xylanase shown in SEQ ID NO: 4 herein derived from a strain of *Rasomsonia byssochlamydoides*; the xylanase shown in SEQ ID NO: 5 herein derived from a strain of *Talaromyces leycettanus*; the xylanase shown in SEQ ID NO: 8 herein derived from a strain of *Aspergillus fumigatus* or a polypeptide having hemicellulase, preferably xylanase activity, having at least 60%, such as at least 70%, such as at least 75% identity, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, such as 100% identity to the mature part of the polypeptides of SEQ ID NOs: 3, 4, 5, 8 and 34 herein.

In an embodiment the optional endoglucoanase has a Melting Point (DSC) above 74° C., such as above 76° C., such as above 78° C., such as above 80° C., such as above 82° C., such as above 84° C., such as above 86° C., such as above 88° C., such as between 70° C. and 95° C., such as between 76° C. and 94° C., such as between 78° C. and 93° C., such as between 80° C. and 92° C., such as between 82° C. and 91° C., such as between 84° C. and 90° C.

In an embodiment the optional endoglucanase has at least 60%, such as at least 70%, such as at least 75% identity, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, such as 100% identity to the mature part of the polypeptide of SEQ ID NOs: 9, 35, 36, 37 or 38 herein.

In an embodiment the endoglucanase has at least 80% identity to the mature part of the polypeptide of SEQ ID NO: 9 herein.

In an embodiment the endoglucanase has at least 90% identity to the mature part of the polypeptide of SEQ ID NO: 9 herein having a Melting Point (DSC) above 70° C.

In an embodiment the *Pyrococcus furiosus* protease (SEQ ID NO: 13 herein) and/or *Thermoascus aurantiacus* protease (SEQ ID NO: 2 herein), or a variant thereof, is the mature protease or corresponding mature protease having at least 80% identity, at least 90% identity, at least 95% identity at least 96% identity at least 97% identity at least 99% identity to the SEQ ID NO: 2 herein or SEQ ID NO: 13 herein, respectively.

In an embodiment 1 the *Penicillium oxalicum* glucoamylase (SEQ ID NO: 14 herein), or a variant thereof, is the mature glucoamylase or corresponding mature glucoamylase having at least 80% identity, at least 90% identity, at least 95% identity at least 96% identity at least 97% identity at least 99% identity to the SEQ ID NO: 14 herein.

Further Aspects of the Invention

In a further aspect of the invention it relates to the use of a composition of the invention for liquefying a starch-containing material.

In a final aspect of the invention is relates to methods of producing liquefied starch, comprising liquefying a starch-containing material with a composition of the invention.

The invention is further summarized in the following paragraphs:

1. A process for producing fermentation products from starch-containing material comprising the steps of:

i) liquefying the starch-containing material at a temperature above the initial gelatinization temperature using:

an alpha-amylase;

a hemicellulase having a Melting Point (DSC) above 80° C.;

ii) saccharifying using a carbohydrate-source generating enzyme;

iii) fermenting using a fermenting organism.

2. The process of paragraph 1, wherein the hemicellulase is a xylanase, in particular a GH10 xylanase or a GH11 xylanase.

3. The process of paragraph 1 or 2, wherein the hemicellulase, in particular xylanase, especially GH10 or GH11 xylanase has a Melting Point (DSC) above 82° C., such as above 84° C., such as above 86° C., such as above 88° C., such as above 88° C., such as above 90° C., such as above 92° C., such as above 94° C., such as above 96° C., such as above 98° C., such as above 100° C., such as between 80° C. and 110° C., such as between 82° C. and 110° C., such as between 84° C. and 110° C.

4. The process of any of paragraphs 1-3, wherein the hemicellulase, in particular xylanase, especially GH10 or GH11 xylanase has at least 60%, such as at least 70%, such as at least 75%, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, such as 100% identity to the mature part of the polypeptide of SEQ ID NO: 3 herein (GH10) or SEQ ID NO: 34 herein (GH11), preferably derived from a strain of the genus *Dictyoglomus*, such as a strain of *Dictyogilomus thermophilum*.

5. The process any of paragraphs 1-3, wherein the hemicellulase, in particular xylanase, especially GH10 xylanase has at least 60%, such as at least 70%, such as at least 75% identity, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, such as 100% identity to the mature part of the polypeptide of SEQ ID NO: 4 herein, preferably derived from a strain of the genus *Rasamsonia*, such as a strain of *Rasomsonia byssochlamydoides*.

6. The process of any of paragraphs 1-3, wherein the hemicellulase, in particular xylanase, especially GH10 xylanase has at least 60%, such as at least 70%, such as at least 75% identity, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, such as 100% identity to the mature part of the polypeptide of SEQ ID NO: 5 herein, preferably derived from a strain of the genus *Talaromyces*, such as a strain of *Talaromyces leycettanus*.

7. The process of paragraphs 1 or 2, wherein the hemicellulase, in particular xylanase, especially GH10 xylanase has at least 60%, such as at least 70%, such as at least 75% identity, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, such as 100% identity to the mature part of the polypeptide of SEQ ID NO: 8 herein, preferably derived from a strain of the genus *Aspergillus*, such as a strain of *Aspergillus fumigatus*.

8. The process of any of paragraphs 1-7, wherein
an alpha-amylase;
a hemicellulase having a Melting Point (DSC) above 80° C., preferably above 85° C., especially above 90° C., in particular 95° C.;
an optional endoglucanase having Melting Point (DSC) above 70° C., preferably above 75° C., in particular above 80° C., especially above 85° C.; are present and/or added in liquefaction step i).

9. The process of any of paragraphs 1-8, further comprises, prior to the liquefaction step i), the steps of:
a) reducing the particle size of the starch-containing material, preferably by dry milling;
b) forming a slurry comprising the starch-containing material and water.

10. The process of any of paragraphs 1-9, wherein at least 50%, preferably at least 70%, more preferably at least 80%, especially at least 90% of the starch-containing material fit through a sieve with #6 screen.

11. The process of any of paragraphs 1-10, wherein the pH during liquefaction is between 4.0-6.5, such as 4.5-6.2, such as above 4.8-6.0, such as between 5.0-5.8.

12. The process of any of paragraphs 1-11, wherein the temperature during liquefaction is in the range from 70-100° C., such as between 70-95° C., such as between 75-90° C., preferably between 80-90° C., such as around 85° C.

13. The process of any of paragraphs 1-12, wherein a jet-cooking step is carried out before liquefaction in step i).

14. The process of paragraph 13, wherein the jet-cooking is carried out at a temperature between 95-160° C., such as between 110-145° C., preferably 120-140° C., such as 125-135° C., preferably around 130° C. for about 1-15 minutes, preferably for about 3-10 minutes, especially around about 5 minutes.

15. The process of any of paragraphs 1-14, wherein saccharification and fermentation is carried out sequentially or simultaneously.

16. The process of any of paragraphs 1-15, wherein saccharification is carried out at a temperature from 20-75° C., preferably from 40-70° C., such as around 60° C., and at a pH between 4 and 5.

17. The process of any of paragraphs 1-16, wherein fermentation or simultaneous saccharification and fermentation (SSF) is carried out at a temperature from 25° C. to 40° C., such as from 28° C. to 35° C., such as from 30° C. to 34° C., preferably around about 32° C., such as for 6 to 120 hours, in particular 24 to 96 hours.

18. The process of any of paragraphs 1-17, wherein the fermentation product is recovered after fermentation, such as by distillation.

19. The process of any of paragraphs 1-18, wherein the fermentation product is an alcohol, preferably ethanol, especially fuel ethanol, potable ethanol and/or industrial ethanol.

19. The process of any of paragraphs 1-18, wherein the starch-containing starting material is whole grains.

20. The process of any of paragraphs 1-19, wherein the starch-containing material is derived from corn, wheat, barley, rye, milo, sago, cassava, manioc, tapioca, sorghum, rice or potatoes.

21. The process of any of paragraphs 1-20, wherein the fermenting organism is yeast, preferably a strain of *Saccharomyces*, especially a strain of *Saccharomyces cerevisiae*.

23. The process of any of paragraphs 1-22, wherein the alpha-amylase is a bacterial alpha-amylase, in particular derived from the genus *Bacillus*, such as a strain of *Bacillus stearothermophilus*, in particular a variant of a *Bacillus stearothermophilus* alpha-amylase, such as the one shown in SEQ ID NO: 3 in WO 99/019467 or SEQ ID NO: 1 herein.

24. The process of paragraph 23, wherein the *Bacillus stearothermophilus* alpha-amylase or variant thereof is truncated, preferably to be around 491 amino acids long, such as from 480-495 amino acids long.

25. The process of any of paragraphs 23 or 24, wherein the *Bacillus stearothermophilus* alpha-amylase has a double deletion in positions I181+G182, and optionally a N193F substitution, or a double deletion in positions R179+G180 (using SEQ ID NO: 1 herein for numbering).

26. The process of any of paragraphs 23-25 wherein the *Bacillus stearothermophilus* alpha-amylase has a substitution in position S242, preferably a S242Q or a S242A substitution (using SEQ ID NO: 1 herein for numbering).

27. The process of any of paragraphs 23-26, wherein the *Bacillus stearothermophilus* alpha-amylase has a substitution in position E188, preferably E188P substitution (using SEQ ID NO: 1 herein for numbering).

28. The process of any of paragraphs 1-27, wherein the alpha-amylase has a T½ (min) at pH 4.5, 85° C., 0.12 mM CaCl₂) of at least 10, such as at least 15, such as at least 20, such as at least 25, such as at least 30, such as at least 40, such as at least 50, such as at least 60, such as between 10-70, such as between 15-70, such as between 20-70, such as between 25-70, such as between 30-70, such as between 40-70, such as between 50-70, such as between 60-70.

29. The process of any of paragraphs 1-28, wherein the alpha-amylase is selected from the group of *Bacillus stearothermophilus* alpha-amylase variants with the following mutations: I181*+G182*, and optionally N193F (using SEQ ID NO: 1 for numbering) and optionally further:

V59A + Q89R + G112D + E129V + K177L + R179E + K220P + N224L + Q254S;
V59A + Q89R + E129V + K177L + R179E + H208Y + K220P + N224L + Q254S;
V59A + Q89R + E129V + K177L + R179E + K220P + N224L + Q254S + D269E + D281N;
V59A + Q89R + E129V + K177L + R179E + K220P + N224L + Q254S + I270L;
V59A + Q89R + E129V + K177L + R179E + K220P + N224L + Q254S + H274K;
V59A + Q89R + E129V + K177L + R179E + K220P + N224L + Q254S + Y276F;
V59A + E129V + R157Y + K177L + R179E + K220P + N224L + S242Q + Q254S;
V59A + E129V + K177L + R179E + H208Y + K220P + N224L + S242Q + Q254S;
V59A + E129V + K177L + R179E + K220P + N224L + S242Q + Q254S;
V59A + E129V + K177L + R179E + K220P + N224L + S242Q + Q254S + H274K;
V59A + E129V + K177L + R179E + K220P + N224L + S242Q + Q254S +Y276F;
V59A + E129V + K177L + R179E + K220P + N224L + S242Q + Q254S + D281N;
V59A + E129V + K177L + R179E + K220P + N224L + S242Q + Q254S + M284T;
V59A + E129V + K177L + R179E + K220P + N224L + S242Q + Q254S + G416V;
V59A + E129V + K177L + R179E + K220P + N224L + Q254S;
V59A + E129V + K177L + R179E + K220P + N224L + Q254S + M284T;
A91L + M96I + E129V + K177L + R179E + K220P + N224L + S242Q + Q254S;
E129V + K177L + R179E;
E129V + K177L + R179E + K220P + N224L + S242Q + Q254S;
E129V + K177L + R179E + K220P + N224L + S242Q + Q254S + Y276F + L427M;
E129V + K177L + R179E + K220P + N224L + S242Q + Q254S + M284T;
E129V + K177L + R179E + K220P + N224L + S242Q + Q254S + N376* + I377*;
E129V + K177L + R179E + K220P + N224L + Q254S;
E129V + K177L + R179E + K220P + N224L + Q254S + M284T;
E129V + K177L + R179E + S242Q;
E129V + K177L + R179V + K220P + N224L + S242Q + Q254S;
K220P + N224L + S242Q + Q254S;
M284V;
V59A Q89R + E129V + K177L + R179E + Q254S + M284V.

30. The process of any of paragraphs 1-29, wherein the alpha-amylase is selected from the group of *Bacillus stearothermophilus* alpha-amylase variants:
I181*+G182*;
I181*+G182*+N193F;
preferably
I181*+G182*+E129V+K177L+R179E;
I181*+G182*+N193F+E129V+K177L+R179E;
I181*+G182*+N193F+V59A+Q89R+E129V+K177L+R179E+H208Y+K220P+N224L+Q254S
I181*+G182*+N193F+V59A Q89R+E129V+K177L+R179E+Q254S+M284V: and
I181*+G182*+N193F+E129V+K177L+R179E+K220P+N224L+S242Q+Q254S (using SEQ ID NO: 1 for numbering).

31. The process of any of paragraphs 1-30, further wherein a protease is present and/or added in liquefaction, wherein the protease has a thermostability value of more than 25% determined as Relative Activity at 80° C./70° C.

32. The process of any of paragraphs 1-31, wherein the protease has a thermostability of more than 30%, more than 40%, more than 50%, more than 60%, more than 70%, more than 80%, more than 90%, more than 100%, such as more than 105%, such as more than 110%, such as more than 115%, such as more than 120% determined as Relative Activity at 80° C./70° C.

33. The process of any of paragraphs 1-26, wherein the protease has a thermostability of between 20 and 50%, such as between 20 and 40%, such as 20 and 30% determined as Relative Activity at 80° C./70° C.

34. The process of any of paragraphs 1-33, wherein the protease has a thermostability between 50 and 115%, such as between 50 and 70%, such as between 50 and 60%, such as between 100 and 120%, such as between 105 and 115% determined as Relative Activity at 80° C./70° C. or wherein the protease has a thermostability of more than 10%, such as more than 12%, more than 14%, more than 16%, more than 18%, more than 20%, more than 30%, more than 40%, more that 50%, more than 60%, more than 70%, more than 80%, more than 90%, more than 100%, more than 110% determined as Relative Activity at 85° C./70° C.

35. The process of any of paragraphs 1-34, wherein the protease has thermostability of between 10 and 50%, such as between 10 and 30%, such as between 10 and 25% determined as Relative Activity at 85° C./70° C.

36. The process of any of paragraphs 1-35, wherein the protease has a themostability above 60%, such as above 90%, such as above 100%, such as above 110% at 85° C. as determined using the Zein-BCA assay.

37. The process of any of paragraphs 1-36, wherein the protease has a themostability between 60-120, such as between 70-120%, such as between 80-120%, such as between 90-120%, such as between 100-120%, such as 110-120% at 85° C. as determined using the Zein-BCA assay.

38. The process of any of paragraphs 1-37, wherein the protease is of fungal origin.

39. The process of any of paragraphs 1-38, wherein the protease is a variant of the metallo protease derived from a strain of the genus *Thermoascus*, preferably a strain of *Thermoascus aurantiacus*, especially *Thermoascus aurantiacus* CGMCC No. 0670, in particular the mature sequence shown in SEQ ID NO: 2.

40. The process of any of paragraphs 1-39, wherein the protease is a variant of the metallo protease disclosed as the mature part of SEQ ID NO: 2 disclosed in WO 2003/048353 or the mature part of SEQ ID NO: 1 in WO 2010/008841 or SEQ ID NO: 2 herein mutations selected from the group of:
S5*+D79L+S87P+A112P+D142L;
D79L+S87P+A112P+T124V+D142L;
S5*+N26R+D79L+S87P+A112P+D142L;
N26R+T46R+D79L+S87P+A112P+D142L;
T46R+D79L+S87P+T116V+D142L;
D79L+P81R+S87P+A112P+D142L;
A27K+D79L+S87P+A112P+T124V+D142L;
D79L+Y82F+S87P+A112P+T124V+D142L;
D79L+Y82F+S87P+A112P+T124V+D142L;

D79L+S87P+A112P+T124V+A126V+D142L;
D79L+S87P+A112P+D142L;
D79L+Y82F+S87P+A112P+D142L;
S38T+D79L+S87P+A112P+A126V+D142L;
D79L+Y82F+S87P+A112P+A126V+D142L;
A27K+D79L+S87P+A112P+A126V+D142L;
D79L+S87P+N98C+A112P+G135C+D142L;
D79L+S87P+A112P+D142L+T141C+M161C;
S36P+D79L+S87P+A112P+D142L;
A37P+D79L+S87P+A112P+D142L;
S49P+D79L+S87P+A112P+D142L;
S50P+D79L+S87P+A112P+D142L;
D79L+S87P+D104P+A112P+D142L;
D79L+Y82F+S87G+A112P+D142L;
S70V+D79L+Y82F+S87G+Y97W+A112P+D142L;
D79L+Y82F+S87G+Y97W+D104P+A112P+D142L;
S70V+D79L+Y82F+S87G+A112P+D142L;
D79L+Y82F+S87G+D104P+A112P+D142L;
D79L+Y82F+S87G+A12P+A126V+D142L;
Y82F+S87G+S70V+D79L+D104P+A112P+D142L;
Y82F+S87G+D79L+D104P+A112P+A126V+D142L,
A27K+D79D+Y82F+S87G+D104P+A112P+A126V+D142L,
A27K+Y82F+S87G+D104P+A112P+A126V+D142L.
A27K+D79L+Y82F+D104P+A112P+A126V+D142L;
A27K+Y82F+D104P+A112P+A126V+D142L;
A27K+D79L+S87P+A112P+D142L; and
D79L+S87P+D142L.

41. The process of any of paragraphs 1-40, wherein the protease is a variant of the metallo protease disclosed as the mature part of SEQ ID NO: 2 disclosed in WO 2003/048353 or the mature part of SEQ ID NO: 1 in WO 2010/008841 or SEQ ID NO: 2 herein with the following mutations:
D79D+S87P+A112P+D142L;
D79L+S87P+D142L; or
A27K+D79L+Y82F+S87G+D104P+A112P+A126V+D142L.

42. The process of any of paragraphs 1-41, wherein the protease variant has at least 75% identity preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the mature part of the polypeptide of SEQ ID NO: 2 disclosed in WO 2003/048353 or the mature part of SEQ ID NO: 1 in WO 2010/008841 or SEQ ID NO: 2 herein.

43. The process of any of paragraphs 1-42, wherein the protease variant of the *Thermoascus aurantiacus* protease shown in SEQ ID NO: 2 is one of the following:
D79L+S87P+D142.
D79D+S87P+A112P+D142L
D79L+Y82F+S87P+A112P+D142L
S38T+D79D+S87P+A112P+A126V+D142L
D79L+Y82F+S87P+A112P+A126V+D142L
A27K+D79L+S87P+A112P+A126V+D142L
S49P+D79L+S87P+A112P+D142L
S50P+D79L+S87P+A112P+D142L
D79L+S87P+D104P+A112P+D142L
D79L+Y82F+S87G+A112P+D142L
S70V+D79L+Y82F+S87G+Y97W+A112P+D142L
D79D+Y82F+S87G+Y97W+D104P+A112P+D142L
S70V+D79L+Y82F+S87G+A112P+D142L
D79D+Y82F+S87G+D104P+A112P+D142L
D79L+Y82F+S87G+A112P+A126V+D142L
Y82F+S87G+S70V+D79L+D104P+A112P+D142L
Y82F+S87G+D79L+D104P+A112P+A126V+D142L
A27K+D79L+Y82F+S87G+D104P+A112P+A126V+D142L.

44. The process of any of paragraphs 1-43, wherein the protease is of bacterial origin.

45. The process of any of paragraphs 1-44, wherein the protease is derived from a strain of *Pyrococcus*, preferably a strain of *Pyrococcus furiosus*.

46. The process of any of paragraphs 1-45, wherein the protease is the one shown in SEQ ID NO: 1 in U.S. Pat. No. 6,358,726 or SEQ ID NO: 13 herein.

47. The process of any of paragraphs 1-46, wherein the protease is one having at least 80%, such as at least 85%, such as at least 90%, such as at least 95%, such as at least 96%, such as at least 97%, such as at least 98%, such as at least 99% identity to in SEQ ID NO: 1 in U.S. Pat. No. 6,358,726 or SEQ ID NO: 13 herein.

48. The process of any of paragraphs 1-47, further wherein a carbohydrate-source generating enzyme is present and/or added during liquefaction step i), preferably a glucoamylase.

49. The process of any of paragraphs 1-48, wherein the carbohydrate-source generating enzyme present and/or added during liquefaction step i) is a glucoamylase having a heat stability at 85° C., pH 5.3, of at least 20%, such as at least 30%, preferably at least 35%.

50. The process of any of paragraphs 48-49, wherein the carbohydrate-source generating enzyme is a glucoamylase having a relative activity pH optimum at pH 5.0 of at least 90%, preferably at least 95%, preferably at least 97%.

51. The process of any of paragraphs 48-50, wherein the carbohydrate-source generating enzyme is a glucoamylase having a pH stability at pH 5.0 of at least at least 80%, at least 85%, at least 90%.

52. The process of any of paragraphs 48-51, wherein the carbohydrate-source generating enzyme present and/or added during liquefaction step i) is a glucoamylase, preferably derived from a strain of the genus *Penicillium*, especially a strain of *Penicillium oxaticum* disclosed as SEQ ID NO: 2 in WO2011/127802 or SEQ ID NO: 14 herein.

53. The process of claim 48-52, wherein the glucoamylase has at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99% or 100% identity to the mature polypeptide shown in SEQ ID NO: 2 in WO 2011/127802 or SEQ ID NO: 14 (mature) herein.

54. The process of any of paragraphs 48-53, wherein the carbohydrate-source generating enzyme is a variant of the glucoamylase derived from a strain of *Penicillium oxaficum* disclosed as SEQ ID NO: 2 in WO 2011/127802 having a K79V substitution (using the mature sequence shown in SEQ ID NO: 14 herein for numbering).

55. The process of any of paragraphs 52-54, wherein the *Penicillium oxalicum* glucoamylase has a K79V substitution (using the mature sequence shown as SEQ ID NO: 14 herein for numbering) and further one of the following:
T65A; or
Q327F; or
E501V; or
Y504T; or
Y504*; or
T65A+Q327F; or
T65A+E501V; or
T65A+Y504T; or T65A+Y504*; or
Q327F+E501V; or
Q327F+Y504T; or
Q327F+Y504*; or
E501V+Y504T; or
E501V+Y504*; or
T65A+Q327F+E501V; or
T65A+Q327F+Y504T; or
T65A+E501V+Y504T; or
Q327F+E501V+Y504T; or
T65A+Q327F+Y504*; or
T65A+E501V+Y504*; or
Q327F+E501V+Y504*; or
T65A+Q327F+E501V+Y504T; or
T65A+Q327F+E501V+Y504*;
E501V+Y504T; or
T65A+K161S; or
T65A+Q405T; or
T65A+Q327W; or
T65A+Q327F; or
T65A+Q327Y; or
P11F+T65A+Q327F; or
R1K+D3W+K5Q+G7V+N8S+T10K+P11S+T65A+Q327F; or
P2N+P4S+P11F+T65A+Q327F; or
P11F+D26C+K33C+T65A+Q327F; or
P2N+P4S+P11F+T65A+Q327W+E501V+Y504T; or
R1E+D3N+P4G+G6R+G7A+N8A+T10D+P11D+T65A+Q327F; or
P11F+T65A+Q327W; or
P2N+P4S+P11F+T65A+Q327F+E501V+Y504T; or
P11F+T65A+Q327W+E501V+Y504T; or
T65A+Q327F+E501V+Y504T; or
T65A+S105P+Q327W; or
T65A+S105P+Q327F; or
T65A+Q327W+S364P; or
T65A+Q327F+S364P; or
T65A+S103N+Q327F; or
P2N+P4S+P11F+K34Y+T65A+Q327F; or
P2N+P4S+P11F+T65A+Q327F+D445N+V447S; or
P2N+P4S+P11F+T65A+I172V+Q327F; or
P2N+P4S+P11F+T65A+Q327F+N502*; or
P2N+P4S+P11F+T65A+Q327F+N502T+P563S+K571E; or
P2N+P4S+P11F+R31S+K33V+T65A+Q327F+N564D+K571S; or
P2N+P4S+P11F+T65A+Q327F+S377T; or
P2N+P4S+P11F+T65A+V325T+Q327W; or
P2N+P4S+P11F+T65A+Q327F+D445N+V447S+E501V+Y504T; or
P2N+P4S+P11F+T65A+I172V+Q327F+E501V+Y504T; or
P2N+P4S+P11F+T65A+Q327F+S377T+E501V+Y504T; or
P2N+P4S+P11F+D26N+K34Y+T65A+Q327F; or
P2N+P4S+P11F+T65A+Q327F+I375A+E501V+Y504T; or
P2N+P4S+P11F+T65A+K218A+K221D+Q327F+E501V+Y504T; or
P2N+P4S+P11F+T65A+S103N+Q327F+E501V+Y504T; or
P2N+P4S+T10D+T65A+Q327F+E501V+Y504T; or
P2N+P4S+F12Y+T65A+Q327F+E501V+Y504T; or
K5A+P11F+T65A+Q327F+E501V+Y504T; or
P2N+P4S+T10E+E18N+T65A+Q327F+E501V+Y504T; or
P2N+T10E+E18N+T65A+Q327F+E501V+Y504T; or
P2N+P4S+P11F+T65A+Q327F+E501V+Y504T+T568N; or
P2N+P4S+P11F+T65A+Q327F+E501V+Y504T+K524T+G526A; or
P2N+P4S+P11F+K34Y+T65A+Q327F+D445N+V447S+E501V+Y504T; or
P2N+P4S+P11F+R31S+K33V+T65A+Q327F+D445N+V447S+E501V+Y504T; or
P2N+P4S+P11F+D26N+K34Y+T65A+Q327F+E501V+Y504T; or
P2N+P4S+P11F+T65A+F80*+Q327F+E501V+Y504T; or
P2N+P4S+P11F+T65A+K112S+Q327F+E501V+Y504T; or
P2N+P4S+P11F+T65A+Q327F+E501V+Y504T+T516P+K524T+G526A; or
P2N+P4S+P11F+T65A+Q327F+E501V+N502T+Y504*; or
P2N+P4S+P11F+T65A+Q327F+E501V+Y504T; or
P2N+P4S+P11F+T65A+S103N+Q327F+E501V+Y504T; or
K5A+P11F+T65A+Q327F+E501V+Y504T; or
P2N+P4S+P11F+T65A+Q327F+E501V+Y504T+T516P+K524T+G526A; or
P2N+P4S+P11F+T65A+K79A+Q327F+E501V+Y504T; or
P2N+P4S+P11F+T65A+K79G+Q327F+E501V+Y504T; or
P2N+P4S+P11F+T65A+K79I+Q327F+E501V+Y504T; or
P2N+P4S+P11F+T65A+K79L+Q327F+E501V+Y504T; or
P2N+P4S+P11F+T65A+K79S+Q327F+E501V+Y504T; or
P2N+P4S+P11F+T65A+L72V+Q327F+E501V+Y504T; or
S255N+Q327F+E501V+Y504T; or
P2N+P4S+P11F+T65A+E74N+V79K+Q327F+E501V+Y504T; or
P2N+P4S+P11F+T65A+G220N+Q327F+E501V+Y504T; or
P2N+P4S+P11F+T65A+Y245N+Q327F+E501V+Y504T; or
P2N+P4S+P11F+T65A+Q253N+Q327F+E501V+Y504T; or
P2N+P4S+P11F+T65A+D279N+Q327F+E501V+Y504T; or
P2N+P4S+P11F+T65A+Q327F+S359N+E501V+Y504T; or
P2N+P4S+P11F+T65A+Q327F+D370N+E501V+Y504T; or
P2N+P4S+P11F+T65A+Q327F+V460S+E501V+Y504T; or
P2N+P4S+P11F+T65A+Q327F+V460T+P468T+E501V+Y504T; or
P2N+P4S+P11F+T65A+Q327F+T463N+E501V+Y504T; or
P2N+P4S+P11F+T65A+Q327F+S465N+E501V+Y504T; or
P2N+P4S+P11F+T65A+Q327F+T477N+E501V+Y504T.

56. The process of any of paragraphs 48-55, further wherein a glucoamylase is present and/or added during saccharification and/or fermentation.

57. The process of any of paragraphs 1-56, wherein the glucoamylase present and/or added during saccharification and/or fermentation is of fungal origin, preferably from a stain of *Aspergillus*, preferably *Aspergillus niger, Aspergillus awamori,* or *Aspergillus oryzae*; or a strain of *Trichoderma*, preferably *T. reesei*; or a strain of *Talaromyces*, preferably *T. emersonii*, or a strain of *Pycnoporus*, or a strain of *Gloephyllum*, or a strain of the *Nigrofomes*.

58. The process of any of paragraphs 1-57, further wherein a pullulanase is present and/or added during liquefaction and/or saccharification.

59. The process of any of paragraphs 1-58, further wherein an endoglucnase is present and/or added during liquefaction step i).

60. The process of paragraphs 59, wherein the endoglucnase is the one shown as SEQ ID NO: 2 in WO 2013/019780 or in SEQ ID NO: 9 herein, e.g., derived from a strain of *Talaromyces leycettanus*, or an endoglucanase having at least 60%, such as at least 70%, such as at least 75% identity, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, such as 100% identity to the mature part of the polypeptide of SEQ ID NO: 9 herein.

61. The process of paragraphs 1-59, wherein a phytase is present and/or added during liquefaction and/or saccharification.

62. The process of any of paragraphs 1-61, comprising the steps of:
i) liquefying the starch-containing material at a temperature in the range from 70-100° C. using:
an alpha-amylase derived from *Bacillus stearothermophilus*;
a hemicellulase, in particular a xylanase, having a Melting Point (DSC) above 80° C., preferably above 85° C., especially above 90° C., in particular above 95° C.;
ii) saccharifying using a glucoamylase enzyme;
iii) fermenting using a fermenting organism.

63. A process of paragraphs 1-62, comprising the steps of:
i) liquefying the starch-containing material at a temperature above the initial gelatinization temperature using:
an alpha-amylase, preferably derived from *Bacillus stearothermophilus*, having a T½ (min) at pH 4.5, 85° C., 0.12 mM CaCl$_2$ of at least 10;
a hemicellulase, in particular a xylanase, having a Melting Point (DSC) above 80° C.; preferably above 85° C., especially above 90° C., in particular above 95° C.;
optionally an endoglucanase, in particular one having a Melting Point (DSC) above 70° C., preferably above 75° C.;
ii) saccharifying using a glucoamylase enzyme;
iii) fermenting using a fermenting organism.

64. A process of paragraphs 1-63, comprising the steps of:
i) liquefying the starch-containing material at a temperature between 70-100° C. using:
a bacterial alpha-amylase, preferably derived from *Bacillus stearothermophilus*, having a T½ (min) at pH 4.5, 85° C., 0.12 mM CaCl$_2$ of at least 10;
a hemicellulase, in particular a xylanase, having a Melting Point (DSC), above 80° C., preferably above 85° C., especially above 90° C., in particular above 95° C.;
optionally a protease, preferably derived from *Pyrococcus furiosus* or *Thermoascus aurantiacus*, having a thermostability value of more than 20% determined as Relative Activity at 80° C./70° C.;
optionally an endoglucanase, in particular one having a Melting Point (DSC) above 70° C.;
ii) saccharifying using a glucoamylase enzyme;
iii) fermenting using a fermenting organism.

65. A process of paragraphs 1-64, comprising the steps of:
i) liquefying the starch-containing material at a pH in the range between from above 4.0-6.5 at a temperature above the initial gelatinization temperature using:
an alpha-amylase derived from *Bacillus stearothermophilus* having a double deletion I181+G182, and optional substitution N193F; and optionally further comprising one of the following set of substitutions:
E129V+K177L+R179E;
V59A+Q89R+E129V+K177L+R179E
V59A+Q89R+E129V+K177L+R179E+H208Y+ K220P+N224L+Q254S;
E129V+K177L+R179E+K220P+N224L+S242Q+ Q254S;
V59A+Q89R+E129V+K177L+R179E+Q254S+ M284V (using SEQ ID NO: 1 herein for numbering);
a hemicellulase, in particular a xylanase, having a Melting Point (DSC) above 80° C., preferably above 85° C., especially above 90° C., in particular above 95° C.; in particular a xylanase having at least 60%, such as at least 70%, such as at least 75% identity, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99% to the mature part of any of the polypeptides shown in SEQ ID NOs: 3, 4, 5, 8 and 34 herein;
optionally a protease having a thermostability value of more than 20% determined as Relative Activity at 80° C./70° C., in particular derived from *Pyrococcus furiosus* and/or *Thermoascus aurantiacus*; and optionally
optionally a *Penicillium oxalicum* glucoamylase in SEQ ID NO: 14 herein having substitutions selected from the group of:
K79V;
K79V+P11F+T65A+Q327F; or
K79V+P2N+P4S+P11F+T65A+Q327F; (using SEQ ID NO: 14 hereinfor numbering);
optionally an endoglucanase, in particular one having a Melting Point (DSC) above 70° C., preferably above 75° C., especially above 80° C.;
ii) saccharifying using a glucoamylase enzyme;
iii) fermenting using a fermenting organism.

66. A process of paragraphs 1-65, comprising the steps of:
i) liquefying the starch-containing material at a temperature between 70-100° C. using:
an alpha-amylase derived from *Bacillus stearothermophilus* having a double deletion I181+G182, and optional substitution N193F; and optionally further comprising one of the following set of substitutions:
E129V+K177L+R179E;
V59A+Q89R+E129V+K177L+R179E;
V59A+Q89R+E129V+K177L+R179E+H208Y+ K220P+N224L+Q254S; or
V59A+Q89R+E129V+K177L+R179E+Q254S+ M284V (using SEQ ID NO: 1 herein for numbering);

a hemicellulase, preferably xylanase, having a Melting Point (DSC), above 80° C., preferably above 85° C., especially above 90° C., in particular above 95° C.; in particular a xylanase having at least 80% identity to the mature part of the polypeptide of SEQ ID NOs: 3, 4, 5, 8 and 34 herein;

optionally an endoglucanase, in particular an having a Melting Point (DSC) above 70° C., preferably above 75° C., especially above 80° C.;

optionally a protease having a thermostability value of more than 20% determined as Relative Activity at 80° C./70° C., in particular a protease derived from *Pyrococcus furiosus* and/or *Thermoascus aurantiacus*; and optionally a *Penicillium oxalicum* glucoamylase in SEQ ID NO: 14 herein comprising substitutions selected from the group of:

K79V; or
K79V+P11F+T65A+Q327F; or
K79V+P2N+P4S+P11F+T65A+Q327F (using SEQ ID NO: 14 for numbering);

ii) saccharifying using a glucoamylase enzyme;
iii) fermenting using a fermenting organism.

67. A process of paragraphs 1-65, comprising the steps of:
i) liquefying the starch-containing material at a temperature between 70-100° C. using:

an alpha-amylase derived from *Bacillus stearothermophilus* having a double deletion I181+G182, and optional substitution N193F; and optionally further comprising one of the following set of substitutions:

E129V+K177L+R179E;
V59A+Q89R+E129V+K177L+R179E;
V59A+Q89R+E129V+K177L+R179E+H208Y+ K220P+N224L+Q254S;
V59A    Q89R+E129V+K177L+R179E+Q254S+ M284V;
E129V+K177L+R179E+K220P+N224L+S242Q+ Q254S (using SEQ ID NO: 1 herein for numbering);

a hemicellulase, in particular a xylanase, having a Melting Point (DSC) above 80° C., preferably above 85° C., especially above 90° C., in particular above 95° C.; in particular a xylanase having at least 60%, such as at least 70%, such as at least 75% identity, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99% to the mature part of any of the polypeptides shown in SEQ ID NOs: 3, 4, 5, 8 and 34 herein;

optionally an endoglucanase having a Melting Point (DSC), above 70° C., preferably above 75° C., especially above 80° C.;

optionally a protease having a thermostability value of more than 20% determined as Relative Activity at 80° C./70° C., in particular one derived from *Pyrococcus furiosus;* optionally a *Penicillium oxalicum* glucoamylase in SEQ ID NO: 14 herein having substitutions selected from the group of:

K79V; or
K79V+P11F+T65A+Q327F; or
K79V+P2N+P45+P11F+T65A+Q327F; or
K79V+P11F+D26C+K33C+T65A+Q327F; or
K79V+P2N+P4S+P11F+T65A+Q327W+E501V+ Y504T; or

K79V+P2N+P4S+P11F+T65A+Q327F+E501V+ Y504T; or
K79V+P11F+T65A+Q327W+E501V+Y504T (using SEQ ID NO: 14 for numbering);

optionally an endoglucanase in particular one having a Melting Point (DSC) above 70° C., preferably above 75° C., especially above 80° C.;

ii) saccharifying using a glucoamylase enzyme;
iii) fermenting using a fermenting organism.

68. The process of any of paragraphs 62-67, wherein the *Bacillus stearothermophilus* alpha-amylase (SEQ ID NO: 1 herein) is the mature alpha-amylase or corresponding mature alpha-amylases having at least 60%, such as at least 70%, such as at least 80% identity, such as at least 90% identity, at least 95% identity at least 96% identity at least 97% identity at least 99% identity to the SEQ ID NO: 1 herein.

69. The process of any of paragraphs 64-68, wherein the *Pyrococcus furiosus* protease (SEQ ID NO: 13 herein) or *Thermoascus aurantiacus* protease (SEQ ID NO: 3) is the mature protease or corresponding mature protease having at least 80% identity, at least 90% identity, at least 95% identity at least 96% identity at least 97% identity at least 99% identity to SEQ ID NO: 13 herein or SEQ ID NO: 3 herein, respectively.

70. The process of any of paragraphs 65-69, wherein the *Penicillium oxalicum* glucoamylase (SEQ ID NO: 14 herein), or a variant thereof, is the mature glucoamylase or corresponding mature glucoamylase having at least 80% identity, at least 90% identity, at least 95% identity at least 96% identity at least 97% identity at least 99% identity to the SEQ ID NO: 14 herein.

71. The process of any of paragraphs 1-70, wherein cellulase or cellulolytic enzyme composition is present or adding during fermentation or simultaneous saccharification and fermentation.

72. The process of any of paragraphs 1-71, wherein a cellulase or cellulolytic enzyme composition and a glucoamylase are present or added during fermentation or simultaneous saccharification and fermentation.

73. The process of any of paragraphs 1-72, wherein cellulase or cellulolytic enzyme composition and glucoamylase present or added during fermentation or simultaneous saccharification and fermentation added.

74. The process of any of paragraphs 71-73 wherein the cellulase or cellulolytic enzyme composition is derived from *Trichoderma reesei, Humicola insolens, Chrysosporium lucknowense* or *Penicillium decumbens*.

75. The process of any of paragraphs 71-74, wherein the cellulase or cellulolytic enzyme composition comprises a beta-glucosidase, a cellobiohydrolase, and an endoglucanase.

76. The process of any of paragraphs 71-75, wherein the cellulase or cellulolytic enzyme composition comprises a beta-glucosidase, preferably one derived from a strain of the genus *Aspergillus*, such as *Aspergillus oryzae*, such as the one disclosed in WO 2002/095014 or the fusion protein having beta-glucosidase activity disclosed in WO 2008/057637, or *Aspergillus fumigatus*, such as one disclosed in SEQ ID NO: 2 in WO 2005/047499 or SEQ ID NO: 29 herein or an *Aspergillus fumigatus* beta-glucosidase variant disclosed in WO 2012/044915; or a strain of the genus a strain *Penicillium*, such as a strain of the *Penicillium brasilianum* disclosed in WO 2007/019442, or a strain of the genus *Trichoderma*, such as a strain of *Trichoderma reesei*.

77. The process of any of paragraphs 71-76, wherein the cellulase or cellulolytic enzyme composition comprises a GH61 polypeptide having cellulolytic enhancing activity such as one derived from the genus *Thermoascus*, such as a strain of *Thermoascus aurantiacus*, such as the one described in WO 2005/074656 or SEQ ID NO: 30 herein; or one derived from the genus *Thielavia*, such as a strain of *Thielavia terrestris*, such as the one described in WO 2005/074647 as SEQ ID NO: 7; or one derived from a strain of *Aspergillus*, such as a strain of *Aspergillus fumigatus*, such as the one described in WO 2010/138754 as SEQ ID NO: 1; or one derived from a strain derived from *Penicillium*, such as a strain of *Penicillium emersonii*, such as the one disclosed in WO 2011/041397 as SEQ ID NO: 2 or SEQ ID NO: 31 herein.

78. The process of any of paragraphs 71-77, wherein the cellulase or cellulolytic enzyme composition comprises a cellobiohydrolase I (CBH I), such as one derived from a strain of the genus *Aspergillus*, such as a strain of *Aspergillus fumigatus*, such as the Cel7a CBH I disclosed in SEQ ID NO: 6 in WO 2011/057140 or SEQ ID NO: 32 herein, or a strain of the genus *Trichoderma*, such as a strain of *Trichoderma reesei*.

79. The process of any of paragraphs 71-78, wherein the cellulase or cellulolytic enzyme composition comprises a cellobiohydrolase II (CBH II), such as one derived from a strain of the genus *Aspergillus*, such as a strain of *Aspergillus fumigatus*; such as the one disclosed as SEQ ID NO: 33 herein or a strain of the genus *Trichoderma*, such as *Trichoderma reesei*, or a strain of the genus *Thielavia*, such as a strain of *Thielavia terrestris*, such as cellobiohydrolase II CEL6A from *Thielavia terrestris*.

80. The process of any of paragraphs 71-79, wherein the cellulase or cellulolytic enzyme composition comprises a GH61 polypeptide having cellulolytic enhancing activity and a beta-glucosidase.

81. The process of any of paragraphs 71-80, wherein the cellulase or cellulolytic enzyme composition comprises a GH61 polypeptide having cellulolytic enhancing activity and a beta-glucosidase.

82. The process of any of paragraphs 71-81, wherein the cellulase or cellulolytic enzyme composition comprises a GH61 polypeptide having cellulolytic enhancing activity, a beta-glucosidase, and a CBH I.

83. The process of any of paragraphs 71-82, wherein the cellulase or cellulolytic enzyme composition comprises a GH61 polypeptide having cellulolytic enhancing activity, a beta-glucosidase, a CBH I, and a CBH II.

84. The process of any of paragraphs 71-83, wherein the cellulase or cellulolytic enzyme composition is a *Trichoderma reesei* cellulolytic enzyme composition, further comprising *Thermoascus aurantiacus* GH61A polypeptide having cellulolytic enhancing activity (SEQ ID NO: 2 in WO 2005/074656 or SEQ ID NO: 30 herein), and *Aspergillus oryzae* beta-glucosidase fusion protein (WO 2008/057637).

85. The process of any of paragraphs 71-84, wherein the cellulase or cellulolytic enzyme composition is a *Trichoderma reesei* cellulolytic enzyme composition, further comprising *Thermoascus aurantiacus* GH61A polypeptide having cellulolytic enhancing activity (SEQ ID NO: 2 in WO 2005/074656 or SEQ ID NO: 30 herein) and *Aspergillus fumigatus* beta-glucosidase (SEQ ID NO: 2 of WO 2005/047499 or SEQ ID NO: 29 herein).

86. The process of any of paragraphs 71-85, wherein the cellulase or cellulolytic enzyme composition is a *Trichoderma reesei* cellulolytic enzyme composition further comprising *Penicillium emersonii* GH61A polypeptide having cellulolytic enhancing activity disclosed in WO 2011/041397 as SEQ ID NO: 2 or SEQ ID NO: 31 herein; and *Aspergillus fumigatus* beta-glucosidase (SEQ ID NO: 2 of WO 2005/047499) or SEQ ID NO: 29 herein or a variant thereof with one or more, such as all, of the following substitutions: F100D, S283G, N456E, F512Y.

87. The process of any of paragraphs 71-86, wherein the cellulase or cellulolytic enzyme composition comprises one or more of the following components (i) an *Aspergillus fumigatus* cellobiohydrolase I;

(ii) an *Aspergillus fumigatus* cellobiohydrolase II;

(iii) an *Aspergillus fumigatus* beta-glucosidase or variant thereof; and (iv) a *Penicillium* sp. GH61 polypeptide having cellulolytic enhancing activity; or homologs thereof.

88. The process of any of paragraphs 71-87, wherein the cellulase or cellulolytic enzyme composition is SPIRIZYME ACHIEVE™, CELLIC CTEC™, CELLIC CTEC2™, CELLIC CTEC3™, ACCELLERASE 1000™, ACCELLERASE 1500™, ACCELLERASE DUET™, ACCELLERASE TRIO™.

89. The process of any of paragraphs 71-88, wherein the glucoamylase present or added during saccharification or simultaneous saccharification and fermentation is of fungal origin, preferably from a stain of *Aspergillus*, preferably *Aspergillus niger*, *Aspergillus awamori*, or *Aspergillus oryzae*: or a strain of *Trichoderma*, preferably *T. reesei*; or a strain of *Talaromyces*, preferably *T. emersonii*, or a strain of *Pycnoporus*, or a strain of *Gloephyllum*, or a strain of the *Nigrofomes*.

90. The process of any of paragraphs 72-89, wherein the glucoamylase is a blend of glucoamylase derived from *Talaromyces emersonii* disclosed in WO 99/28448 or SEQ ID NO: 28 herein, *Trametes cingulata* glucoamylase disclosed as SEQ ID NO: 2 in WO 06/69289 or SEQ ID NO: 26 herein, and *Rhizomucor pusillus* alpha-amylase with *Aspergillus niger* glucoamylase linker and SBD disclosed as V039 in Table 5 in WO 2006/069290 or SEQ ID NO: 27 herein.

91. The process of any of paragraphs 72-90, wherein the alpha-amylase is the *Rhizomucor pusillus* alpha-amylase having an *Aspergillus niger* glucoamylase linker and starch-binding domain (SBD) (SEQ ID NO: 27 herein) which further comprises at least one of the following substitutions or combinations of substitutions: D165M; Y141W; Y141R; K136F; K192R; P224A; P224R; S123H+Y141W; G20S+Y141W; A76G+Y141W; G128D+Y141W; G128D+D143N; P219C+Y141W; N142D+D143N; Y141W+K192R; Y141W+D143N; Y141W+N383R; Y141W+P219C+A265C; Y141W+N142D+D143N; Y141W+K192R V410A: G128D+Y141W+D143N; Y141W+D143N+P2190; Y141W+D143N+K192R; G128D+D143N+K192R; Y141W+D143N+K192R+P2190; G128D+Y141W+D143N+K192R; or G128D+Y141W+D143N+K192R+P219C (using SEQ ID NO: 27 herein for numbering).

92. A composition comprising:

an alpha-amylase;

a hemicellulase, in particular a xylanase, having a Melting Point (DSC) above 80° C., preferably above 85° C., especially above 90° C., in particular above 95° C.;

optionally an endoglucanase;

optionally a protease;

optionally a carbohydrate-source generating enzyme.

93. The composition of paragraph 92, wherein the alpha-amylase is a bacterial or fungal alpha-amylase.

94. The composition of any of paragraphs 92-93, wherein the alpha-amylase is a bacterial alpha-amaylase, in particular from the genus *Bacillus*, such as a strain of *Bacillus stearothermophilus*, in particular a variant of a *Bacillus*

*stearothermophilus* alpha-amylase, such as the one shown in SEQ ID NO: 3 in WO 99/019467 or SEQ ID NO: 1 herein.

95. The composition of paragraph 94, wherein the *Bacillus stearothermophilus* alpha-amylase or variant thereof is truncated, preferably to be around 491 amino acids long, such as from 480-495 amino acids long.

96. The composition of any of paragraphs 92-95, wherein the *Bacillus stearothermophilus* alpha-amylase has a double deletion in positions I181+G182, and optionally a N193F substitution, or a double deletion in positions R179+G180 (using SEQ ID NO: 1 herein for numbering).

97. The composition of any of paragraphs 92-96 wherein the *Bacillus stearothermophilus* alpha-amylase has a substitution in position S242, preferably S2420 substitution (using SEQ ID NO: 1 herein for numbering), 98. The composition of any of paragraphs 92-97, wherein the *Bacillus stearothermophilus* alpha-amylase has a substitution in position E188, preferably E188P substitution (using SEQ ID NO: 1 herein for numbering).

99. The composition of any of paragraphs 92-98, wherein the alpha-amylase has a T½ (min) at pH 4.5, 85° C., 0.12 mM $CaCl_2$) of at least 10, such as at least 15, such as at least 20, such as at least 25, such as at least 30, such as at least 40, such as at least 50, such as at least 60, such as between 10-70, such as between 15-70, such as between 20-70, such as between 25-70, such as between 30-70, such as between 40-70, such as between 50-70, such as between 60-70.

100. The composition of any of paragraphs 92-99, wherein the alpha-amylase is selected from the group of *Bacillus stearomthermphilus* alpha-amylase variants shown in SEQ ID NO: 1 herein having a double deletion in I181*+G182*, and optionally a subsitution in N193F, in particular further having one of the following set of substitutions:

E129V+K177L+R179E;
V59A+Q89R+E129V+K177L+R179E;
V59A+Q89R+E129V+K177L+R179E+H208Y+K220P+N224L+Q254S;
V59A Q89R+E129V+K177L+R179E+Q254S+M284V; and
E129V+K177L+R179E+K220P+N224L+S242Q+Q254S
(using SEQ ID NO: 1 herein for numbering).

101, The composition of any of paragraphs 92-100, wherein the hemicellulase, in particular xylanase, such as GH10 xylanase or GH11 xylanase, has a Melting Point (DSC) above 82° C., such as above 84° C., such as above 86° C., such as above 88° C., such as above 90° C., such as above 92° C., such as above 94° C., such as above 96° C., such as above 98° C., such as above 100° C.

102. The composition of any of paragraphs 92-101, wherein the hemicellulase, in particular xylanase, especially GH10 or GH11 xylanase has at least 60%, such as at least 70%, such as at least 75%, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, such as 100% identity to the mature part of the polypeptide of SEQ ID NO: 3 herein (GH10 xylanase) or SEQ ID NO: 34 (GH11 xylanase), preferably derived from a strain of the genus *Dictyoglomus*, such as a strain of *Dictyogllomus thermophilum*.

103. The composition of any of paragraphs 92-101, wherein the hemicellulase, in particular xylanase, especially GH10 xylanase has at least 60%, such as at least 70%, such as at least 75% identity, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, such as 100% identity to the mature part of the polypeptide of SEQ ID NO: 4 herein, preferably derived from a strain of the genus *Rasamsonia*, such as a strain of *Rasomsonia byssochlamydoides*.

104. The composition of any of paragraphs 92-101, wherein the hemicellulase, in particular xylanase, especially GH10 xylanase has at least 60%, such as at least 70%, such as at least 75% identity, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, such as 100% identity to the mature part of the polypeptide of SEQ ID NO: 5 herein, preferably derived from a strain of the genus *Talaromyces*, such as a strain of *Talaromyces leycettanus*.

105. The composition of any of paragraphs 92-101, wherein the hemicellulase, in particular xylanase, especially GH10 xylanase has at least 60%, such as at least 70%, such as at least 75% identity, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, such as 100% identity to the mature part of the polypeptide of SEQ ID NO: 8 herein, preferably derived from a strain of the genus *Aspergillus*, such as a strain of *Aspergillus fumigatus*.

106. The composition of any of paragraphs 92-105, comprising
an alpha-amylase;
a hemicellulase having a Melting Point (DSC) above 80° C. preferably above 85° C., especially above 90° C., in particular above 95° C.;
an endoglucanase having Melting Point (DSC) above 70° C., preferably above 75° C., especially above 80° C., in particular above 85° C.

107. The composition of any of paragraphs 92-106, wherein the protease with a thermostability value of more than 20%, such as more than 25% determined as Relative Activity at 80° C./70° C.

108. The composition of any of paragraphs 92-107, wherein the protease has a thermostability of more than 30%, more than 40%, more than 50%, more than 60%, more than 70%, more than 80%, more than 90%, more than 100%, such as more than 105%, such as more than 110%, such as more than 115%, such as more than 120% determined as Relative Activity at 80° C./70° C.

109. The composition of any of paragraphs 92-108, wherein the protease has a thermostability of between 20 and 50%, such as between 20 and 40%, such as 20 and 30% determined as Relative Activity at 8° C./70° C.

110. The composition of any of paragraphs 92-109, wherein the protease has a thermostability between 50 and 115%, such as between 50 and 70%, such as between 50 and 60%, such as between 100 and 120%, such as between 105 and 115% determined as Relative Activity at 80° C./70° C.

111. The composition of any of paragraphs 92-110, wherein the protease has a thermostability of more than 10%, such as more than 12%, more than 14%, more than 16%, more than 18%, more than 20%, more than 30%, more than 40%, more that 50%, more than 60%, more than 70%, more than 80%, more than 90%, more than 100%, more than 110% determined as Relative Activity at 85° C./70° C.

112. The composition of any of paragraphs 92-111, wherein the protease has thermostability of between 10 and 50%, such as between 10 and 30%, such as between 10 and 25% determined as Relative Activity at 85° C./70° C.

113. The composition of any of paragraphs 92-112, wherein the protease has a thermostability above 60%, such as above 90%, such as above 100%, such as above 110% at 85° C. as determined using the Zein-BCA assay.

114. The composition of any of paragraphs 92-113, wherein the protease has a thermostability between 60-120, such as between 70-120%, such as between 80-120%, such as between 90-120%, such as between 100-120%, such as 110-120% at 85° C. as determined using the Zein-BCA assay.

115. The composition of any of paragraphs 92-114, wherein the protease is of fungal origin.

116. The composition of any of paragraphs 92-115, wherein the protease is a variant of the metallo protease derived from a strain of the genus *Thermoascus*, preferably a strain of *Thermoascus aurantiacus*, especially *Thermoascus aurantiacus* CGMCC No. 0670, in particular the one shown in SEQ ID NO: 2 herein.

117. The composition of any of paragraphs 92-116, wherein the protease is a variant of the protease disclosed as the mature part of SEQ ID NO: 2 disclosed in WO 2003/048353 or the mature part of SEQ ID NO: 1 in WO 2010/008841 or SEQ ID NO: 2 herein with the following mutations:
D79L+S87P+A112P+D142L:
D79L+S87P+D142L; or
A27K+D79L+Y82F+S87G+D104P+A112P+A126V+D142L (using SEQ ID NO: 2 herein for numbering).

118. The composition of any of paragraphs 92-118, wherein the protease variant has at least 75% identity preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the mature part of the polypeptide of SEQ ID NO: 2 disclosed in WO 2003/048353 or the mature part of SEQ ID NO: 1 in WO 2010/008841 or SEQ ID NO: 2 herein.

119. The composition of any of paragraphs 92-118, wherein the protease variant of the *Thermoascus aurantiacus* protease shown in SEQ ID NO: 2 herein is one of the following:
D79L+S87P+D142L
D79L+S87P+A112P+D142L
D79L+Y82F+S87P+A112P+D142L
S38T+D79L+S87P+A112P+A126V+D142L
D79L+Y82F+S87P+A112P+A126V+D142L
A27K+D79D+S87P+A112P+A126V+D142L
S49P+D79L+S87P+A112P+D142L
S50P+D79L+S87P+A112P+D142L
D79L+S87P+D104P+A112P+D142L
D79L+Y82F+S87G+A112P+D142L
S70V+D79D+Y82F+387G+Y97W+A112P+D142L
D79L+Y82F+S87G+Y97W+D104P+A112P+D142L
S70V+D79L+Y82F+S87G+A112P+D142L
D79L+Y82F+S87G+D104P+A112P+D142L
D79L+Y82F+S87G+A112P+A126V+D142L
Y82F+S87G+S70V+D79L+D104P+A112P+D142L
Y82F+S87G+D79L+D104P+A112P+A126V+D142L
A27K+D79L+Y82F+S87G+D104P+A112P+A126V+D142L.

120. The composition of any of paragraphs 92-119, wherein the protease is of bacterial origin.

121. The composition of any of paragraphs 92-120, wherein the protease is derived from a strain of *Pyrococcus*, preferably a strain of *Pyrococcus furiosus*.

122. The composition of any of paragraphs 92-121, wherein the protease is the one shown in SEQ ID NO: 1 in U.S. Pat. No. 6,358,726 or SEQ ID NO: 13 herein.

123. The composition of any of paragraphs 92-122, wherein the protease is one having at least 80%, such as at least 85%, such as at least 90%, such as at least 95%, such as at least 96%, such as at least 97%, such as at least 98%, such as at least 99% identity to SEQ ID NO: 1 in U.S. Pat. No. 6,358,726 or SEQ ID NO: 13 herein.

124. The composition of any of paragraphs 92-123, wherein a carbohydrate-source generating enzyme is a glucoamylase.

125. The composition of any of paragraphs 92-124, wherein the carbohydrate-source generating enzyme is a glucoamylase having a heat stability at 85° C., pH 5.3, of at least 20%, such as at least 30%, preferably at least 35%.

126. The composition of any of paragraphs 92-125, wherein the carbohydrate-source generating enzyme is a glucoamylase having a relative activity pH optimum at pH 5.0 of at least 90%, preferably at least 95%, preferably at least 97%.

127. The composition of any of paragraphs 92-126, wherein the carbohydrate-source generating enzyme is a glucoamylase having a pH stability at pH 5.0 of at least at least 80%, at least 85%, at least 90%.

128. The composition of any of paragraphs 92-127, wherein the carbohydrate-source generating enzyme is a glucoamylase, preferably derived from a strain of the genus *Penicillium*, especially a strain of *Penicillium oxalicum* disclosed as SEQ ID NO: 2 in WO 2011/127802 or SEQ ID NO: 14 herein.

129. The composition of paragraphs 92-128, wherein the glucoamylase has at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99% or 100% identity to the mature polypeptide shown in SEQ ID NO: 2 in WO 2011/127802 or SEQ ID NO: 14 herein.

130. The composition of any of paragraphs 92-129, wherein the carbohydrate-source generating enzyme is a variant of the glucoamylase derived from a strain of *Penicillium oxalicum* disclosed as SEQ ID NO: 2 in WO 2011/127802 having a K79V substitution (using the mature sequence shown in SEQ ID NO: 14 for numbering), 131. The composition of any of paragraphs 92-130, further comprising a pullulanase, in particular a pullulanase of family GH57, wherein the pullulanase preferably includes an X47 domain as disclosed in WO 2011/087836.

132. The composition of any of paragraphs 92-131, further comprising a phytase.

133. The composition of paragraph 132, wherein the phytase is derived from *Buttiauxelia*, such as *Buttiauxella gaviniae, Buttiauxella agrestis*, or *Buttiauxella noackies* disclosed in WO 2008/092901, or *Citrobacter braakii*, such as one disclosed in WO 2006/037328.

134. The composition of any of paragraphs 92-136 comprising
an alpha-amylase derived from *Bacillus stearothermophius;*
a hemicellulase, in particular a xylanase, having a Melting Point (DSC) above 80° C., preferably above 85° C., especially above 90° C., in particular above 95° C.;
optionally a protease having a thermostability value of more than 20% determined as Relative Activity at 80° C./70° C. derived from *Pyrococcus furiosus* or *Thermoascus aurantiacus*; and
optionally an endoglucanase in particular one having a Melting Point (DSC) above 70° C., preferably above 75° C., especially above 80° C., in particular above 85° C.; in particular a xylanase having at least 60%, such as at least 70%, such as at least 75% identity, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99% to the mature part of any of the polypeptides shown in SEQ ID NOs: 9, 35, 36, 37 and 38 herein;
optionally a glucoamylase, such as one derived from *Penicillium oxalicum.*

135. The composition of any of paragraphs 92-134, comprising
an alpha-amylase, preferably derived from *Bacillus stearothermophilus*, having a T½ (min) at pH 4.5, 85° C., 0.12 mM CaCl$_2$ of at least 10;
a hemicellulase, in particular a xylanase, having a Melting Point (DSC) above 80° C. preferably above 75° C., especially above 80° C., in particular above 85° C.;
optionally an endoglucanase, in particular one having a Melting Point (DSC) above 70° C., preferably above 75° C., especially above 80° C.; in particular above 85° C.; in particular a xylanase having at least 60%, such as at least 70%, such as at least 75% identity, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99% to the mature part of any of the polypeptides shown in SEQ ID NOs: 9, 35, 36, 37 or 38 herein;
optionally a protease, preferably derived from *Pyrococcus furiosus* or *Thermoascus aurantiacus*, having a thermostability value of more than 20% determined as Relative Activity at 80° C./70° C.; and
optionally a glucoamylase, e.g., derived from *Penicillium oxalicum.*

136. The composition of any of paragraphs 92-135, comprising
an alpha-amylase derived from *Bacillus stearothermophilus* having a double deletion I181+G182 and optionally substitution N193F; and optionally further one of the following set of substitutions:
E129V+K177L+R179E;
V59A+Q89R+E129V+K177L+R179E+H208Y+K220P+N224L+Q254S;
V59A+Q89R+E129V+K177L+R179E+Q254S+M284V; and
E129V+K177L+R179E+K220P+N224L+S242Q+Q254S (using SEQ ID NO: 1 herein for numbering);
a hemicellulase, in particular a xylanase having a Melting Point (DSC) above 70° C., preferably above 75° C., in particular above 80° C., especially above 85° C.; in particular a xylanase having at least 60%, such as at least 70%, such as at least 75% identity, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99% to the mature part of any of the polypeptides shown in SEQ ID NOs: 3, 4, 5, 8 and 34 herein;
optionally an endoglucanase, in particular one having a Melting Point (DSC) above 70° C., preferably above 75° C., especially above 80° C., in particular above 85° C.; in particular a xylanase having at least 60%, such as at least 70%, such as at least 75% identity, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99% to the mature part of any of the polypeptides shown in SEQ ID NOs: 9, 35, 36, 37 and 38 herein;
optionally a protease, preferably derived from *Pyrococcus furiosus* and/or *Thermoascus aurantiacus*, having a thermostability value of more than 20% determined as Relative Activity at 80° C./70° C.; and
optionally a *Penicillium oxalicum* glucoamylase in SEQ ID NO: 14 herein having substitutions selected from the group of:
K79V;
K79V+P11F+T65A+Q327F; or
K79V+P2N+P4S+P11F+T65A+Q327F; or
K79V+P11F+D26C+K33C+T65A+Q327F; or
K79V+P2N+P4S+P11F+T65A+Q327W+E501V+Y504T; or
K79V+P2N+P4S+P11F+T65A+Q327F+E501V+Y504T; or
K79V+P11F+T65A+Q327W+E501V+Y504T (using SEQ ID NO: 14 herein for numbering), 137. The composition of any of paragraphs 92-136, wherein the alpha-amylase is a bacterial alpha-amylase in particular derived from *Bacillus stearothermophllus* (SEQ ID NO: 1 herein), or a variant thereof, is the mature alpha-amylase or corresponding mature alpha-amylases having at least 80% identity, at least 90% identity, at least 95% identity at least 96% identity at least 97% identity at least 99% identity to the SEQ ID NO: 1 herein.

138. Use of a composition of paragraphs 92-137 for liquefying a starch-containing material. hemicellulase, in particular xylanase, in liquefaction in a fermentation product production process.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control. Various references are cited herein, the disclosures of which are incorporated by reference in their entireties. The present invention is further described by the following examples which should not be construed as limiting the scope of the invention.

Materials & Methods

Materials:

Alpha-Amylase 369 (AA369): *Bacillus stearothermophilus* alpha-amylase with the mutations: I181*1+G182*+N193F+V59A+Q89R+E129V+K177L+R179E+Q254S+M284V truncated to 491 amino acids (SEQ ID NO: 1 herein). Endoglucanase TL (EG TL): Endoglucoanase GH5 from *Talaromyces leycettanus* disclosed in WO2013/019780 as SEQ ID NO: 2 and SEQ ID NO: 9 herein. (P23YSQ).

Xylalanase TL (Tl Xyl): Family GH10 xylanase from *Talaromyces leycettanus* shown in SEQ ID NO: 5 herein.

Xylanase DT (Dt Xyl): Family GH11 xylanase from *Dictyoglomus thermophilum* shown in SEQ ID NO: 34 herein.

Endoglucanase PC (EG PC): Endoglucanase GH5 from *Penicillium capsulatum* disclosed as SEQ ID NO: 35 herein. (P244HZ)

Endoglucanase TS (EG TS): Endoglucanase GH5 from *Trichophaea saccata* disclosed as SEQ ID NO: 36 herein. (P2PJ)

Endoglucanase TT (EG TT): Endoglucoanase GH45 from *Thielavia terrestris* disclosed in SEQ ID NO: 37 herein. (P24PYU)

Endoglucanase SF (EG SF): Endoglucanase GH45 from *Sordaria fimicola* disclosed in co-pending application PCT/CN2012/080220 as SEQ ID NO: 2 and SEQ IDNO: 38 herein (P2CF).

Protease Pfu: Protease derived from *Pyrococcus furiosus* purchased from Takara Bio (Japan) as Pfu Protease S (activity 10.5 mg/mL) and also shown in SEQ ID NO: 13 herein.

Glucoamylase Po: Mature part of the *Penicillium oxalicum* glucoamylase disclosed as SEQ ID NO: 2 in WO 2011/127802 and shown in SEQ ID NO: 14 herein.

Glucoamylase PE001: Variant of the *Penicillium oxalicum* glucoamylase having a K79V substitution using the mature sequence shown in SEQ ID NO: 14 for numbering.

Protease Pfu: Protease derived from *Pyrococcus furiosus* shown in SEQ ID NO: 13 herein.

Glucoamylase Po 498 (GA498): Variant of *Penicillium oxalicum* glucoamylase having the following mutations: K79V+P2N+P4S+P11F+T65A+Q327F (using SEQ ID NO: 14 for numbering).

Glucoamylase SA (GSA): Blend comprising *Talaromyces emersonii* glucoamylase disclosed as SEQ ID NO: 34 in WO99/28448 or SEQ ID NO: 28 herein, *Trametes cingulata* glucoamylase disclosed as SEQ ID NO: 2 in WO 06/69289 or SEQ ID NO: 26 herein, and *Rhizomucor pusillus* alpha-amylase with *Aspergillus niger* glucoamylase linker and starch binding domain (SBD) disclosed in SEQ ID NO: 27 herein having the following substitutions G128D+D143N (activity ratio in AGU:AGU:FAU-F is about 20:5:1).

Protease X: Metallo protease derived from *Thermoascus aurantiacus* CGMCC No. 0670 disclosed as amino acids 1-177 in SEQ ID NO: 2 herein and amino acids 1-177 in SEQ ID NO: 2 in WO 2003/048353

Yeast: ETHANOL RED™ available from Red Star/Lesaffre, USA.

Methods

Determination of Td by Differential Scanning calorimetry for Endoglucanases and Hemicellulases The thermostability of an enzyme is determined by Differential Scanning calorimetry (DSC) using a VP-Capillary Differential Scanning calorimeter (MicroCal Inc., Piscataway, N.J., USA). The thermal denaturation temperature, Td (° C.), is taken as the top of denaturation peak (major endothermic peak) in thermograms (Cp vs. T) obtained after heating enzyme solutions (approx. 0.5 mg/ml) in buffer (50 mM acetate, pH 5.0) at a constant programmed heating rate of 200 K/hr.

Sample- and reference-solutions (approx. 0.2 ml) are loaded into the calorimeter (reference: buffer without enzyme) from storage conditions at 10° C. and thermally pre-equilibrated for 20 minutes at 20° C. prior to DSC scan from 20° C. to 120° C. Denaturation temperatures are determined at an accuracy of approximately +/−1° C.

Identity: The relatedness between two amino acid sequences or between two nucleotide sequences is described by the parameter "identity".

For purposes of the present invention the degree of identity between two amino acid sequences, as well as the degree of identity between two nucleotide sequences, may be determined by the program "align" which is a Needleman-Wunsch alignment (i.e. a global alignment). The program is used for alignment of polypeptide, as well as nucleotide sequences. The default scoring matrix BLOSUM50 is used for polypeptide alignments, and the default identity matrix is used for nucleotide alignments. The penalty for the first residue of a gap is −12 for polypeptides and −16 for nucleotides. The penalties for further residues of a gap are −2 for polypeptides, and −4 for nucleotides.

"Align" is part of the FASTA package version v20u6 (see W. R. Pearson and D. J. Lipman (1988), "Improved Tools for Biological Sequence Analysis", PNAS 85:2444-2448, and W. R. Pearson (1990) "Rapid and Sensitive Sequence Comparison with FASTP and FASTA," Methods in Enzymology 183:63-98). FASTA protein alignments use the Smith-Waterman algorithm with no limitation on gap size (see "Smith-Waterman algorithm", T. F. Smith and M. S. Waterman (1981) J. Mol. Biol. 147:195-197).

Protease Assays

AZCL-Casein Assay

A solution of 0.2% of the blue substrate AZCL-casein is suspended in Borax/NaH$_2$PO$_4$ buffer pH9 while stirring. The solution is distributed while stirring to microtiter plate (100 microL to each well), 30 microL enzyme sample is added and the plates are incubated in an Eppendorf Thermomixer for 30 minutes at 45° C. and 600 rpm. Denatured enzyme sample (100° C. boiling for 20 min) is used as a blank. After incubation the reaction is stopped by transferring the microtiter plate onto ice and the coloured solution is separated from the solid by centrifugation at 3000 rpm for 5 minutes at 4° C. 60 microL of supernatant is transferred to a microtiter plate and the absorbance at 595 nm is measured using a BioRad Microplate Reader.

pNA-Assay 50 microL protease-containing sample is added to a microtiter plate and the assay is started by adding 100 microL 1 mM pNA substrate (5 mg dissolved in 100 microL DMSO and further diluted to 10 mL with Borax/NaH$_2$PO$_4$ buffer pH 9.0). The increase in OD$_{405}$ at room temperature is monitored as a measure of the protease activity.

Glucoamylase Activity (AGU)

Glucoamylase activity may be measured in Glucoamylase Units (AGU).

The Novo Glucoamylase Unit (AGU) is defined as the amount of enzyme, which hydrolyzes 1 micromole maltose per minute under the standard conditions 37° C., pH 4.3, substrate: maltose 23.2 mM, buffer: acetate 0.1 M, reaction time 5 minutes.

An autoanalyzer system may be used. Mutarotase is added to the glucose dehydrogenase reagent so that any alpha-D-glucose present is turned into beta-D-glucose. Glucose dehydrogenase reacts specifically with beta-D-glucose in the reaction mentioned above, forming NADH which is determined using a photometer at 340 nm as a measure of the original glucose concentration.

| AMG incubation: | |
| --- | --- |
| Substrate: | maltose 23.2 mM |
| Buffer: | acetate 0.1M |
| pH: | 4.30 ± 0.05 |
| Incubation temperature: | 37° C. ± 1 |
| Reaction time: | 5 minutes |
| Enzyme working range: | 0.5-4.0 AGU/mL |

| Color reaction: | |
| --- | --- |
| GlucDH: | 430 U/L |
| Mutarotase: | 9 U/L |
| NAD: | 0.21 mM |
| Buffer: | phosphate 0.12M; 0.15M NaCl |
| pH: | 7.60 ± 0.05 |
| Incubation temperature: | 37° C. ± 1 |
| Reaction time: | 5 minutes |
| Wavelength: | 340 nm |

A folder (EB-SM-0131.02/01) describing this analytical method in more detail is available on request from Novozymes A/S, Denmark, which folder is hereby included by reference.

Alpha-Amylase Activity (KNU)

The alpha-amylase activity may be determined using potato starch as substrate. This method is based on the break-down of modified potato starch by the enzyme, and the reaction is followed by mixing samples of the starch/enzyme solution with an iodine solution. Initially, a blackish-blue color is formed, but during the break-down of the starch the blue color gets weaker and gradually turns into a reddish-brown, which is compared to a colored glass standard.

One Kilo Novo alpha amylase Unit (KNU) is defined as the amount of enzyme which, under standard conditions (i.e., at 37° C.+/−0.05; 0.0003 M $Ca^{2+}$; and pH 5.6) dextrinizes 5260 mg starch dry substance Merck Amylum solubile.

A folder EB-SM-0009.02/01 describing this analytical method in more detail is available upon request to Novozymes A/S, Denmark, which folder is hereby included by reference.

Alpha-Amylase Activity (KNU-A)

Alpha amylase activity is measured in KNU(A) Kilo Novozymes Units (A), relative to an enzyme standard of a declared strength.

Alpha amylase in samples and α-glucosidase in the reagent kit hydrolyze the substrate (4,6-ethylidene($G_7$)-p-nitrophenyl($G_1$)-α,D-maltoheptaoside (ethylidene-$G_7$PNP) to glucose and the yellow-colored p-nitrophenol.

The rate of formation of p-nitrophenol can be observed by Konelab 30. This is an expression of the reaction rate and thereby the enzyme activity.

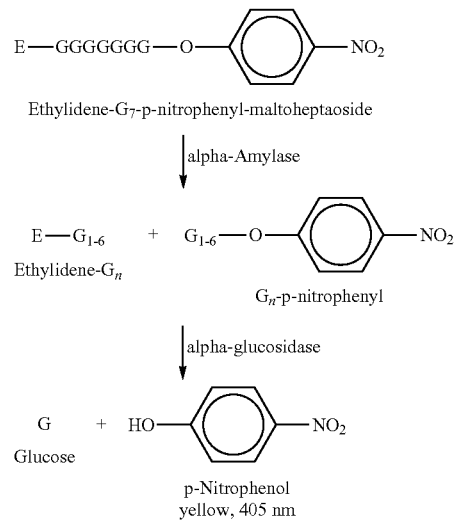

The enzyme is an alpha-amylase pith the enzyme classification number EC 3.2.1.1.

| Parameter | Reaction conditions |
| --- | --- |
| Temperature | 37° C. |
| pH | 7.00 (at 37° C.) |
| Substrate conc. | Ethylidene-$G_7$PNP, R2: 1.86 mM |
| Enzyme conc. (conc. of high/low standard in reaction mixture) | 1.35-4.07 KNU(A)/L |
| Reaction time | 2 min |
| Interval kinetic measuring time | 7/18 sec. |
| Wave length | 405 nm |
| Conc. of reagents/chemicals critical for the analysis | α-glucosidase, R1: ≥3.39 kU/L |

A folder EB-SM-5091.02-D on determining KNU-A actitvity is available upon request to Novozymes A/S, Denmark, which folder is hereby included by reference.

Alpha-Amylase Activity KNU(S)

BS-amylase in samples and the enzyme alpha-glucosidase in the reagent kit hydrolyze substrate (4,6-ethylidene(G7)-p-nitrophenyl(G1)-alpha-D-maltoheptaoside (ethylidene-G7PNP)) to glucose and the yellow-colored p-nitrophenol.

The rate of formation of p-nitrophenol can be observed by Konelab 30. This is an expression of the reaction rate and thereby the enzyme activity.

Reaction Conditions

| Reaction | |
| --- | --- |
| pH | 7.15 |
| Temperature | 37° C. |
| Reaction Time | 180 sec |
| Detection | |
| Wavelength | 405 nm |
| Measuring Time | 120 sec |

Unit definition: *Bacillus stearothermophilus* amylase (BS-amylase) activity is measured in KNU(S), Kilo Novo Units (*sterarothermophilus*), relative to an enzyme standard of a declared strength. This analytical method is described in more details in EB-SM-0221.02 (incorporated by reference) available from Novozymes A/S, Denmark, on request.
Determination of FAU Activity One Fungal Alpha-Amylase Unit (FAU) is defined as the amount of enzyme, which breaks down 5.26 g starch (Merck Amylum solubile Erg. B.6, Batch 9947275) per hour based upon the following standard conditions:

| Substrate | Soluble starch |
|---|---|
| Temperature | 37° C. |
| pH | 4.7 |
| Reaction time | 7-20 minutes |

Determination of Acid Alpha-Amylase Activity (AFAU)

Acid alpha-amylase activity is measured in AFAU (Acid Fungal Alpha-amylase Units), which are determined relative to an enzyme standard.

The standard used is AMG 300 L (from Novozymes A/S, glucoamylase wildtype *Aspergillus niger* G1, also disclosed in Boel et al, (1984), EMBO J. 3 (5), p. 1097-1102) and WO 92/00381). The neutral alpha-amylase in this AMG falls after storage at room temperature for 3 weeks from approx. 1 FAU/mL to below 0.05 FAU/mL.

The acid alpha-amylase activity in this AMG standard is determined in accordance with the following description. In this method, 1 AFAU is defined as the amount of enzyme, which degrades 5.260 mg starch dry matter per hour under standard conditions.

Iodine forms a blue complex with starch but not with its degradation products. The intensity of colour is therefore directly proportional to the concentration of starch. Amylase activity is determined using reverse colorimetry as a reduction in the concentration of starch under specified analytic conditions.

| Alpha-amylase | | |
|---|---|---|
| _Starch + Iodine | _→ | _Dextrins + Oligosaccharides |
| | 40° C., pH 2.5 | |
| _Blue/violet | _t = 23 sec. | _Decoloration |

Standard Conditions/Reaction Conditions: (Per Minute)

| _Substrate: | _Starch, approx. 0.17 g/L |
|---|---|
| Buffer: | Citate, approx. 0.03M |
| Iodine ($I_2$): | 0.03 g/L |
| $CaCl_2$: | 1.85 mM |
| pH: | 2.50 ± 0.05 |
| Incubation temperature: | 40° C. |
| _Reaction time: | _23 seconds |
| _Wavelength: | _lambda = 590 nm |
| Enzyme concentration: | 0.025 AFAU/mL |
| Enzyme working range: | 0.01-0.04 AFAU/mL |

If further details are preferred these can be found in EB-SM-0259.02/01 available on request from Novozymes A/S, and incorporated by reference.
Determination of Pullulanase Activity (NPUN)

Endo-pullulanase activity in NPUN is measured relative to a Novozymes pullulanase standard. One pullulanase unit (NPUN) is defined as the amount of enzyme that releases 1 micro mol glucose per minute under the standard conditions (0.7% red pullulan (Megazyme), pH 5, 40° C., 20 minutes). The activity is measured in NPUN/ml using red pullulan.

1 mL diluted sample or standard is incubated at 40° C. for 2 minutes. 0.5 mL 2% red pullulan, 0.5 M KCl, 50 mM citric acid, pH 5 are added and mixed. The tubes are incubated at 40° C. for 20 minutes and stopped by adding 2.5 ml 80% ethanol. The tubes are left standing at room temperature for 10-60 minutes followed by centrifugation 10 minutes at 4000 rpm. OD of the supernatants is then measured at 510 nm and the activity calculated using a standard curve.

EXAMPLES

Example

Stability of Alpha-Amylase Variants

The stability of a reference alpha-amylase (*Bacillus stearothermophilus* alpha-amylase with the mutations I181*+G182*+N193F truncated to 491 amino acids (SEQ ID NO: 1 herein for numbering)) and alpha-amylase variants thereof was determined by incubating the reference alpha-amylase and variants at pH 4.5 and 5.5 and temperatures of 75° C. and 85° C. with 0.12 mM $CaCl_2$ followed by residual activity determination using the EnzChek® substrate (EnzChek® Ultra Amylase assay kit, E33651, Molecular Probes).

Purified enzyme samples were diluted to working concentrations of 0.5 and 1 or 5 and 10 ppm (micrograms/ml) in enzyme dilution buffer (10 mM acetate, 0.01% Triton X100, 0.12 mM $CaCl_2$, pH 5.0). Twenty microliters enzyme sample was transferred to 48-well PCR MTP and 180 microliters stability buffer (150 mM acetate, 150 mM MES, 0.01% Triton X100, 0.12 mM $CaCl_2$, pH 4.5 or 5.5) was added to each well and mixed. The assay was performed using two concentrations of enzyme in duplicates. Before incubation at 75° C. or 85° C., 20 microliters was withdrawn and stored on ice as control samples. Incubation was performed in a PCR machine at 75° C. and 85° C. After incubation samples were diluted to 15 ng/mL in residual activity buffer (100 mM Acetate, 0.01% Triton X100, 0.12 mM $CaCl_2$, pH 5.5) and 25 microliters diluted enzyme was transferred to black 384-MTP. Residual activity was determined using the EnzChek substrate by adding 25 microliters substrate solution (100 micrograms/ml) to each well. Fluorescence was determined every minute for 15 minutes using excitation filter at 485-P nm and emission filter at 555 nm (fluorescence reader is Polarstar, BMG). The residual activity was normalized to control samples for each setup.

Assuming logarithmic decay half life time (T½ (min)) was calculated using the equation: T½ (min)=T(min)*LN (0.5)/LN(% RA/100), where T is assay incubation time in minutes, and % RA is % residual activity determined in assay.

Using this assay setup the half life time was determined for the reference alpha-amylase and variant thereof as shown in Table 1.

TABLE 1

| Mutations | T½ (min) (pH 4.5, 75° C., 0.12 mM CaCl₂) | T½ (min) (pH 4.5, 85° C., 0.12 mM CaCl₂) | T½ (min) (pH 5.5, 85° C., 0.12 mM CaCl₂) |
|---|---|---|---|
| Reference Alpha-Amylase A | 21 | 4 | 111 |
| Reference Alpha-Amylase A with the substitution V59A | 32 | 6 | 301 |
| Reference Alpha-Amylase A with the substitution V59E | 28 | 5 | 230 |
| Reference Alpha-Amylase A with the substitution V59I | 28 | 5 | 210 |
| Reference Alpha-Amylase A with the substitution V59Q | 30 | 6 | 250 |
| Reference Alpha-Amylase A with the substitutions V59A + Q89R + G112D + E129V + K177L + R179E + K220P + N224L + Q254S | 149 | 22 | ND |
| Reference Alpha-Amylase A with the substitutions V59A + Q89R + E129V + K177L + R179E + H208Y + K220P + N224L + Q254S | >180 | 28 | ND |
| Reference Alpha-Amylase A with the substitutions V59A + Q89R + E129V + K177L + R179E + K220P + N224L + Q254S + D269E + D281N | 112 | 16 | ND |
| Reference Alpha-Amylase A with the substitutions V59A + Q89R + E129V + K177L + R179E + K220P + N224L + Q254S + I270L | 168 | 21 | ND |
| Reference Alpha-Amylase A with the substitutions V59A + Q89R + E129V + K177L + R179E + K220P + N224L + Q254S + H274K | >180 | 24 | ND |
| Reference Alpha-Amylase A with the substitutions V59A + Q89R + E129V + K177L + R179E + K220P + N224L + Q254S + Y276F | 91 | 15 | ND |
| Reference Alpha-Amylase A with the substitutions V59A + E129V + R157Y + K177L + R179E + K220P + N224L + S242Q + Q254S | 141 | 41 | ND |
| Reference Alpha-Amylase A with the substitutions V59A + E129V + K177L + R179E + H208Y + K220P + N224L + S242Q + Q254S | >180 | 62 | ND |
| Reference Alpha-Amylase A with the substitutions V59A + E129V + K177L + R179E + K220P + N224L + S242Q + Q254S | >180 | 49 | >480 |
| Reference Alpha-Amylase A with the substitutions V59A + E129V + K177L + R179E + K220P + N224L + S242Q + Q254S + H274K | >180 | 53 | ND |
| Reference Alpha-Amylase A with the substitutions V59A + E129V + K177L + R179E + K220P + N224L + S242Q + Q254S + Y276F | >180 | 57 | ND |
| Reference Alpha-Amylase A with the substitutions V59A + E129V + K177L + R179E + K220P + N224L + S242Q + Q254S + D281N | >180 | 37 | ND |
| Reference Alpha-Amylase A with the substitutions V59A + E129V + K177L + R179E + K220P + N224L + S242Q + Q254S + M284T | >180 | 51 | ND |
| Reference Alpha-Amylase A with the substitutions V59A + E129V + K177L + R179E + K220P + N224L + S242Q + Q254S + G416V | >180 | 45 | ND |
| Reference Alpha-Amylase A with the substitutions V59A + E129V + K177L + R179E + K220P + N224L + Q254S | 143 | 21 | >480 |
| Reference Alpha-Amylase A with the substitutions V59A + E129V + K177L + R179E + K220P + N224L + Q254S + M284T | >180 | 22 | ND |

TABLE 1-continued

| Mutations | T½ (min) (pH 4.5, 75° C., 0.12 mM CaCl$_2$) | T½ (min) (pH 4.5, 85° C., 0.12 mM CaCl$_2$) | T½ (min) (pH 5.5, 85° C., 0.12 mM CaCl$_2$) |
|---|---|---|---|
| Reference Alpha-Amylase A with the substitutions A91L + M96I + E129V + K177L + R179E + K220P + N224L + S242Q + Q254S | >180 | 38 | ND |
| Reference Alpha-Amylase A with the substitutions E129V + K177L + R179E | 57 | 11 | 402 |
| Reference Alpha-Amylase A with the substitutions E129V + K177L + R179E + K220P + N224L + S242Q + Q254S | 174 | 44 | >480 |
| Reference Alpha-Amylase A with the substitutions E129V + K177L + R179E + K220P + N224L + S242Q + Q254S + Y276F + L427M | >180 | 49 | >480 |
| Reference Alpha-Amylase A with the substitutions E129V + K177L + R179E + K220P + N224L + S242Q + Q254S + M284T | >180 | 49 | >480 |
| Reference Alpha-Amylase A with the substitutions E129V + K177L + R179E + K220P + N224L + S242Q + Q254S + N376* + I377* | 177 | 36 | >480 |
| Reference Alpha-Amylase A with the substitutions E129V + K177L + R179E + K220P + N224L + Q254S | 94 | 13 | >480 |
| Reference Alpha-Amylase A with the substitutions E129V + K177L + R179E + K220P + N224L + Q254S + M284T | 129 | 24 | >480 |
| Reference Alpha-Amylase A with the substitutions E129V + K177L + R179E + S242Q | 148 | 30 | >480 |
| Reference Alpha-Amylase A with the substitutions E129V + K177L + R179V | 78 | 9 | >480 |
| Reference Alpha-Amylase A with the substitutions E129V + K177L + R179V + K220P + N224L + S242Q + Q254S | 178 | 31 | >480 |
| Reference Alpha-Amylase A with the substitutions K220P + N224L + S242Q + Q254S | 66 | 17 | >480 |
| Reference Alpha-Amylase A with the substitutions K220P + N224L + Q254S | 30 | 6 | 159 |
| Reference Alpha-Amylase A with the substitution M284T | 35 | 7 | 278 |
| Reference Alpha-Amylase A with the substitutions M284V | 59 | 13 | ND |

ND not determined

The results demonstrate that the alpha-amylase variants have a significantly greater half-life and stability than the reference alpha-amylase.

Example 2

Preparation of Protease Variants and Test of Thermostability
Strains and Plasmids E. coli DH12S (available from Gibco BRL) was used for yeast plasmid rescue. pJTP000 is a S. cerevisiae and E. coli shuttle vector under the control of TPI promoter, constructed from pJC039 described in WO 01/92502, in which the Thermoascus aurantiacus M35 protease gene (WO 03/048353) has been inserted.

Saccharomyces cerevisiae YNG318 competent cells: MATa Dpep4[cir+] ura3-52, leu2-D2, his 4-539 was used for protease variants expression. It is described in J. Biol. Chem. 272 (15), pp 9720-9727, 1997.

Media and Substrates

10× Basal solution: Yeast nitrogen base w/o amino acids (DIFCO) 66.8 g/l, succinate 100 g/l, NaOH 60 g/l.

SC-glucose: 20% glucose (i.e., a final concentration of 2%=2 g/100 ml)) 100 ml/l, 5% threonine 4 ml/l, 1% tryptophan10 ml/l, 20% casamino acids 25 ml/l, 10× basal solution 100 ml/l. The solution is sterilized using a filter of a pore size of 0.20 micrometer. Agar (2%) and H$_2$O (approx. 761 ml) is autoclaved together, and the separately sterilized SC-glucose solution is added to the agar solution.

YPD: Bacto peptone 20 g/l, yeast extract 10 g/I, 20% glucose 100 ml/l.

YPD+Zn: YPD+0.25 mM ZnSO$_4$

PEG/LiAc solution: 40% PEG4000 50 ml, 5 M Lithium Acetate 1 ml.

96 well Zein micro titre plate:

Each well contains 200 microL of 0.05-0.1% of zein (Sigma), 0.25 mM ZnSO$_4$ and 1% of agar in 20 mM sodium acetate buffer, pH 4.5.

DNA Manipulations

Unless otherwise stated, DNA manipulations and transformations were performed using standard methods of molecular biology as described in Sambrook et al. (1989) Molecular cloning: A laboratory manual, Cold Spring Harbor lab. Cold Spring Harbor, N.Y.; Ausubel, F. M. et al. (eds.) "Current protocols in Molecular Biology", John Wiley and Sons, 1995; Harwood, C. R, and Cutting, S. M. (Eds.), Yeast Transformation Yeast transformation was performed using the lithium acetate method. 0.5 microL of vector (digested by restriction endnucleases) and 1 microL of PCR fragments is mixed. The DNA mixture, 100 microL of YNG318 competent cells, and 10 microL of YEAST MAKER carrier DNA (Clontech) is added to a 12 ml polypropylene tube (Falcon 2059). Add 0.6 ml PEG/LiAc solution and mix gently. Incubate for 30 min at 30° C., and 200 rpm followed by 30 min at 42° C. (heat shock). Transfer to an eppendorf tube and centrifuge for 5 sec. Remove the supernatant and resolve in 3 ml of YPD. Incubate the cell suspension for 45 min at 200 rpm at 30° C. Pour the suspension to SC-glucose plates and incubate 30° C. for 3 days to grow colonies. Yeast total DNA are extracted by Zymoprep Yeast Plasmid Miniprep Kit (ZYMO research).

DNA Sequencing

E. coli transformation for DNA sequencing was carried out by electroporation (BIO-RAD Gene Pulser). DNA Plasmids were prepared by alkaline method (Molecular Cloning, Cold Spring Harbor) or with the Qiagen® Plasmid Kit. DNA fragments were recovered from agarose gel by the Qiagen gel extraction Kit. PCR was performed using a PTC-200 DNA Engine. The ABI PRISM™ 310 Genetic Analyzer was used for determination of all DNA sequences.

Construction of Protease Expression Vector

The Themoascus M35 protease gene was amplified with the primer pair Prot F (SEQ ID NO: 15 herein) and Prot R (SEQ ID NO: 16 herein). The resulting PCR fragments were introduced into S. cerevisiae YNG318 together with the pJC039 vector (described in WO2001/92502) digested with restriction enzymes to remove the Humicola insolens cutinase gene.

The Plasmid in yeast clones on SC-glucose plates was recovered to confirm the internal sequence and termed as pJTP001.

Construction of Yeast Library and Site-Directed Variants

Library in yeast and site-directed variants were constructed by SOE PCR method (Splicing by Overlap Extension, see "PCR: A practical approach", p. 207-209, Oxford University press, eds. McPherson, Quirke, Taylor), followed by yeast in vivo recombination.

General Primers for Amplification and Sequencing

The primers AM34 (SEQ ID NO: 17 herein) and AM35 (SEQ ID NO: 18 herein) were used to make DNA fragments containing any mutated fragments by the SOE method together with degenerated primers (AM34+ Reverse primer and AM35+ forward primer) or just to amplify a whole protease gene (AM34+AM35).

| PCR reaction system: | Conditions: |
|---|---|
| 48.5 microL H$_2$O | 1  94° C. 2 min |
| 2 beads puRe Taq Ready-To-Go PCR (Amersham Biosciences) | 2  94° C. 30 sec |
| | 3  55° C. 30 sec |
| 0.5 micro L X 2 100 pmole/microL of primers | 4  72° C. 90 sec |
| 0.5 microL template DNA | 2-4 25 cycles |
| | 5  72° C. 10 min |

DNA fragments were recovered from agarose gel by the Qiagen gel extraction Kit. The resulting purified fragments were mixed with the vector digest. The mixed solution was introduced into Saccharomyces cerevisiae to construct libraries or site-directed variants by in vivo recombination.

Relative Activity Assay

Yeast clones on SC-glucose were inoculated to a well of a 96-well micro titre plate containing YPD+Zn medium and cultivated at 28° C. for 3 days. The culture supernatants were applied to a 96-well zein micro titer plate and incubated at at least 2 temperatures (ex. 60° C. and 65° C., 70° C. and 75° C., 70° C. and 80° C.) for more than 4 hours or overnight. The turbidity of zein in the plate was measured as A630 and the relative activity (higher/lower temperatures) was determined as an indicator of thermoactivity improvement. The clones with higher relative activity than the parental variant were selected and the sequence was determined.

Remaining Activity Assay

Yeast clones on SC-glucose were inoculated to a well of a 96-well micro titre plate and cultivated at 28° C. for 3 days. Protease activity was measured at 65° C. using azo-casein (Megazyme) after incubating the culture supernatant in 20 mM sodium acetate buffer, pH 4.5, for 10 min at a certain temperature (80° C. or 84° C. with 4° C. as a reference) to determine the remaining activity. The clones with higher remaining activity than the parental variant were selected and the sequence was determined.

Azo-Casein Assay 20 microL of samples were mixed with 150 microL of substrate solution (4 ml of 12.5% azo-casein in ethanol in 96 ml of 20 mM sodium acetate, pH 4.5, containing 0.01% triton-100 and 0.25 mM ZnSO$_4$) and incubated for 4 hours or longer.

After adding 20 microL/well of 100% trichloroacetic acid (TCA) solution, the plate was centrifuge and 100 microL of supernatants were pipette out to measure A440.

Expression of Protease Variants in Aspergillus oryzae

The constructs comprising the protease variant genes were used to construct expression vectors for Aspergillus. The Aspergillus expression vectors consist of an expression cassette based on the Aspergillus niger neutral amylase II promoter fused to the Aspergillus nidulans triose phosphate isomerase non translated leader sequence (Pna2/tpi) and the Aspergillus niger amyloglycosidase terminator (Tamg). Also present on the plasmid was the Aspergillus selective marker amdS from Aspergillus nidulans enabling growth on acetamide as sole nitrogen source. The expression plasmids for protease variants were transformed into Aspergillus as described in Lassen et al. (2001), Appl. Environ. Microbiol, 67, 4701-4707. For each of the constructs 10-20 strains were isolated, purified and cultivated in shake flasks.

Purification of Expressed Variants

1. Adjust pH of the 0.22 μm filtered fermentation sample to 4.0.
2. Put the sample on an ice bath with magnetic stirring. Add (NH4)2SO4 in small aliquots (corresponding to approx. 2.0-2.2 M (NH4)2SO4 not taking the volume increase into account when adding the compound).
3. After the final addition of (NH4)2SO4, incubate the sample on the ice bath with gentle magnetic stirring for min. 45 min.

4. Centrifugation: Hitachi himac CR20G High-Speed Refrigerated Centrifuge equipped with R20A2 rotor head, 5° C., 20,000 rpm, 30 min.
5. Dissolve the formed precipitate in 200 ml 50 mM Na-acetate pH 4.0.
6. Filter the sample by vacuum suction using a 0.22 μm PES PLUS membrane (IWAKI).
7. Desalt/buffer-exchange the sample to 50 mM Na-acetate pH 4.0 using ultrafiltration (Vivacell 250 from Vivascience equipped with 5 kDa MWCO PES membrane) overnight in a cold room. Dilute the retentate sample to 200 ml using 50 mM Na-acetate pH 4.0. The conductivity of sample is preferably less than 5 mS/cm.
8. Load the sample onto a cation-exchange column equilibrated with 50 mM Na-acetate pH 4.0. Wash unbound sample out of the column using 3 column volumes of binding buffer (50 mM Na-acetate pH 4.0), and elute the sample using a linear gradient, 0-100% elution buffer (50 mM Na-acetate+1 M NaCl pH 4.0) in 10 column volumes.
9. The collected fractions are assayed by an endo-protease assay (cf. below) followed by standard SDS-PAGE (reducing conditions) on selected fractions. Fractions are pooled based on the endo-protease assay and SDS-PAGE.

Endo-Protease Assay
1. Protazyme OL tablet/5 ml 250 mM Na-acetate pH 5.0 is dissolved by magnetic stirring (substrate: endo-protease Protazyme AK tablet from Megazyme—cat. #PRAK 11/08).
2. With stirring, 250 microL of substrate solution is transferred to a 1.5 ml Eppendorf tube.
3. 25 microL of sample is added to each tube (blank is sample buffer).
4. The tubes are incubated on a Thermomixer with shaking (1000 rpm) at 50° C. for 15 minutes.
5. 250 microL of 1 M NaOH is added to each tube, followed by vortexing.
6. Centrifugation for 3 min. at 16,100×G and 25° C.
7. 200 microL of the supernatant is transferred to a MTP, and the absorbance at 590 nm is recorded.

Results

TABLE 2

Relative activity of protease variants. Numbering of substitution(s) starts from N-terminal of the mature peptide in amino acids 1 to 177 of SEQ ID NO: 2 herein.

| Variant | Substitution(s) | Relative activity 65° C./60° C. |
|---|---|---|
| WT | None | 31% |
| JTP004 | S87P | 45% |

TABLE 2-continued

Relative activity of protease variants. Numbering of substitution(s) starts from N-terminal of the mature peptide in amino acids 1 to 177 of SEQ ID NO: 2 herein.

| Variant | Substitution(s) | Relative activity 65° C./60° C. |
|---|---|---|
| JTP005 | A112P | 43% |
| JTP008 | R2P | 71% |
| JTP009 | D79K | 69% |
| JTP010 | D79L | 75% |
| JTP011 | D79M | 73% |
| JTP012 | D79L/S87P | 86% |
| JTP013 | D79L/S87P/A112P | 90% |
| JTP014 | D79L/S87P/A112P | 88% |
| JTP016 | A73C | 52% |
| JTP019 | A126V | 69% |
| JTP021 | M152R | 59% |

TABLE 3

Relative activity of protease variants. Numbering of substitution(s) starts from N-terminal of the mature peptide in amino acids 1 to 177 of SEQ ID NO: 2 herein.

| | | Relative activity | | |
|---|---|---|---|---|
| Variant | Substitution(s) and/or deletion (S) | 70° C./65° C. | 75° C./65° C. | 75° C./70° C. |
| WT | None | 59% | 17% | |
| JTP036 | D79L/S87P/D142L | 73% | 73% | |
| JTP040 | T54R/D79L/S87P | | 71% | |
| JTP042 | Q53K/D79L/S87P/I173V | | 108% | |
| JTP043 | Q53R/D79L/S87P | | 80% | |
| JTP045 | S41R/D79L/S87P | | 82% | |
| JTP046 | D79L/S87P/Q158W | | 96% | |
| JTP047 | D79L/S87P/S157K | | 85% | |
| JTP048 | D79L/S87P/D104R | | 88% | |
| JTP050 | D79L/S87P/A112P/D142L | | 88% | |
| JTP051 | S41R/D79L/S87P/A112P/D142L | | | 102% |
| JTP052 | D79L/S87P/A112P/D142L/S157K | | | 111% |
| JTP053 | S41R/D79L/S87P/A112P/D142L/S157K | | | 113% |
| JTP054 | ΔS5/D79L/S87P | | | 92% |
| JTP055 | ΔG8/D79L/S87P | | | 95% |
| JTP059 | C6R/D79L/S87P | | | 92% |
| JTP061 | T46R/D79L/S87P | | | 111% |
| JTP063 | S49R/D79L/S87P | | | 94% |
| JTP064 | D79L/S87P/N88R | | | 92% |
| JTP068 | D79L/S87P/T114P | | | 99% |
| JTP069 | D79L/S87P/S115R | | | 103% |
| JTP071 | D79L/S87P/T116V | | | 105% |
| JTP072 | N26R/D79L/S87P | | 92% | |
| JTP077 | A27K/D79L/S87P/A112P/D142L | | | 106% |
| JTP078 | A27V/D79L/S87P/A112P/D142L | | | 100% |
| JTP079 | A27G/D79L/S87P/A112P/D142L | | | 104% |

TABLE 4

Relative activity of protease variants. Numbering of substitution(s) starts from N-terminal of the mature peptide in amino acids 1 to 177 of SEQ ID NO: 2 herein.

| | | Relative activity | Remaining activity | |
|---|---|---|---|---|
| Variant | Substitution(s) and/or deletion(s) | 75° C./65° C. | 80° C. | 84° C. |
| JTP082 | ΔS5/D79L/S87P/A112P/D142L | 129% | | 53% |
| JTP083 | T46R/D79L/S87P/A112P/D142L | 126% | | |
| JTP088 | Y43F/D79L/S87P/A112P/D142L | 119% | | |
| JTP090 | D79L/S87P/A112P/T124L/D142L | 141% | | |
| JTP091 | D79L/S87P/A112P/T124V/D142L | 154% | 43% | |
| JTP092 | ΔS5/N26R/D79L/S87P/A112P/D142L | | | 60% |

TABLE 4-continued

Relative activity of protease variants. Numbering of substitution(s) starts from N-terminal of the mature peptide in amino acids 1 to 177 of SEQ ID NO: 2 herein.

| Variant | Substitution(s) and/or deletion(s) | Relative activity 75° C./65° C. | Remaining activity 80° C. | 84° C. |
|---|---|---|---|---|
| JTP095 | N26R/T46R/D79L/S87P/A112P/D142L | | | 62% |
| JTP096 | T46R/D79L/S87P/T116V/D142L | | | 67% |
| JTP099 | D79L/P81R/S87P/A112P/D142L | | | 80% |
| JTP101 | A27K/D79L/S87P/A112P/T124V/D142L | | 81% | |
| JTP116 | D79L/Y82F/S87P/A112P/T124V/D142L | | 59% | |
| JTP117 | D79L/Y82F/S87P/A112P/T124V/D142L | | 94% | |
| JTP127 | D79L/S87P/A112P/T124V/A126V/D142L | | 53% | |

TABLE 5

Relative activity of protease variants. Numbering of substitution(s) starts from N-terminal of the mature peptide in amino acids 1 to 177 of SEQ ID NO: 2 herein.

| | | Relative activity | | |
|---|---|---|---|---|
| Variant | Substitutions | 75° C./70° C. | 80° C./70° C. | 85° C./70° C. |
| JTP050 | D79L S87P A112P D142L | 55% | 23% | 9% |
| JTP134 | D79L Y82F S87P A112P D142L | | 40% | |
| JTP135 | S38T D79L S87P A112P A126V D142L | | 62% | |
| JTP136 | D79L Y82F S87P A112P A126V D142L | | 59% | |
| JTP137 | A27K D79L S87P A112P A126V D142L | | 54% | |
| JTP140 | D79L S87P N98C A112P G135C D142L | 81% | | |
| JTP141 | D79L S87P A112P D142L T141C M161C | 68% | | |
| JTP143 | S36P D79L S87P A112P D142L | 69% | | |
| JTP144 | A37P D79L S87P A112P D142L | 57% | | |
| JTP145 | S49P D79L S87P A112P D142L | 82% | 59% | |
| JTP146 | S50P D79L S87P A112P D142L | 83% | 63% | |
| JTP148 | D79L S87P D104P A112P D142L | 76% | 64% | |
| JTP161 | D79L Y82F S87G A112P D142L | | 30% | 12% |
| JTP180 | S70V D79L Y82F S87G Y97W A112P D142L | | 52% | |
| JTP181 | D79L Y82F S87G Y97W D104P A112P D142L | | 45% | |
| JTP187 | S70V D79L Y82F S87G A112P D142L | | 45% | |
| JTP188 | D79L Y82F S87G D104P A112P D142L | | 43% | |
| JTP189 | D79L Y82F S87G A112P A126V D142L | | 46% | |
| JTP193 | Y82F S87G S70V D79L D104P A112P D142L | | | 15% |
| JTP194 | Y82F S87G D79L D104P A112P A126V D142L | | | 22% |
| JTP196 | A27K D79L Y82F S87G D104P A112P A126V D142L | | | 18% |

TABLE 6

Relative activity of protease variants. Numbering of substitution(s) starts from N-terminal of the mature peptide in amino acids 1 to 177 of SEQ ID NO: 2 herein.

| | | Relative activity | |
|---|---|---|---|
| Variant | Substitutions | 75° C./70° C. | 80° C./70° C. |
| JTP196 | A27K D79L Y82F S87G D104P A112P A126V D142L | 102% | 55% |
| JTP210 | A27K Y82F S87G D104P A112P A126V D142L | 107% | 36% |
| JTP211 | A27K D79L Y82F D104P A112P A126V D142L | 94% | 44% |
| JTP213 | A27K Y82F D104P A112P A126V D142L | 103% | 37% |

Example 3

Temperature Profile of Selected Variants Using Purified Enzymes

Selected variants showing good thermo-stability were purified and the purified enzymes were used in a zein-BCA assay as described below. The remaining protease activity was determined at 60° C. after incubation of the enzyme at elevated temperatures as indicated for 60 min, Zein-BCA Assay:

Zein-BCA assay was performed to detect soluble protein quantification released from zein by variant proteases at various temperatures, Protocol:

1) Mix 10 microliters of 10 micrograms/ml enzyme solutions and 100 ul of 0.025% zein solution in a micro titer plate (MTP).
2) Incubate at various temperatures for 60 min.
3) Add 10 microliters of 100% trichloroacetic acid (TCA) solution,
4) Centrifuge MTP at 3500 rpm for 5 min.
5) Take out 15 microliters to a new MTP containing 100 microliters of BCA assay solution (Pierce Cat#:23225, BCA Protein Assay Kit).
6) Incubate for 30 min. at 60° C.
7) Measure A562.

The results are shown in Table 7. All of the tested variants showed an improved thermo-stability as compared to the wt protease.

TABLE 7

Zein-BCA assay

| WT/Variant | Sample incubated 60 min at indicated temperatures (° C.) (μg/ml Bovine serum albumin equivalent peptide released) | | | | | | |
|---|---|---|---|---|---|---|---|
| | 60° C. | 70° C. | 75° C. | 80° C. | 85° C. | 90° C. | 95° C. |
| WT | 94 | 103 | 107 | 93 | 58 | 38 | |
| JTP050 | 86 | 101 | 107 | 107 | 104 | 63 | 36 |

TABLE 7-continued

Zein-BCA assay

| WT/Variant | Sample incubated 60 min at indicated temperatures (° C.) (μg/ml Bovine serum albumin equivalent peptide released) | | | | | | |
|---|---|---|---|---|---|---|---|
| | 60° C. | 70° C. | 75° C. | 80° C. | 85° C. | 90° C. | 95° C. |
| JTP077 | 82 | 94 | 104 | 105 | 99 | 56 | 31 |
| JTP188 | 71 | 83 | 86 | 93 | 100 | 75 | 53 |
| JTP196 | 87 | 99 | 103 | 106 | 117 | 90 | 38 |

Example 4

Characterization of *Penicillium oxalicum* Glucoamylase

The *Penicillium oxalicum* glucoamylase is disclosed in SEQ ID NO: 14 (mature) herein.

Substrate. Substrate: 1% soluble starch (Sigma S-9765) in deionized water

Reaction buffer: 0.1M Acetate buffer at pH 5.3

Glucose concentration determination kit: Wako glucose assay kit (LabAssay glucose, WAKO, Cat#298-65701), Reaction condition. 20 microL soluble starch and 50 microL acetate buffer at pH 5.3 were mixed. 30 microL enzyme solution (50 micro g enzyme protein/rill) was added to a final volume of 100 microL followed by incubation at 37° C. for 15 min.

The glucose concentration was determined by Wako kits.

All the work carried out in parallel.

Temperature optimum. To assess the temperature optimum of the *Penicillium oxalicum* glucoamylase the "Reaction condition"-assay described above was performed at 20, 30, 40, 50, 60, 70, 80, 85, 90 and 95° C. The results are shown in Table 8.

TABLE 8

Temperature optimum

| | Temperature (° C.) | | | | | | | | | |
|---|---|---|---|---|---|---|---|---|---|---|
| | 20 | 30 | 40 | 50 | 60 | 70 | 80 | 85 | 90 | 95 |
| Relative activity (%) | 63.6 | 71.7 | 86.4 | 99.4 | 94.6 | 100.0 | 92.9 | 92.5 | 82.7 | 82.8 |

From the results it can be seen that the optimal temperature for *Penicillium oxalicum* glucoamylase at the given conditions is between 50° C. and 70° C. and the glucoamylase maintains more than 80% activity at 95° C.

Heat stability. To assess the heat stability of the *Penicillium oxalicum* glucoamylase the Reaction condition assay was modifed in that the the enzyme solution and acetate buffer was preincubated for 15 min at 20, 30, 40, 50, 60, 70, 75, 80, 85, 90 and 95° C. Following the incubation 20 microL of starch was added to the solution and the assay was performed as described above.

The results are shown in Table 9.

TABLE 9

Heat stability

| | Temperature (° C.) | | | | | | | | | |
|---|---|---|---|---|---|---|---|---|---|---|
| | 20 | 30 | 40 | 50 | 60 | 70 | 80 | 85 | 90 | 95 |
| Relative activity (%) | 91.0 | 92.9 | 88.1 | 100.0 | 96.9 | 86.0 | 34.8 | 36.0 | 34.2 | 34.8 |

From the results it can be seen that *Penicillium oxalicum* glucoamylase is stable up to 70° C. after preincubation for 15 min in that it maintains more than 80% activity.

pH optimum. To assess the pH optimum of the *Penicillium oxalicum* glucoamylase the Reaction condition assay described above was performed at pH 2.0, 3.0, 3.5, 4.0, 4.5, 5.0, 6.0 7.0, 8.0, 9.0, 10.0 and 11.0. Instead of using the acetate buffer described in the Reaction condition assay the following buffer was used 100 mM Succinic acid, HEPES, CHES, CAPSO, 1 mM CaCl$_2$, 150 mM KCl, 0.01% Triton X-100, pH adjusted to 2.0, 3.0, 3.5, 4.0, 4.5, 5.0, 6.0 7.0, 8.0, 9.0, 10.0 or 11.0 with HCl or NaOH.

The results are shown in Table 10.

TABLE 10

| | pH optimum | | | | | | | | | | | |
|---|---|---|---|---|---|---|---|---|---|---|---|---|
| | pH | | | | | | | | | | | |
| | 2.0 | 3.0 | 3.5 | 4.0 | 4.5 | 5.0 | 6.0 | 7.0 | 8.0 | 9.0 | 10.0 | 11.0 |
| Relative activity (%) | 71.4 | 78.6 | 77.0 | 91.2 | 84.2 | 100.0 | 55.5 | 66.7 | 30.9 | 17.8 | 15.9 | 16.1 |

From the results it can be seen that *Penicillium oxalicum* glucoamylase at the given conditions has the highest activity at pH 5.0. The *Penicillium oxalicum* glucoamylase is active in a broad pH range in the it maintains more than 50% activity from pH 2 to 7.

pH stability. To assess the heat stability of the *Penicillium oxalicum* glucoamylase the Reaction condition assay was modfied in that the enzyme solution (50 micro g/mL) was preincubated for 20 hours in buffers with pH 2.0, 3.0, 3.5, 4.0, 4.5, 5.0, 6.0 7.0, 8.0, 9.0, 10.0 and 11.0 using the buffers described under pH optimum. After preincubation, 20 microL soluble starch to a final volume of 100 microL was added to the solution and the assay was performed as described above.

The results are shown in Table 11.

TABLE 11

| | pH stability | | | | | | | | | | | |
|---|---|---|---|---|---|---|---|---|---|---|---|---|
| | pH | | | | | | | | | | | |
| | 2.0 | 3.0 | 3.5 | 4.0 | 4.5 | 5.0 | 6.0 | 7.0 | 8.0 | 9.0 | 10.0 | 11.0 |
| Relative activity (%) | 17.4 | 98.0 | 98.0 | 103.2 | 100.0 | 93.4 | 71.2 | 90.7 | 58.7 | 17.4 | 17.0 | 17.2 |

From the results it can be seen that *Penicillium oxalicum* glucoamylase, is stable from pH 3 to pH 7 after preincubation for 20 hours and it decreases its activity at pH 8.

Example 5

Thermostability of Protease Pfu.

The thermostability of the *Pyrococcus furiosus* protease (Pfu S) purchased from Takara Bio Inc, (Japan) was tested using the same methods as in Example 2. It was found that the thermostability (Relative Activity) was 110% at (80° C./70° C.) and 103% (90° C./70° C.) at pH 4.5.

Example 6

Cloning of *Penicillium oxalicum* Strain Glucoamylase Gene
Preparation of *Penicillium oxalicum* Strain cDNA.

The cDNA was synthesized by following the instruction of 3' Rapid Amplifiction of cDNA End System (Invitrogen Corp., Carlsbad, Calif., USA).

Cloning of *Penicillium oxalicum* Strain Glucoamylase Gene.

The *Penicillium oxalicum* glucoamylase gene was cloned using the oligonucleotide primer shown below designed to amplify the glucoamylase gene from 5' end.

```
Sense primer:
                                    (SEQ ID NO: 19)
5'-ATGCGTCTCACTCTATTATCAGGTG-3'
```

The full length gene was amplified by PCR with Sense primer and AUAP (supplied by 3' Rapid Amplifiction of cDNA End System) by using Platinum HIFI Taq DNA polymerase (Invitrogen Corp., Carlsbad, Calif., USA). The amplification reaction was composed of 5 µl of 10× PCR buffer, 2 µl of 25 mM MgCl$_2$, 1 µl of 10 mM dNTP, 1 µl of 10 uM Sense primer, 1 µl of 10 uM AUAP, 2 µl of the first strand cDNA, 0.5 µl of HIFI Taq, and 37.5 µl of deionized water. The PCR program was: 94° C., 3 mins; 10 cycles of 94° C. for 40 secs, 60° C. 40 secs with 1° C. decrease per cycle, 68° C. for 2 min; 25 cycles of 94° C. for 40 secs, 50° C. for 40 secs, 68° C. for 2 min; final extension at 68° C. for 10 mins.

The obtained PCR fragment was cloned into pGEM-T vector (Promega Corporation, Madison, Wis., USA) using a pGEM-T Vector System (Promega Corporation, Madison, Wis., USA) to generate plasmid AMG 1. The glucoamylase gene inserted in the plasmid AMG 1 was sequencing confirmed. *E. coli* strain TOP10 containing plasmid AMG 1 (designated NN059173), was deposited with the Deutsche Sammlung von Mikroorganismen Lind Zellkulturen GmbH (DSMZ) on Nov. 23, 2009, and assigned accession number as DSM 23123.

Example 7

Expression of Cloned *Penicillium oxalicum* Glucoamylase

The *Penicillium oxalicum* glucoamylase gene was re-cloned from the plasmid AMG 1 into an *Aspergillus* expression vector by PCR using two cloning primer F and primer R shown below, which were designed based on the known sequence and added tags for direct cloning by IN-FUSION™ strategy.

```
Primer F:
                                        (SEQ ID NO: 20)
5' ACACAACTGGGGATCCACCATGCGTCTCACTCTATTATC Primer R:
                                        (SEQ ID NO: 21)
5' AGATCTCGAGAAGCTTAAAACTGCCACACGTCGTTGG
```

A PCR reaction was performed with plasmid AMG 1 in order to amplify the full-length gene. The PCR reaction was composed of 40 µg of the plasmid AMG 1 DNA, 1 µl of each primer (100 µM); 12.5 µl of 2× Extensor Hi-Fidelity master mix (Extensor Hi-Fidelity Master Mix, ABgene, United Kingdom), and 9.5 µl of PCR-grade water. The PCR reaction was performed using a DYAD PCR machine (Bio-Rad Laboratories, Inc., Hercules, Calif., USA) programmed for 2 minutes at 94° C. followed by a 25 cycles of 94° C. for 15 seconds, 50° C. for 30 seconds, and 72° C. for 1 minute; and then 10 minutes at 72° C.

The reaction products were isolated by 1.0% agarose gel electrophoresis using 1×TAE buffer where an approximately 1.9 kb PCR product band was excised from the gel and purified using a GFX® PCR DNA and Gel Band Purification Kit (GE Healthcare, United Kingdom) according to manufacturer's instructions. DNA corresponding to the *Penicillium oxalicum* glucoamylase gene was cloned into an *Aspergillus* expression vector linearized with BamHI and HindIII, using an IN-FUSION™ Dry-Down PCR Cloning Kit (BD Biosciences, Palo Alto, Calif., USA) according to the manufacturer's instructions. The linearized vector construction is as described in WO 2005/042735 A1.

A 2 µl volume of the ligation mixture was used to transform 25 µl of Fusion Blue *E. coli* cells (included in the IN-FUSION™ Dry-Down PCR Cloning Kit). After a heat shock at 42° C. for 45 sec, and chilling on ice, 250 µl of SOC medium was added, and the cells were incubated at 37° C. at 225 rpm for 90 min before being plated out on LB agar plates containing 50 µg of ampicillin per ml, and cultivated overnight at 37° C. Selected colonies were inoculated in 3 ml of LB medium supplemented with 50 µg of ampicillin per ml and incubated at 37° C. at 225 rpm overnight. Plasmid DNA from the selected colonies was purified using Mini JETSTAR (Genomed, Germany) according to the manufacturer's instructions. *Penicillium oxalicum* glucoamylase gene sequence was verified by Sanger sequencing before heterologous expression. One of the plasmids was selected for further expression, and was named XYZ XYZ1471-4.

Protoplasts of *Aspergillus niger* MBin118 were prepared as described in WO 95/02043. One hundred µl of protoplast suspension were mixed with 2.5 µg of the XYZ1471-4 plasmid and 250 microliters of 60% PEG 4000 (Applichem) (polyethylene glycol, molecular weight 4,000), 10 mM CaCl$_2$, and 10 mM Tris-HCl pH 7.5 were added and gently mixed. The mixture was incubated at 37° C. for 30 minutes and the protoplasts were mixed with 6% low melting agarose (Biowhittaker Molecular Applications) in COVE sucrose (Cove, 1996, Biochim. Biophys, Acta 133:51-56) (1M) plates supplemented with 10 mM acetamide and 15 mM CsCl and added as a top layer on COVE sucrose (1M) plates supplemented with 10 mM acetamide and 15 mM CsCl for transformants selection (4 ml topagar per plate). After incubation for 5 days at 37° C. spores of sixteen transformants were picked up and seed on 750 µl YP-2% Maltose medium in 96 deepwell MT plates. After 5 days of stationary cultivation at 30° C., 10 µl of the culture-broth from each well was analyzed on a SDS-PAGE (Sodium dodecyl sulfate-polyacrylamide gel electrophoresis) gel, Griton XT Precast gel (BioRad, CA, USA) in order to identify the best transformants based on the ability to produce large amount of glucoamylase. A selected transformant was identified on the original transformation plate and was preserved as spores in a 20% glycerol stock and stored frozen (−80° C.).

Cultivation. The selected transformant was inoculated in 100 ml of MLC media and cultivated at 30° C. for 2 days in 500 ml shake flasks on a rotary shaker. 3 ml of the culture broth was inoculated to 100 ml of M410 medium and cultivated at 30° C. for 3 days. The culture broth was centrifugated and the supernatant was filtrated using 0.2 µm membrane filters.

Alpha-cyclodextrin affinity gel. Ten grams of Epoxy-activated Sepharose 6B (GE Healthcare, Chalfont St, Giles, U.K) powder was suspended in and washed with distilled water on a sintered glass filter. The gel was suspended in coupling solution (100 ml of 12.5 mg/ml alpha-cyclodextrin, 0.5 M NaOH) and incubated at room temperature for one day with gentle shaking. The gel was washed with distilled water on a sintered glass filter, suspended in 100 ml of 1 M ethanolamine, pH 10, and incubated at 50° C. for 4 hours for blocking. The gel was then washed several times using 50 mM Tris-HCl, pH 8 and 50 mM NaOAc, pH 4.0 alternatively. The gel was finally packed in a 35-40 ml column using equilibration buffer (50 mM NaOAc, 150 mM NaCl, pH 4.5).

Purification of glucoamylase from culture broth. Culture broth from fermentation of *A. niger* MBin118 harboring the glucoamylase gene was filtrated through a 0.22 µm RES filter, and applied on a alpha-cyclodextrin affinity gel column previously equilibrated in 50 mM NaOAc, 150 mM NaCl, pH 4.5 buffer. Unbound material was washed off the column with equilibration buffer and the glucoamylase was eluted using the same buffer containing 10 mM beta-cyclodextrin over 3 column volumes.

The glucoamylase activity of the eluent was checked to see, if the glucoamylase had bound to the alpha-cyclodextrin affinity gel. The purified glucoamylase sample was then dialyzed against 20 mM NaOAc, pH 5.0. The purity was finally checked by SDS-PAGE, and only a single band was found.

Example 8

Construction and Expression of a Site-Directed Variant of *Penicillium oxalicum* Glucoamylase (PEON)

Two PCR reactions were performed with plasmid XYZ1471-4, described in Example 9, using primers K79V F and K79VR shown below, which were designed to substitute lysine K at position 79 from the mature seequence to varin V and primers F-NP003940 and R-NP003940 shown below, which were designed based on the known sequence and added tags for direct cloning by IN-FUSION™ strategy.

```
Primer K79V F 18mer
                                        (SEQ ID NO: 22)
GCAGTCTTTCCAATTGAC Primer K79V R 18mer
                                        (SEQ ID NO: 23)
AATTGGAAAGACTGCCCG Primer F-NP003940:
                                        (SEQ ID NO: 24)
5' ACACAACTGGGGATCCACCATGCGTCTCACTCTATTATC
```

-continued

Primer R-NP003940:
(SEQ ID NO: 25)
5' AGATCTCGAGAAGCTTAAAACTGCCACACGTCGTTGG

The PCR was performed using a PTC-200 DNA Engine under the conditions described below.

| PCR reaction system: | | Conditions: |
|---|---|---|
| 48.5 micro L H2O | 1 | 94° C. 2 min |
| 2 beads puRe Taq Ready-To-Go PCR | 2 | 94° C. 30 sec |
| Beads (Amersham bioscineces) | 3 | 55° C. 30 sec |
| 0.5micro L X 2100 pmole/micro L Primers | 4 | 72° C. 90 sec |
| (K79V F + Primer R-NP003940, K79V R + | 2-4 | 25 cycles |
| Primer F-NP003940) | 5 | 72° C. 10 min |
| 0.5 micro L Template DNA | | |

DNA fragments were recovered from agarose gel by the Qiagen gel extraction Kit according to the manufacturer's instruction. The resulting purified two fragments were cloned into an *Aspergillus* expression vector linearized with BamHI and HindIII, using an IN-FUSION™ Dry-Down PCR Cloning Kit (BD Biosciences, Palo Alto, Calif., USA) according to the manufacturer's instructions. The linearized vector construction is as described in WO 2005/042735 A1.

The ligation mixture was used to transform *E. coli* DH5α cells (TOYOBO). Selected colonies were inoculated in 3 ml of LB medium supplemented with 50 µg of ampicillin per ml and incubated at 37° C. at 225 rpm overnight. Plasmid DNA from the selected colonies was purified using Qiagen plasmid mini kit (Qiagen) according to the manufacturer's instructions. The sequence of *Penicillium oxalicum* glucoamylase site-directed variant gene sequence was verified before heterologous expression and one of the plasmids was selected for further expression, and was named pPoPE001.

Protoplasts of *Aspergillus niger* MBin118 were prepared as described in WO 95/02043. One hundred microliters of protoplast suspension were mixed with 2.5 µg of the pPoPE001 plasmid and 250 microliters of 60% PEG 4000 (Applichem) (polyethylene glycol, molecular weight 4,000), 10 mM CaCl$_2$, and 10 mM Tris-HCl pH 7.5 were added and gently mixed. The mixture was incubated at 37° C. for 30 minutes and the protoplasts were mixed with 1% agarose L (Nippon Gene) in COVE sucrose (Cove, 1996, Biochim. Biophys. Acta 133:51-56) supplemented with 10 mM acetamide and 15 mM CsCl and added as a top layer on COVE sucrose plates supplemented with 10 mM acetamide and 15 mM CsCl for transformants selection (4 ml topagar per plate). After incubation for 5 days at 37° C. spores of sixteen transformants were picked up and seed on 750 µl YP-2% Maltose medium in 96 deepwell MT plates. After 5 days of stationary cultivation at 30° C., 10 µl of the culture-broth from each well was analyzed on a SDS-PAGE gel in order to identify the best transformants based on the ability to produce large amount of the glucoamylase.

Example 9

Purification of Site-Directed Po AMG Variant PE001

The selected transformant of the variant and the strain expressing the wild type *Penicillium oxalicum* glucoamylase described in Example 8 was cultivated in 100 ml of YP-2% maltose medium and the culture was filtrated through a 0.22 µm RES filter, and applied on a alpha-cyclodextrin affinity gel column previously equilibrated in 50 mM NaOAc, 150 mM NaCl, pH 4.5 buffer. Unbound materias was washed off the column with equilibration buffer and the glucoamylase was eluted using the same buffer containing 10 mM beta-cyclodextrin over 3 column volumes.

The glucoamylase activity of the eluent was checked to see, if the glucoamylase had bound to the alpha-cyclodextrin affinity gel. The purified glucoamylase samples were then dialyzed against 20 mM NaOAc, pH 5.0.

Example 10

Characterization of PE001 Protease Stability

40 µl enzyme solutions (1 mg/ml) in 50 mM sodium acetate buffer, pH 4.5, was mixed with 1/10 volume of 1 mg/ml protease solutions such as aspergillopepsinI described in *Biochem J*. 1975 April; 147(1): 45-53 or the commercially availble product from Sigma and aorsin described in Biochemical journal [0264-6021] Ichishima, 2003, 371(2): 541 and incubated at 4 or 32° C. overnight. As a control experiment, H$_2$O was added to the sample instead of proteases. The samples were loaded on SDS-PAGE to see if the glucoamylases are cleaved by proteases.

In SDS-PAGE, PE001 only showed one band corresponding to the intact molecule, while the wild type glucoamylase was degraded by proteases and showed a band at lower molecular size at 60 kCa.

TABLE 12

The result of SDS-PAGE after protease treatment

| | Wild type glucoamylase | | | | PE001 | | | | |
|---|---|---|---|---|---|---|---|---|---|
| | Protease | | | | | | | | |
| | aspergillopepsin I | | aorsin | | aspergillopepsin I | | aorsin | | control |
| | Incubation temperature (° C.) | | | | | | | | |
| | 4 | 32 | 4 | 32 | 4 | 32 | 4 | 32 | 4 |
| intact glucoamylase (ca. 70 kDa) | 100% | 90% | 40% | 10% | 100% | 100% | 100% | 100% | 100% |
| cleaved glucoamylase (ca. 60 kDa) | N.D. | 10% | 60% | 90% | N.D. | N.D. | N.D. | N.D. | N.D. |

N.D.: not detected.

Example 11

Less Cleavage During Cultivation

*Aspergillus* transformant of the variant (PE001) and the wild type *Penicillium oxalicum* glucoamylase were cultivated in 6-well MT plates containing 4× diluted YR-2% maltose medium supplemented with 10 mM sodium acetate buffer, pH4.5, at 32° C. for 1 week.

The culture supernatants were loaded on SDS-PAGE.

TABLE 13

The result of SDS-PAGE of the culture supernatants

|  | Wild type glucoamylase | PE001 |
| --- | --- | --- |
| intact glucoamylase (ca. 70 kDa) | 90% | 100% |
| cleaved glucoamylase (ca. 60 kDa) | 10% | N.D. |

N.D.: not detected.

The wild type glucoamylase was cleaved by host proteasaes during fermentation, while the variant yielded only intact molecule.

Example 12

Glucoamylase Activity of Variant PE001 Compared to Parent

The glucoamylase activity measures as AGU as described above was checked for the purified enzymes of the wild type *Penicillium oxalicum* and the variant glucoamylase.

The Glucoamylase Unit (AGU) was defined as the amount of enzyme, which hydrolyzes 1 micromole maltose per minute under the standard conditions (37° C., pH 4.3, substrate: maltose 100 mM, buffer: acetate 0.1 M, reaction time 6 minutes).

TABLE 14

| Relative specific activity | AGU/mg |
| --- | --- |
| *Penicillium oxalicum* wt | 100% |
| *Penicillium oxalicum* PE001 | 102% |

Example 13

Purification of Glucoamylase Variants Having Increased Thermostability

The variants showing increased thermostability may be constructed and expressed similar to the procedure described in Example 8. All variants were derived from the PE001. After expression in YPM medium, variants comprising the T65A or Q327F (SEQ ID NO: 14 numbering) substitution was micro-purified as follows:

Mycelium was removed by filtration through a 0.22 μm filter, 50 μl column material (alpha-cyclodextrin coupled to Mini-Leak divinylsulfone-activated agarose medium according to manufacturers recommendations) was added to the wells of a filter plate (Whatman, Unifilter 800 μl, 25-30 μm MBPP). The column material was equilibrated with binding buffer (200 mM sodium acetate pH 4.5) by two times addition of 200 μl buffer, vigorous shaking for 10 min (Heidolph, Titramax 101, 1000 rpm) and removal of buffer by vacuum (Whatman, UniVac 3), Subsequently, 400 μl culture supernatant and 100 μl binding buffer was added and the plate incubated 30 min with vigorous shaking. Unbound material was removed by vacuum and the binding step was repeated. Normally 4 wells were used per variant. Three washing steps were then performed with 200 μl buffer of decreasing ionic strength added (50/10/5 mM sodium acetate, pH 4.5), shaking for 15 min and removal of buffer by vacuum. Elution of the bound AMG was achieved by two times addition of 100 μl elution buffer (250 mM sodium acetate, 0.1% alpha-cyclodextrin, pH 6.0), shaking for 15 min and collection of eluted material in a microtiter plate by vacuum. Pooled eluates were concentrated and buffer changed to 50 mM sodium acetate pH 4.5 using centrifugal filter units with 10 kDa cut-off (Millipore Microcon Ultracel YM-10). Micropurified samples were stored at −18° C. until testing of thermostability.

Example 14

Protein Thermal Unfolding Analysis (TSA, Thermal Shift Assay)

Protein thermal unfolding of the T65A and Q327F variants, was monitored using Sypro Orange (In-vitrogen, S-6650) and was performed using a real-time PCR instrument (Applied Biosystems; Step-One-Plus).

In a 96-well plate, 25 microliter micropurified sample in 50 mM Acetate pH4.5 at approx. 100 microgram/ml was mixed (5:1) with Sypro Orange (resulting conc.=5×; stock solution from supplier=5000×). The plate was sealed with an optical PCR seal. The PCR instrument was set at a scan-rate of 76° C. pr. hr, starting at 25° C. and finishing at 96° C.

Protein thermal unfolding of the E501V+Y504T variant, was monitored using Sypro Orange (In-vitrogen, S-6650) and was performed using a real-time PCR instrument (Applied Biosystems; Step-One-Plus).

In a 96-well plate, 15 microliter purified sample in 50 mM Acetate pH4.5 at approx. 50 microgram/ml was mixed (1:1) with Sypro Orange (resulting conc.=5×; stock solution from supplier=5000×) with or without 200 ppm Acarbose (Sigma A8980). The plate was sealed with an optical PCR seal. The PCR instrument was set at a scan-rate of 76 degrees C. pr. hr, starting at 25° C. and finishing at 96° C.

Fluorescence was monitored every 20 seconds using in-built LED blue light for excitation and ROX-filter (610 nm, emission).

Tm-values were calculated as the maximum value of the first derivative (dF/dK) (ref.: Gregory et al., 2009, *J. Biomol. Screen.* 14: 700).

TABLE 15 a.

| Sample | Tm (Deg. Celsius) +/− 0.4 |
| --- | --- |
| PO-AMG (PE001) | 80.3 |
| Variant Q327F | 82.3 |
| Variant T65A | 81.9 |

TABLE 15-continued b.

| Sample | Tm (Deg. Celsius) +/− 0.4 | |
|---|---|---|
| Acarbose: | − | + |
| PO-AMG (PE001) | 79.5 | 86.9 |
| Variant E501V Y504T | 79.5 | 95.2 |

Example 15

Thermostability Analysis by Differential Scanning Calorimetry (DSC)

Additional site specific variants having substitutions and/or deletions at specific positions were constructed basically as described in Example 8 and purified as described in Example 9.

The thermostability of the purified Po-AMG PE001 derived variants were determined at pH 4.0 or 4.8 (50 mM Sodium Acetate) by Differential Scanning calorimetry (DSC) using a VP-Capillary Differential Scanning calorimeter (MicroCal Inc., Piscataway, N.J., USA). The thermal denaturation temperature, Td (° C.), was taken as the top of the denaturation peak (major endothermic peak) in thermograms (Cp vs. T) obtained after heating enzyme solutions in selected buffers (50 mM Sodium Acetate, pH 4.0 or 4.8) at a constant programmed heating rate of 200 K/hr.

Sample- and reference-solutions (approximately 0.3 ml) were loaded into the calorimeter (reference: buffer without enzyme) from storage conditions at 10° C. and thermally pre-equilibrated for 10 minutes at 20° C. prior to DSC scan from 20° C. to 110° C. Denaturation temperatures were determined with an accuracy of approximately +/−1° C.

The isolated variants and the DSC data are disclosed in Table 16 below.

TABLE 16

| Po-AMG name | Mutations Mutations relative to PE001 | DSC Td (° C.) @ pH 4.0 | DSC Td (° C.) @ pH 4.8 |
|---|---|---|---|
| PE001 | | 82.1 | 83.4 |
| GA167 | E501V Y504T | 82.1 | |
| GA481 | T65A K161S | 84.1 | 86.0 |
| GA487 | T65A Q405T | 83.2 | |
| GA490 | T65A Q327W | 87.3 | |
| GA491 | T65A Q327F | 87.7 | |
| GA492 | T65A Q327Y | 87.3 | |
| GA493 | P11F T65A Q327F | 87.8 | 88.5 |
| GA497 | R1K D3W K5Q G7V N8S T10K P11S T65A Q327F | 87.8 | 88.0 |
| GA498 | P2N P4S P11F T65A Q327F | 88.3 | 88.4 |
| GA003 | P11F D26C K33C T65A Q327F | 83.3 | 84.0 |
| GA009 | P2N P4S P11F T65A Q327W E501V Y504T | 88.8 | |
| GA002 | R1E D5N P4G G6R G7A N8A T10D P11D T65A Q327F | 87.5 | 88.2 |
| GA005 | P11F T65A Q327W | 87.4 | 88.0 |
| GA008 | P2N P4S P11F T65A Q327F E501V Y504T | 89.4 | 90.2 |
| GA010 | P11F T65A Q327W E501V Y504T | | 89.7 |
| GA507 | T65A Q327F E501V Y504T | | 89.3 |
| GA513 | T65A S105P Q327W | | 87.0 |
| GA514 | T65A S105P Q327F | | 87.4 |
| GA515 | T65A Q327W S364P | | 87.8 |
| GA516 | T65A Q327F S364P | | 88.0 |
| GA517 | T65A S103N Q327F | | 88.9 |

TABLE 16-continued

| Po-AMG name | Mutations Mutations relative to PE001 | DSC Td (° C.) @ pH 4.0 | DSC Td (° C.) @ pH 4.8 |
|---|---|---|---|
| GA022 | P2N P4S P11F K34Y T65A Q327F | | 89.7 |
| GA023 | P2N P4S P11F T65A Q327F D445N V447S | | 89.9 |
| GA032 | P2N P4S P11F T65A I172V Q327F | | 88.7 |
| GA049 | P2N P4S P11F T65A Q327F N502* | | 88.4 |
| GA055 | P2N P4S P11F T65A Q327F N502T P563S K571E | | 88.0 |
| GA057 | P2N P4S P11F R31S K33V T65A Q327F N564D K571S | | 89.5 |
| GA058 | P2N P4S P11F T65A Q327F S377T | | 88.6 |
| GA064 | P2N P4S P11F T65A V325T Q327W | | 88.0 |
| GA068 | P2N P4S P11F T65A Q327F D445N V447S E501V Y504T | | 90.2 |
| GA069 | P2N P4S P11F T65A I172V Q327F E501V Y504T | | 90.2 |
| GA073 | P2N P4S P11F T65A Q327F S377T E501V Y504T | | 90.1 |
| GA074 | P2N P4S P11F D26N K34Y T65A Q327F | | 89.1 |
| GA076 | P2N P4S P11F T65A Q327F I375A E501V Y504T | | 90.2 |
| GA079 | P2N P4S P11F T65A K218A K221D Q327F E501V Y504T | | 90.9 |
| GA085 | P2N P4S P11F T65A S103N Q327F E501V Y504T | | 91.3 |
| GA086 | P2N P4S T10D T65A Q327F E501V Y504T | | 90.4 |
| GA088 | P2N P4S F12Y T65A Q327F E501V Y504T | | 90.4 |
| GA097 | K5A P11F T65A Q327F E501V Y504T | | 90.0 |
| GA101 | P2N P4S T10E E18N T65A Q327F E501V Y504T | | 89.9 |
| GA102 | P2N T10E E18N T65A Q327F E501V Y504T | | 89.8 |
| GA084 | P2N P4S P11F T65A Q327F E501V Y504T T568N | | 90.5 |
| GA108 | P2N P4S P11F T65A Q327F E501V Y504T K524T G526A | | 88.6 |
| GA126 | P2N P4S P11F K34Y T65A Q327F D445N V447S E501V Y504T | | 91.8 |
| GA129 | P2N P4S P11F R31S K33V T65A Q327F D445N V447S E501V Y504T | | 91.7 |
| GA087 | P2N P4S P11F D26N K34Y T65A Q327F E501V Y504T | | 89.8 |
| GA091 | P2N P4S P11F T65A F80* Q327F E501V Y504T | | 89.9 |
| GA100 | P2N P4S P11F T65A K112S Q327F E501V Y504T | | 89.8 |
| GA107 | P2N P4S P11F T65A Q327F E501V Y504T T516P K524T G526A | | 90.3 |
| GA110 | P2N P4S P11F T65A Q327F E501V N502T Y504* | | 90.6 |

Example 16

Thermostability Analysis by Thermo-Stress Test and pNPG Assay

Starting from one of the identified substitution variants from Example 10, identified as PE008, additional variants were tested by a thereto-stress assay in which the supernatant from growth cultures were assayed for glucoamylase (AMG) activity after a heat shock at 83° C. for 5 min.

After the heat-shock the residual activity of the variant was measured as well as in a non-stressed sample.

Description of Po-AMG pNPG Activity Assay:

The *Penicillium oxalicum* glucoamylase pNPG activity assay is a spectrometric endpoint assay where the samples are split in two and measured thereto-stressed and nonthermo-stressed. The data output is therefore a measurement of residual activity in the stressed samples.

Growth:

A sterile micro titer plate (MTP) was added 200 microliters rich growth media (FT X-14 without Dowfax) to each well. The strains of interest were inoculated in triplicates directly from frozen stocks to the MTP. Benchmark was inoculated in 20 wells. Non-inoculated wells with media were used as assay blanks. The MTP was placed in a plastic box containing wet tissue to prevent evaporation from the wells during incubation. The plastic box was placed at 34° C. for 4 days.

Assay:

50 microliters supernatant was transferred to 50 microliters 0.5 M NaAc pH 4.8 to obtain correct sample pH.

50 microliters dilution was transferred to a PCR plate and thermo-stressed at 83° C. for 5 minutes in a PCR machine. The remaining half of the dilution was kept at RT.

20 microliters of both stressed and unstressed samples was transferred to a standard MTP, 20 microliters pNPG-substrate was added to start the reaction. The plate was incubated at RT for 1 h.

The reaction was stopped and the colour developed by adding 50 microliters 0.5 M $Na_2CO_3$. The yellow colour was measured on a plate reader (Molecular Devices) at 405 nm.

Buffers:

0.5 M NaAc pH 4.8

0.25 M NaAc pH 4.8

Substrate, 6 mM pNPG:

15 mg 4-nitrophenyl D-glucopyranoside in 10 mL 0.25 NaAc pH 4.8

Stop/Developing Solution:

0.5 M $Na_2CO_3$

Data Treatment:

In Excel the raw Abs405 data from both stressed and unstressed samples were blank subtracted with their respective blanks. The residual activity (% res. act.=($Abs_{unstressed}$($Abs_{unstressed}$-$Abs_{stressed}$))/$Abs_{unstressed}$*100%) was calculated and plotted relative to benchmark, Po-amg0008.

TABLE 17

| Po-AMG name | Mutations | % residual activity |
| --- | --- | --- |
| GA008 | P2N P4S P11F T65A Q327F E501V Y504T | 100 |
| GA085 | P2N P4S P11F T65A S103N Q327F E501V Y504T | 127 |
| GA097 | K5A P11F T65A Q327F E501V Y504T | 106 |
| GA107 | P2N P4S P11F T65A Q327F E501V Y504T T516P K524T G526A | 109 |
| GA130 | P2N P4S P11F T65A V79A Q327F E501V Y504T | 111 |
| GA131 | P2N P4S P11F T65A V79G Q327F E501V Y504T | 112 |
| GA132 | P2N P4S P11F T65A V79I Q327F E501V Y504T | 101 |
| GA133 | P2N P4S P11F T65A V79L Q327F E501V Y504T | 102 |
| GA134 | P2N P4S P11F T65A V79S Q327F E501V Y504T | 104 |
| GA150 | P2N P4S P11F T65A L72V Q327F E501V Y504T | 101 |
| GA155 | S255N Q327F E501V Y504T | 105 |

TABLE 18

| Po-AMG name | Mutations | % residual activity |
| --- | --- | --- |
| GA008 | P2N P4S P11F T65A Q327F E501V Y504T | 100 |
| GA179 | P2N P4S P11F T65A E74N V79K Q327F E501V Y504T | 108 |
| GA180 | P2N P4S P11F T65A G220N Q327F E501V Y504T | 108 |
| GA181 | P2N P4S P11F T65A Y245N Q327F E501V Y504T | 102 |
| GA184 | P2N P4S P11F T65A Q253N Q327F E501V Y504T | 110 |
| GA185 | P2N P4S P11F T65A D279N Q327F E501V Y504T | 108 |
| GA186 | P2N P4S P11F T65A Q327F S359N E501V Y504T | 108 |
| GA187 | P2N P4S P11F T65A Q327F D370N E501V Y504T | 102 |
| GA192 | P2N P4S P11F T65A Q327F V460S E501V Y504T | 102 |
| GA193 | P2N P4S P11F T65A Q327F V460T P468T E501V Y504T | 102 |
| GA195 | P2N P4S P11F T65A Q327F T463N E501V Y504T | 103 |
| GA196 | P2N P4S P11F T65A Q327F S465N E501V Y504T | 106 |
| GA198 | P2N P4S P11F T65A Q327F T477N E501V Y504T | 106 |

Example 17

Test for Glucoamylase Activity of Thermo-Stable Variants According to the Invention All of the above described variants disclosed in tables 16, 17, and 18 have been verified for Glucoamylase activity on culture supernatants using the pNPG assay described in Example 16.

Example 18

Determination of Thermostablity of Endo-beta-glucanases (EG) by Differential Scanning Calorimitry (DSC)

The thermostability of EGs was tested as described in the "Materials & Methods" section under "Determination of Td by Differential Scanning calorimetry for Endoglucanases and Hemicellulases"

TABLE 19

| ID | Family | Donor | Melting point ° C. (DSC) |
| --- | --- | --- | --- |
| Endoglucanase TL (SEQ ID NO: 9) | GH5 | Talaromyces leycettanus | 89 |
| Endoglucanase PC (SEQ ID NO: 35) | GH5 | Penicillium capsulatum | 83 |
| Endoglucanase TS (SEQ ID NO: 36) | GH5 | Trichophaea saccata | 81 |
| Endoglucanase SF (SEQ ID NO: 38) | GH45 | Sordaria fimicola | 75 |

Example 19

Adding Thermostable Xylanase in Liquefaction—Effect on Ethanol Yield and Corn Fiber Degradation All treatments were evaluated via 100 g small-scale liquefaction. Corn flour obtained from industrial corn ethanol plants was used for the experiments. The dry solids (DS) of the corn flour was 85.12%, determined by Mettler-Toledo HB43 halogen moisture balance. For liquefaction, 38.77 g corn flour and 61.23 g tap water were added to reach DS of 33% and mass of 100 g in each canister of Lab-O-Mat. The pH of the corn slurry was found to be about 5.9 without adjustment. 40% $H_2SO_4$ was added to each canister to adjust pH to 5.0 for liquefaction. Each canister was dosed with the appropriate amount of diluted enzyme as shown in Table 21 below. The alpha-amylase (AA369) and the endo-glucanase (TI EG) was used. Two thermostable xylanases were evaluated as shown in Table 20. Final DS of the corn slurry after all additions and prior to liquefaction was 31.4%. The canisters were then sealed with caps, and loaded into Lab-O-Mat. Liquefaction happened at 85° C. for two hours with constant rotation.

After liquefaction done, the canisters were taken off from Lab-O-Mat and put on ice for fast cooling. The cooled corn mashes were then removed from canisters to beakers, and prepared for simultaneous saccharification and fermentation (SSF). Each SSF treatment was run in five replicate. 3 ppm penicillin and 800 ppm urea was supplemented before SSF started, Approximately 5 g of each corn mash (liquefied above) was added to 15 ml polypropylene tube. The tubes were prepared by drilling a 1/32 inch (1.5 mm) hole and the empty tubes were then weighed before corn slurry was added. The tubes were weighed again after mash was added to determine the exact weight of mash in each tube. Each tube was dosed with 0.6 AGU/gDS of Glucoamylase SA (GSA). Actual enzyme dosages were based on the exact weight of corn slurry in each tube. After enzyme dosage, each tube was added with 100 ul of ETHANOL RED™ yeast propagate, and then were incubated in 32° C. water bath for 54 hrs. Samples were taken at the end of fermentation for HPLC analysis. The HPLC preparation consisted of stopping the reaction by addition of 50 micro liters of 40% $H_2SO_4$, centrifuging, and filtering through a 0.45 micrometer filter. Samples were stored at 4° C. until analysis. Agilent™ 1100 HPLC system coupled with RI detector was used to determine ethanol and oligosaccharides concentration. The separation column was aminex HPX-87H ion exclusion column (300 mm×7.8 mm) from BioRad™.

TABLE 20

Xylanase tested in liquefaction

| Source | Family | Action | DSC, ° C. |
|---|---|---|---|
| *Talaromyces leycettanus* (SEQ ID NO: 5 herein) | GH10 | Xylanase | 89 |
| *Dictyoglomus thermophilum* (SEQ ID NO: 34 herein) | GH11 | Xylanase | 106 |

TABLE 21

Enzyme dosage in liquefaction

| Liquefaction treatment | AA dose (KNU-A/g DS) | EG dose (μg EP/gDS) | Xyl dose (μg EP/gDS) |
|---|---|---|---|
| AA control | 0.12 | | |
| AA + EG | 0.12 | 100 | |
| AA + EG + Xyl | 0.12 | 50 | 50 |
| AA + Xyl | 0.12 | | 50 |

Results:

The ethanol yield from each treatment was summarized in Table 22 below. The Tl xylanase has good performance by itself and on top of EG. By the same enzyme dosage of 100 ug/gDS, the combination of xylanase and EG gave higher ethanol yield than EG itself. From GPC data after liquefaction, it was found that the treatment with combination of Tl xylanase and Tl EG yielded smaller fragments than treatment with Tl EG alone, indicating the Tl xylanase was able to cut the corn fiber into smaller fragments, hence help to release more bound starch.

TABLE 22

Summarized Ethanol Yield and Percent Change Results

| Liquefaction Treatment | Ethanol (% w/v) | Ethanol Increase (%) |
|---|---|---|
| AA only control | 13.40 | — |
| AA + EG100 | 13.50 | 0.7% |
| AA + EG50 + Tl Xyl50 | 13.65 | 1.9% |
| AA + Tl Xyl50 | 13.50 | 0.8% |
| AA + EG50 + Dt Xyl50 | 13.55 | 1.1% |
| AA + Dt Xyl50 | 13.44 | 0.3% |

Example 20

Adding Thermostable Hemicellulase in Liquefaction of Corn with Alpha-Amylase—Effect on Ethanol Yield All treatments were evaluated via 18 g liquefaction. Ground corn flour was obtained from an industrial corn ethanol plant to be used for the experiment. The dry solids (% DS) of the corn flour was 86.5% as determined by Mettler-Toledo HB43 halogen moisture balance in duplicate. For liquefaction of the corn flour, 6.4±0.1 g corn flour was weighed into a 40 ml Oak Ridge tube. Tap water was added to reach % DS of 32.2% and mass of 17.2±0.2 g corn slurry. The pH of the corn slurry was found to be about 6.0; 23 μl of 40% $H_2SO_4$ was added to each tube to reduce the pH to 5.0 for liquefaction.

The alpha-amylase (AA369) was used. In addition to the AA-only control, six thermostable hemicellulases were evaluated as shown in Table 23. Each tube was dosed with the appropriate amount of diluted enzyme as shown in Table 24 below. Each liquefaction treatment was tested in quadruplicate along with six controls without hemicellulase added. Actual enzyme dosages were calculated based on the mass of corn slurry in each tube; tap water was added to bring the calculated % DS of all tubes to 31.0%. The final volume of the corn slurry after all additions and prior to liquefaction was 18.1±0.4 g. After enzyme and water addition, the tubes were sealed tightly, shaken thoroughly, and then placed in a Boekel Big SHOT III hybridization oven Model 230402 with a rack that holds and rotates the tubes vertically around a fixed axis. The oven was preheated to 80.0±0.5° C. as determined by a calibrated thermometer attached to the oven rack. The incubator temperature decreased while the door was open for loading; the temperature on the thermometer was monitored until it reached 75° C. at which time the timer was started for a two hour incubation with rotation set at speed 20 rpm.

TABLE 23

List of Hemicellulase Source, family and Sequence ID

| Source of Hemicellulase | Family | Action | DSC (° C.) | Sequence ID |
|---|---|---|---|---|
| *Dictyoglomus thermophilum* | GH10 | Xylanase | 99 | (SEQ ID NO: 3 herein) |
| *Rasamsonia byssochlamydoides* | GH10 | Xylanase | 96 | (SEQ ID NO: 4 herein) |
| *Aspergilius fumigatus* | GH10 | Xylanase | 89 | (SEQ ID NO: 8 herein) |
| *Talaromyces emersonii* | GH3 | Beta-xylosidase | 78 | (SEQ ID NO: 6 herein) |
| *Dictyoglomus thermophilum* | GH11 | Xylanase | — | (SEQ ID NO: 34 herein) |
| *Trichoderma reesei* | CE5 | Acetylxylan esterase | 69 | (SEQ ID NO: 7 herein) |

TABLE 24

Enzyme Dosage in Liquefaction

| Liquefaction Treatments | AA dose (KNU-A/g DS) | Hemicellulase dose (μg EP (Enzyme Protein)/g DS) |
|---|---|---|
| AA | 0.12 | |
| AA + Hemicellulase | 0.12 | 100 |

After incubating the tubes for two hours at 80° C., the tubes were removed from the hybridization oven and submerged in cool water with occasional mixing for about 30 minutes until they were cool to the touch. The caps were removed and a small spatula was used to push material stuck to the sides of the tubes down. Urea and penicillin solutions prepared in-house were added to each tube to reach final concentrations of 700 ppm and 3 ppm, respectively. Each tube was dosed with the appropriate amount of diluted Glucoamylase SA (GSA). Actual enzyme dosage was 0.77 AGU/g DS based on the average weight of liquefied corn mash in each tube; tap water was added as needed to bring the DS of each tube to 31%. All tubes had 400 μL of yeast rehydrated in tap water added; the volume is based on the average mash weight in each tube and a yeast dose of 20 μl/g corn mash rounded up to the nearest 100 μl. The tubes were then covered with caps with septa, vented by inserting a 22 gauge needle, and placed in an Infors HT MultitronPro humidity controlled incubator for Simultaneous Saccharification and Fermentation (SSF). The temperature was 32° C. and humidity was set at 80%; the tubes were mixed by hand twice a day throughout fermentation.

Samples were collected for HPLC analysis after 65 hours of fermentation. This process began with stopping the enzyme and yeast reactions by adding 200 μL of 40% $H_2SO_4$ (10 μl/g corn mash, rounded up to the nearest 100 μl) and mixing to distribute the acid; final calculated DS was 29.7% at the end of SSF. HPLC sample preparation consisted of transferring about 5 g of fermented corn mash to a 15 ml Falcon tube, centrifuging at 3000 rpm for 8 minutes, and passing the supernatant through a 0.45 μm filter into an HPLC vial. Samples were stored at 4° C. until analysis. The system used to determine ethanol and oligosaccharides concentration was an Agilent™ 100 HPLC system coupled with an RI detector. The separation column was a BioRad™ Aminex HPX-87H ion exclusion column (300 mm×7.8 mm).

Results

The final ethanol and percentage of ethanol increase by addition of hemicellulase are summarized in Table 25 below.

TABLE 25

Summarized Ethanol Yield and Percent Change Results

| Liquefaction Treatment | Ethanol (% w/v) | Ethanol Increase (%) |
|---|---|---|
| AA only control | 13.33 | — |
| AA + *Dictyoglomus thermophilum* GH10 xylanase | 13.59 | 2.0% |
| AA + *Rasamsonia byssochlamydoides* GH10 xylanase | 13.74 | 3.1% |
| AA + *Aspergillus fumigatus* GH10 xylanase | 13.47 | 1.1% |
| AA + *Talaromyces emersonii* GH3 beta-xylosidase | 13.29 | −0.3% |
| AA + *Dictyoglomus thermophilum* GH11 xylanase | 13.39 | 0.5% |
| AA + *Trichoderma reesei* CE5 acetylxylan esterase | 13.35 | 0.2% |

Example 21

Adding Thermostable Hemicellulase in Liquefaction of Corn—Effect on Ethanol Yield All treatments were evaluated via 18 g liquefaction. Ground corn flour was obtained from an industrial corn ethanol plant to be used for the experiment. The dry solids (% DS) of the corn flour was 86.5% as determined by Mettler-Toledo HB43 halogen moisture balance in duplicate. For liquefaction of the corn flour, 6.4±0.1 g corn flour was weighed into a 40 ml Oak Ridge tube. Tap water was added to reach % DS of 31.5% and mass of 17.6±0.2 g corn slurry. The pH of the corn slurry was found to be about 6.0; 23 μl of 40% $H_2SO_4$ was added to each tube to reduce the pH to 5.0 for liquefaction.

A thermostable hemicellulase from *Talaromyces leycettanus* (Tl Xyl) was evaluated as shown in Table 26. This hemicellulase was combined with alpha-amylase (AA369), thermostable glucoamylase (Po 498), thermostable protease (Protease Pfu) as indicated in the Table 26 below to evaluate the effect of the thermostable hemicellulase in liquefaction. Each tube was dosed with the appropriate amount of diluted enzyme as shown in Table 26 below. Each liquefaction treatment was tested in triplicate along with three controls without hemicellulase added. Actual enzyme dosages were calculated based on the mass of corn slurry in each tube; tap water was added to bring the calculated % DS of all tubes to 31.0%. The final volume of the corn slurry after all additions and prior to liquefaction was 18.1±0.4 g. After enzyme and water addition, the tubes were sealed tightly, shaken thoroughly, and then placed in a Boekel Boekel Big SHOT III hybridization oven Model 230402 with a rack that holds and rotates the tubes vertically around a fixed axis. The oven was preheated to 80.0±0.5° C. as determined by a calibrated thermometer attached to the oven rack. The incubator temperature decreased while the door was open for loading; the temperature on the thermometer was monitored until it reached 75° C. at which time the timer was started for a two-hour incubation with rotation set at speed 20 rpm.

| Source of Enzyme | Family | Action | Sequence ID |
|---|---|---|---|
| *Talaromyces leycettanus* | GH10 | Xylanase | (SEQ ID NO: 5 herein) |

TABLE 26

Enzyme Dosage in Liquefaction

| Liquefaction Treatments | AA 369 dose (KNU-A/g DS) | GA498 dose (μg EP*/g DS) | Protease Pfu dose (μg EP*/g DS) | Hemicellulase Tl xylanase dose (μg EP*/g DS) |
|---|---|---|---|---|
| AA | 0.12 | — | — | — |
| AA + GA | 0.12 | 4.5 | — | — |
| AA + High Protease | 0.12 | — | 3.0 | — |
| AA + Protease + GA | 0.12 | 4.5 | 0.0385 | — |
| AA + High Protease + GA | 0.12 | 4.5 | 3.0 | — |
| AA + Hemicellulase | 0.12 | — | — | 100 |
| AA + GA + Hemicellulase | 0.12 | 4.5 | — | 100 |
| AA + Protease + Hemicellulase | 0.12 | — | 3.0 | 100 |
| AA + Protease + GA + Hemicellulase | — | — | — | 100 |
| AA + Protease + GA + Hemicellulase | — | — | — | 100 |

*EP is enzyme protein

After incubating the tubes for two hours at 80° C., the tubes were removed from the hybridization oven and submerged in cool water with occasional mixing for about 30 minutes until they were cool to the touch. The caps were removed and a small spatula was used to push material stuck to the sides of the tubes down. Urea and penicillin solutions were added to each tube to reach final concentrations of 700 ppm and 3 ppm, respectively. Each tube was dosed with the appropriate amount of diluted glucoamylase (GSA). Actual enzyme dosage was 0.6 AGU/g DS based on the average weight of liquefied corn mash in each tube; tap water was added as needed to bring the DS of each tube to 31.2±0.1%. All tubes had 400 μL of yeast rehydrated in tap water added; the volume is based on the average mash weight in each tube and a yeast dose of 20 μl/g corn mash rounded up to the nearest 100 μl. The tubes were then covered with caps with septa, vented by inserting a 22 gauge needle, and placed in an Infors HT MultitronPro humidity controlled incubator for Simultaneous Saccharification and Fermentation (SSF). The temperature was 32° C. and humidity was set at 80%; the tubes were mixed by hand twice a day throughout fermentation.

Samples were collected for HPLC analysis after 65 hours of fermentation. This process involved stopping the enzyme and yeast reactions by adding 200 μL of 40% $H_2SO_4$ (10 μl/g corn mash, rounded up to the nearest 100 μl) and mixing to distribute the acid; final calculated DS was 30±0.1% at the end of SSF. HPLC sample preparation consisted of transferring about 5 g of fermented corn mash to a 15 ml Falcon tube, centrifuging at 3000 rpm for 8 minutes, and passing the supernatant through a 0.45 μm filter into an HPLC vial. Samples were stored at 4° C. until analysis. The system used to determine ethanol and oligosaccharides concentration was an Agilent™ 100 HPLC system coupled with an RI detector. The separation column was a BioRad™ Aminex HPX-87H ion exclusion column (300 mm×7.8 mm).

Additionally, the samples were analysed for solubilized feruloyated arabinoxylan (SFA) as an indication of hydrolysis of xylan in corn. Analysis was completed using a Tecan Safire V 2.20 08/02 plate reader using XFLUOR4BETA Version: E 4.22d. To prepare samples for analysis, a portion of the 0.45 μm filtered supernatant was diluted eight-fold in deionized water. 200 μl of the resulting solution was transferred to a UV-compatible 96-well microtiter plate and A320 was measured; several wells with 200 μl deionized water were included to use a blanks.

Results

The final ethanol and percentage of ethanol increase by addition of hemicellulase to thermostable GA, thermostable protease and formulated products in liquefaction are summarized in Table 27 below. Treatments containing hemicellulase all showed at least 1% increase in ethanol yield over the same treatment without hemicelluase. The treatments with only AA and AA+Protease+GA were found to have statistically higher ethanol yield of 2.0% and 2.1%, respectively, when hemicellulase was added in liquefaction. Statistical analysis was completed using Dunnett's test for mean comparison (Statistics program used was SAS JMP).

SFA and percentage of SFA increase by addition of hemicellulase on top of various activities and formulated products in liquefaction are summarized in Table 27 below. Thermostable hemicellulase in liquefaction increased SFA in supernatant over the same treatment without hemicellulase in all cases.

TABLE 27

Summarized Ethanol Yield and Percent Change Over Same Treatment Without Hemicellulase

| Liquefaction Treatment | Ethanol (% w/v) | Ethanol Increase (%) |
|---|---|---|
| AA | 12.99 | — |
| AA + GA | 13.13 | — |
| AA + High Protease | 13.31 | — |
| AA + Protease + GA | 13.07 | — |
| AA + High Protease + GA | 13.40 | — |
| AA + Hemicellulase | 13.25 | 2.0% |
| AA + GA + Hemicellulase | 13.32 | 1.5% |
| AA + Protease + Hemicellulase | 13.52 | 1.5% |
| AA + Protease + GA + Hemicellulase | 13.35 | 2.1% |
| AA + High Protease + GA + Hemicellulase | 13.58 | 1.3% |

TABLE 27

Summarized Solubilized Feruloyated Arabinoxylan (SFA) by A320 Results and Percent Change Over Same Treatment Without Hemicellulase

| Liquefaction Treatment | Corrected* Absorbance | Percent Change |
|---|---|---|
| AA | 7.79 | — |
| AA + GA | 7.8 | — |
| AA + Protease | 7.52 | — |
| AA + Protease + GA | 7.67 | — |

TABLE 27-continued

Summarized Solubilized Feruloyated Arabinoxylan (SFA) by A320 Results and Percent Change Over Same Treatment Without Hemicellulase

| Liquefaction Treatment | Corrected* Absorbance | Percent Change |
|---|---|---|
| AA + High Protease + GA | 7.95 | — |
| AA + Hemicellulase | 8.33 | 7.0% |
| AA + GA + Hemicellulase | 8.07 | 3.5% |
| AA + Protease + Hemicellulase | 8.66 | 15.1% |
| AA + Protease + GA + Hemicellulase | 9.07 | 18.3% |
| AA + High Protease + GA + Hemicellulase | 8.91 | 12.0% |

*Value corrected for eight-fold dilution and blank subtracted.

Example 22

The Impact of Grind Size and Thermostable Xylanase Addition in Liquefaction—Effect on Ethanol Yield All treatments were evaluated via 100 g small-scale liquefaction. Corn flour obtained from an industrial corn ethanol plant was used for the experiment. To obtain the "Turkish ground" corn, the industrial corn flour was ground in-lab using a Bunn® Coffee Mill. A sieve analysis was performed on the industrial corn flour and Turkish ground corn flour. To perform sieve analysis, 30 g of corn flour sample was weighed and placed in the Advantech Sonic Sifter. The sifter was run for 2 minutes using the sift/pulse setting at an amplitude of 8. Table 28 displays the resulting grind size distribution of the corn flour. The dry solids (DS) of the industrial ground corn was 86.48% and the Turkish ground corn was 86.58%, as determined by Mettler-Toledo HB43 halogen moisture balance. Each of the three liquefaction treatments were run in triplicate in the Lab-O-Mat (nine canisters total). Corn and tap water were added to each canister such that each corn slurry had a DS of 32%. The corn flour type, corn weight and tap water weight added the canisters for each treatment is as shown in Table 29. The pH of each corn slurry was adjusted to 5.0 using 40% $H_2SO_4$. Each canister was dosed with the appropriate amount of diluted enzyme as shown in Table 29. The total weight of corn, tap water and diluted enzyme equaled 100 g. The alpha-amylase (AA369) and the *Dictyoglomus thermophilum* GH11 xylanase (Dt xylanase from Table 20) were used. The canisters were then sealed with caps and loaded into the Lab-O-Mat. Liquefaction happened at 80° C. for two hours with constant rotation.

After liquefaction was done, the canisters were taken off from the Lab-O-Mat and put on ice for fast cooling. The cooled corn mashes were then removed from canisters to beakers, and prepared for simultaneous saccharification and fermentation (SSF). Five SSF replicates were run for each canister, thus providing 15 total SSF replicates per liquefaction treatment. To all SSF corn mashes, 3 ppm of penicillin and 1000 ppm of urea was added. Approximately 5 g of each corn mash (liquefied above) was added to a 15 ml polypropylene tube. The tubes were prepared by drilling a ¹⁄₃₂ inch (1.5 mm) hole and empty tubes were then weighed before liquefied corn mash was added. The tubes were weighted again after mash was added to determine the exact weight of mash in each tube. Each tube was dosed with 0.6 AGU/gDS of SPIRIZYME EXCEL XHS. Actual enzyme dosages were based on the exact weight of the corn mash in each tube. After enzyme dosage, 100 µl of ETHANOL RED™ yeast propagate was added to each tube and tubes were then incubated in a 32° C. water bath for 54 hours. Samples were taken at the end of fermentation for HPLC analysis. The HPLC preparation consisted of stopping the reaction by addition of 50 µl of 40% $H_2SO_4$, centrifuging and filtering through a 0.45µ filter. Samples were stored at 4° C. until analysis. Agilent™ 1100 HPLC system couple with RI detector was used to determine concentrations of ethanol and oligosaccharides. The separation column was aminex HPX-87H ion exclusion column (300 mm×7.8 mm) from BioRad™.

TABLE 28

Sieve Analysis.

| Sieve Size (µm) | Industrial Corn Flour | Turkish Ground Corn Flour |
|---|---|---|
| 2000 | 0.5% | 0.6% |
| 1000 | 16.6% | 6.7% |
| 850 | 8.6% | 9.1% |
| 425 | 35.5% | 44.7% |
| 250 | 11.2% | 15.2% |
| 180 | 5.5% | 5.5% |
| <180 | 13.7% | 13.6% |

TABLE 29

Summary of Contents in Liquefaction Canisters.

| Corn Flour Type | Corn Weight/ Canister (g) | Tap Water Weight/Canister (g) | AA369 Dose (KNU(AH)/gDS) | Xylanase Dose (µg EP/gDS) |
|---|---|---|---|---|
| Industrial | 37.00 | 62.70 | 0.12 | 0 |
| Industrial | 37.00 | 62.57 | 0.12 | 100 |
| Turkish | 36.96 | 62.61 | 0.12 | 100 |

Results:

The ethanol yield from each treatment is summarized in Table 30 below. The Dt xylanase provided a boost in ethanol when added to both corn flours. The increased ethanol yield of the Dt xylanase in combination with the industrial corn flour indicates that the Dt xylanase was able to break down the corn fiber and thus help to release fiber-bound starch, Dt xylanase in combination with Turkish ground industrial corn flour delivered the highest ethanol performance, indicating optimal performance when fiber-bound starch release and further mechanical grinding of the corn flour are combined.

TABLE 30

Summarized Ethanol Yield and Percent Change Results.

| Liquefaction Treatment | Ethanol (% w/v) | Ethanol Increase (%) |
|---|---|---|
| Industrial Corn Flour + AA only | 13.16 | — |
| Industrial Corn Flour + AA + Dt Xyl | 13.33 | 1.3% |
| Turkish Ground Corn Flour + AA + Dt Xyl | 13.60 | 3.3% |

The invention claimed is:

1. A process for producing fermentation products from starch-containing material comprising the steps of:
   i) liquefying the starch-containing material at a temperature above the initial gelatinization temperature using:
      an alpha-amylase;
      a GH10 xylanase having a Melting Point (DSC) above 80° C.;
   ii) saccharifying using a glucoamylase enzyme;
   iii) fermenting using a fermenting organism, wherein the starch-containing material is corn.

2. The process of claim 1, wherein the xylanase has a Melting Point (DSC) above 82° C., above 84° C., above 86° C., above 88° C., above 88° C., above 90° C., above 92° C., above 94° C., above 96° C., above 98° C., or above 100° C.

3. The process of claim 1, wherein:
   an alpha-amylase;
   a GH10 xylanase having a Melting Point (DSC) above 80° C., above 85° C., above 90° C., or 95° C.; and
   an GH5 endoglucanase having Melting Point (DSC) above 70° C., above 75° C., above 80° C., or above 85° C.; are present and/or added in liquefaction step i).

4. The process of claim 1 further comprises, prior to the liquefaction step i), the steps of:
   a) reducing a particle size of the starch-containing material;

b) forming a slurry comprising the starch-containing material and water.

5. The process of claim 1, wherein:
i) at least 50%, at least 70%, at least 80%, or at least 90% of the starch-containing material fit through a sieve with #6 screen;
ii) at least 50%, at least 59% or 60%, of the starch-containing material fit through a sieve with a 0.25 to 0.425 mm screen;
iii) at least 75% of the starch-containing material fit through a sieve with less than a 0.5 mm screen; or
iv) at least 79% or 80% of the starch-containing material fit through a sieve with equal to or less than a 0.425 mm screen.

6. The process of claim 1 wherein saccharification is carried out at a temperature from 20-75° C., from 40-70° C., and at a pH between 4 and 5.

7. The process of claim 1, wherein fermentation or simultaneous saccharification and fermentation (SSF) is carried out at a temperature from 25° C. to 40° C., from 28° C. to 35° C., from 30° C. to 34° C., for 6 to 120 hours, or 24 to 96 hours.

8. The process of claim 1, wherein the fermentation product is recovered after fermentation.

9. The process of claim 1, wherein the pH during liquefaction is between 4.0-6.5.

10. The process of claim 1, wherein the pH during liquefaction is between 4.5-6.2.

11. The process of claim 1, wherein the pH during liquefaction is between 4.8-6.0.

12. The process of claim 1, wherein the pH during liquefaction is between 5.0-5.8.

13. The process of claim 1, wherein the temperature during liquefaction is in the range from 70-100° C.

14. The process of claim 1, wherein the temperature during liquefaction is in the range from between 70-95° C.

15. The process of claim 1, wherein the temperature during liquefaction is in the range from 75-90° C.

16. The process of claim 1, wherein the temperature during liquefaction is in the range from 80-90° C.

17. The process of claim 1, wherein saccharification and fermentation is carried out simultaneously.

18. The process of claim 1, wherein saccharification and fermentation is carried out sequentially.

19. The process of claim 1, wherein the fermentation product is an alcohol.

20. The process of claim 1, wherein the fermentation product is ethanol.

21. The process of claim 1, wherein the fermentation product is fuel ethanol.

22. The process of claim 1, wherein the fermenting organism is yeast.

23. The process of claim 1, wherein the fermenting organism is a strain of *Saccharomyces* yeast.

24. The process of claim 1, wherein the fermenting organism is a strain of *Saccharomyces cerevisiae* yeast.

25. The process of claim 1, wherein the alpha-amylase is a bacterial alpha-amylase.

26. The process of claim 1, wherein the alpha-amylase is a thermostable alpha-amylase.

27. The process of claim 1, wherein the xylanase has at least 85% identity to the polypeptide of SEQ ID NO: 3.

28. The process of claim 1, wherein the xylanase has at least 90% identity to the polypeptide of SEQ ID NO: 3.

29. The process of claim 1, wherein the xylanase has at least 95% identity to the polypeptide of SEQ ID NO: 3.

* * * * *